United States Patent
Ouzounov et al.

(10) Patent No.: US 11,028,148 B2
(45) Date of Patent: *Jun. 8, 2021

(54) RECOMBINANT COLLAGEN AND ELASTIN MOLECULES AND USES THEREOF

(71) Applicant: Geltor, Inc., San Leandro, CA (US)

(72) Inventors: Nikolay Ouzounov, Alameda, CA (US); Alexander Lorestani, Oakland, CA (US); Monica Bhatia, San Ramon, CA (US)

(73) Assignee: GELTOR, INC., San Leandro, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/839,042

(22) Filed: Apr. 2, 2020

(65) Prior Publication Data

US 2020/0247875 A1 Aug. 6, 2020

Related U.S. Application Data

(63) Continuation of application No. 16/144,914, filed on Sep. 27, 2018.

(60) Provisional application No. 62/657,591, filed on Apr. 13, 2018, provisional application No. 62/564,964, filed on Sep. 28, 2017.

(51) Int. Cl.
| | | |
|---|---|---|
| *C07K 14/78* | (2006.01) | |
| *A61K 38/39* | (2006.01) | |
| *A61K 8/65* | (2006.01) | |
| *A61Q 17/04* | (2006.01) | |
| *A61Q 19/08* | (2006.01) | |

(52) U.S. Cl.
CPC .............. *C07K 14/78* (2013.01); *A61K 8/65* (2013.01); *A61K 38/39* (2013.01); *A61Q 17/04* (2013.01); *A61Q 19/08* (2013.01)

(58) Field of Classification Search
CPC ........ A61Q 19/08; A61Q 17/04; C07K 14/78; A61K 38/39; A61K 8/65
See application file for complete search history.

(56) References Cited

U.S. PATENT DOCUMENTS

| | | |
|---|---|---|
| 4,515,893 A | 5/1985 | Kung et al. |
| 4,816,397 A | 3/1989 | Boss et al. |
| 4,816,567 A | 3/1989 | Cabilly et al. |
| 4,946,778 A | 8/1990 | Ladner et al. |
| 5,091,313 A | 2/1992 | Chang |
| 5,602,183 A | 2/1997 | Martin et al. |
| 5,622,700 A | 4/1997 | Jardieu et al. |
| 5,672,347 A | 9/1997 | Aggarwal et al. |
| 5,693,762 A | 12/1997 | Queen et al. |
| 5,714,338 A | 2/1998 | Wai Fei et al. |
| 5,721,108 A | 2/1998 | Robinson et al. |
| 5,725,856 A | 3/1998 | Hudziak et al. |
| 5,736,137 A | 4/1998 | Anderson et al. |
| 6,413,742 B1 | 7/2002 | Olsen et al. |
| 6,428,978 B1 | 8/2002 | Olsen et al. |
| 6,617,431 B1 | 9/2003 | Gruber et al. |
| 6,653,450 B1 | 11/2003 | Berg et al. |
| 6,682,760 B2 | 1/2004 | Noff et al. |
| 6,903,200 B1 | 6/2005 | Chou et al. |
| 6,992,172 B1 | 1/2006 | Chang et al. |
| 7,495,076 B2 | 2/2009 | Gu et al. |
| 7,700,126 B2 | 4/2010 | Ng et al. |
| 7,754,447 B2 | 7/2010 | Glover et al. |
| 7,759,090 B2 | 7/2010 | Chou et al. |
| 7,803,577 B2 | 9/2010 | Weiss |
| 7,932,053 B2 | 4/2011 | Bank et al. |
| 7,932,353 B2 | 4/2011 | Van Es et al. |
| 8,252,553 B2 | 8/2012 | Hook et al. |
| 8,507,652 B2 | 8/2013 | Da Cruz |
| 8,618,250 B2 | 12/2013 | Russell et al. |
| 8,759,487 B2 | 6/2014 | Shoseyov et al. |
| 8,889,626 B2 | 11/2014 | Lin et al. |
| 8,956,632 B2 | 2/2015 | Boutros |
| 9,040,484 B2 | 5/2015 | Marinkovich et al. |
| 9,072,724 B2 | 7/2015 | Hausmanns et al. |
| 9,156,950 B2 | 10/2015 | Garralda et al. |
| 9,328,154 B2 | 5/2016 | Chilkoti |
| 9,382,310 B2 | 7/2016 | Mirochnitchenko et al. |
| 9,591,853 B2 | 3/2017 | Belgorodsky et al. |
| 9,675,635 B2 | 6/2017 | Minatelli et al. |
| 9,676,837 B2 | 6/2017 | Viswanathan et al. |

(Continued)

FOREIGN PATENT DOCUMENTS

| | | |
|---|---|---|
| EP | 0036776 A2 | 9/1981 |
| EP | 0535446 A1 | 4/1993 |

(Continued)

OTHER PUBLICATIONS

Lucas et al, A molecular, morphometric and mechanical comparison of the structural elements of byssus from Mytilus edulis and Mytilus galloprovincialis, The Journal of Experimental Biology, 2002, 205, pp. 1807-1817.*
Shin et al, Enhancement of the Tumor Penetration of Monoclonal Antibody by Fusion of a Neuropilin-Targeting Peptide Improves the Antitumor Efficacy, Mol Cancer Ther., 2014, 13, pp. 651-661, with supplementary information pp. 1-27.*
Phosphate buffered saline, from https://www.protocolsonline.com/recipes/phosphate-buffered-saline-pbs/, Oct. 3, 2016, pp. 1-3.*
U.S. Appl. No. 16/839,044 Office Action dated Aug. 7, 2020.
Anonymous, "ColF1—Fibrillar collagen—*Podocoryna carnera* (Hydrozoan)—colF1 gene & protein" (Jan. 1, 1998), XP055541622, Retrieved from the Internet: URL:https://www.uniportorg/uniport/076966#entry_information [retrieved on Jan. 14, 2019].

(Continued)

*Primary Examiner* — Li N Komatsu
(74) *Attorney, Agent, or Firm* — Wilson Sonsini Goodrich & Rosati

(57) ABSTRACT

This disclosure provides non-naturally occurring collagen and elastin molecules. The non-naturally occurring collagens and elastins include truncated collagens, truncated elastins, as well as fusion proteins thereof. The non-naturally occurring collagen and elastin are useful in foods, cosmetics and many other products and uses.

19 Claims, 5 Drawing Sheets

Specification includes a Sequence Listing.

(56) References Cited

U.S. PATENT DOCUMENTS

| | | | |
|---|---|---|---|
| 9,725,498 | B2 | 8/2017 | Russell et al. |
| 9,962,582 | B2 | 5/2018 | Antku |
| 10,053,501 | B2 | 8/2018 | Ramshaw et al. |
| 10,155,793 | B2 | 12/2018 | Ramshaw et al. |
| 10,232,008 | B1 | 3/2019 | Moran |
| 10,358,464 | B2 | 7/2019 | Hook et al. |
| 2013/0078209 | A1 | 3/2013 | Yu et al. |
| 2013/0237486 | A1 | 9/2013 | Bella |
| 2014/0309401 | A1 | 10/2014 | Hayashida et al. |
| 2015/0150764 | A1 | 6/2015 | Pinsky |
| 2016/0130315 | A1* | 5/2016 | Kim ............ C07K 14/4703 424/450 |
| 2016/0215018 | A1 | 7/2016 | Yang et al. |
| 2018/0282776 | A1 | 10/2018 | Douchin et al. |
| 2019/0106702 | A1 | 4/2019 | Ouzounov |
| 2019/0153068 | A1 | 5/2019 | Ouzounov et al. |
| 2019/0276515 | A1 | 9/2019 | Bruno-Bonnet et al. |
| 2020/0009184 | A1 | 1/2020 | Akthakul et al. |

FOREIGN PATENT DOCUMENTS

| | | |
|---|---|---|
| EP | 0420937 B1 | 11/1994 |
| EP | 1323820 A2 | 7/2003 |
| EP | 2941277 B1 | 9/2018 |
| EP | 3395860 A1 | 10/2018 |
| JP | 2013095708 A | 5/2013 |
| WO | WO-9304173 A1 | 3/1993 |
| WO | WO-9404690 A1 | 3/1994 |
| WO | WO-9519181 A1 | 7/1995 |
| WO | WO-9523865 A1 | 9/1995 |
| WO | WO-9630046 A1 | 10/1996 |
| WO | WO-9640210 A1 | 12/1996 |
| WO | WO-9726912 A2 | 7/1997 |
| WO | WO-9738710 A1 | 10/1997 |
| WO | WO-9806248 A2 | 2/1998 |
| WO | WO-9823761 A1 | 6/1998 |
| WO | WO-9845331 A2 | 10/1998 |
| WO | WO-9851793 A1 | 11/1998 |
| WO | WO-9903886 A1 | 1/1999 |
| WO | WO-0009018 A1 | 2/2000 |
| WO | WO-0075348 A1 | 12/2000 |
| WO | WO-0140309 A2 | 6/2001 |
| WO | WO-2004056312 A2 | 7/2004 |
| WO | WO-2005021772 A1 | 3/2005 |
| WO | WO-2015012682 A2 | 1/2015 |
| WO | WO-2015012683 A1 | 1/2015 |
| WO | WO-2016004334 A1 | 1/2016 |
| WO | WO-2017083398 A1 | 5/2017 |
| WO | WO-2017125585 A2 | 7/2017 |
| WO | WO-2017156418 A1 | 9/2017 |
| WO | WO-2017160636 A1 | 9/2017 |
| WO | WO-2017125585 A9 | 10/2017 |
| WO | WO-2017172994 A1 | 10/2017 |
| WO | WO-2017206326 A1 | 12/2017 |
| WO | WO-2018014453 A1 | 1/2018 |
| WO | WO-2018041684 A1 | 3/2018 |
| WO | WO-2018078276 A1 | 5/2018 |
| WO | WO-2018119530 A1 | 7/2018 |
| WO | WO-2019023555 A1 | 1/2019 |
| WO | WO-2019046943 A1 | 3/2019 |
| WO | WO-2019068018 A2 | 4/2019 |
| WO | WO-2019077312 A1 | 4/2019 |
| WO | WO-2019166418 A1 | 9/2019 |
| WO | WO-2020205848 A1 | 10/2020 |
| WO | WO-2020210440 A1 | 10/2020 |

OTHER PUBLICATIONS

Bornert, Olivier et al. "Analysis of the functional consequences of targeted exon deletion in COL7A1 reveals prospects for dystrophic epidermolysis bullosa therapy", Molecular Therapy. Jul. 1, 2016;24(7):1302-11.

Bornhorst Ja, Falke JJ. [16] Purification of proteins using polyhistidine affinity tags. In Methods in enzymology Jan. 1, 2000 (vol. 326, pp. 245-254). Academic Press.

Cayley, D. Scott, et al., "Biophysical characterization of changes in amounts and activity of *Escherichia coli* cell and compartment water and turgor pressure in response to osmotic stress", Biophysical Journal, (Apr. 2000), 78(4):1748-1764.

Chandrakasan et al. Preparation of intact monomeric collagen from rat tail tendon and skin and the structure of the nonhelical ends in solution. J Biol Chem. Oct. 10, 1976;251(19):6062-7.

Chou, M-Y, et al., "Genomic organization and characterization of the human type XXI collagen (COL21A1) gene", Genomics. Mar. 1, 2002;79(3):395-401.

Co-pending U.S. Appl. No. 16/839,035, filed Apr. 2, 2020.
Co-pending U.S. Appl. No. 16/839,044, filed Apr. 2, 2020.
Co-pending U.S. Appl. No. 16/839,047, filed Apr. 2, 2020.
Co-pending U.S. Appl. No. 16/844,226, filed Apr. 9, 2020.

Dinh et al. Using superfolder green fluorescent protein for periplasmic protein localization studies. J Bacteriol 193(18):4984-4987 (Sep. 2011). Epub Jul. 15, 2011. doi: 10.1128/JB.00315-11.

Fleischmajer et al. Rotary shadowing of collagen monomers, oligomers, and fibrils during tendon fibrillogenesis. J Histochem Cytochem. Jan. 1991;39(1):51-8.

GenBank Accession No. AJ009690. Version No. AJ009690.1. Podocoryne carnea mRNA for fibrillar collagen, partial. Record created Jul. 30, 1988. 2 pages. Retrieved Mar. 26, 2020 at URL:<https://www.ncbi.nlm.nih.gov/nucleotide/3355656?report=genbank&log$=nuclalign&blast_rank=1&RID=TSYP7CMV014>.

Gortz, H.-D. et al., "Changes in Fine Structure and Polypeptide Pattern during Development of Holospora obtuse, a bacterium Infecting the macronucleus of Paramecium caudatum", Journal of Bacteriology, (Oct. 1, 1990), 172(10):5664-5669, XP055373233, Retrieved from the Internet: URL: https://www.ncbi.nlm.nih.gov/pmc/articles/PMC526880/pdf/jbacter00164-0156.pdf, [retrieved May 16, 2017].

Gumpert et al. Characteristic properties and biological significance of stable protoplast type L-forms. In Protoplasts, Lecture Proceedings of the 6th International Protoplast Symposium: Basel. Experientia 1983, 46(suppl):227-241.

Haworth, R.S. et al., "Uncoupler resistance in *E. coli* Tuv and Cuv is due to the exclusion of uncoupler by the outer membrane", Biochim Biophys Acta., (Aug. 9, 1990), 1019(1):67-72, XP023349580, ISBN: 0005-2728, DOI: 10.1016/0005-2728(90)90125-N [retrieved on Aug. 9, 1990]. Abstract only.

Hoischen et al. Lipid and fatty acid composition of cytoplasmic membranes from Streptomyces hygroscopicus and its stable protoplast-type L form. J Bacteriol 179(11):3430-3436 (Jun. 1997).

International Preliminary Report on Patentability, dated Oct. 2, 2018, for International Patent Application No. PCT/US2017/024857.

International Search Report and Written Opinion of the Searching Authority for International Patent Application No. PCT/US2017/024857, dated May 31, 2017.

International Search Report and Written Opinion of the Searching Authority for International Patent Application No. PCT/US2018/053601, dated Apr. 10, 2019.

Joly et al. Chapter 20: Practical Applications for Periplasmic Protein Accumulation, in The Periplasm, ed. Ehrmann, M., ASM Press, Washington D.C., pp. 345-360 (2007).

Krapf et al. Deciphering the aggregation mechanism of bacteria (*Shewanella oneidensis* MR1) in the presence of polyethyleneimine: Effects of the exopolymeric superstructure and polymer molecular weight. Colloids Surf B Biointerfaces. Mar. 1, 2016;139:285-93. doi: 10.1016/j.colsurfb.2015.12.015. Epub Dec. 8, 2015.

Paul-Dauphin et al. Bias and precision in visual analogue scales: a randomized controlled trial. Am J Epidemiol. Nov. 15, 1999;150(10):1117-27.

Pilizota, Teuta and J. W. Shaevitz, "Fast, Multiphase Volume Adaptation to Hyperosmotic Shock by *Escherichia coli*", PLoS One, (Apr. 2012), 7(4): e35205. https://doi.org/10.1371/journal.pone.0035205.

(56) References Cited

OTHER PUBLICATIONS

Ramshaw, John A. M., et al., "Gly-XY tripeptide frequencies in collagen: a context for host-guest triple-helical peptides", Journal of structural biology. Jan. 1, 1998;122(1-2):86-91.
Schmid, V. et al., "The extracellular matrix (mesoglea) of hydrozoan jellyfish and its ability to support cell adhesion and spreading", In Hydrobiologia Jun. 1, 1991 (vol. 216, No. 1, pp. 3-10). Kluwer Academic Publishers.
Tomaro-Duchesneau et al. Microencapsulation for the Therapeutic Delivery of Drugs, Live Mammalian and Bacterial Cells, and Other Biopharmaceutics: Current Status and Future Directions. J Pharm (Cairo) 2013:103527 (2013). Published online Dec. 4, 2012. doi: 10.1155/2013/103527.
Amino acid sequence of SEQ ID No. 572 in US20130237486A1, pp. 1-2, accessed Jul. 15, 2020 at URL: http://seqdata.uspto.gov/?pageRequest=viewSequence&DocID=US20130237486A1&seqID=572. United States Patent and Trademark Office Publication Site for Issued and Published Sequences (PSIPS).
Co-pending U.S. Appl. No. 16/462,196, filed May 17, 2019.
Drumm et al. Genetic Variation and Clinical Heterogeneity in Cystic Fibrosis. Annu Rev Pathol. 2012; 7: 267-282. Published online Oct. 17, 2011. doi: 10.1146/annurev-pathol-011811-120900.
Dulbecco's Modified Eagle Medium (DMEM). Product Information. Product Code: AT068. HiMedia Laboratories Pvt Ltd., Mumbai, India. 2011. 2 pages.
GenBank Accession No. CAA08789. Version No. CAA08789.1. fibrillar collagen, partial [Podocoryna carnea]. Record created Mar. 9, 1999. 2 pages. Retrieved Apr. 28, 2020 at URL: <https://www.ncbi.nlm.nih.gov/protein/4379341?report=genbank&log$=protalign&blast_rank=1&RID=T1N9ZEUW014>.
GenBank Accession No. XP_016874317. Version No. XP_016874317.1. collagen alpha-1(II) chain isoform X1 [*Homo sapiens*]. Record created Jun. 6, 2016. 3 pages. Accessed Jun. 18, 2020 at URL: <https://www.ncbi.nlm.nih.gov/protein/XP_016874317.1?report=genbank&log$=protalign&blast_rank=11&RID=ER8N7H11014>.
Grosso et al. PGAIPG, a Repeated Hexapeptide of Bovine Tropoelastin, Is a Ligand for the 67-kDa Bovine Elastin Receptor.Matrix. Mar. 1993;13(2):157-64.doi: 10.1016/s0934-8832(11)80074-0.
Hong et al., Fibrillar Type I Collagen Enhances the Differentiation and Proliferation of Myofibroblasts by Lowering alpha2beta1 Integrin Expression in Cardiac Fibrosis. Biomed Res Int. 2017; 2017: 1790808. Published online Jan. 30, 2017. doi: 10.1155/2017/1790808. 11 pages.
Kuzan et al. An Estimation of the Biological Properties of Fish Collagen in an Experimental In Vitro Study. Adv Clin Exp Med. May-Jun. 2015;24(3):385-92.doi: 10.17219/acem/31704.
Luo et al. Collagen-like peptides and peptide-polymer conjugates in the design of assembled materials. Eur Polym J. Oct. 2013; 49(10): 2998-3009. doi: 10.1016/j.eurpolymj.2013.05.013. Available online Jun. 4, 2013.
PCT/US2020/025934 International Search Report and Written Opinion dated Jul. 2, 2020.
PCT/US2020/027399 International Search Report and Written Opinion dated Jun. 26, 2020.
Rodriguez et al. Collagen: A Review on Its Sources and Potential Cosmetic Applications. J Cosmet Dermatol. Feb. 2018;17(1):20-26. doi: 10.1111/jocd.12450. Epub Nov. 16, 2017.
Shigemura et al. Effect of Prolyl-hydroxyproline (Pro-Hyp), a food-derived collagen peptide in human blood, on growth of fibroblasts from mouse skin. J Agric Food Chem. Jan. 28, 2009;57(2):444-9. doi: 10.1021/jf802785h.
U.S. Appl. No. 16/144,914 Office Action dated Jul. 10, 2020.
U.S. Appl. No. 16/839,035 Office Action dated Jul. 24, 2020.
Water, from http://www.biology-online.org/dictionary/Water, accessed Apr. 24, 2014, 3 pages.
What Is Sorbic Acid? From https://www.healthline.com/health/food-nutrition/what-is-sorbic-acid, accessed Sep. 9, 2019, 3 pages.
Yampolsky et al. The Exchangeability of Amino Acids in Proteins. Genetics. Aug. 2005; 170(4): 1459-1472. doi: 10.1534/genetics.104.039107.
Zhuang et al. Effects of Collagen and Collagen Hydrolysate From Jellyfish (*Rhopilema esculentum*) on Mice Skin Photoaging Induced by UV Irradiation. J Food Sci. Aug. 2009;74(6):H183-8.doi: 10.1111/j.1750-3841.2009.01236.x.
Protease cleavage of SEQ ID No. 61 in WO 2019/068018A2, from ExPASy- PeptideCutter, SIB Swiss Institute of Bioinformatics, accessed Oct. 15, 2020 at URL: https://web.expasy.org/cgi-bin/peptide_cutter/peptidecutter.pl, pp. 1-2.
Sewing et al. Jellyfish collagen matrices conserve the chondrogenic phenotype in two- and three-dimensional collagen matrices. J Tissue Eng Regen Med. Mar. 2017;11(3):916-925.doi: 10.1002/term.1993. Epub Jan. 29, 2015.
U.S. Appl. No. 16/839,047 Office Action dated Oct. 21, 2020.
U.S. Appl. No. 16/844,226 Office Action dated Oct. 29, 2020.
U.S. Appl. No. 16/839,044 Final Office Action dated Dec. 10, 2020.
Peptidecutter of SEQ ID No. 4 in Chou et al., from https://web.expasy.org/cgi-bin/peptide_cutter/peptidecutter.ol, pp. 1-8, accessed Jan. 29, 2021.
Teale et al., Ultraviolet fluorescence of the aromatic amino acids. Biochem J. 65(3):476-482 (1957).
Turczynski et al., Targeted Exon Skipping Restores Type VII Collagen Expression and Anchoring Fibril Formation in an In Vivo RDEB Model. Journal of Investigative Dermatology 136: 2387-2395 (2016).
U.S. Appl. No. 16/144,914 Final Office Action dated Feb. 5, 2021.
U.S. Appl. No. 16/839,047 Notice of Allowance dated Feb. 23, 2021.
U.S. Appl. No. 16/844,226 Final Office Action dated Feb. 4, 2021.
Woodley et al., Intravenously Injected Recombinant Human Type VII Collagen Homes to Skin Wounds and Restores Skin Integrity of Dystrophic Epidermolysis Bullosa. Journal of Investigative Dermatology 133: 1910-1913 (2013).

\* cited by examiner

RECOMBINANT COLLAGEN AND ELASTIN MOLECULES AND USES THEREOF

CROSS-REFERENCE

This application is a continuation application of U.S. patent application Ser. No. 16/144,914, filed Sep. 27, 2018, which application claims priority from U.S. Provisional Patent Application No. 62/564,964, filed Sep. 28, 2017, and U.S. Provisional Patent Application No. 62/657,591, filed Apr. 13, 2018, the disclosures of which are incorporated by reference herein in their entirety.

SEQUENCE LISTING

The instant application contains a Sequence Listing which has been submitted electronically in ASCII format and is hereby incorporated by reference in its entirety. Said ASCII copy, created on Nov. 21, 2018, is named 57607702SL.txt and is 320,570 bytes in size.

FIELD

The present disclosure relates to non-naturally occurring full-length and truncated collagen molecules and full-length and truncated elastin molecules and uses thereof.

BACKGROUND

Collagens and similar proteins are the most abundant proteins in the biosphere. Collagens and elastins are structural proteins found in the skin, connective tissue and bone of animals and other tissues. In humans, the amount of collagen present in the body is approximately one third of the total proteins and accounts for about three fourths of the dry weight of skin. Elastin is a highly elastic protein found in connective tissue and other types of tissue.

The structure of collagen is a triple helix in which three polypeptide strands together form a helical coil. The individual polypeptide strands are composed of repeating triplet amino acid sequences designated as GLY-X-Y. X and Y can be any amino acid and the third amino acid is glycine. The amino acids proline and hydroxyproline are found in high concentrations in collagen. The most common triplet is proline-hydroxyproline-glycine (Gly-Pro-Hyp) accounting for approximately 10.5% of the triplets in collagen.

Gelatin is a product obtained by partial hydrolysis of collagen. Typically, gelatin is produced by acid hydrolysis, alkaline hydrolysis, and enzymatic hydrolysis or by exposing collagen to heat in an aqueous solution (e.g., boiling the bones and skins of animal, boiling fish scales, etc.).

Gelatin is used in many products including cosmetics, foods, pharmaceuticals, medical devices, photographic films, adhesives, binders and many others. The physical and chemical properties of gelatin are tuned to the particular application. These physical/chemical properties include gel strength, melting point temperature, viscosity, color, turbidity, pH, isoelectric point and others.

Elastin is an elastic protein that is crucial for the proper functioning of arteries, lung, tendons, ligament, skin and other tissue. Elastin provides the tissues with the ability to stretch and return to its original shape. The protein tropoelastin is the building block of elastin. In contrast to collagen that include a family of genes, there is one tropoelastin gene in humans. When expressed, the single elastin gene is spliced to produce different forms of the tropoelastin protein. Many tropoelastin molecules associate together to form elastin.

L-form bacteria, or L-forms, are bacterial strains derived from parent species (N-forms) that are able to grow as cell wall-deficient (spheroplast type) or as cell wall-less (protoplast type) cells. See, Madoff S (Ed): The Bacterial L-Forms. New York: Marcel Dekker Inc., 1986; Mattmann LH (Ed): Cell Wall Deficient Forms. Boca Raton: CRC Press; 1993; and Gumpert J, Taubeneck U: Characteristic properties and biological significance of stable protoplast type L-forms. In Protoplasts, Lecture Proceedings of the 6th International Protoplast Symposium: Basel. Experientia 1983, 46(suppl): 227-241.

Protoplast type L-forms have been cultivated in the cell wall-less state and represent genetically stable mutants showing extreme pleiotropic changes, including the inability to form cell walls, capsules, flagella, pili, spores and mesosomes, altered colony and cell morphology, qualitative and quantitative changes in the lipid and protein components of the cytoplasmic membrane, the absence of extracellular proteolytic activities, resistance against bacteriophages and the incapability to propagate outside laboratory conditions. See, Gumpert and Taubeneck (supra); and Hoischen et al., Lipid and fatty acid composition of cytoplasmic membranes from *Streptomyces* hygroscopic and its stable protoplast type L-form. J Bacteriol 1997, 179:3430-3436.

SUMMARY

In one aspect, a non-naturally occurring collagen produced by a host cell is provided. The non-naturally occurring collagen is jellyfish (Hydrozoan) collagen, human collagen, *Chondrosia reniformis* (kidney sponge) collagen, or *Rhincodon typus* (whale shark) collagen. In an embodiment, the non-naturally occurring collagen is a full-length or a truncated collagen. In one embodiment, the collagen is truncated by an internal truncation of between 50 amino acids and 500 amino acids. In another embodiment, the truncation is at the C-terminal end or the N-terminal end of the collagen polypeptide. The non-naturally occurring collagens are SEQ ID NO: 10, SEQ ID NO: 12, SEQ ID NO: 14, SEQ ID NO: 16, SEQ ID NO: 18, SEQ ID NO: 20, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 91, SEQ ID NO: 92, SEQ ID NO: 94, SEQ ID NO: 96, SEQ ID NO: 102, SEQ ID NO: 104, SEQ ID NO: 106, SEQ ID NO: 108, SEQ ID NO:110, or SEQ ID NO: 112.

In another aspect, the non-naturally occurring collagen further comprises amino acid sequences including a secretion tag, a histidine tag, a green fluorescent protein tag, a protease cleavage site, a Beta-lactamase and/or GEK amino acid trimer repeats and/or GDK amino acid trimer repeats. When the non-naturally occurring collagen comprises one or more amino acid trimer repeats of the sequence glycine-glutamic acid-lysine (GEK) and/or glycine-aspartic acid-lysine (GDK), the number of GEK and/or GDK trimer repeats can range from 2 to 50 trimer repeats (SEQ ID NOS: 130-131, respectively). In one aspect, the secretion tag is DsbA, PelB, OmpA, TolB, MalE, lpp, TorA, or Hy1A, or a hybrid secretion tag that comprises a portion of one secretion tag fused to a portion of a second secretion tag. An exemplary secretion tag is DsbA.

In one aspect, provided are compositions that comprise between 0.005% and 30% w/w non-naturally occurring collagen. The compositions can further comprise at least one additional ingredient comprising a topical carrier or a preservative.

Compositions comprising non-naturally occurring collagen are in one aspect topical compositions for applying to skin. The topical compositions are used for decreasing skin damage or promoting the repair of damaged skin.

One aspect provides methods for decreasing skin damage or promoting the repair of damaged skin. The method comprises applying the composition comprising elastin to the skin of a subject. The method increases the viability of the fibroblast cells or keratinocytes of the skin of the subject. In another aspect the application of the composition increases the synthesis of procollagen by the fibroblast cells of the subject's skin. In another aspect the topical application of the composition protects skin or keratinocytes against UV damage. In yet another embodiment, thymine-thymine (TT) dimer formation is decreased by the collagens or elastins disclosed herein.

Another aspect provided herein are methods of increasing the viability of skin cells. The method comprises applying collagen or elastin molecules to the skin or skin cell. The collagen or elastin as provided increases the viability of keratinocytes and/or fibroblasts is increased upon exposure to UV radiation, urban dust or other damaging stimuli.

In another aspect provided herein are methods for decreasing the production of inflammatory cytokines in a skin cell. In one embodiment the skin cell is a keratinocyte. The method comprises applying a collagen or elastin molecule to a skin cell. The production of inflammatory cytokines including TNFα, IL-1α, IL-1β, IL-3, IL-6, IL-7, IL-8, IL-10, IL-18, and IL-1RA.

In another aspect, provided are methods of protecting skin cells against the effect of exposure to urban dust. The method comprises the step of applying the collagen or elastin disclosed herein to the skin cell. The exposure of skin cell to collagen or elastin increases the viability of the skin cell. In an embodiment, the skin cell is a keratinocyte or a fibroblast.

In one aspect, a non-naturally occurring elastin produced by a host cell is provided. The non-naturally occurring elastin is jellyfish elastin, human elastin, *Chondrosia reniformis* (kidney sponge) elastin, or *Rhincodon typus* elastin. In an embodiment, the non-naturally occurring elastin is a full-length or truncated elastin. In one embodiment, the elastin is truncated by an internal truncation of between 50 amino acids and 500 amino acids. In another embodiment, the truncation is at the C-terminal end or the N-terminal end of the elastin polypeptide. The non-naturally occurring elastins are SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55 SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 98, or SEQ ID NO: 110.

In another aspect, the non-naturally occurring elastin further comprises amino acid sequences including a secretion tag, a histidine tag, a green fluorescent protein tag, a protease cleavage site, a Beta-lactamase and/or GEK amino acid trimer repeats and/or GDK amino acid trimer repeats. When the non-naturally occurring collagen comprises one or more amino acid trimer repeats of the sequence glycine-glutamic acid-lysine (GEK) and/or glycine-aspartic acid-lysine (GDK), the number of GEK and/or GDK trimer repeats can range from 2 to 50 trimer repeats (SEQ ID NOS: 130-131, respectively). In one aspect, the secretion tag is DsbA, PelB, OmpA, TolB, MalE, lpp, TorA, or Hy1A, or a hybrid secretion tag that comprises a portion of one secretion tag fused to a portion of a second secretion tag. An exemplary secretion tag is DsbA.

In another embodiment, compositions that comprise between 0.005% and 30% w/w non-naturally occurring elastin are provided. The compositions can further comprise at least one additional ingredient comprising a topical carrier or a preservative.

Compositions comprising non-naturally occurring elastin are in one aspect topical compositions for applying to skin. The topical compositions are used for decreasing skin damage or promoting the repair of damaged skin.

One embodiment provides methods for decreasing skin damage or promoting the repair of damaged skin. The method comprises applying the composition comprising elastin to the skin of a subject. The method increases the viability of the fibroblast cells of the skin of the subject. In another aspect the application of the composition increases the synthesis of procollagen by the fibroblast cells of the subject's skin. In another aspect the topical application of the compositions protects skin or keratinocytes against UV damage. In yet another embodiment, thymine-thymine (TT) dimer formation is decreased by the collagens or elastins disclosed herein.

Another embodiment provides polynucleotides that encode a non-naturally occurring collagen or a non-naturally occurring elastin. The polynucleotides encode collagen or elastin from jellyfish, human, *Chondrosia reniformis* (kidney sponge), or *Rhincodon typus*. The encoded collagen or elastin may be full length or truncated. In one embodiment, the collagen or elastin is truncated by an internal truncation of between 50 amino acids and 500 amino acids.

In one embodiment polynucleotides that encode fusion proteins comprising a secretion tag, a histidine tag, a green fluorescent protein tag, a protease cleavage site, a Beta-lactamase along and/or GEK amino acid trimer repeat and/or GDK amino acid trimer repeats together with collagen or elastin are provided. The non-naturally occurring collagen or elastin may comprise one or more amino acid trimer repeats of the sequence glycine-glutamic acid-lysine (GEK) and/or glycine-aspartic acid-lysine (GDK), the number of GEK and/or GDK trimer repeats can range from 2 to 50 trimer repeats (SEQ ID NOS: 130-131, respectively). In one aspect, the secretion tag is DsbA, PelB, OmpA, TolB, MalE, lpp, TorA, or Hy1A, or a hybrid secretion tag that comprises a portion of one secretion tag fused to a portion of a second secretion tag. An exemplary embodiment secretion tag is DsbA.

The polynucleotides and vectors can be used to transform host cells and express the polynucleotides. Polynucleotides encoding a non-naturally occurring collagen, wherein the polynucleotide is SEQ ID NO: 9, SEQ ID NO: 11, SEQ ID NO: 13, SEQ ID NO: 15, SEQ ID NO: 17, SEQ ID NO: 19 SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 90, SEQ ID NO: 93, SEQ ID NO: 95, SEQ ID NO: 97, SEQ ID NO: 103, SEQ ID NO: 105, SEQ ID NO: 107, SEQ ID NO: 109, SEQ ID NO:111, SEQ ID NO: 113, or SEQ ID NO:105 are provided. Polynucleotides encoding a non-naturally occurring elastin, wherein the polynucleotide is SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, and SEQ ID NO: 72, SEQ ID NO: 99, or SEQ ID NO:101provided.

Host cells that express the polynucleotides of the invention are disclosed. Host cells can be any host cell including bacterial cells, yeast cells, fungal cells, insect cells, mammalian cells, plant cells and any other cells used to express exogenous polynucleotides.

Bacterial host cells in which the cells have been modified to inhibit cell division and the periplasmic space is increased are provided. An exemplary host cell is *E. coli*.

One embodiment provides a method of producing a non-naturally occurring collagen or a non-naturally occurring elastin. The method comprises the steps of inoculating a culture medium with a recombinant host cell comprising polynucleotides that encode the collagen or elastin, cultivating the host cell, and isolating the non-naturally occurring collagen or the non-naturally occurring elastin from the host cell.

DESCRIPTION

Figure 1:
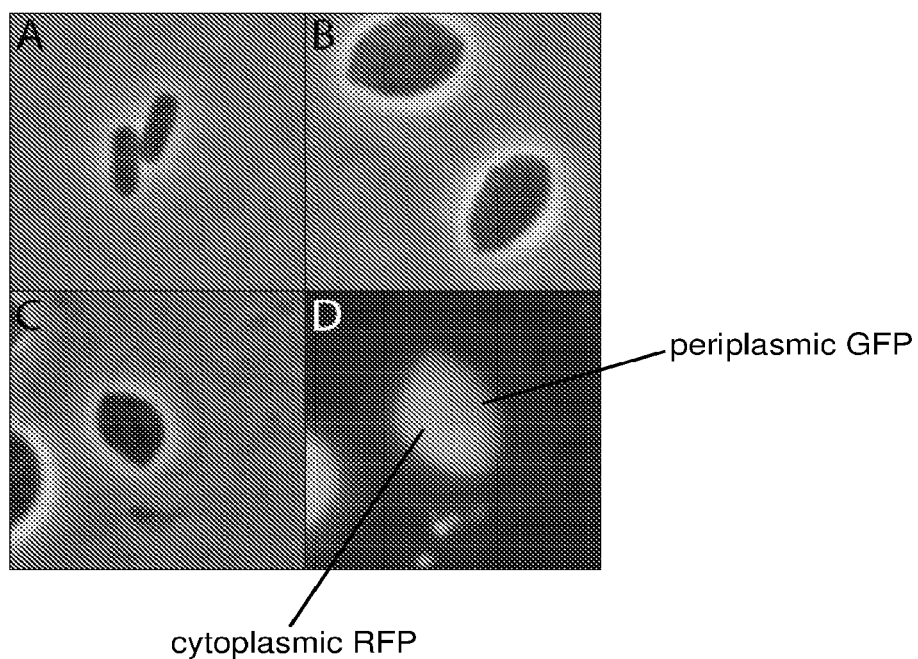
FIG. 1 depicts the physiological state difference between switched and unswitched cells. A) Unswitched *Escherichia coli* cells. B) Same *Escherichia coli* population as figure A but has undergone the physiological switch. C) Phase contrast of switched *Escherichia coli* cell containing cytoplasmic RFP and periplasmic GFP. D) Fluorescent imaging of cell in figure C illustrates targeted protein localization.
Figure 2:
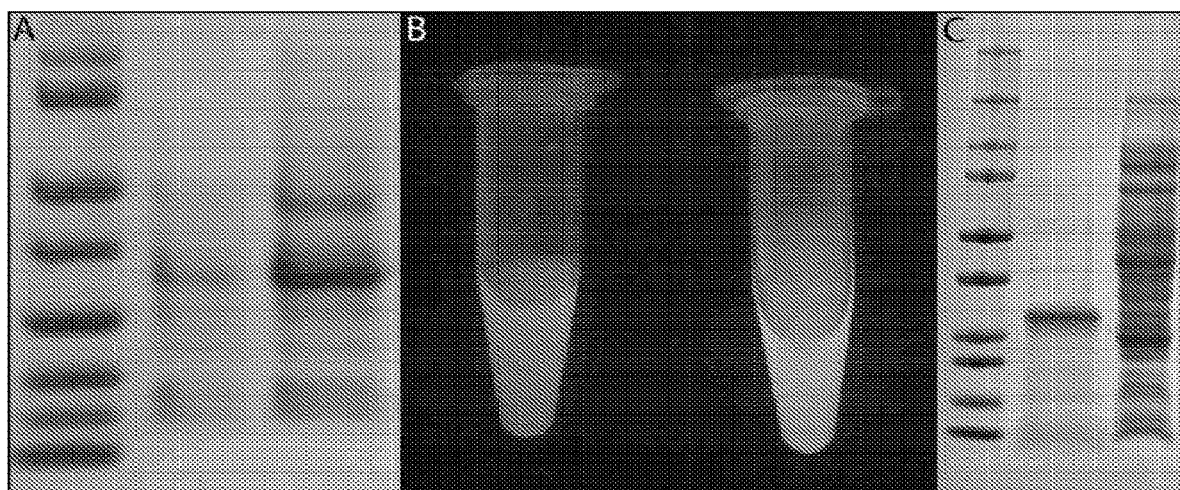
FIG. 2 depicts enhanced protein production in switched cells. A-B) Target protein for T7 inducible protein production is periplasmic expressed GFP, produced in *Escherichia coli* BL21. The same population of cells was used and induced at OD 1.1. A) Protein ladder (lane 1), IPTG induced protein production (lane 2), IPTG induced protein production with physiological switch (lane 3). B) Two vials of the cell GFP induced cultures with IPTG only on left and IPTG+Switch on right. C) Expression of a 22 kDa collagen using switched cells showing protein ladder (lane 1), supernatant after protein production (lane 2), cell pellet (lane 3).
Figure 3:
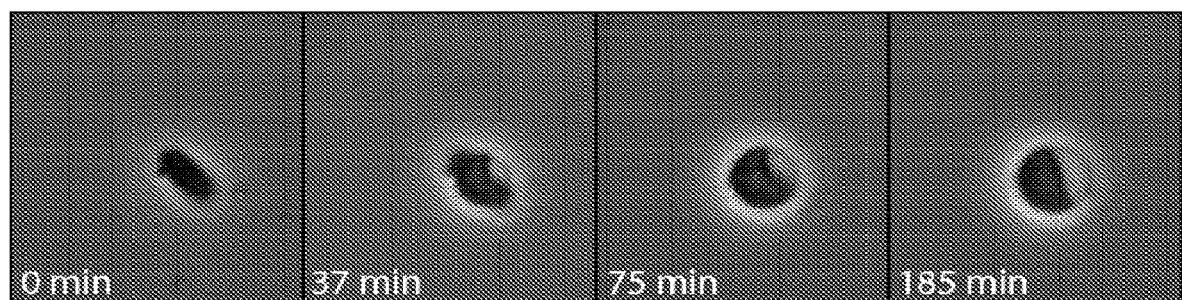
FIG. 3 depicts a time-lapse of *Escherichia coli* cell switching over time.
Figure 4:
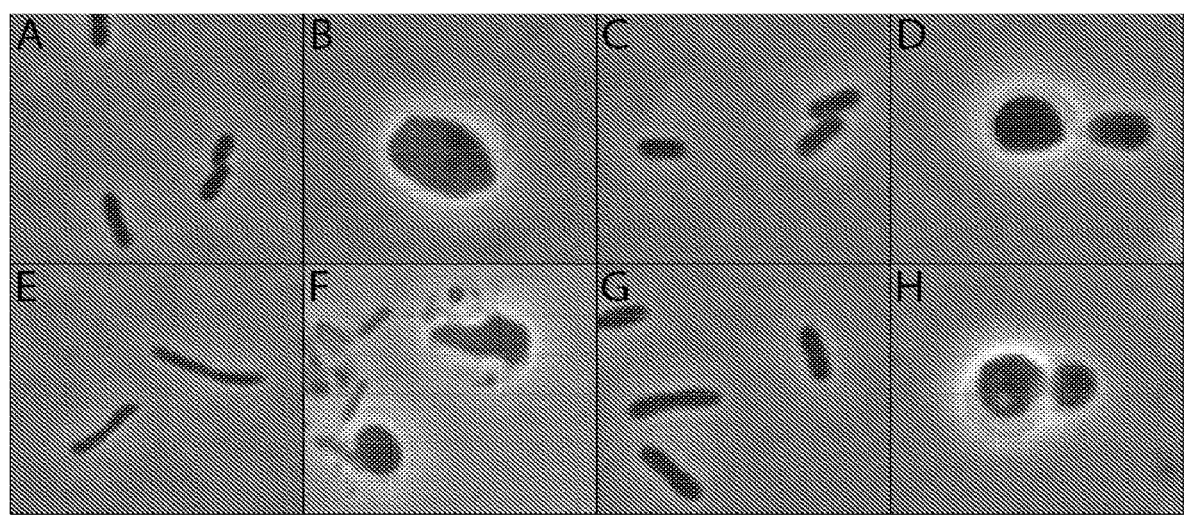
FIG. 4 illustrates other organisms undergoing the physiological switch. A) *Agrobacterium tumefaciens* normal physiology. B) *Agrobacterium tumefaciens* switched physiology. C) *Pseudomonas aeruginosa* PAO1 normal physiology. D) *Pseudomonas aeruginosa* PAO1 switched physiology. E) *Brevundimonas diminuta* normal physiology. F) *Brevundimonas diminuta* switched physiology. G) *Agrobacterium tumefaciens* normal physiology. H) *Agrobacterium tumefaciens* switched physiology.

In the following description, certain specific details are set forth in order to provide a thorough understanding of various embodiments of the disclosure. However, one skilled in the art will understand that the disclosure may be practiced without these details.

As used herein the term "about" refers to ±10%.

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this disclosure may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The term "collagen" or "collagen-like" as used herein refers to a monomeric polypeptide that can associate with one or more collagen or collagen-like polypeptides to form a quaternary structure. Collagen can be treated with acid, base or heat to prepare gelatin. The quaternary structure of natural collagen is a triple helix typically composed of three polypeptides. Of the three polypeptides that form natural collagen, two are usually identical and are designated as the alpha chain. The third polypeptide is designated as the beta chain. Thus a typical natural collagen can be designated as AAB, wherein the collagen is composed of two alpha ("A") strands and one beta ("B") strand. The term "procollagen" as used herein refers to polypeptides produced by cells that can be processed to naturally occurring collagen.

The terms "elastin" as used herein refers to a polypeptide that is elastic and functions to stretch or contract and return to its original shape. Elastin is found naturally in connective tissue.

The term "expression vector" or "vector" as used herein refers to a nucleic acid assembly which is capable of directing the expression of the exogenous gene. The expression vector may include a promoter which is operably linked to the exogenous gene, restriction endonuclease sites, nucleic acids that encode one or more selection markers, and other nucleic acids useful in the practice of recombinant technologies.

The term "fibroblast" as used herein refers to a cell that synthesizes procollagen and other structural proteins. Fibroblasts are widely distributed in the body and found in skin, connective tissue and other tissues.

The term "fluorescent protein" is a protein that is commonly used in genetic engineering technologies used as a reporter of expression of an exogenous polynucleotide. The protein when exposed to ultraviolet or blue light fluoresces and emits a bright visible light. Proteins that emit green light is green fluorescent protein (GFP) and proteins that emit red light is red fluorescent protein (RFP).

The term "gelatin" as used herein refers to collagen that has been further processed by exposure to acid, base or heat. While not wishing to be bound by theory or mechanism, treatment of collagen with acid, base or heat is thought to denature the collagen polypeptides. Aqueous denatured collagen solutions form reversible gels used in foods, cosmetics, pharmaceuticals, industrial products, medical products, laboratory culture growth media, and many other applications.

The term "gene" as used herein refers to a polynucleotide that encodes a specific protein, and which may refer to the coding region alone or may include regulatory sequences preceding (5' non-coding sequences) and following (3' non-coding sequences) the coding sequence.

The term "histidine tag" is a 2-30 contiguous series of histidine residues on a recombinant polypeptide.

The term "host cell" is a cell that is engineered to express an introduced exogenous polynucleotide.

The term "keratinocyte" is a cell that produces keratins found in the epidermal layer of the skin.

The term "lactamase" as used herein refer to enzymes that hydrolyze antibiotics that contain a lactam (cyclic amide) moiety. "Beta-lactamase" or "β-lactamase" are enzymes that hydrolyze antibiotics that contain a β-lactam moiety.

The term "non-naturally occurring" as used herein refers to collagen or elastin that is not normally found in nature. The non-naturally occurring collagen or elastin are recombinantly prepared. The non-naturally occurring collagen or elastin is a recombinant collagen or recombinant elastin. The non-naturally occurring collagen is in one embodiment a truncated collagen. Other non-naturally occurring collagen polypeptides include chimeric collagens. A chimeric collagen is a polypeptide wherein one portion of a collagen polypeptide is contiguous with a portion of a second collagen polypeptide. For example, a collagen molecule comprising a portion of a jellyfish collagen contiguous with a portion of a human collagen is a chimeric collagen. In another embodiment, the non-naturally occurring collagen comprises a fusion polypeptide that includes additional amino acids such as a secretion tag, histidine tag, green fluorescent protein, protease cleavage site, GEK repeats, GDK repeats, and/or beta-lactamase. The non-naturally occurring elastin in one embodiment a truncated elastin. Other non-naturally occurring elastin polypeptides include chimeric elastins. A chimeric elastin is a polypeptide wherein one portion of an elastin polypeptide is contiguous with a portion of a second elastin polypeptide. For example, a collagen molecule comprising a portion of a jellyfish elastin contiguous with a portion of a human elastin is a chimeric elastin. In another embodiment, the non-naturally occurring elastin comprises a fusion polypeptide that includes additional amino acids such as a secretion tag, histidine tag, green fluorescent protein, protease cleavage site and/or beta-lactamase. The chimeric gelatin or the chimeric elastin can comprise additional amino acids such as a secretion tag, histidine tag, green fluorescent protein, protease cleavage site, GEK repeats, GDK repeats, and/or beta-lactamase.

The term "protease cleavage site" is an amino acid sequence that is cleaved by a specific protease.

The term "secretion tag" or "signal peptide" refers to an amino acid sequence that recruits the host cell's cellular machinery to transport an expressed protein to a particular location or cellular organelle of the host cell.

The term "truncated collagen" refers to a monomeric polypeptide that is smaller than a full-length collagen wherein one or more portions of the full-length collagen is not present. Collagen polypeptides are truncated at the C-terminal end, the N-terminal end, or truncated by removal of internal portion(s) of the full-length collagen polypeptide.

The term "truncated elastin" refers to a monomeric polypeptide that is smaller than a full-length elastin wherein one or more portions of the full-length elastin is not present. Elastin polypeptides are truncated at the C-terminal end, the N-terminal end, or truncated by removal of internal portion(s) of the full-length elastin polypeptide.

In co-owned application PCT/US17/24857, incorporated by reference, an expression system that uses modified bacterial cells (switched cells) in which cell division is inhibited and growth of the periplasmic space is greatly enhanced was disclosed. In this expression system, the expressed proteins are targeted to the periplasmic space. Recombinant protein production in these switched cells is dramatically increased compared with that in non-switched cells. Structurally, the cells comprise both inner and outer membranes but lack a functional peptidoglycan cell wall, while the cell shape is spherical and increases in volume over time. Notably, while the periplasmic space normally comprises only 10-20% of the total cell volume, the periplasmic compartment of the switched state described herein can comprise more than 20%, 30%, 40% or 50% and up to 60%, 70%, 80% or 90% of the total cell volume.

The modified bacterial cells of PCT/US17/24857 are derived from Gram-negative bacteria, e.g. selected from: gammaproteobacteria and alphaproteobacteria. In some embodiments, the bacterium is selected from: *Escherichia coli, Vibrio natriegens, Pseudomonas fluorescens, Caulobacter crescentus, Agrobacterium tumefaciens*, and *Brevundimonas diminuta*. In specific embodiments, the bacterium is *Escherichia coli*, e.g. strain BL21(DE3).

In another aspect, the host bacterial cells have an enlarged periplasmic space in a culture medium comprising a magnesium salt, wherein the concentration of magnesium ions in the medium is at least about 3, 4, 5 or 6 mM. In further embodiments, the concentration of magnesium ions in the medium is at least about 7, 8, 9 or 10 mM. In some embodiments, the concentration of magnesium ions in the medium is between about 5 mM and 25 mM, between about 6 mM and/or about 20, or 10 mM. In some embodiments, the magnesium salt is selected from: magnesium sulfate and magnesium chloride.

In other embodiments, the culture medium further comprises an osmotic stabilizer, including, e.g. sugars (e.g., arabinose, glucose, sucrose, glycerol, sorbitol, mannitol, fructose, galactose, saccharose, maltotrioseerythritol, ribitol, pentaerythritol, arabitol, galactitol, xylitol, iditol, maltotriose, and the like), betaines (e.g., trimethylglycine), proline, sodium chloride, wherein the concentration of the osmotic stabilizer in the medium is at least about 4%, 5%, 6%, or 7% (w/v). In further embodiments, the concentration of osmotic stabilizer is at least about 8%, 9%, or 10% (w/v). In some embodiments, the concentration of the osmotic stabilizer in the medium is between about 5% to about 20% (w/v).

In some embodiments, the cell culture may further comprise ammonium chloride, ammonium sulfate, calcium chloride, amino acids, iron(II) sulfate, magnesium sulfate, peptone, potassium phosphate, sodium chloride, sodium phosphate, and yeast extract.

The host bacterial cell may be cultured continuously or discontinuously; in a batch process, a fed-batch process or a repeated fed-batch process.

In some embodiments, the antibiotic is selected from: β-lactam antibiotics (e.g. penicillins, cephalosporins, carbapenems, and monobactams), phosphonic acid antibiotics, polypeptide antibiotics, and glycopeptide antibiotics. In particular embodiments, the antibiotic is selected from alafosfalin, amoxicillin, ampicillin, aztreonam, bacitracin, carbenicillin, cefamandole, cefotaxime, cefsulodin, cephalothin, fosmidomycin, methicillin, nafcillin, oxacillin, penicillin g, penicillin v, fosfomycin, primaxin, and vancomycin.

Without being bound by theory, the cell morphology that promotes recombinant protein production and inhibits cell division appears to be driven by the removal of the cell wall under the media conditions stated above. In some embodiments, the methods for removal/inhibition of cell wall synthesis can be through the use of antibiotics that inhibit peptidoglycan synthesis (such as ampicillin, carbenicillin, penicillins or fosfomycin), or other methods known in the art.

When having an appropriate periplasmic targeting signal sequence, recombinantly produced polypeptides can be secreted into the periplasmic space of bacterial cells. Joly, J. C. and Laird, M. W., in The Periplasm ed. Ehrmann, M., ASM Press, Washington D.C., (2007) 345-360. In the chemically oxidizing environment of the periplasm the formation of disulfide bonds and thereby the functionally correct folding of polypeptides is favored.

In general, the signal sequence may be a component of the expression vector, or it may be a part of the exogenous gene that is inserted into the vector. The signal sequence selected should be one that is recognized and processed (i.e., cleaved by a signal peptidase) by the host cell. For bacterial host cells that do not recognize and process the native signal sequence of the exogenous gene, the signal sequence is substituted by any commonly known bacterial signal sequence. In some embodiments, recombinantly produced polypeptides can be targeted to the periplasmic space using the DsbA signal sequence. Dinh and Bernhardt, J Bacteriol, September 2011, 4984-4987.

In one aspect, a non-naturally occurring collagen or elastin is produced by a host cell is provided. The non-naturally occurring collagen or elastin is jellyfish collagen or elastin, human collagen or elastin, or *Chondrosia reniformis* (kidney sponge) collagen or elastin, or *Rhincodon typus* collagen or elastin. The non-naturally occurring collagen or elastin is a truncated collagen. The truncation is an internal truncation, a truncation at the N-terminal portion of the collagen or elastin, or a truncation at the C-terminal portion of the collagen or elastin. The collagen or elastin is truncated by a truncation of between 50 amino acids and 1000 amino acids, between, 50 amino acids and 950 amino acids, between 50 amino acids and 900 amino acids, between 50 amino acids and 850 amino acids, between 50 amino acids and 800 amino acids, between 50 amino acids and 850 amino acids, between 50 amino acids and 800 amino acids, between 50 amino acids and 750 amino acids, between 50 amino acids and 700 amino acids, between 50 amino acids and 650 amino acids, between 50 amino acids and 600 amino acids, between 50 amino acids and 650 amino acids, between 50 amino acids and 500 amino acids, between 50 amino acids and 450 amino acids, between 50 amino acids and 400 amino acids, between 50 amino acids and 350 amino acids, between 50 amino acids and 300 amino acids, between 50 amino acids and 250 amino acids, between 50 amino acids and 200 amino acids, between 50 amino acids and 150 amino acids, or between 50 amino acids and 100 amino acids. In another embodiment, the collagen or elastin is truncated by 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900, 950, or 1000 amino acids. The non-naturally occurring collagen or elastin are encoded by a portion of a polynucleotide sequence or the entire polynucleotide sequence disclosed herein.

The non-naturally occurring collagen or elastin further comprises amino acid sequences including a secretion tag. The secretion tag directs the collagen or elastin to the periplasmic space of the host cell. In particular embodiments, the signal peptide is derived from DsbA, PelB, OmpA, TolB, MalE, lpp, TorA, or Hy1A, or a hybrid secretion tag that comprises a portion of one secretion tag fused to a portion of a second secretion tag. In one aspect the secretion tag is attached to the non-naturally occurring collagen or elastin. In another aspect the secretion tag is cleaved from the non-naturally occurring collagen or elastin.

The non-naturally occurring collagen or the non-naturally occurring elastin o further comprises a histidine tag. The histidine tag or polyhistidine tag is a sequence of 2 to 20 histidine residues (SEQ ID NO: 117) that are attached to the collagen or elastin. The histidine tag comprises 2 to 20 histidine residues (SEQ ID NO: 117), 5 to histidine residues (SEQ ID NO: 118), 5 to 18 histidine residues (SEQ ID NO: 119), 5 to 16 histidine residues (SEQ ID NO: 120), 5 to 15 histidine residues (SEQ ID NO: 118), 5 to 14 histidine residues (SEQ ID NO: 121), 5 to 13 histidine residues (SEQ ID NO: 122), 5 to 12 histidine residues (SEQ ID NO: 123), 5 to 11 (SEQ ID NO: 124), 5 to 10 histidine residues (SEQ ID NO: 125), 6 to 12 histidine residues (SEQ ID NO: 126), 6 to 11 histidine residues (SEQ ID NO: 127), or 7 to 10 histidine residues (SEQ ID NO: 128). The histidine tags are useful in purification of proteins by chromatographic methods utilizing nickel based chromatographic media. Exemplary fluorescent proteins include green fluorescent protein (GFP) or red fluorescent protein (RFP). Fluorescent proteins are well known in the art. In one embodiment the non-naturally occurring collagen or the on-naturally occurring elastin comprises a GFP and/or RFP. In one embodiment a superfolder GFP is fused to the on-naturally occurring collagen or elastin. The superfolder GFP is a GFP that folds properly even when fused to a poorly folded polypeptide. In one aspect the histidine tag is attached to the non-naturally occurring collagen or elastin. In another aspect the histidine tag is cleaved from the non-naturally occurring collagen or elastin.

The non-naturally occurring collagen or non-naturally occurring elastin further comprises a protease cleavage site. The protease cleavage site is useful to cleave the recombinantly produced collagen or elastin to remove portions of the polypeptide. The portions of the polypeptide that may be removed include the secretion tag, the histidine tag, the fluorescent protein tag and/or the Beta-lactamase. The proteases comprise endoproteases, exoproteases, serine proteases, cysteine proteases, threonine proteases, aspartic proteases, glutamic proteases, and metalloproteases. Exemplary protease cleavage sites include amino acids that are cleaved by Thrombin, TEV protease, Factor Xa, Enteropeptidase, and Rhinovirus 3C Protease. In one aspect the cleavage tag is attached to the non-naturally occurring collagen or elastin. In another aspect the cleavage tag is removed by an appropriate protease from the non-naturally occurring collagen or elastin.

The non-naturally occurring collagen or non-naturally occurring elastin further comprises an enzyme that is a Beta-lactamase. The beta-lactamase is useful as a selection marker. In one aspect the beta-lactamase is attached to the non-naturally occurring collagen or elastin. In another aspect the beta-lactamase is cleaved from the non-naturally occurring collagen or elastin.

The non-naturally occurring collagen or non-naturally occurring elastin further comprises GEK amino acid trimer repeats and/or GDK amino acid trimer repeats. The GEK and the GDK trimer repeats facilitate the gelling of the collagen and/or the gelatin. In one embodiment, the non-naturally occurring collagen or the non-naturally occurring elastin comprises 2-50 GEK and/or 2-50 GDK trimer repeats (SEQ ID NOS: 130-131, respectively), 2-40 GEK and/or 2-40 GDK trimer repeats (SEQ ID NOS: 132-133, respectively), 2-30 GEK and/or 2-30 GDK trimer repeats (SEQ ID NOS: 134-135, respectively), 2-20 GEK and/or 2-20 GDK trimer repeats (SEQ ID NOS: 136-137, respectively), 2-15 GEK and/or 2-15 GDK trimer repeats (SEQ ID NOS: 138-139, respectively). 2-10 GEK and/or 2-10 GDK trimer repeats (SEQ ID NOS: 140-141, respectively), 2-9 GEK and/or 2-9 GDK trimer repeats (SEQ ID NOS: 142-143, respectively), 2-8 GEK and/or 2-8 GDK trimer repeats (SEQ ID NOS: 144-145, respectively), 2-7 GEK and/or 2-7 GDK trimer repeats (SEQ ID NOS: 146-147, respectively), 2-6 GEK and/or 2-6 GDK trimer repeats (SEQ ID NOS: 148-149, respectively), 2-5 GEK and/or 2-5 GDK trimer repeats (SEQ ID NOS: 150-151, respectively), or 2-4 GEK and/or 2-4 GDK trimer repeats (SEQ ID NOS: 152-153, respectively). In one aspect the GEK trimer repeat or the GDK trimer repeat is attached to the non-naturally occurring collagen or elastin. In another aspect the GEK trimer repeat or the GDK trimer repeat is cleaved from the non-naturally occurring collagen or elastin.

Provided herein are compositions that comprise between 0.005% and 30% w/w non-naturally occurring collagen and/or non-naturally occurring elastin. The composition comprises between 0.005% and 20% w/w non-naturally occurring collagen and/or non-naturally occurring elastin, between 0.005% and 10% w/w non-naturally occurring collagen and/or non-naturally occurring elastin, between 0.005% and 5% w/w non-naturally occurring collagen and/or non-naturally occurring elastin, between 0.005% and 2% w/w non-naturally occurring collagen and/or non-naturally occurring elastin, between 0.005% and 1% w/w non-naturally occurring collagen and/or non-naturally occurring elastin, between 0.005% and 0.5% w/w non-naturally occurring collagen and/or non-naturally occurring elastin, and between 0.005% and 0.2% w/w non-naturally occurring collagen and/or non-naturally occurring elastin.

The compositions that comprise the between non-naturally occurring collagen and/or non-naturally occurring elastin are personal care products. In some embodiments the compositions are formulated for topical administration. The compositions can contain other cosmetic ingredients suitable for human use. The personal care products are useful for preventing or treating ultraviolet radiation damage to human skin or hair. The personal care products are applied to skin or hair. The personal care products include, for example, masks, skin cleaners such as soap, cleansing creams, cleansing lotions, cleansing milks, cleansing pads, facial washes, hair shampoo, hair conditioner and body shampoos.

The compositions that comprise the non-naturally occurring collagen and/or non-naturally occurring elastin can further comprise at least one additional ingredient comprising a topical carrier or a preservative. The topical carrier comprises a topical carrier selected from the group consisting of liposome, biodegradable microcapsule, lotion, spray, aerosol, dusting powder, biodegradable polymer, mineral oil, triglyceride oil, silicone oil, glycerin, glycerin monostearate, alcohols, emulsifying agents, liquid petroleum, white petrolatum, propylene glycol, polyoxyethylene, polyoxypropylene, wax, sorbitan monostearate, polysorbate, cetyl ester wax, cetearyl alcohol, 2-octyldodecanol, benzyl alcohol, cyclomethicone, cyclopentasiloxane, and water. The preservative comprises a preservative selected from the group consisting of tocopherol, diiodomethyl-p-tolylsulfone, 2-Bromo-2-nitropropane-1,3-diol, cis isomer 1-(3-chloroallyl)-3,5,7-triaza-1-azoniaadamantane chloride, glutaraldehyde, 4,4-dimethyl oxazolidine, 7-Ethylbicyclooxazolidine, methyl paraben, sorbic acid, GERMABEN® II, rosemary extract, and EDTA.

Provided are methods of decreasing skin damage, promoting the repair of damaged skin, protecting skin against UV damage, protecting skin cells against the effects of exposure to urban dust. The method comprises the step of applying the composition comprising the non-naturally occurring collagen and/or non-naturally occurring elastin to the skin of a subject. Without being bound to a particular theory or mechanism, the collagen and/or the elastin in the composition decrease skin damage by protecting against UV damage, and/or promotes the repair of damaged skin by increasing the viability of cells and/or increasing procollagen synthesis when applied to skin, and/or promotes the viability of skin cells. The collagens and elastins in one aspect decrease the formation of thymine-thymine (TT) dimer formation.

One aspect provides polynucleotides that encode a non-naturally occurring collagen or a non-naturally occurring elastin. The polynucleotides encode collagen or elastin from jellyfish, human, *Chondrosia reniformis* (kidney sponge), or *Rhincodon typus*. The polynucleotides encode for collagen or elastin that is full length or truncated.

Another aspect provides polynucleotides that encode collagen or elastin fusion proteins. The elastin or collagen fusion proteins comprise a secretion tag, a histidine tag, a fluorescent protein tag, a protease cleavage site, a Beta-lactamase along and/or GEK amino acid trimer repeats and/or GDK amino acid trimer repeats together with collagen or elastin.

The polynucleotides are in one aspect vectors used to transform host cells and express the polynucleotides. The polynucleotides further comprise nucleic acids that encode enzymes that permit the host organism to grow in the presence of a selection agent. The selection agents include certain sugars including galactose containing sugars or antibiotics including ampicillin, hygromycin, G418 and others. Enzymes that are used to confer resistance to the selection agent include β-galactosidase or a β-lactamase.

In one aspect host cells that express the polynucleotides of the invention are provided. Host cells can be any host cell including gram negative bacterial cells, gram positive bacterial cells, yeast cells, insect cells, mammalian cells, plant cells or any other cells used to express exogenous polynucleotides. An exemplary gram-negative host cell is *E. coli*.

Bacterial host cells in which the cells have been modified to inhibit cell division and the periplasmic space is increased are taught. As discussed herein and taught in example 1, Beta-lactam antibiotics are useful as a switch to convert wild-type bacterial cells to a modified bacterial cell in which cell replication is inhibited and the periplasmic space is increased. Exemplary Beta-lactam antibiotics including penicillins, cephalosporins, carbapenems, and monobactams.

The switched form of bacteria (L-form) are cultivated in culture media that include certain salts and other nutrients. Salts and media compositions that support the physiological switch physiology that have been tested are M63 salt media, M9 salt media, PYE media, and Luria-Bertani (LB) media. Any necessary supplements besides carbon, nitrogen, and inorganic phosphate sources may also be included at appropriate concentrations introduced alone or as a mixture with another supplement or medium such as a complex nitrogen source. In certain embodiments, the medium further comprises one or more ingredients selected from: ammonium chloride, ammonium sulfate, calcium chloride, casamino acids, iron(II) sulfate, magnesium sulfate, peptone, potassium phosphate, sodium chloride, sodium phosphate, and yeast extract.

Beta-lactamases are enzymes that confer resistance to lactam antibiotics in prokaryotic cells. Typically when Beta-lactamases are expressed in bacterial host cells, the expressed Beta-lactamase protein also includes targeting sequences (secretion tag) that direct the Beta-lactamase protein to the periplasmic space. Beta-lactamases are not functional unless they are transported to the periplasmic space. Beta-lactamase targeted to the periplasmic without the use of an independent secretion tag that targets the enzyme to the periplasmic space are provided. By creating a fusion protein in which a periplasmic secretion tag added to the N-terminus of a protein such as GFP, collagen, or GFP/collagen chimeras, the functionality of the Beta-lactamase lacking a native secretion tag can be used to select for full translation and secretion of the N-terminal fusion proteins. Using this approach, we have used a DsbA-GFP-Collagen-Beta-lactamase fusion to select for truncation products in the target collagens that favor translation and secretion.

Another embodiment provides methods of producing a non-naturally occurring collagen or a non-naturally occurring elastin. The method comprises the steps of inoculating a culture medium with a recombinant host cell comprising polynucleotides that encode the collagen or elastin, cultivating the host cell, and isolating the non-naturally occurring collagen or the non-naturally occurring elastin from the host cell.

A process for fermentative preparation of a protein is provided. The process comprises the steps of:
  a) culturing a recombinant Gram-negative bacterial cell in a medium comprising a magnesium salt, wherein the concentration of magnesium ions in the medium is at least about 6 mM, and wherein the bacterial cell comprises an exogenous gene encoding the protein;
  b) adding an antibiotic to the medium, wherein the antibiotic inhibits peptidoglycan biogenesis in the bacterial cell; and
  c) harvesting the protein from the medium.

The bacteria may be cultured continuously—as described, for example, in WO 05/021772—or discontinuously in a batch process (batch cultivation) or in a fed-batch or repeated fed-batch process for the purpose of producing the target protein. In some embodiments, protein production is conducted on a large-scale. Various large-scale fermentation procedures are available for production of recombinant proteins. Large-scale fermentations have at least 1,000 liters of capacity, preferably about 1,000 to 100,000 liters of capacity. These fermentors use agitator impellers to distribute oxygen and nutrients, especially glucose (the preferred carbon/energy source). Small-scale fermentation refers generally to fermentation in a fermentor that is no more than approximately 20 liters in volumetric capacity.

For accumulation of the target protein, the host cell is cultured under conditions sufficient for accumulation of the target protein. Such conditions include, e.g., temperature, nutrient, and cell-density conditions that permit protein expression and accumulation by the cell. Moreover, such conditions are those under which the cell can perform basic cellular functions of transcription, translation, and passage of proteins from one cellular compartment to another for the secreted proteins, as are known to those skilled in the art.

The bacterial cells are cultured at suitable temperatures. For $E.\ coli$ growth, for example, the typical temperature ranges from about 20° C. to about 39° C. In one embodiment, the temperature is from about 20° C. to about 37° C. In another embodiment, the temperature is at about 30° C. In one embodiment, the host cells, in the non-switched state or switched state are cultivated at one temperature and switched to a different temperature to induce protein production. The host cells are cultivated first at one temperature to propagate the cells, then to induce protein production the cell are cultivated at a lower temperature. The first temperature is 23°, 24°, 25°, 26°, 27°, 28°, 29°, 30°, 31°, 32°, 33°, 34°, 35°, 36°, or 37° C. The second temperature is 20°, 21°, 22°, 23°, 24°, 25°, 26°, 27°, 28°, 29°, 30°, 31°, 32°, 33°, 34°, 35° or 36° C. The cultivation at the second temperature is conducted between 1 hour and 100 hours, between 5 hours and 90 hours, between 5 hours and 80 hours, between hours and 80 hours, between 5 hours and 70 hours, between 10 hours and 70 hours, between 15 hours and 70 hours, between 15 hours and 65 hours, between 15 hours and 60 hours, between 20 hours and 60 hours, between 20 hours and 55 hours, between 20 hours and 50 hours, between 24 hours and 50 hours, between 24 hours and 48 hours, between 30 hours and 50 hours, between 30 hours and 45 hours, or between 30 hours and 40 hours.

The pH of the culture medium may be any pH from about 5-9, depending mainly on the host organism. For $E.\ coli$, the pH is from about 6.8 to about 7.4, or about 7.0.

For induction of gene expression, typically the cells are cultured until a certain optical density is achieved, e.g., an OD600 of about 1.1, at which point induction is initiated (e.g., by addition of an inducer, by depletion of a repressor, suppressor, or medium component, etc.) to induce expression of the exogenous gene encoding the target protein. In some embodiments, expression of the exogenous gene is inducible by an inducer selected from, e.g. isopropyl-β-d-1-thiogalactopyranoside, lactose, arabinose, maltose, tetracycline, anhydrotetracycline, vavlycin, xylose, copper, zinc, and the like. The induction of gene expression can also be accomplished by decreasing the dissolved oxygen levels during fermentation. The dissolved oxygen levels of the fermentation during cell propagation is between 10% and 30%. To induce gene expression the dissolved oxygen level is reduced to below 10%, 9%, 8%, 7%, 6%, 5%, 4%, 3%, 2%, 1%, or 0%. In host cells, in either the physiological state or the switched state, protein production can be induced by lowering the temperature of the fermentation as disclosed herein.

After product accumulation, the cells are vortexed and centrifuged in order to induce lysis and release of recombinant proteins. The majority of the proteins is found in the supernatant but any remaining membrane bound proteins can be released using detergents (such as TRITON™ X-100).

In a subsequent step, the target protein, as a soluble or insoluble product released from the cellular matrix, is recovered in a manner that minimizes co-recovery of cellular debris with the product. The recovery may be done by any means, but in one embodiment, can comprise histidine tag purification through a nickel column. See, e.g., Purification of Proteins Using Polyhistidine Affinity Tags, Methods Enzymology. 2000; 326: 245-254.

EXAMPLES

Example 1: Expression System

Materials and Methods:
Strains:
Tested Physiological Switch and Protein Production:
*E. coli* BL21(DE3)—From NEB, product #c2527
*E. coli* K12 NCM3722—From The *Coli* Genetic Stock Center, CGSC #12355
Tested Physiological Switch:
Gammaproteobacteria:
*Vibrio natriegens*—From ATCC, product #14048
*Pseudomonas fluorescens*—From ATCC, product #31948
*Pseudomonas aeruginosa* PAO1—From ATCC, product #BAA-47
Alphaproteobacteria:
*Caulobacter crescentus*—From ATCC, product #19089
*Agrobacterium tumefaciens/Rhizobium radiobacter*—From ATCC, product #33970
*Brevundimonas diminuta*—From ATCC, product #13184
Media Compositions:
1 Liter 5×m63 Salts:
g (NH4)2SO4—From P212121, product #7783-20-2
68 g KH2PO4—From P212121, product #7778-77-0
2.5 mg FeSO4.7H2O—From Sigma Aldrich, product #F7002
Bring volume up to 1 liter with milliQ water
Adjust to pH 7 with KOH (From P212121, product #1310-58-3)
Autoclave mixture
1 Liter of 1M MgSO4:
246.5 g MgSO4 7H2O—From P212121, (Sigma Aldrich, product #10034-99-8)
Bring volume up to 1 liter with milliQ water.
Autoclave mixture.
1 Liter of Switch Media 1:
133.4 mL 5×m63 salts
mL 1M MgSO4
38.6 g Glucose—From P212121, product #50-99-7
66.6 g Sucrose—From P212121, product #57-50-1
8.33 g LB mix—From P212121, product #lb-miller
Bring volume up to 1 liter with milliQ water.
Filter sterilize mixture through a 0.22 µM pore vacuum filter (Sigma Aldrich, product #CLS430517).
1 Liter of Switch Media 2:
133.4 mL 5×m63 salts
mL 1M MgSO4
38.6 g Glucose—From P212121, product #50-99-7
66.6 g Sucrose—From P212121, product #57-50-1
g Yeast Extract—From FisherSci.com, product #J60287A1
Bring volume up to 1 liter with milliQ water.
Filter sterilize mixture through a 0.22 µM pore vacuum filter (Sigma Aldrich, product #CLS430517).

For Bioreactor Growth:
liter of bioreactor media MGZ12:
1) Autoclave 1 L of Glucose at concentration of 500 g/L in DI water. (VWR, product #97061-170).
2) Autoclave 1 L of Sucrose at concentration of 500 g/L in DI water. (Geneseesci.com, product #62-112).
3) Autoclave in 3946 mL of DI water:
g (NH4)2HPO4. (VWR, product #97061-932).
66.5 g KH2PO4. (VWR, product #97062-348).
22.5 g H3C6H5O7. (VWR, product #BDH9228-2.5KG).
2.95 g MgSO4.7H2O. (VWR, product #97062-134).
mL Trace Metals (Teknova), 1000×. (Teknova, product #T1001).
After autoclaving add 400 mL of (1) to (3), 65 mL of 10M NaOH (VWR, product #97064-480) to (3), and 666 mL of (2) to (3).
A feed of 500 g/L of glucose can be used during fermentation run as needed.
At induction add:
50 mL of 1M MgSO4.7H2O to a 5 L bioreactor
1 to 10 mM concentration of IPTG. (carbosynth.com, product #EI05931).
Add Fosfomycin (50 µg/mL or higher) and Carbenicillin (100 µg/mL or higher).
Physiological Switch:
The physiological switch is optimally flipped at an OD 600 of 1 to 1.1 for *E. coli* for growth in shake flasks at volumes up to 1 L. For the other species tested, cultures were grown in switch media and subcultured once cultures reached maximal OD 600. In all cases the physiological switch is flipped through the addition of 100-200 ug/mL Carbenicillin (From P212121, product #4800-94-6) and 50-100 ug/mL Fosfomycin (From P212121, product #26016-99-9). The majority of the population is in the switched state within a few hours. To confirm that cells underwent a physiological switch, cells were imaged on a Nikon Ti-E with perfect focus system, Nikon CFI60 Plan Apo 100×NA 1.45 objective, Prior automated filter wheels and stage, LED-CFP/YFP/mCherry and LED-DA/FI/TX filter sets (Semrock), a Lumencor Sola II SE LED illumination system, and a Hamamatsu Flash 4.0 V2 CMOS camera.
Image Analysis of Physiological Switch:
Images were analyzed using ImageJ to measure dimensions. In the switched state, the spherical outline of the outer membrane is treated as a sphere to calculate total volume ($V=(4/3)\pi r3$). The cytoplasmic volume is calculated as an ellipsoid that exists within the sphere ($V=(4/3)\pi*$(longest radius)*(short radius)2). To calculate the periplasmic volume, the cytoplasmic volume is subtracted from the total volume of the cell.
Protein Expression and Quantification:
*E. coli* BL21(DE3) (NEB product #c2527) containing pET28a (emd Millipore product #69864) and its derivatives carrying GFP or collagen derivatives were grown in a shaking incubator at 37° C. overnight in switch media containing 50 mg/mL kanamycin (p212121 product #2251180). Next day, subcultures are started with a 1:10 dilution of the overnight culture into fresh switch media containing 50 mg/mL kanamycin. The culture is then physiologically switched and protein production is induced simultaneously at an OD 600 of 1 to 1.1 (Read on a Molecular Devices SPECTRAMAX® M2 microplate reader). The physiologically switch and protein production are flipped through the addition of 100 ug/mL Carbenicillin, 50 ug/mL Fosfomycin, and 100 ug/mL IPTG (p212121 product #367-93-1). Protein expression is continued in the switched state from between 8 hours to overnight at room temperature (approximately 22° C.) on an orbital shaker. In order to quantify total protein levels, QUICK START™ Bradford Protein Assay was used on mixed portion of culture and standard curves are quantitated on a Molecular Devices Spectramax M2 microplate reader. In order to quantitate the relative intensity of target protein production relative to the rest of the protein population the mixed portion of the cultures were run on MINI-PROTEAN® TGX™ Gels and stained with BIO-SAFE™ Coomassie Stain.

Induction of Protein Production:

Standard procedures have been followed to induce protein production in the physiological state. We have been using the strain BL21(DE3) containing the plasmid pET28a driving the IPTG/lactose inducible production of recombinant proteins and targeting them to the periplasmic space using the DsbA signal sequence. Using the GFP protein, targeted to the periplasmic space as described above, we have demonstrated the ability to gain and increase of 5-fold in protein production when compared to un-switched cell populations induced at the same optical density, for the same amount of time (figures). The induction was optimal at an OD600 of 1.1 and induction was continued for 10 hours at which point the protein produced was measured at about 200 mg/mL.

Example 2: Production of Full-Length Collagen

Full length jellyfish collagen was produced using the expression system discussed in Example 1 herein. The wild-type amino acid sequence of *Podocoryna carnea* (jellyfish or Hydrozoan) collagen is provided in SEQ ID NO: 1.

(SEQ ID NO: 1)
GPQGVVGADGKDGTPGEKGEQGRTGAAGKQGSPGADGARGPLGSIGQQGA

RGEPGDPGSPGLRGDTGLAGVKGVAGPSGRPGQPGANGLPGVNGRGGLRG

KPGAKGIAGSDGEAGESGAPGQSGPTGPRGQRGPSGEDGNPGLQGLPGSD

GEPGEEGQPGRSGQPGQQGPRGSPGEVGPRGSKGPSGDRGDRGERGVPGQ

TGSAGNVGEDGEQGGKGVDGASGPSGALGARGPPGSRGDTGAVGPPGPTG

RSGLPGNAGQKGPSGEPGSPGKAGSAGEQGPPGKDGSNGEPGSPGKEGER

GLAGPPGPDGRRGETGSPGIAGALGKPGLEGPKGYPGLRGRDGTNGKRGE

QGETGPDGVRGIPGNDGQSGKPGIDGIDGTNGQPGEAGYQGGRGTRGQLG

ETGDVGQNGDRGAPGPDGSKGSAGRPGLR

<//www.ncbi.nlm.nih.gov/protein/
4379341?report=genbank&log$=protalign&blast_r
ank=1&RID=T1N9ZEUW014>

The non-codon optimized polynucleotide sequence encoding the full length jellyfish collagen is disclosed in SEQ ID NO: 2.

(SEQ ID NO: 2)
ggaccacaaggtgttgtaggagctgatggcaaagatggaacaccgggaga gaaaggtgagcaaggacgaaccggagctgcaggaaaacagggaagccctg gagcagatggagcaagaggccctcttggatcaattggacaacaaggtgct cgtggagaacctggtgatccaggatctcccggcttaagaggagatactgg attggctggagtcaaaggagtagcaggaccatctggtcgacctggacaac ccggtgcaaatggattacctggtgtgaatggcagaggcggtttgagaggc aaacctggtgctaaaggaattgctggcagtgatggagaagcgggagaatc tggcgcacctggacagtccggacctaccggtccacgtggtcaacgaggac caagtggtgaggatggtaatcctggattacagggattgcctggttctgat ggagagcccggagaggaaggacaacctggaagatctggtcaaccaggaca gcaaggaccacgtggttccctggagaggtaggaccaagaggatctaaag gtccatcaggagatcgtggtgacaggggagagagaggtgttcctggacaa acaggttcggctggaaatgtaggagaagatggagagcaaggaggcaaagg tgtcgatggagcgagtggaccaagtggagctcttggtgctcgtggtcccc caggaagtagaggtgacaccggggcagtgggacctcccggacctactggg cgatctggtttacctggaaacgcaggacaaaagggaccaagtggtgaacc aggtagtccaggaaaagcaggatcagctggtgaacagggtcctcctggta aagacggatcaaatggtgaacctggatctcctggcaaagagggtgaacgt ggtcttgctggtccaccaggtccagatggcagacgtggtgaaacgggatc tccaggtatcgctggtgctcttggtaaaccaggttttggaaggacctaaag gttatccaggattaagaggaagagatggaaccaatggcaaacgaggagaa caaggagaaactggtcctgatggagtcagaggtattcctggaaatgatgg acaatctggcaaaccaggtattgatggtattgacggaacaaatggtcaac caggtgaggctggataccaaggtggtagaggtacacgtggtcagttaggt gaaactggtgatgtcggacagaatggagatcgaggagctcctggtcctga tggatctaaaggttctgctggtagaccaggacttcgtgg <https://www.ncbi.nlm.nih.gov/nucleotide/
3355656?report=genbank&log$=nuclalign
&blast_rank=1&RID=TSYP7CMV014>

Two different codon optimized polynucleotide sequences encoding the wild-type, full-length jellyfish collagen were synthesized. The two polynucleotide sequences were slightly different due to slightly different codon optimization methods. In addition to the non-truncated, full-length jellyfish collagen, the polynucleotides also encoded a secretion tag, a 9 amino acid his tag (SEQ ID NO: 129), a short linker, and a thrombin cleavage site. The DsbA secretion tag is encoded by nucleotides 1-71. The histidine tag comprising 9 histidine residues (SEQ ID NO: 129) is encoded by nucleotides 73-99 and encodes amino acids 25-33. The linker is encoded by nucleotides 100-111. The thrombin cleavage tag is encoded by nucleotides 112-135 and encodes amino acids 38-45. The truncated collagen is encoded by nucleotides 136-1422. The two polynucleotides are disclosed below in SEQ ID NO: 3 and 4.

(SEQ ID NO: 4)
ATGAAAAAGATTTGGCTGGCGCTGGCTGGTTTAGTTTTAGCGTTTAGCGC

ATCGGCGGCGCAGTATGAAGATCACCATCACCACCACCACCATCACCACT

CTGGCTCGAGCCTGGTGCCGCGCGGCAGCCATATGGGTCCGCAGGGTGTT

GTTGGTGCAGATGGTAAAGACGGTACCCCGGGTGAAAAAGGAGAACAGGG

ACGTACAGGTGCAGCAGGTAAACAGGGCAGCCCGGGTGCCGATGGTGCC

CGTGGCCCGCTGGGTAGCATTGGTCAGCAGGGTGCAAGAGGCGAACCGG

```
GCGATCCGGGTAGTCCGGGCCTGCGTGGTGATACGGGTCTGGCCGGTGTT

AAAGGCGTTGCAGGTCCTTCAGGTCGTCCAGGTCAACCGGGTGCAAATGG

TCTGCCGGGTGTTAATGGTCGTGGCGGTCTGCGTGGCAAACCGGGAGCAA

AAGGTATTGCAGGTAGCGATGGAGAAGCCGGTGAAAGCGGTGCCCCGGG

TCAGAGTGGTCCGACCGGTCCGCGCGGTCAGCGTGGTCCGTCTGGTGAAG

ATGGCAATCCGGGTCTGCAGGGTCTGCCTGGTAGTGATGGCGAACCAGGT

GAAGAAGGTCAGCCGGGTCGTTCAGGCCAGCCGGGCCAGCAGGGCCCGC

GTGGTAGCCCGGGCGAAGTTGGCCCGCGGGGTAGTAAAGGTCCTAGTGGC

GATCGCGGTGATCGTGGTGAACGCGGTGTTCCTGGTCAGACCGGTAGCGC

AGGTAATGTTGGCGAAGATGGTGAACAGGGTGGCAAAGGTGTTGATGGTG

CAAGCGGTCCGAGCGGTGCACTGGGTGCACGTGGTCCTCCGGGCAGCCGT

GGTGACACCGGTGCAGTTGGTCCGCCTGGCCCGACCGGCCGTAGTGGCTT

ACCGGGTAATGCAGGTCAGAAAGGTCCGTCAGGTGAACCTGGCAGCCCTG

GTAAAGCAGGTAGTGCCGGTGAGCAGGGTCCGCCGGGCAAAGATGGTAG

TAATGGTGAGCCGGGTAGCCCTGGCAAAGAAGGTGAACGTGGTCTGGCAG

GACCGCCGGGTCCTGATGGTCGCCGCGGTGAAACGGGTTCACCGGGTATT

GCCGGTGCCCTGGGTAAACCAGGTCTGGAAGGTCCGAAAGGTTATCCTGG

TCTGCGCGGTCGTGATGGTACCAATGGCAAACGTGGCGAACAGGGCGAAA

CCGGTCCAGATGGTGTTCGTGGTATTCCGGGTAACGATGGTCAGAGCGGT

AAACCGGGCATTGATGGTATTGATGGCACCAATGGTCAGCCTGGCGAAGC

AGGTTATCAGGGTGGTCGCGGTACCCGTGGTCAGCTGGGTGAAACAGGTG

ATGTTGGTCAGAATGGTGATCGCGGCGCACCGGGTCCGGATGGTAGCAAA

GGTAGCGCCGGTCGTCCGGGTTTACGTtaa
                                                (SEQ ID NO: 3)
ATGAAAAAGATTTGGCTGGCGCTGGCTGGTTTAGTTTTAGCGTTTAGCGC

ATCGGCGGCGCAGTATGAAGATCACCATCACCACCACCACCATCACCACT

CTGGCTCGAGCCTGGTGCCGCGCGGCAGCCATATGGGTCCGCAGGGTGTT

GTTGGTGCAGATGGTAAAGACGGTACCCCGGGTGAAAAGGtGAACAGGG tCGTACcGGTGCAGCAGGTAAACAGGGCAGCCCGGGTGCCGATGGTGCCC

GTGGCCCGCTGGGTAGCATTGGTCAGCAGGGTGCAcgtGGCGAACCGGGC

GATCCGGGTAGcCCGGGCCTGCGTGGTGATACGGGTCTGGCCGGTGTTAA

AGGCGTTGCAGGTCCTTCtGGTCGTCCAGGTCAACCGGGTGCAAATGGTC

TGCCGGGTGTTAATGGTCGTGGCGGTCTGCGTGGCAAACCGGGtGCAAAA

GGTATTGCAGGTAGCGATGGcGAAGCCGGTGAAAGCGGTGCCCCGGGTCA

GAGcGGTCCGACCGGTCCGCGCGGTCAGCGTGGTCCGTCTGGTGAAGATG

GCAATCCGGGTCTGCAGGGTCTGCCTGGTAGcGATGGCGAACCAGGTGAA

GAAGGTCAGCCGGGTCGTTCtGGCCAGCCGGGCCAGCAGGGCCCGCGTGG

TAGCCCGGGCGAAGTTGGCCCGCGcGGTtcTAAAGGTCCTAGcGGCGATC

GCGGTGATCGTGGTGAACGCGGTGTTCCTGGTCAGACCGGTAGCGCAGGT

AATGTTGGCGAAGATGGTGAACAGGGTGGCAAAGGTGTTGATGGTGCAAG

CGGTCCGAGCGGTGCACTGGGTGCACGTGGTCCTCCGGGCAGCCGTGGTG

ACACCGGTGCAGTTGGTCCGCCTGGCCCGACCGGCCGTAGcGGCctgCCG

GGTAATGCAGGTCAGAAAGGTCCGTCtGGTGAACCTGGCAGCCCTGGTAA

AGCAGGTAGcGCCGGTGAGCAGGGTCCGCCGGGCAAAGATGGTAGcAATG

GTGAGCCGGGTAGCCCTGGCAAAGAAGGTGAACGTGGTCTGGCAGGtCCG

CCGGGTCCTGATGGTCGCCGCGGTGAAACGGGTTCtCCGGGTATTGCCGG

TGCCCTGGGTAAACCAGGTCTGGAAGGTCCGAAAGGTTATCCTGGTCTGC

GCGGTCGTGATGGTACCAATGGCAAACGTGGCGAACAGGGCGAAACCGGT

CCAGATGGTGTTCGTGGTATTCCGGGTAACGATGGTCAGAGCGGTAAACC

GGGCATTGATGGTATTGATGGCACCAATGGTCAGCCTGGCGAAGCAGGTT

ATCAGGGTGGTCGCGGTACCCGTGGTCAGCTGGGTGAAACcGGTGATGTT

GGTCAGAATGGTGATCGCGGCGCACCGGGTCCGGATGGTAGCAAAGGTAG

CGCCGGTCGTCCGGGTctgCGTtaa
```

The amino acid sequence encoded by the polynucleotides of SEQ ID NO: 3 and SEQ ID NO:4 is disclosed in SEQ ID NO:5 below. In SEQ ID NO: 5 the DsbA secretion tag is encoded by nucleotides 1-71 and encodes amino acids 1-24; the histidine tag comprising 9 histidine residues (SEQ ID NO: 129) is encoded by nucleotides 73-99 and encodes amino acids 25-33; the linker is encoded by nucleotides 100-111 and encodes amino acids 34-37; the thrombin cleavage tag is encoded by nucleotides 112-135 and encodes amino acids 38-45; the full-length collagen is encoded by nucleotides 136-1422 and encodes amino acids 46-474.

```
                                                (SEQ ID NO: 5)
MKKIWLALAGLVLAFSASAAQYEDHHHHHHHHHSGSSLVPRGSHMGPQGV

VGADGKDGTPGEKGEQGRTGAAGKQGSPGADGARGPLGSIGQQGARGEPG

DPGSPGLRGDTGLAGVKGVAGPSGRPGQPGANGLPGVNGRGGLRGKPGAK

GIAGSDGEAGESGAPGQSGPTGPRGQRGPSGEDGNPGLQGLPGSDGEPGE

EGQPGRSGQPGQQGPRGSPGEVGPRGSKGPSGDRDGRGERGVPGQTGSAG

NVGEDGEQGGKGVDGASGPSGALGARGPPGSRGDTGAVGPPGPTGRSGLP

GNAGQKGPSGEPGSPGKAGSAGEQGPPGKDGSNGEPGSPGKEGERGLAGP

PGPDGRRGETGSPGIAGALGKPGLEGPKGYPGLRGRDGTNGKRGEQGETG

PDGVRGIPGNDGQSGKPGIDGIDGTNGQPGEAGYQGGRGTRGQLGETGDV

GQNGDRGAPGPDGSKGSAGRPGLR
```

A jellyfish collagen without the DsbA secretion tag, the histidine tag, linker and thrombin cleavage site is disclosed in SEQ ID NO: 89.

```
                                                (SEQ ID NO: 89)
GPQGVVGADGKDGTPGEKGEQGRTGAAGKQGSPGADGARGPLGSIGQQGA

RGEPGDPGSPGLRGDTGLAGVKGVAGPSGRPGQPGANGLPGVNGRGGLRG

KPGAKGIAGSDGEAGESGAPGQSGPTGPRGQRGPSGEDGNPGLQGLPGSD

GEPGEEGQPGRSGQPGQQGPRGSPGEVGPRGSKGPSGDRDGRGERGVPGQ

TGSAGNVGEDGEQGGKGVDGASGPSGALGARGPPGSRGDTGAVGPPGPTG

RSGLPGNAGQKGPSGEPGSPGKAGSAGEQGPPGKDGSNGEPGSPGKEGER

GLAGPPGPDGRRGETGSPGIAGALGKPGLEGPKGYPGLRGRDGTNGKRGE
```

-continued

QGETGPDGVRGIPGNDGQSGKPGIDGIDGTNGQPGEAGYQGGRGTRGQLG

ETGDVGQNGDRGAPGPDGSKGSAGRPGLR

The polynucleotides of SEQ ID NO: 3 and SEQ ID NO: 4 were synthesized by Gen9 DNA, now Ginkgo Bioworks internal synthesis. Overlaps between the pET28 vector and SEQ ID NO: 3 and SEQ ID NO: 4 were designed to be between 30 and 40 bp long and added using PCR with the enzyme PRIMESTAR® GXL polymerase (<http://www.clontech.com/US/Products/PCR/GC Rich/PrimeSTAR_GXL_DNA_P olymerase?sitex=10020:22372:US>). The opened pET28a vector and insert DNA (SEQ ID NO: 3 or SEQ ID NO: 4) were then assembled together into the final plasmid using SGI GIBSON ASSEMBLY® (<https://us.vwr.com/store/product/17613857/gibson-assembly-hifi-1-step-kit-synthetic-genomics-inc>). Sequence of plasmid was then verified through Sanger sequencing through Eurofins Genomics (<www.eurofinsgenomics.com>).

The transformed cells were cultivated in minimal media and frozen in 1.5 aliquots with glycerol at a ratio of 50:50 of cells to glycerol. One vial of this frozen culture was revived in 50 ml of minimal media overnight at 37° C., 200 rpm. Cells were transferred into 300 ml of minimal media and grown for 6-9 hours to reach an OD600 of 5-10.

Minimal media used in this example and throughout this application is prepared as follows. The minimal media (Table 1) was autoclaved in several separate fractions, Salts mix (Ammonium Phosphate dibasic, Potassium phosphate monobasic, Citric acid anhydrous, Magnesium sulfate heptahydrate), the Sucrose at 500 g/L, the Glucose at 55%, the Trace Metals TM5 (table 2), and Sodium Hydroxide 10M. The minimal media was then mixed together at the above concentrations post-autoclaving in the hood.

TABLE 1

Minimal media recipe for shake flask cultures

| chemical | Formula | MW | Conc (g/L) |
| --- | --- | --- | --- |
| Ammonium Phosphate dibasic | $(NH_4)_2HPO_4$ | 133 | 4 |
| Potassium phosphate monobasic | $KH_2PO_4$ | 137 | 13.3 |
| Citric acid anhydrous | $H_3C_6H_5O_7$ | 192.14 | 4.5 |
| Magnesium sulfate heptahydrate | $MgSO_4 \cdot 7H_2O$ | 246 | 0.59 |
| Trace Metals TM5 | | | 2 |
| Glucose | $C_6H_{12}O_6$ | 500 | 40 |
| Sodium Hydroxide 10M | NaOH | 400 | 5.2 |
| Sucrose 500 g/L | $C_{12}H_{22}O_{11}$ | 500 | 66.6 |

TABLE 2

Trace Metals TM5 composition

| chemical | Formula | MW | Conc (g/L) |
| --- | --- | --- | --- |
| Ferrous Sulfate Heptahydrate | $FeSO_4 \cdot 7H_2O$ | 278.02 | 27.8 |
| Calcium Chloride | $CaCl_2 \cdot 2H_2O$ | 147 | 2.94 |
| Manganese Chloride | $MnCl_2$ | 125.84 | 1.26 |
| Zinc Sulfate | $ZnSO_4 \cdot H_2O$ | 179.5 | 1.8 |
| Nickel Chloride | $NiCl_2 \cdot 6H_2O$ | 237.69 | 0.48 |
| Sodium Molybate | $Na_2MoO_4 \cdot 2H_2O$ | 241.95 | 0.48 |
| Sodium Selenite | $Na_2SeO_3$ | 172.94 | 0.35 |
| Boric Acid | $H_3BO_3$ | 61.83 | 0.12 |

The harvested cells were disrupted in a homogenizer at 14,000 psi pressure in 2 passes. Resulting slurry contained the collagen protein along with other proteins.

The collagen was purified by acid treatment of homogenized cell broth. The pH of the homogenized slurry was decreased to 3 using 6M Hydrochloric acid. Acidified cell slurry was incubated overnight at 4° C. with mixing, followed by centrifugation. Supernatant of the acidified slurry was tested on a polyacrylamide gel and found to contain collagen in relatively high abundance compared to starting pellet. The collagen slurry thus obtained was high in salts. To obtain volume and salt reduction, concentration and diafiltration steps were performed using an EMD Millipore Tangential Flow Filtration system with ultrafiltration cassettes of 0.1 m² each. Total area of filtration was 0.2 m² using 2 cassettes in parallel. A volume reduction of 5× and a salt reduction of 19× was achieved in the TFF stage. Final collagen slurry was run on an SDS-PAGE gel to confirm presence of the collagen. This slurry was dried using a multi-tray lyophilizer over 3 days to obtain a white, fluffy collagen powder.

The purified collagen was analyzed on an SDS-PAGE gel and a thick and clear band was observed at the expected size of 42 kilodaltons. The purified collagen was also analyzed by mass spectrometry and it was confirmed that the 42 kilodalton protein was jellyfish collagen.

The fermentations were performed at various temperature ranging from 25° to 28° C. For some fermentations, the temperature of the fermentation was maintained at a constant temperature and immediately upon completion of fermentation (OD600 of 5-10) the collagen was purified. For other fermentations, the temperature of the fermentations was maintained for a desired period of time and when cell densities of OD600 of 5-10 were reached, the temperature was reduced to induce protein production. Typically, the temperature was reduced from 28° C. to 25° C. After the fermentation at 25° C. was continued for 40-60 hours, the collagen was isolated.

Additional Full Length Jellyfish Collagens

A full length jellyfish collagen without a His tag, linker, and thrombin cleavage site is disclosed below. Two codon-optimized nucleotide sequence encoding this collagen are provided in SEQ ID NO: 6 and SEQ ID NO: 7. The differences in the nucleotide sequences are due to different codon-optimization strategies but encode the same protein. The amino acid sequence is disclosed in SEQ ID NO: 8. The DsbA secretion tag is encoded by nucleotides 1-72 and encodes amino acids 1-24. The collagen sequence is encoded by nucleotides 73-1359 and encodes amino acids 25-453.

(SEQ ID NO: 6)
ATGAAAAAGATTTGGCTGGCGCTGGCTGGTTTAGTTTTAGCGTTTAGCGC

ATCGGCGGCGCAGTATGAAGATGGTCCGCAGGGTGTTGTTGGTGCAGATG

GTAAAGACGGTACCCCGGGTGAAAAAGGAGAACAGGGACGTACAGGTGCA

GCAGGTAAACAGGGCAGCCCGGGTGCCGATGGTGCCCGTGGCCCGCTGG

GTAGCATTGGTCAGCAGGGTGCAAGAGGCGAACCGGGCGATCCGGGTAG

TCCGGGCCTGCGTGGTGATACGGGTCTGGCCGGTGTTAAAGGCGTTGCAG

GTCCTTCAGGTCGTCCAGGTCAACCGGGTGCAAATGGTCTGCCGGGTGTT

AATGGTCGTGGCGGTCTGCGTGGCAAACCGGGAGCAAAAGGTATTGCAGG

TAGCGATGGAGAAGCCGGTGAAAGCGGTGCCCCGGGTCAGAGTGGTCCG

ACCGGTCCGCGCGGTCAGCGTGGTCCGTCTGGTGAAGATGGCAATCCGGG

```
TCTGCAGGGTCTGCCTGGTAGTGATGGCGAACCAGGTGAAGAAGGTCAGC
CGGGTCGTTCAGGCCAGCCGGGCCAGCAGGGCCCGCGTGGTAGCCCGGGC
GAAGTTGGCCCGCGGGGTAGTAAAGGTCCTAGTGGCGATCGCGGTGATCG
TGGTGAACGCGGTGTTCCTGGTCAGACCGGTAGCGCAGGTAATGTTGGCG
AAGATGGTGAACAGGGTGGCAAAGGTGTTGATGGTGCAAGCGGTCCGAG
CGGTGCACTGGGTGCACGTGGTCCTCCGGGCAGCCGTGGTGACACCGGTG
CAGTTGGTCCGCCTGGCCCGACCGGCCGTAGTGGCTTACCGGGTAATGCA
GGTCAGAAAGGTCCGTCAGGTGAACCTGGCAGCCCTGGTAAAGCAGGTAG
TGCCGGTGAGCAGGGTCCGCCGGGCAAAGATGGTAGTAATGGTGAGCCG
GGTAGCCCTGGCAAAGAAGGTGAACGTGGTCTGGCAGGACCGCCGGGTCC
TGATGGTCGCCGCGGTGAAACGGGTTCACCGGGTATTGCCGGTGCCCTGG
GTAAACCAGGTCTGGAAGGTCCGAAAGGTTATCCTGGTCTGCGCGGTCGT
GATGGTACCAATGGCAAACGTGGCGAACAGGGCGAAACCGGTCCAGATG
GTGTTCGTGGTATTCCGGGTAACGATGGTCAGAGCGGTAAACCGGGCATT
GATGGTATTGATGGCACCAATGGTCAGCCTGGCGAAGCAGGTTATCAGGG
TGGTCGCGGTACCCGTGGTCAGCTGGGTGAAACAGGTGATGTTGGTCAGA
ATGGTGATCGCGGCGCACCGGGTCCGGATGGTAGCAAAGGTAGCGCCGGT
CGTCCGGGTTTACGTtaa
                                     (SEQ ID NO: 7)
ATGAAAAAGATTTGGCTGGCGCTGGCTGGTTTAGTTTTAGCGTTTAGCGC
ATCGGCGGCGCAGTATGAAGATGGTCCGCAGGGTGTTGTTGGTGCAGATG
GTAAAGACGGTACCCCGGGTGAAAAAGGtGAACAGGGtCGTACcGGTGCA
GCAGGTAAACAGGGcAGCCCGGGTGCCGATGGTGCCCGTGGCCCGCTGGG
TAGCATTGGTCAGCAGGGTGCAcgtGGCGAACCGGGCGATCCGGGTAGcC
CGGGCCTGCGTGGTGATACGGGTCTGGCCGGTGTTAAAGGCGTTGCAGGT
CCTTCtGGTCGTCCAGGTCAACCGGGTGCAAATGGTCTGCCGGGTGTTAA
TGGTCGTGGCGGTCTGCGTGGCAAACCGGGtGCAAAAGGTATTGCAGGTA
GCGATGGcGAAGCCGGTGAAAGCGGTGCCCCGGGTCAGAGcGGTCCGACC
GGTCCGCGCGGTCAGCGTGGTCCGTCTGGTGAAGATGGCAATCCGGGTCT
GCAGGGTCTGCCTGGTAgcGATGGCGAACCAGGTGAAGAAGGTCAGCCGG
GTCGTTCtGGCCAGCCGGGCCAGCAGGGCCCGCGTGGTAGCCCGGGCGAA
GTTGGCCCGCGcGGTtcTAAAGGTCCTAGcGGCGATCGCGGTGATCGTGG
TGAACGCGGTGTTCCTGGTCAGACCGGTAGCGCAGGTAATGTTGGCGAAG
ATGGTGAACAGGGTGGCAAAGGTGTTGATGGTGCAAGCGGTCCGAGCGGT
GCACTGGGTGCACGTGGTCCTCCGGGCAGCCGTGGTGACACCGGTGCAGT
TGGTCCGCCTGGCCCGACCGGCCGTAGcGGCctgCCGGGTAATGCAGGTC
AGAAAGGTCCGTCtGGTGAACCTGGCAGCCCTGGTAAAGCAGGTAGcGCC
GGTGAGCAGGGTCCGCCGGGCAAAGATGGTAGcAATGGTGAGCCGGGTAG
CCCTGGCAAAGAAGGTGAACGTGGTCTGGCAGGtCCGCCGGGTCCTGATG
GTCGCCGCGGTGAAACGGGTTCtCCGGGTATTGCCGGTGCCCTGGGTAAA
CCAGGTCTGGAAGGTCCGAAAGGTTATCCTGGTCTGCGCGGTCGTGATGG
TACCAATGGCAAACGTGGCGAACAGGGCGAAACCGGTCCAGATGGTGTTC
GTGGTATTCCGGGTAACGATGGTCAGAGCGGTAAACCGGGCATTGATGGT
ATTGATGGCACCAATGGTCAGCCTGGCGAAGCAGGTTATCAGGGTGGTCG
CGGTACCCGTGGTCAGCTGGGTGAAACcGGTGATGTTGGTCAGAATGGTG
ATCGCGGCGCACCGGGTCCGGATGGTAGCAAAGGTAGCGCCGGTCGTCCG
GGTctgCGTtaa
                                     (SEQ ID NO: 8)
MKKIWLALAGLVLAFSASAAQYEDGPQGVVGADGKDGTPGEKGEQGRTGA
AGKQGSPGADGARGPLGSIGQQGARGEPGDPGSPGLRGDTGLAGVKGVAG
PSGRPGQPGANGLPGVNGRGGLRGKPGAKGIAGSDGEAGESGAPGQSGPT
GPRGQRGPSGEDGNPGLQGLPGSDGEPGEEGQPGRSGQPGQQGPRGSPGE
VGPRGSKGPSGDRGDRGERGVPGQTGSAGNVGEDGEQGGKGVDGASGPSG
ALGARGPPGSRGDTGAVGPPGPTGRSGLPGNAGQKGPSGEPGSPGKAGSA
GEQGPPGKDGSNGEPGSPGKEGERGLAGPPGPDGRRGETGSPGIAGALGK
PGLEGPKGYPGLRGRDGTNGKRGEQGETGPDGVRGIPGNDGQSGKPGIDG
IDGTNGQPGEAGYQGGRGTRGQLGETGDVGQNGDRGAPGPDGSKGSAGRP
GLR
```

Example 3: Production of Truncated Collagen

A codon optimized DNA sequence, optimized for expression in E. coli, encoding a jellyfish collagen with a truncation of 240 internal amino acids was synthesized and expressed. The DNA sequence is shown below in SEQ ID NO: 9. In SEQ ID NO: 9, The DsbA secretion tag is encoded by nucleotides 1-72 and encodes amino acids 1-24 of SEQ ID NO: 10. The histidine tag comprising 9 histidine (SEQ ID NO: 129) residues is encoded by nucleotides 73-99 and encodes amino acids 25-33 of SEQ ID NO: 10. The linker is encoded by nucleotides 100-111 and encodes amino acids 34-37 of SEQ ID NO: 10. The thrombin cleavage site is encoded by nucleotides 112-135 and encodes amino acids 38-45 of SEQ ID NO: 10. The truncated collagen is encoded by nucleotides 136-822 and encodes amino acids 46-274 of SEQ ID NO: 10.

```
                                     (SEQ ID NO: 9)
ATGAAAAAGATTTGGCTGGCGCTGGCTGGTTTAGTTTTAGCGTTTAGCGC
ATCGGCGGCGCAGTATGAAGATCACCATCACCACCACCACCATCACCACT
CTGGCTCGAGCCTGGTGCCGCGCGGCAGCCATATGGGTCCGCAGGGTGTT
GTTGGTGCAGATGGTAAAGACGGTACCCCGGGTGAAAAAGGAGAACAGGG
ACGTACAGGTGCAGCAGGTAAACAGGGCAGCCCGGGTGCCGATGGTGCC
CGTGGCCCGCTGGGTAGCATTGGTCAGCAGGGTGCAAGAGGCGAACCGG
GCGATCCGGGTAGTCCGGGCCTGCGTGGTGATACGGGTCTGGCCGGTGTT
AAAGGCGTTGCAGGTCCTTCAGGTCGTCCAGGTCAACCGGGTGCAAATGG
TCTGCCGGGTGTTAATGGTCGTGGCGGTCTGGAACTGGTCTGGCAGGAC
CGCCGGGTCCTGATGGTCGCCGCGGTGAAACGGGTTCACCGGGTATTGCC
GGTGCCCTGGGTAAACCAGGTCTGGAAGGTCCGAAAGGTTATCCTGGTCT
GCGCGGTCGTGATGGTACCAATGGCAAACGTGGCGAACAGGGCGAAACC
```

-continued

```
GGTCCAGATGGTGTTCGTGGTATTCCGGGTAACGATGGTCAGAGCGGTAA

ACCGGGCATTGATGGTATTGATGGCACCAATGGTCAGCCTGGCGAAGCAG

GTTATCAGGGTGGTCGCGGTACCCGTGGTCAGCTGGGTGAAACAGGTGAT

GTTGGTCAGAATGGTGATCGCGGCGCACCGGGTCCGGATGGTAGCAAAGG

TAGCGCCGGTCGTCCGGGTTTACGTtaa
```

The truncated collagen is approximately 54% of the full length collagen and is disclosed below in SEQ ID NO:10.

```
                                        (SEQ ID NO: 10)
MKKIWLALAGLVLAFSASAAQYEDHHHHHHHHHSGSSLVPRGSHMGPQGV

VGADGKDGTPGEKGEQGRTGAAGKQGSPGADGARGPLGSIGQQGARGEPG

DPGSPGLRGDTGLAGVKGVAGPSGRPGQPGANGLPGVNGRGGLERGLAGP

PGPDGRRGETGSPGIAGALGKPGLEGPKGYPGLRGRDGTNGKRGEQGETG

PDGVRGIPGNDGQSGKPGIDGIDGTNGQPGEAGYQGGRGTRGQLGETGDV

GQNGDRGAPGPDGSKGSAGRPGLR
```

The polynucleotide encoding the truncated jellyfish collagen without the DsbA secretion tag, the histidine tag, linker and thrombin cleavage site is disclosed in SEQ ID NO: 85

```
                                        (SEQ ID NO: 85)
GTCCGCAGGGTGTTGTTGGTGCAGATGGTAAAGACGGTACCCCGGGTGAA

AAAGGAGAACAGGGACGTACAGGTGCAGCAGGTAAACAGGGCAGCCCGG

GTGCCGATGGTGCCCGTGGCCCGCTGGGTAGCATTGGTCAGCAGGGTGCA

AGAGGCGAACCGGGCGATCCGGGTAGTCCGGGCCTGCGTGGTGATACGG

GTCTGGCCGGTGTTAAAGGCGTTGCAGGTCCTTCAGGTCGTCCAGGTCAA

CCGGGTGCAAATGGTCTGCCGGGTGTTAATGGTCGTGGCGGTCTGGAACG

TGGTCTGGCCAGGACCGCCGGGTCCTGATGGTCGCCGCGGTGAAACGGGTT

CACCGGGTATTGCCGGTGCCCTGGGTAAACCAGGTCTGGAAGGTCCGAAA

GGTTATCCTGGTCTGCGCGGTCGTGATGGTACCAATGGCAAACGTGGCGA

ACAGGGCGAAACCGGTCCAGATGGTGTTCGTGGTATTCCGGGTAACGATG

GTCAGAGCGGTAAACCGGGCATTGATGGTATTGATGGCACCAATGGTCAG

CCTGGCGAAGCAGGTTATCAGGGTGGTCGCGGTACCCGTGGTCAGCTGGG

TGAAACAGGTGATGTTGGTCAGAATGGTGATCGCGGCGCACCGGGTCCGG

ATGGTAGCAAAGGTAGCGCCGGTCGTCCGGGTTTACGTtaa
```

The truncated jellyfish collagen without the DsbA secretion tag, the histidine tag, linker and thrombin cleavage site is disclosed in SEQ ID NO: 86

```
                                        (SEQ ID NO: 86)
GPQGVVGADGKDGTPGEKGEQGRTGAAGKQGSPGADGARGPLGSIGQQGA

RGEPGDPGSPGLRGDTGLAGVKGVAGPSGRPGQPGANGLPGVNGRGGLER

GLAGPPGPDGRRGETGSPGIAGALGKPGLEGPKGYPGLRGRDGTNGKRGE

QGETGPDGVRGIPGNDGQSGKPGIDGIDGTNGQPGEAGYQGGRGTRGQLG

ETGDVGQNGDRGAPGPDGSKGSAGRPGLR
```

The polynucleotides of SEQ ID NO: 9 was codon optimized and synthesized by Gen9 DNA, now Ginkgo Bioworks internal synthesis. Overlaps between the pET28 vector and SEQ ID NO: 9 were designed to be between 30 and 40 bp long and added using PCR with the enzyme PRIMESTAR® GXL polymerase (<http://www.clontech.com/US/Products/PCR/GC Rich/PrimeSTAR_GXL_DNA_P olymerase?sitex=10020:22372:US>). The opened pET28a vector and insert DNA (SEQ ID NO: 9) was then assembled together into the final plasmid using SGI GIBSON ASSEMBLY® (<https://us.vwr.com/store/product/17613857/gibson-assembly-hifi-1-step-kit-synthetic-genomics-inc>). Sequence of plasmid was then verified through sanger sequencing through Eurofins Genomics (<www.eurofinsgenomics.com>).

The transformed cells were cultivated in minimal media and frozen in 1.5 aliquots with glycerol at a ratio of 50:50 of cells to glycerol. One vial of this frozen culture was revived in 50 ml of minimal media overnight at 37° C., 200 rpm. Cells were transferred into 300 ml of minimal media and grown for 6-9 hours to reach an OD600 of 5-10.

A bioreactor was prepared with 2.7 L of minimal media+glucose and 300 ml of OD600 of 5-10 culture was added to bring the starting volume to 3 L. Cells were grown at 28° C., pH7 with Dissolved Oxygen maintained at 20% saturation using a cascade containing agitation, air and oxygen. pH was controlled using 28% w/w Ammonium hydroxide solution. Fermentation was run in a fed-batch mode using a DO-stat based feeding algorithm once the initial bolus of 40 g/L was depleted around 13 hours. After 24-26 hours of initial growth, the OD600 reached above 100. At this point, 300 mL of 500 g/L sucrose was added and temperature was reduced to 25 C. High density culture was induced for protein production using 1 mM IPTG. Fermentation was continued for another 20-24 hours and cells were harvested using a bench top centrifuge at 9000 rcf, 15 C for 60 minutes. Cell pellet recovered from centrifugation was resuspended in a buffer containing 0.5M NaCl and 0.1M KH2PO4 at pH8 in a weight by weight ratio of 2× buffer to 1× cells.

The harvested cells were disrupted in a homogenizer at 14,000 psi pressure in 2 passes. Resulting slurry contained the collagen protein along with other proteins.

The fermentations were performed at various temperature ranging from 25° to 28° C. For some fermentations, the temperature of the fermentation was maintained at a constant temperature and immediately upon completion of fermentation (OD600 of 5-10) the collagen was purified. For other fermentations, the temperature of the fermentations was maintained for a desired period of time and when cell densities of OD600 of 5-10 were reached, the temperature was reduced to induce protein production. Typically, the temperature was reduced from 28° C. to 25° C. After the fermentation at 25° C. was continued for 40-60 hours, the collagen was isolated.

The collagen was purified by acid treatment of homogenized cell broth. Additionally, acid treatment was also performed on non-homogenized whole cells recovered from the bioreactor after centrifugation and resuspension in the buffer described above. The pH of either the homogenized slurry of the resuspended whole cells was decreased to 3 using 6M Hydrochloric acid. Acidified cell slurry was incubated overnight at 4° C. with mixing, followed by centrifugation. Supernatant of the acidified slurry was tested on a polyacrylamide gel and found to contain collagen in relatively high abundance compared to starting pellet. The collagen slurry thus obtained was high in salts. To obtain volume and salt reduction, concentration and diafiltration steps were performed using an EMD Millipore Tangential Flow Filtration system with ultrafiltration cassettes of 0.1 m² each. Total area of filtration was 0.2 m² using 2 cassettes in parallel. A volume reduction of 5× and a salt reduction of 19× was achieved in the TFF stage. Final collagen slurry was run on an SDS-PAGE gel to confirm presence of the collagen. This slurry was dried using a multi-tray lyophilizer over 3 days to obtain a white, fluffy collagen powder.

The purified truncated collagen obtained from homogenized cell broth or non-homogenized cells were analyzed on an SDS-PAGE gel and a thick and clear band was observed at the expected size of 27 kilodaltons. The purified collagen was also analyzed by mass spectrometry and it was confirmed that the 27 kilodalton protein was jellyfish collagen.

An alternative purification method of the full length and truncated collagens is provided below.

The fermentation broth was mixed with 0.3-0.5% w/v of Poly Ethyl Imine (PEI). After 15 minutes of incubation with PEI, the fermentation broth was centrifuged at 9000 rcf for 15 minutes to recover the supernatant, which contained the collagen protein. The pellet containing the cells was discarded and the PEI-treated collagen containing supernatant was mixed with Sodium Bentonite (0.2% final w/v) (WYOPURE™, Wyoming Bentonite) and centrifuged. The bentonite containing pellet was discarded and the supernatant was recovered.

The Bentonite treated supernatant was concentrated between 3-6 fold on a tangential flow filtration system (TFF) (EMD Millipore) using a 5 kDa cassette. The collagen was retained with almost no losses in the permeate stream. To remove salts, the retentate from the concentration step was diafiltered using the same TFF set-up. Final conductivity of the protein solution was <10 milliSiemens. The typical conductivity was between 400 microsiemens and 1.5 millisiemens. Highly concentrated collagen solutions had higher conductivities approaching 4 milliSiemens. A skilled artisan will understand that conductivities higher than 10 milliSiemens may be observed depending on the concentration of the collagen. Next, the desalted and concentrated protein was subjected to treatment with activated carbon using the W-L 9000 10×40 granulated resin (Carbon Activated Corporation). 5% w/v of the carbon resin was mixed with collagen containing protein feed and mixed at 45-50° C. with mild agitation. The carbon-treated slurry was filtered using a Buchner funnel lined with an Ertel Filter Press Pad M-953 (Ertel Alsop) in presence or absence of a filtration aid such as Diatomaceous Earth (Sigma Aldrich). Post-filtration, the collagen solution was filtered through a 0.2 micron filter followed by one to several hours of treatment with Sodium Bentonite (0.2% w/v final) (WYOPURE™, Wyoming Bentonite) and centrifuged at 9000 rcf, 15-30 minutes to obtain a highly pure, clear and particulate free collagen solution. When removal of endotoxin proteins was desired, the protein was passed through a chromatographic filter like SARTOBIND® Q (Sartorius-Stedim) to specifically remove endotoxin proteins.

The purified collagen was analyzed on an SDS-PAGE gel and a thick and clear band was observed at 30 kilodaltons. The upshift in size is due to the structure of the collagen molecule and the high glycine/proline amino acid content. The purified collagen was also analyzed by mass spectrometry and it was confirmed that the 30 kilodalton protein was the truncated collagen.

The truncated collagens were further analyzed by HPLC using an Agilent 1100 series HPLC. The column was the 50 mm Agilent PLRP-S reverse phase column with an inner diameter of 4.6 mm, µM particle size and 1000 Angstrom pore size.

The sample was prepared by diluting 1:1 in a 0.04% sodium azide solution in HPLC-grade water. After dilution, the resulting mixture was filtered through a 0.45 um filter to remove any large particles that can clog the HPLC column. For analysis, the samples are diluted appropriately with a 20 mM ammonium acetate buffer in HPLC-grade water at a pH of about 4.5. After mixing the sample, it was transferred to a 300 µL microvial that was then placed in the autosampler. Using ChemStation, the software that operates the HPLC, the analysis parameters such as sample flowrate, column temperature, mobile phase flowrate, mobile phase composition, etc. can be altered. In one exemplary, but non-limiting analysis the parameters were: sample flow rate of 1 mL/min, column temperature of 80° C., column pressure of 60-70 bar, mobile phase composition of 97.9% water/1.9% acetonitrile with 0.2% trifluoroacetic acid; UV wavelength for analysis of 214.4 nm, injection volume of 10 µL, and sample run time of 10 minutes.

Under these conditions, the truncated jellyfish collation of SEQ ID NO: 91 has an elution time of about 5.4 minutes. ChemStation quantifies the peak area of the elution peak and calculates the protein concentration using a calibration curve that directly relates peak area to protein concentration. The calibration curve is generated using a known collagen solution that is serially diluted to contain collagen concentration ranges of 0.06 mg/mL to 1.00 mg/mL.

Truncated Collagen without His Tag-Linker-Thrombin Cleavage Site

A truncated jellyfish collagen without a His tag, linker, and thrombin cleavage site is disclosed below. The codon-optimized nucleotide sequence encoding this collagen is provided in SEQ ID NO: 11. The amino acid sequence is disclosed in SEQ ID NO: 12. The DsbA secretion tag is encoded by nucleotides 1-72 and encodes amino acids 1-24. The truncated collagen sequence is encoded by nucleotides 73-639 and encodes amino acids 25-213.

```
                                            (SEQ ID NO: 11)
ATGAAAAAGATTTGGCTGGCGCTGGCTGGTTTAGTTTTAGCGTTTAGCGC

ATCGGCGGCGCAGTATGAAGATGGTCCGCAGGGTGTTGTTGGTGCAGATG

GTAAAGACGGTACCCCGGGTAATGCAGGTCAGAAAGGTCCGTCAGGTGAA

CCTGGCAGCCCTGGTAAAGCAGGTAGTGCCGGTGAGCAGGGTCCGCCGGG

CAAAGATGGTAGTAATGGTGAGCCGGGTAGCCCTGGCAAAGAAGGTGAAC

GTGGTCTGGCAGGACCGCCGGGTCCTGATGGTCGCCGCGGTGAAACGGGT

TCACCGGGTATTGCCGGTGCCCTGGGTAAACCAGGTCTGGAAGGTCCGAA

AGGTTATCCTGGTCTGCGCGGTCGTGATGGTACCAATGGCAAACGTGGCG

AACAGGGCGAAACCGGTCCAGATGGTGTTCGTGGTATTCCGGGTAACGAT

GGTCAGAGCGGTAAACCGGGCATTGATGGTATTGATGGCACCAATGGTCA

GCCTGGCGAAGCAGGTTATCAGGGTGGTCGCGGTACCCGTGGTCAGCTGG

GTGAAACAGGTGATGTTGGTCAGAATGGTGATCGCGGCGCACCGGGTCCG

GATGGTAGCAAAGGTAGCGCCGGTCGTCCGGGTTTACGTtaa (SEQ ID NO: 12)
MKKIWLALAGLVLAFSASAAQYEDGPQGVVGADGKDGTPGNAGQKGPSGE

PGSPGKAGSAGEQGPPGKDGSNGEPGSPGKEGERGLAGPPGPDGRRGETG
```

SPGIAGALGKPGLEGPKGYPGLRGRDGTNGKRGEQGETGPDGVRGIPGND

GQSGKPGIDGIDGTNGQPGEAGYQGGRGTRGQLGETGDVGQNGDRGAPGP

DGSKGSAGRPGLR

A polynucleotide encoding a truncated jellyfish collagen without a His tag, linker and thrombin cleavage site disclosed in SEQ ID NO: 90

(SEQ ID NO: 90)
GGTCCGCAGGGTGTTGTTGGTGCAGATGGTAAAGACGGTACCCCGGGTAA

TGCAGGTCAGAAAGGTCCGTCAGGTGAACCTGGCAGCCCTGGTAAAGCAG

GTAGTGCCGGTGAGCAGGGTCCGCCGGGCAAAGATGGTAGTAATGGTGA

GCCGGGTAGCCCTGGCAAAGAAGGTGAACGTGGTCTGGCAGGACCGCCG

GGTCCTGATGGTCGCCGCGGTGAAACGGGTTCACCGGGTATTGCCGGTGC

CCTGGGTAAACCAGGTCTGGAAGGTCCGAAAGGTTATCCTGGTCTGCGCG

GTCGTGATGGTACCAATGGCAAACGTGGCGAACAGGGCGAAACCGGTCC

AGATGGTGTTCGTGGTATTCCGGGTAACGATGGTCAGAGCGGTAAACCGG

GCATTGATGGTATTGATGGCACCAATGGTCAGCCTGGCGAAGCAGGTTAT

CAGGGTGGTCGCGGTACCCGTGGTCAGCTGGGTGAAACAGGTGATGTTGG

TCAGAATGGTGATCGCGGCGCACCGGGTCCGGATGGTAGCAAAGGTAGCG

CCGGTCGTCCGGGTTTACGTtaa

A truncated jellyfish collagen without a His tag, linker and thrombin cleavage site disclosed in SEQ ID NO: 91

(SEQ ID NO: 91)
GPQGVVGADGKDGTPGNAGQKGPSGEPGSPGKAGSAGEQGPPGKDGSNGE

PGSPGKEGERGLAGPPGPDGRRGETGSPGIAGALGKPGLEGPKGYPGLRG

RDGTNGKRGEQGETGPDGVRGIPGNDGQSGKPGIDGIDGTNGQPGEAGYQ

GGRGTRGQLGETGDVGQNGDRGAPGPDGSKGSAGRPGLR

Truncated Collagen with GEK Repeats

A jellyfish collagen with GEK repeats is disclosed below. The codon-optimized nucleotide sequence encoding this collagen is provided in SEQ ID NO: 13. The amino acid sequence is disclosed in SEQ ID NO: 14. The DsbA secretion tag is encoded by nucleotides 1-72 and encodes amino acids 1-24. The GEK repeat is encoded by nucleotides 73-126 and encodes the GEK repeats of amino acids 25-42. The truncated collagen sequence is encoded by nucleotides 127-693 and encodes amino acids 43-231.

(SEQ ID NO: 13)
ATGAAAAAGATTTGGCTGGCGCTGGCTGGTTTAGTTTTAGCGTTTAGCGC

ATCGGCGGCGCAGTATGAAGATGGTGAAAAGGTGAaAAGGGCGAGAAAG

GTGAGAAAGGCGAAAAGGGTGAAAAAGGTCCGCAGGGTGTTGTTGGTGC

AGATGGTAAAGACGGTACCCCGGGTAATGCAGGTCAGAAAGGTCCGTCA

GGTGAACCTGGCAGCCCTGGTAAAGCAGGTAGTGCCGGTGAGCAGGGTCC

GCCGGGCAAAGATGGTAGTAATGGTGAGCCGGGTAGCCCTGGCAAAGAA

GGTGAACGTGGTCTGGCAGGACCGCCGGGTCCTGATGGTCGCCGCGGTGA

AACGGGTTCACCGGGTATTGCCGGTGCCCTGGGTAAACCAGGTCTGGAAG

GTCCGAAAGGTTATCCTGGTCTGCGCGGTCGTGATGGTACCAATGGCAAA

CGTGGCGAACAGGGCGAAACCGGTCCAGATGGTGTTCGTGGTATTCCGGG

TAACGATGGTCAGAGCGGTAAACCGGGCATTGATGGTATTGATGGCACCA

ATGGTCAGCCTGGCGAAGCAGGTTATCAGGGTGGTCGCGGTACCCGTGGT

CAGCTGGGTGAAACAGGTGATGTTGGTCAGAATGGTGATCGCGGCGCACC

GGGTCCGGATGGTAGCAAAGGTAGCGCCGGTCGTCCGGGTTTACGTtaa (SEQ ID NO: 14)
MKKIWLALAGLVLAFSASAAQYEDGEKGEKGEKGEKGEKGPQGVVGA

DGKDGTPGNAGQKGPSGEPGSPGKAGSAGEQGPPGKDGSNGEPGSPGKEG

ERGLAGPPGPDGRRGETGSPGIAGALGKPGLEGPKGYPGLRGRDGTNGKR

GEQGETGPDGVRGIPGNDGQSGKPGIDGIDGTNGQPGEAGYQGGRGTRGQ

LGETGDVGQNGDRGAPGPDGSKGSAGRPGLR

The polynucleotides of SEQ ID NO: 13 was codon optimized and synthesized by Gen9 DNA, now Ginkgo Bioworks internal synthesis. Overlaps between the pET28 vector and SEQ ID NO: 13 was designed to be between 30 and 40 bp long and added using PCR with the enzyme PRIMESTAR® GXL polymerase (<http://www.clontech-.com/US/Products/PCR/GC Rich/PrimeSTAR_GXL_D-NA_P olymerase?sitex=10020:22372:US>). The opened pET28a vector and insert DNA (SEQ ID NO: 13) was then assembled together into the final plasmid using SGI GIBSON ASSEMBLY® (<https://us.vwr.com/store/product/17613857/gibson-assembly-hifi-1-step-kit-synthetic-genomics-inc>). Sequence of plasmid was then verified through Sanger sequencing through Eurofins Genomics (<www.eurofinsgenomics.com>).

The transformed cells were cultivated in minimal media and frozen in 1.5 aliquots with glycerol at a ratio of 50:50 of cells to glycerol. One vial of this frozen culture was revived in 50 ml of minimal media overnight at 37° C., 200 rpm. Cells were transferred into 300 ml of minimal media and grown for 6-9 hours to reach an OD600 of 5-10.

A bioreactor was prepared with 2.7 L of minimal media+ glucose and 300 ml of OD600 of 5-10 culture was added to bring the starting volume to 3 L. Cells were grown at 28° C., pH7 with Dissolved Oxygen maintained at 20% saturation using a cascade containing agitation, air and oxygen. pH was controlled using 28% w/w Ammonium hydroxide solution. Fermentation was run in a fed-batch mode using a DO-stat based feeding algorithm once the initial bolus of 40 g/L was depleted around 13 hours. After 24-26 hours of initial growth, the OD600 reached above 100. At this point, 300 mL of 500 g/L sucrose was added and temperature was reduced to 25 C. High density culture was induced for protein production using 1 mM IPTG. Fermentation was continued for another 20-24 hours and cells were harvested using a bench top centrifuge at 9000 rcf, 15 C for 60 minutes. Cell pellet recovered from centrifugation was resuspended in a buffer containing 0.5M NaCl and 0.1M KH2PO4 at pH8 in a weight by weight ratio of 2× buffer to 1× cells.

The harvested cells were disrupted in a homogenizer at 14,000 psi pressure in 2 passes. Resulting slurry contained the collagen protein along with other proteins.

The collagen was purified by acid treatment whole cells recovered from bioreactor after centrifugation and resuspension in a buffer as described above The pH of either the homogenized slurry or the resuspended suspension was decreased to 3 using 6M Hydrochloric acid. Acidified cell slurry was incubated overnight at 4° C. with mixing, followed by centrifugation. Supernatant of the acidified slurry was tested on a polyacrylamide gel and found to contain collagen in relatively high abundance compared to starting pellet. The collagen slurry thus obtained was high in salts. To obtain volume and salt reduction, concentration and diafiltration steps were performed using an EMD Millipore Tangential Flow Filtration system with ultrafiltration cassettes of 0.1 m$^2$ each. Total area of filtration was 0.2 m$^2$ using 2 cassettes in parallel. A volume reduction of 5× and a salt reduction of 19× was achieved in the TFF stage. Final collagen slurry was run on an SDS-PAGE gel to confirm presence of the collagen. This slurry was dried using a multi-tray lyophilizer over 3 days to obtain a white, fluffy collagen powder.

The purified collagen was analyzed on an SDS-PAGE gel and was observed to run at an apparent molecular weight of 35 kilodaltons. The 35 kilodalton band does not correspond to the expected size of 22 kilodaltons. The upshift between the expected size and the apparent size is thought to be due to the GEK repeats interacting with the gel matrix. The 35 kDa band was confirmed by mass spectrometry to be the correct collagen with the GEK repeats.

Truncated Collagen With GDK Repeats

A jellyfish collagen with GDK repeats is disclosed below. The codon-optimized nucleotide sequence encoding this collagen is provided in SEQ ID NO: 15. The amino acid sequence is disclosed in SEQ ID NO: 16. The DsbA secretion tag is encoded by nucleotides 1-72 and encodes amino acids 1-24. The GDK repeat is encoded by nucleotides 73-126 and encodes the GDK repeats of amino acids 25-42. The truncated collagen sequence is encoded by nucleotides 127-693 and encodes amino acids 43-231.

```
                                          (SEQ ID NO: 15)
ATGAAAAAGATTTGGCTGGCGCTGGCTGGTTTAGTTTTAGCGTTTAGCGC

ATCGGCGGCGCAGTATGAAGATGGTGATAAAGGTGATAAGGGCGACAAAG

GTGACAAAGGCGATAAGGGTGATAAAGGTCCGCAGGGTGTTGTTGGTGCA

GATGGTAAAGACGGTACCCCGGGTAATGCAGGTCAGAAAGGTCCGTCAGG

TGAACCTGGCAGCCCTGGTAAAGCAGGTAGTGCCGGTGAGCAGGGTCCGC

CGGGCAAAGATGGTAGTAATGGTGAGCCGGGTAGCCCTGGCAAAGAAGGT

GAACGTGGTCTGGCAGGACCGCCGGGTCCTGATGGTCGCCGCGGTGAAAC

GGGTTCACCGGGTATTGCCGGTGCCCTGGGTAAACCAGGTCTGGAAGGTC

CGAAAGGTTATCCTGGTCTGCGCGGTCGTGATGGTACCAATGGCAAACGT

GGCGAACAGGGCGAAACCGGTCCAGATGGTGTTCGTGGTATTCCGGGTAA

CGATGGTCAGAGCGGTAAACCGGGCATTGATGGTATTGATGGCACCAATG

GTCAGCCTGGCGAAGCAGGTTATCAGGGTGGTCGCGGTACCCGTGGTCAG

CTGGGTGAAACAGGTGATGTTGGTCAGAATGGTGATCGCGGCGCACCGGG

TCCGGATGGTAGCAAAGGTAGCGCCGGTCGTCCGGGTTTACGTaa
```

```
                                          (SEQ ID NO: 16)
MKKIWLALAGLVLAFSASAAQYEDGDKGDKGDKGDKGDKGDKGPQGVVGA

DGKDGTPGNAGQKGPSGEPGSPGKAGSAGEQGPPGKDGSNGEPGSPGKEG

ERGLAGPPGPDGRRGETGSPGIAGALGKPGLEGPKGYPGLRGRDGTNGKR
```

GEQGETGPDGVRGIPGNDGQSGKPGIDGIDGTNGQPGEAGYQGGRGTRGQ

LGETGDVGQNGDRGAPGPDGSKGSAGRPGLR

The polynucleotides of SEQ ID NO: 15 was codon optimized and synthesized by Gen9 DNA, now Ginkgo Bioworks internal synthesis. Overlaps between the pET28 vector and SEQ ID NO: 15 was designed to be between 30 and 40 bp long and added using PCR with the enzyme PRIMESTAR® GXL polymerase (<http://www.clontech-.com/US/Products/PCR/GC Rich/PrimeSTAR_GXL_D-NA_P olymerase?sitex=10020:22372:US>). The opened pET28a vector and insert DNA (SEQ ID NO: 15) was then assembled together into the final plasmid using SGI GIBSON ASSEMBLY® (<https://us.vwr.com/store/product/17613857/gibson-assembly-hifi-1-step-kit-synthetic-genomics-inc>). Sequence of plasmid was then verified through Sanger sequencing through Eurofins Genomics (<www.eurofinsgenomics.com>).

The transformed cells were cultivated in minimal media and frozen in 1.5 aliquots with glycerol at a ratio of 50:50 of cells to glycerol. One vial of this frozen culture was revived in 50 ml of minimal media overnight at 37° C., 200 rpm. Cells were transferred into 300 ml of minimal media and grown for 6-9 hours to reach an OD600 of 5-10.

A bioreactor was prepared with 2.7 L of minimal media+glucose and 300 ml of OD600 of 5-10 culture was added to bring the starting volume to 3 L. Cells were grown at 28° C., pH7 with Dissolved Oxygen maintained at 20% saturation using a cascade containing agitation, air and oxygen. pH was controlled using 28% w/w Ammonium hydroxide solution. Fermentation was run in a fed-batch mode using a DO-stat based feeding algorithm once the initial bolus of 40 g/L was depleted around 13 hours. After 24-26 hours of initial growth, the OD600 reached above 100. At this point, 300 mL of 500 g/L sucrose was added and temperature was reduced to 25 C. High density culture was induced for protein production using 1 mM IPTG. Fermentation was continued for another 20-24 hours and cells were harvested using a bench top centrifuge at 9000 rcf, 15 C for 60 minutes. Cell pellet recovered from centrifugation was resuspended in a buffer containing 0.5M NaCl and 0.1M KH2PO4 at pH8 in a weight by weight ratio of 2× buffer to 1× cells.

The harvested cells were disrupted in a homogenizer at 14,000 psi pressure in 2 passes. Resulting slurry contained the collagen protein along with other proteins.

The collagen was purified by acid treatment of whole cells recovered from bioreactor after centrifugation and resuspension in a buffer as described above. The pH of either the homogenized slurry was decreased to 3 using 6M Hydrochloric acid. Acidified cell slurry was incubated overnight at 4° C. with mixing, followed by centrifugation. Supernatant of the acidified slurry was tested on a polyacrylamide gel and found to contain collagen in relatively high abundance compared to starting pellet. The collagen slurry thus obtained was high in salts. To obtain volume and salt reduction, concentration and diafiltration steps were performed using an EMD Millipore Tangential Flow Filtration system with ultrafiltration cassettes of 0.1 m$^2$ each. Total area of filtration was 0.2 m$^2$ using 2 cassettes in parallel. A volume reduction of 5× and a salt reduction of 19× was achieved in the TFF stage. Final collagen slurry was run on an SDS-PAGE gel to confirm presence of the collagen. This slurry was dried using a multi-tray lyophilizer over 3 days to obtain a white, fluffy collagen powder.

The purified collagen was analyzed on an SDS-PAGE gel and was observed to run at an apparent molecular weight of 35 kilodaltons. The 35 kilodalton band does not correspond to the expected size of 22 kilodaltons. The upshift between the expected size and the apparent size is thought to be due to the GDK repeats interacting with the gel matrix. The 35 kDa band was confirmed by mass spectrometry to be the correct collagen with the GDK repeats.

Truncated Collagen with DsbA Secretion Tag-His Tag-Linker-Thrombin Cleavage Site and GFP Beta-Lactamase Fusion (Version 1):

A jellyfish collagen with DsbA secretion tag-His tag-Linker-Thrombin cleavage site and GFP Beta-lactamase fusion is disclosed below. The codon-optimized nucleotide sequence encoding this collagen is provided in SEQ ID NO: 17. The amino acid sequence is disclosed in SEQ ID NO: 18. The DsbA secretion tag is encoded by nucleotides 1-72 and encodes amino acids 1-24. The His tag is encoded by nucleotides 73-99 and encodes a 9 histidine tag (SEQ ID NO: 129) of amino acids 25-33. The linker is encoded by nucleotides 100-111 and encodes amino acids 34-37. The thrombin cleavage side is encoded by nucleotides 112-135 and encodes amino acids 38-45. The green fluorescent protein (GFP) with linker is encoded by nucleotides 136-873 and encodes amino acids 46-291. The truncated collagen sequence is encoded by nucleotides 874-1440 and encodes amino acids 292-480. The Beta-lactamase with linker is encoded by nucleotides 1441-2232 and encodes amino acids 481-744. The Beta-lactamase was properly targeted to the periplasmic space even though the polypeptide did not have an independent secretion tag. The DsbA secretion tag directed the entire transcript (Truncated Collagen with DsbA secretion tag-His tag-Linker-Thrombin cleavage site and GFP Beta-lactamase fusion protein) to the periplasmic space and the Beta-lactamase functioned properly.

(SEQ ID NO: 17)
ATGAAAAAGATTTGGCTGGCGCTGGCTGGTTTAGTTTTAGCGTTTAGCGC

ATCGGCGGCGCAGTATGAAGATCACCATCACCACCACCACCATCACCACT

CTGGCTCGAGCCTGGTGCCGCGCGGCAGCCATATGTCTGGCTCGAGCAGT

AAAGGTGAAGAACTGTTCACCGGTGTTGTTCCGATCCTGGTTGAACTGGA

TGGTGATGTTAACGGCCACAAATTCTCTGTTCGTGGTGAAGGTGAAGGTG

ATGCAACCAACGGTAAACTGACCCTGAAATTCATCTGCACTACCGGTAAA

CTGCCGGTTCCATGGCCGACTCTGGTGACTACCCTGACCTATGGTGTTCA

GTGTTTTCTCGTTACCCGGATCACATGAAGCAGCATGATTTCTTCAAAT

CTGCAATGCCGGAAGGTTATGTACAGGAGCGCACCATTTCTTTCAAAGAC

GATGGCACCTACAAACCCGTGCAGAGGTTAAATTTGAAGGTGATACTCT

GGTGAACCGTATTGAACTGAAAGGCATTGATTTCAAAGAGGACGGCAACA

TCCTGGGCCACAAACTGGAATATAACTTCAACTCCCATAACGTTTACATC

ACCGCAGACAAACAGAAGAACGGTATCAAAGCTAACTTCAAAATTCGCCA

TAACGTTGAAGACGGTAGCGTACAGCTGGCGGACCACTACCAGCAGAACA

CTCCGATCGGTGATGGTCCGGTTCTGCTGCCGGATAACCACTACCTGTCC

ACCCAGTCTaaaCTGTCCAAAGACCCGAACGAAAAGCGCGACCACATGGT

GCTGCTGGAGTTCGTTACTGCAGCAGGTATCACGCACGGCATGGATGAAC

TCTACAAATCTGGCGCGCCGGGCGGTCCGCAGGGTGTTGTTGGTGCAGAT

GGTAAAGACGGTACCCCGGGTAATGCAGGTCAGAAAGGTCCGTCAGGTGA

ACCTGGCAGCCCTGGTAAAGCAGGTAGTGCCGGTGAGCAGGGTCCGCCGG

GCAAAGATGGTAGTAATGGTGAGCCGGGTAGCCCTGGCAAAGAAGGTGAA

CGTGGTCTGGCCAGGACCGCCGGGTCCTGATGGTCGCCGCGGTGAAACGGG

TTCACCGGGTATTGCCGGTGCCCTGGGTAAACCAGGTCTGGAAGGTCCGA

AAGGTTATCCTGGTCTGCGCGGTCGTGATGGTACCAATGGCAAACGTGGC

GAACAGGGCGAAACCGGTCCAGATGGTGTTCGTGGTATTCCGGGTAACGA

TGGTCAGAGCGGTAAACCGGGCATTGATGGTATTGATGGCACCAATGGTC

AGCCTGGCGAAGCAGGTTATCAGGGTGGTCGCGGTACCCGTGGTCAGCTG

GGTGAAACAGGTGATGTTGGTCAGAATGGTGATCGCGGCGCACCGGGTCC

GGATGGTAGCAAAGGTAGCGCCGGTCGTCCGGGTTTACGTcacccagaaa cgctggtgaaagtaaaagatgctgaagatcagttgggtgcacgagtgggt tacatcgaactggatctcaacagcggtaagatccttgagagttttcgccc cgaagaacgttttccaatgatgagcacttttaaagttctgctatgtggcg cggtattatcccgtattgacgccgggcaagagcaactcggtcgccgcata cactattctcagaatgacttggttgagtactcaccagtcacagaaaagca tcttacggatggcatgacagtaagagaattatgcagtgctgccataacca tgagtgataacactgcggccaacttacttctgacaacgatcggaggaccg aaggagctaaccgcttttttgcacaacatggggggatcatgtaactcgcct tgatcgttgggaaccggagctgaatgaagccataccaaacgacgagcgtg acaccacgatgcctgtagcaatggcaacaacgttgcgcaaactattaact ggcgaactacttactctagcttcccggcaacaattaatagactggatgga ggcggataaagttgcaggaccacttctgcgctcggcccttccggctggct ggtttattgctgataaatctggagccggtgagcgtgggtctcgcggtatc attgcagcactggggccagatggtaagccctcccgtatcgtagttatcta cacgacggggagtcaggcaactatggatgaacgaaatagacagatcgctg agataggtgcctcactgattaagcattggtaa (SEQ ID NO: 18)
MKKIWLALAGLVLAFSASAAQYEDHHHHHHHHHSGSSLVPRGSHMSGSSS

KGEELFTGVVPILVELDGDVNGHKFSVRGEGEGDATNGKLTLKFICTTGK

LPVPWPTLVTTLTYGVQCFSRYPDHMKQHDFFKSAMPEGYVQERTISFKD

DGTYKTRAEVKFEGDTLVNRIELKGIDFKEDGNILGHKLEYNFNSHNVYI

TADKQKNGIKANFKIRHNVEDGSVQLADHYQQNTPIGDPVLLPDNHYLS

TQSKLSKDPNEKRDHMVLLEFVTAAGITHGMDELYKSGAPGGPQGVVGAD

GKDGTPGNAGQKGPSGEPGSPGKAGSAGEQGPPGKDGSNGEPGSPGKEGE

RGLAGPPGPDGRRGETGSPGIAGALGKPGLEGPKGYPGLRGRDGTNGKRG

EQGETGPDGVRGIPGNDGQSGKPGIDGIDGTNGQPGEAGYQGGRGTRGQL

GETGDVGQNGDRGAPGPDGSKGSAGRPGLRHPETLVKVKDAEDQLGARVG

YIELDLNSGKILESFRPEERFPMMSTFKVLLCGAVLSRIDAGQEQLGRRI

HYSQNDLVEYSPVTEKHLTDGMTVRELCSAAITMSDNTAANLLLTTIGGP

KELTAFLHNMGDHVTRLDRWEPELNEAIPNDERDTTMPVAMATTLRKLLT

-continued

GELLTLASRQQLIDWMEADKVAGPLLRSALPAGWFIADKSGAGERGSRGI

IAALGPDGKPSRIVVIYTTGSQATMDERNRQIAEIGASLIKHW

The polynucleotides of SEQ ID NO: 17 was constructed by assembling several DNA fragments. The collagen containing sequence was codon optimized and synthesized by Gen9 DNA, now Ginkgo Bioworks internal synthesis. The GFP was also synthesized by Gen9. The Beta-lactamase was cloned out of the plasmid pKD46 (<http://cgsc2.biology.yale.edu/Strain.php?ID=68099>) using PCR with the enzyme PRIMESTAR® GXL polymerase (<http://www.clontech.com/US/Products/PCR/GC Rich/PrimeSTAR_GXL_DNA_P olymerase?sitex=10020:22372:US>). Overlaps between the pET28 vector, GFP, Collagen, and Beta-lactamase was designed to be between 30 and 40 bp long and added using PCR with the enzyme PRIMESTAR® GXL polymerase. The opened pET28a vector and inserts were then assembled together into the final plasmid using SGI GIBSON ASSEMBLY® (<https://us.vwr.com/store/product/17613857/gibson-assembly-hifi-1-step-kit-synthetic-genomics-inc>). Sequence of plasmid was then verified through Sanger sequencing through Eurofins Genomics (<www.eurofinsgenomics.com>).

The transformed cells were cultivated in minimal media and frozen in 1.5 aliquots with glycerol at a ratio of 50:50 of cells to glycerol. One vial of this frozen culture was revived in 50 ml of minimal media overnight at 37° C., 200 rpm. Cells were transferred into 300 ml of minimal media and grown for 6-9 hours to reach an OD600 of 5-10.

A bioreactor was prepared with 2.7 L of minimal media+ glucose and 300 ml of OD600 of 5-10 culture was added to bring the starting volume to 3 L. Cells were grown at 28° C., pH7 with Dissolved Oxygen maintained at 20% saturation using a cascade containing agitation, air and oxygen. pH was controlled using 28% w/w Ammonium hydroxide solution. Fermentation was run in a fed-batch mode using a DO-stat based feeding algorithm once the initial bolus of 40 g/L was depleted around 13 hours. After 24-26 hours of initial growth, the OD600 reached above 100. At this point, 300 mL of 500 g/L sucrose was added and temperature was reduced to 25 C. High density culture was induced for protein production using 1 mM IPTG. Fermentation was continued for another 20-24 hours and cells were harvested using a bench top centrifuge at 9000 rcf, 15 C for 60 minutes. Cell pellet recovered from centrifugation was resuspended in a buffer containing 0.5M NaCl and 0.1M KH2PO4 at pH8 in a weight by weight ratio of 2x buffer to 1x cells.

The harvested cells were disrupted in a homogenizer at 14,000 psi pressure in 2 passes. Resulting slurry contained the collagen protein along with other proteins.

The collagen was purified by acid treatment of non-homogenized whole cells recovered from the bioreactor after centrifugation and resuspension in the buffer described above. The pH of the resuspended suspension-was decreased to 3 using 6M Hydrochloric acid. Acidified cell slurry was incubated overnight at 4° C. with mixing, followed by centrifugation. The pH was then raised to 9 using 10N NaOH and the supernatant of the slurry was tested on a polyacrylamide gel and found to contain collagen in relatively high abundance compared to starting pellet. The collagen slurry thus obtained was high in salts. To obtain volume and salt reduction, concentration and diafiltration steps were performed using an EMD Millipore Tangential Flow Filtration system with ultrafiltration cassettes of 0.1 m2 each. Total area of filtration was 0.2 m2 using 2 cassettes in parallel. A volume reduction of 5× and a salt reduction of 19× was achieved in the TFF stage. Final collagen slurry was run on an SDS-PAGE gel to confirm presence of the collagen. This slurry was dried using a multi-tray lyophilizer over 3 days to obtain a white, fluffy collagen powder.

The purified collagen-GFP-Beta-lactamase fusion protein was analyzed on an SDS-PAGE gel and was observed to run at an apparent molecular weight of 90 kilodaltons. The expected size of the fusion protein is 85 kd. The 90 kDa band was confirmed by mass spectrometry to be the correct collagen fusion protein.

Truncated Collagen with DsbA Secretion Tag-His Tag-Linker-Thrombin Cleavage Site and GFP Beta-Lactamase Fusion (Version 2):

A jellyfish collagen with DsbA secretion tag-His tag-Linker-Thrombin cleavage site and GFP Beta-lactamase fusion is disclosed below. The codon-optimized nucleotide sequence encoding this collagen is provided in SEQ ID NO: 19. The amino acid sequence is disclosed in SEQ ID NO: 20. The DsbA secretion tag is encoded by nucleotides 1-72 and encodes amino acids 1-24. The His tag is encoded by nucleotides 73-99 and encodes a 9 histidine tag (SEQ ID NO: 129) of amino acids 25-33. The linker is encoded by nucleotides 100-111 and encodes amino acids 34-37. The thrombin cleavage side is encoded by nucleotides 112-135 and encodes amino acids 38-45. The green fluorescent protein (GFP) with linker is encoded by nucleotides 136-873 and encodes amino acids 46-291 The truncated collagen sequence is encoded by nucleotides 874-1440 and encodes amino acids 292-480. The Beta-lactamase with linker is encoded by nucleotides 1441-2232 and encodes amino acids 481-744.

```
                                             (SEQ ID NO: 19)
ATGAAAAAGATTTGGCTGGCGCTGGCTGGTTTAGTTTTAGCGTTTAGCGC

ATCGGCGGCGCAGTATGAAGATCACCATCACCACCACCACCATCACCACT

CTGGCTCGAGCCTGGTGCCGCGCGGCAGCCATATGTCTGGCTCGAGCAGT

AAAGGTGAAGAACTGTTCACCGGTGTTGTTCCGATCCTGGTTGAACTGGA

TGGTGATGTTAACGGCCACAAATTCTCTGTTCGTGGTGAAGGTGAAGGTG

ATGCAACCAACGGTAAACTGACCCTGAAATTCATCTGCACTACCGGTAAA

CTGCCGGTTCCATGGCCGACTCTGGTGACTACCCTGACCTATGGTGTTCA

GTGTTTTTCTCGTTACCCGGATCACATGAAGCAGCATGATTTCTTCAAAT

CTGCAATGCCGGAAGGTTATGTACAGGAGCGCACCATTTCTTTCAAAGAC

GATGGCACCTACAAAACCCGTGCAGAGGTTAAATTTGAAGGTGATACTCT

GGTGAACCGTATTGAACTGAAAGGCATTGATTTCAAAGAGGACGGCAACA

TCCTGGGCCACAAACTGGAATATAACTTCAACTCCCATAACGTTTACATC

ACCGCAGACAAACAGAAGAACGGTATCAAAGCTAACTTCAAAATTCGCCA

TAACGTTGAAGACGGTAGCGTACAGCTGGCGGACCACTACCAGCAGAACA

CTCCGATCGGTGATGGTCCGGTTCTGCTGCCGGATAACCACTACCTGTCC

ACCCAGTCTaaaCTGTCCAAAGACCCGAACGAAAAGCGCGACCACATGGT

GCTGCTGGAGTTCGTTACTGCAGCAGGTATCACGCACGGCATGGATGAAC

TCTACAAATCTGGCGCGCCGGGCGGTCCGCAGGGTGTTGTTGGTGCAGAT

GGTAAAGACGGTACCCCGGGTAATGCAGGTCAGAAAGGTCCGTCAGGTGA
```

-continued
```
ACCTGGCAGCCCTGGTAAAGCAGGTAGTGCCGGTGAGCAGGGTCCGCCGG
GCAAAGATGGTAGTAATGGTGAGCCGGGTAGCCCTGGCAAAGAAGGTGAA
CGTGGTCTGGCAGGACCGCCGGGTCCTGATGGTCGCCGCGGTGAAACGGG
TTCACCGGGTATTGCCGGTGCCCTGGGTAAACCAGGTCTGGAAGGTCCGA
AAGGTTATCCTGGTCTGCGCGGTCGTGATGGTACCAATGGCAAACGTGGC
GAACAGGGCGAAACCGGTCCAGATGGTGTTCGTGGTATTCCGGGTAACGA
TGGTCAGAGCGGTAAACCGGGCATTGATGGTATTGATGGCACCAATGGTC
AGCCTGGCGAAGCAGGTTATCAGGGTGGTCGCGGTACCCGTGGTCAGCTG
GGTGAAACAGGTGATGTTGGTCAGAATGGTGATCGCGGCGCACCGGGTCC
GGATGGTAGCAAAGGTAGCGCCGGTCGTCCGGGTTTACGTcacccagaaa
cgctggtgaaagtaaaagatgctgaagatcagttgggtgcacgagtgggt
tacatcgaactggatctcaacagcggtaagatccttgagagttttcgccc
cgaagaacgttttccaatgatgagcacttttaaagttctgctatgtggcg
cggtattatccgtattgacgccgggcaagagcaactcggtcgccgcata
cactattctcagaatgacttggttgagtactcaccagtcacagaaaagca
tcttacggatggcatgacagtaagagaattatgcagtgctgccataacca
tgagtgataacactgcggccaacttacttctgacaacgatcggaggaccg
aaggagctaaccgcttttttgcacaacatgggggatcatgtaactcgcct
tgatcgttgggaaccggagctgaatgaagccataccaaacgacgagcgtg
acaccacgatgcctgtagcaatggcaacaacgttgcgcaaactattaact
ggcgaactacttactctagcttcccggcaacaattaatagactggatgga
ggcggataaagttgcaggaccacttctgcgctcggcccttccggctggct
ggtttattgctgataaatctggagccggtgagcgtgggtctcgcggtatc
attgcagcactggggccagatggtaagccctcccgtatcgtagttatcta
cacgacggggagtcaggcaactatggatgaacgaaatagacagatcgctg
agataggtgcctcactgattaagcattggtaa
```

(SEQ ID NO: 20)
MKKIWLALAGLVLAFSASAAQYEDHHHHHHHHHGSSLVPRGSHMSGSSS
KGEELFTGVVPILVELDGDVNGHKFSVRGEGEGDATNGKLTLKFICTTGK
LPVPWPTLVTTLTYGVQCFSRYPDHMKQHDFFKSAMPEGYVQERTISFKD
DGTYKTRAEVKFEGDTLVNRIELKGIDFKEDGNILGHKLEYNFNSHNVYI
TADKQKNGIKANFKIRHNVEDGSVQLADHYQQNTPIGDGPVLLPDNHYLS
TQSKLSKDPNEKRDHMVLLEFVTAAGITHGMDELYKSGAPGPQGVVGAD
GKDGTPGNAGQKGPSGEPGSPGKAGSAGEQGPPGKDGSNGEPGSPGKEGE
RGLAGPPGPDGRRGETGSPGIAGALGKPGLEGPKGYPGLRGRDGTNGKRG
EQGETGPDGVRGIPGNDGQSGKPGIDGIDGTNGQPGEAGYQGGRGTRGQL
GETGDVGQNGDRGAPGPDGSKGSAGRPGLRHPETLVKVKDAEDQLGARVG
YIELDLNSGKILESFRPEERFPMMSTFKVLLCGAVLSRIDAGQEQLGRRI
HYSQNDLVEYSPVTEKHLTDGMTVRELCSAAITMSDNTAANLLLTTIGGP

KELTAFLHNMGDHVTRLDRWEPELNEAIPNDERDTTMPVAMATTLRKLLT
GELLTLASRQQLIDWMEADKVAGPLLRSALPAGWFIADKSGAGERGSRGI
IAALGPDGKPSRIVVIYTTGSQATMDERNRQIAEIGASLIKHW

Example 4: Production of Full-Length Elastin

Full length human elastin were expressed as described below. The wild-type, full length amino acid sequence of human elastin is provided below.

(SEQ ID NO: 21)
MAGLTAAAPRPGVLLLLLSILHPSRPGGVPGAIPGGVPGGVFYPGAGLGA
LGGGALGPGGKPLKPVPGGLAGAGLGAGLGAFPAVTFPGALVPGGVADAA
AAYKAAKAGAGLGGVPGVGGLGVSAGAVVPQPGAGVKPGKVPGVGLPGVY
PGGVLPGARFPGVGVLPGVPTGAGVKPKAPGVGGAFAGIPGVGPFGGPQP
GVPLGYPIKAPKLPGGYGLPYTTGKLPYGYGPGGVAGAAGKAGYPTGTGV
GPQAAAAAAAKAAAKFGAGAAGVLPGVGGAGVPGVPGAIPGIGGIAGVGT
PAAAAAAAAAKAAKYGAAAGLVPGGPGFGPGVVVGVPGAGVPGVGVPGAG
IPVVPGAGIPGAAVPGVVSPEAAAKAAAKAAKYGARPGVGVGGIPTYGVG
AGGFPGFGVGVGGIPGVAGVPGVGGVPGVGGVPGVGISPEAQAAAAAKAA
KYGAAGAGVLGGLVPGPQAAVPGVPGTGGVPGVGTPAAAAAKAAAKAAQF
GLVPGVGVAPGVGVAPGVGVAPGVGLAPGVGVAPGVGVAPGVGVAPGIGP
GGVAAAAKSAAKVAAKAQLRAAAGLGAGIPGLGVGVGVPGLGVGAGVPGL
GVGAGVPGFGAGADEGVRRSLSPELREGDPSSSQHLPSTPSSPRVPGALA
AAKAAKYGAAVPGVLGGLGALGGVGIPGGVVGAGPAAAAAAAKAAAKAAQ
FGLVGAAGLGGLGVGGLGVPGVGGLGGIPPAAAAKAAKYGAAGLGGVLGG
AGQFPLGGVAARPGFGLSPIFPGGACLGKACGRKRK

<http://www.uniprot.org/uniprot/P15502>

The non-codon optimized polynucleotide sequence encoding the full length elastin is disclosed below. In SEQ ID NO: 22, nucleotides 1-78 encode the DsbA secretion tag and nucleotides 79-2358 encode the full length human elastin.

(SEQ ID NO: 22)
```
ATGGCGGGTCTGACGGCGGCGGCCCCGCGGCCCGGAGTCCTCCTGCTCCT
GCTGTCCATCCTCCACCCCTCTCGGCCTGGAGGGGTCCCTGGGGCCATTC
CTGGTGGAGTTCCTGGAGGAGTCTTTTATCCAGGGGCTGGTCTCGGAGCC
CTTGGAGGAGGAGCGCTGGGGCCTGGAGGCAAACCTCTTAAGCCAGTTCC
CGGAGGGCTTGCGGGTGCTGGCCTTGGGGCAGGGCTCGGCGCCTTCCCCG
CAGTTACCTTTCCGGGGGCTCTGGTGCCTGGTGGAGTGGCTGACGCTGCT
GCAGCCTATAAAGCTGCTAAGGCTGGCGCTGGGCTTGGTGGTGTCCCAGG
AGTTGGTGGCTTAGGAGTGTCTGCAGGTGCGGTGGTTCCTCAGCCTGGAG
CCGGAGTGAAGCCTGGGAAAGTGCCGGGTGTGGGGCTGCCAGGTGTATAC
CCAGGTGGCGTGCTCCCAGGAGCTCGGTTCCCCGGTGTGGGGGTGCTCCC
TGGAGTTCCCACTGGAGCAGGAGTTAAGCCCAAGGCTCCAGGTGTAGGTG
```

```
GAGCTTTTGCTGGAATCCCAGGAGTTGGACCCTTTGGGGACCGCAACCT

GGAGTCCCACTGGGGTATCCCATCAAGGCCCCCAAGCTGCCTGGTGGCTA

TGGACTGCCCTACACCACAGGGAAACTGCCCTATGGCTATGGGCCCGGAG

GAGTGGCTGGTGCAGCGGGCAAGGCTGGTTACCCAACAGGGACAGGGGTT

GGCCCCCAGGCAGCAGCAGCAGCGGCAGCTAAAGCAGCAGCAAAGTTCGG

TGCTGGAGCAGCCGGAGTCCTCCCTGGTGTTGGAGGGGCTGGTGTTCCTG

GCGTGCCTGGGGCAATTCCTGGAATTGGAGGCATCGCAGGCGTTGGGACT

CCAGCTGCAGCTGCAGCTGCAGCAGCAGCCGCTAAGGCAGCCAAGTATGG

AGCTGCTGCAGGCTTAGTGCCTGGTGGGCCAGGCTTTGGCCCGGGAGTAG

TTGGTGTCCCAGGAGCTGGCGTTCCAGGTGTTGGTGTCCCAGGAGCTGGG

ATTCCAGTTGTCCCAGGTGCTGGGATCCCAGGTGCTGCGGTTCCAGGGGT

TGTGTCACCAGAAGCAGCTGCTAAGGCAGCTGCAAAGGCAGCCAAATACG

GGGCCAGGCCCGGAGTCGGAGTTGGAGGCATTCCTACTTACGGGGTTGGA

GCTGGGGGCTTTCCCGGCTTTGGTGTCGGAGTCGGAGGTATCCCTGGAGT

CGCAGGTGTCCCTGGTGTCGGAGGTGTTCCCGGAGTCGGAGGTGTCCCGG

GAGTTGGCATTTCCCCCGAAGCTCAGGCAGCAGCTGCCGCCAAGGCTGCC

AAGTACGGTGCTGCAGGAGCAGGAGTGCTGGGTGGGCTAGTGCCAGGTCC

CCAGGCGGCAGTCCCAGGTGTGCCGGGCACGGGAGGAGTGCCAGGAGTGG

GGACCCCAGCAGCTGCAGCTGCTAAAGCAGCCGCCAAAGCCGCCCAGTTT

GGGTTAGTTCCTGGTGTCGGCGTGGCTCCTGGAGTTGGCGTGGCTCCTGG

TGTCGGTGTGGCTCCTGGAGTTGGCTTGGCTCCTGGAGTTGGCGTGGCTC

CTGGAGTTGGTGTGGCTCCTGGCGTTGGCGTGGCTCCCGGCATTGGCCCT

GGTGGAGTTGCAGCTGCAGCAAAATCCGCTGCCAAGGTGGCTGCCAAAGC

CCAGCTCCGAGCTGCAGCTGGGCTTGGTGCTGGCATCCCTGGACTTGGAG

TTGGTGTCGGCGTCCCTGGACTTGGAGTTGGTGCTGGTGTTCCTGGACTT

GGAGTTGGTGCTGGTGTTCCTGGCTTCGGGGCAGGTGCAGATGAGGGAGT

TAGGCGGAGCCTGTCCCCTGAGCTCAGGGAAGGAGATCCCTCCTCCTCTC

AGCACCTCCCCAGCACCCCCTCATCACCCAGGGTACCTGGAGCCCTGGCT

GCCGCTAAAGCAGCCAAATATGGAGCAGCAGTGCCTGGGGTCCTTGGAGG

GCTCGGGGCTCTCGGTGGAGTAGGCATCCCAGGCGGTGTGGTGGGAGCCG

GACCCGCCGCCGCTGCCGCAGCCAAAGCTGCTGCCAAAGCCGCCCAG

TTTGGCCTAGTGGGAGCCGCTGGGCTCGGAGGACTCGGAGTCGGAGGGCT

TGGAGTTCCAGGTGTTGGGGGCCTTGGAGGTATACCTCCAGCTGCAGCCG

CTAAAGCAGCTAAATACGGTGCTGCTGGCCTTGGAGGTGTCCTAGGGGGT

GCCGGGCAGTTCCCACTTGGAGGAGTGGCAGCAAGACCTGGCTTCGGATT

GTCTCCCATTTTCCCAGGTGGGGCCTGCCTGGGGAAAGCTTGTGGCCGGA

AGAGAAAATGA
```

Codon Optimized Elastin with DsbA Secretion Tag-His Tag-Linker-Thrombin Cleavage Site The codon optimized polynucleotide sequence encoding the full length human elastin with DsbA secretion tag-His tag-Linker-Thrombin cleavage site is disclosed below. In SEQ ID NO: 23: nucleotides 1-72 encode the DsbA secretion tag encoding amino acids 1-24 of SEQ ID NO: 24; nucleotides 73-99 encode the 9 His tag (SEQ ID NO: 129) encoding amino acids 25-33 of SEQ ID NO: 24; nucleotides 100-111 encode the linker encoding amino acids 34-37 of SEQ ID NO: 24; nucleotides 112-135 encode the thrombin cleavage tag encoding amino acids 38-45 of SEQ ID NO: 24; nucleotides 136-2415 encode the amino acids 46-805 of the full length human elastin of SEQ ID NO: 24.

```
                                          (SEQ ID NO: 23)
ATGAAAAAGATTTGGCTGGCGCTGGCTGGTTTAGTTTTAGCGTTTAGCGC

ATCGGCGGCGCAGTATGAAGATCACCATCACCACCACCACCATCACCACT

CTGGCTCGAGCCTGGTGCCGCGCGGCAGCCATATGGGTGGCGTACCAGGC

GCAATTCCTGGGGGTGTCCCAGGCGGTGTTTTTTATCCGGGCGCCGGTCT

TGGCGCACTGGGTGGCGGTGCACTGGGCCCGGGCGGCAAACCGCTGAAAC

CGGTACCAGGTGGTTTAGCAGGCGCCGGCTTAGGCGCAGGTCTGGGAGCA

TTTCCGGCAGTTACCTTTCCAGGGGCACTGGTTCCTGGAGGTGTGGCCGA

TGCAGCCGCGGCATATAAAGCCGCTAAAGCCGGTGCGGGTTTAGGAGGCG

TCCCAGGTGTCGGTGGCCTGGGTGTTAGCGCCGGTGCAGTTGTTCCGCAG

CCGGGAGCAGGGGTTAAACCTGGTAAAGTGCCGGGAGTAGGTCTGCCAGG

CGTTTATCCTGGTGGTGTTTTGCCGGGTGCCCGTTTCCGGGCGTTGGTG

TTCTTCCAGGCGTGCCGACCGGAGCCGGTGTTAAACCGAAAGCCCCCGGT

GTTGGAGGTGCATTTGCAGGCATCCCGGGAGTTGGCCCGTTTGGTGGTCC

GCAACCTGGGGTTCCGTTAGGTTATCCGATTAAAGCACCGAAACTGCCCG

GCGGTTATGGTCTGCCGTACACAACCGGTAAACTGCCGTATGGTTATGGC

CCGGGTGGAGTTGCGGGTGCAGCAGGTAAAGCGGGTTATCCTACCGGAAC

CGGTGTAGGTCCGCAGGCCGCTGCTGCCGCCGCCGCAAAAGCAGCGGCTA

AATTTGGCGCCGGAGCAGCGGGTGTTCTGCCTGGAGTTGGTGGTGCGGGC

GTGCCAGGGGTACCTGGTGCAATTCCGGGTATTGGTGGTATTGCCGGTGT

CGGCACCCCGGCCGCGGCAGCTGCGGCAGCGGCGGCTGCCAAAGCTGCTA

AATACGGTGCCGCGGCGGGTCTGGTGCCAGGAGGTCCGGGTTTTGGTCCG

GGAGTGGTTGGCGTGCCTGGCGCAGGCGTTCCTGGTGTGGGCGTTCCAGG

TGCAGGGATTCCTGTTGTGCCTGGTGCCGGTATTCCCGGCGCGGCCGTTC

CGGGGGTGGTTAGCCCGGAAGCCGCAGCGAAGGCTGCGGCAAAGGCAGCA

AAGTATGGCGCACGCCCAGGAGTCGGCGTGGGTGGTATCCCGACCTATGG

GGTGGGCGCAGGGGGTTTTCCTGGTTTCGGCGTAGGCGTAGGAGGTATAC

CGGGCGTGGCCGGTGTACCAGGGGTTGGTGGCGTCCCTGGTGTTGGCGGT

GTGCCAGGTGTTGGTATTTCACCGGAAGCACAGGCAGCAGCCGCAGCTAA

GGCAGCGAAATATGGTGCCGCCGGCGCAGGAGTTTTAGGTGGGCTGGTTC

CGGGCCCGCAGGCAGCTGTGCCGGGGGTTCCAGGCACCGGTGGTGTCCCT

GGAGTCGGTACGCCGGCTGCAGCGGCAGCCAAAGCGGCTGCGAAAGCAGC

ACAGTTTGGCTTAGTACCGGGTGTGGGAGTTGCCCCCGGCGTTGGCGTTG

CTCCAGGGGTGGGTGTTGCTCCTGGCGTCGGTCTGGCTCCTGGAGTGGGC

GTAGCACCCGGTGTGGGGGTGGCCCCGGGTGTTGGGGTTGCACCGGGTAT

CGGTCCGGGCGGTGTCGCAGCAGCAGCTAAAAGCGCGGCGAAAGTTGCGG
```

```
CCAAAGCCCAACTGCGCGCCGCCGCGGGCCTCGGTGCAGGTATTCCGGGG
CTGGGTGTCGGAGTTGGAGTCCCGGGTTTGGGCGTGGGCGCGGGAGTTCC
GGGACTGGGAGTGGGTGCCGGAGTTCCTGGCTTTGGTGCAGGCGCAGATG
AAGGTGTTCGTCGTAGCCTGAGTCCGGAACTGCGTGAAGGTGATCCGAGT
AGCAGCCAGCATCTGCCGAGCACCCCGAGCAGCCCGCGTGTTCCGGGTGC
ATTAGCTGCAGCAAAAGCCGCCAAGTATGGTGCAGCCGTGCCGGGCGTCT
TAGGTGGTCTGGGCGCCCTGGGTGGTGTAGGCATTCCGGGAGGTGTTGTG
GGTGCAGGACCGGCCGCCGCAGCTGCGGCCGCCAAAGCAGCTGCAAAAGC
GGCCCAGTTTGGTTTAGTGGGCGCCGCAGGTTTAGGCGGTTTAGGTGTGG
GTGGACTGGGTGTACCTGGCGTAGGCGGTCTGGGTGGAATTCCGCCCGCA
GCGGCCGCGAAAGCGGCAAAATATGGCGCGGCAGGCCTGGGCGGCGTGCT
GGGTGGGGCAGGTCAGTTTCCGCTGGGCGGGGTTGCCGCACGTCCGGGAT
TTGGTCTGAGCCCGATTTTCCCTGGCGGCGCATGTCTGGGTAAAGCATGT
GGTCGTAAACGTAAAtaa
```
(SEQ ID NO: 24)
```
MKKIWLALAGLVLAFSASAAQYEDHHHHHHHHHSGSSLVPRGSHMGGVPG
AIPGGVPGGVFYPGAGLGALGGGALGPGGKPLKPVPGGLAGAGLGAGLGA
FPAVTFPGALVPGGVADAAAAYKAAKAGAGLGGVPGVGGLGVSAGAVVPQ
PGAGVKPGKVPGVGLPGVYPGGVLPGARFPGVGVLPGVPTGAGVKPKAPG
VGGAFAGIPGVGPFGGPQPGVPLGYPIKAPKLPGGYGLPYTTGKLPYGYG
PGGVAGAAGKAGYPTGTGVGPQAAAAAAAKAAAKFGAGAAGVLPGVGGAG
VPGVPGAIPGIGGIAGVGTPAAAAAAAAAAKAAKYGAAAGLVPGGPGFGP
GVVGVPGAGVPGVGVPGAGIPVVPGAGIPGAAVPGVVSPEAAAKAAAKAA
KYGARPGVGVGGIPTYGVGAGGFPGFGVGVGGIPGVAGVPGVGGVPGVGG
VPGVGISPEAQAAAAAKAAKYGAAGAGVLGGLVPGPQAAVPGVPGTGGVP
GVGTPAAAAAKAAAKAAQFGLVPGVGVAPGVGVAPGVGVAPGVGLAPGVG
VAPGVGVAPGVGVAPGIGPGGVAAAAKSAAKVAAKAQLRAAAGLGAGIPG
LGVGVGVPGLGVGAGVPGLGVGAGVPGFGAGADEGVRRSLSPELREGDPS
SSQHLPSTPSSPRVPGALAAAKAAKYGAAVPGVLGGLGALGGVGIPGGVV
GAGPAAAAAAAKAAAKAAQFGLVGAAGLGGLGVGGLGVPGVGGLGGIPPA
AAAKAAKYGAAGLGGVLGGAGQFPLGGVAARPGFGLSPIFPGGACLGKAC
GRKRK
```

The polynucleotide encoding the full length human elastin without the native sequence tag is disclosed in SEQ ID NO: 87.

(SEQ ID NO: 87)
```
GGTGGCGTACCAGGCGCAATTCCTGGGGGTGTCCCAGGCGGTGTTTTTTA
TCCGGGCGCCGGTCTTGGCGCACTGGGTGGCGGTGCACTGGGCCCGGGCG
GCAAACCGCTGAAACCGGTACCAGGTGGTTTAGCAGGCGCCGGCTTAGGC
GCAGGTCTGGGAGCATTTCCGGCAGTTACCTTTCCAGGGGCACTGGTTCC
TGGAGGTGTGGCCGATGCAGCCGCGGCATATAAAGCCGCTAAAGCCGGTG
CGGGTTTAGGAGGCGTCCCAGGTGTCGGTGGCCTGGGTGTTAGCGCCGGT
GCAGTTGTTCCGCAGCCGGGAGCAGGGGTTAAACCTGGTAAAGTGCCGGG
AGTAGGTCTGCCAGGCGTTTATCCTGGTGGTGTTTTGCCGGGTGCCCGTT
TTCCGGGCGTTGGTGTTCTTCCAGGCGTGCCGACCGGAGCCGGTGTTAAA
CCGAAAGCCCCCGGTGTTGGAGGTGCATTTGCAGGCATCCCGGGAGTTGG
CCCGTTTGGTGGTCCGCAACCTGGGGTTCCGTTAGGTTATCCGATTAAAG
CACCGAAACTGCCCGGCGGTTATGGTCTGCCGTACACAACCGGTAAACTG
CCGTATGGTTATGGCCCGGGTGGAGTTGCGGGTGCAGCAGGTAAAGCGGG
TTATCCTACCGGAACCGGTGTAGGTCCGCAGGCCGCTGCTGCCGCCGCCG
CAAAAGCAGCGGCTAAATTTGGCGCCGGAGCAGCGGGTGTTCTGCCTGGA
GTTGGTGGTGCGGGCGTGCCAGGGGTACCTGGTGCAATTCCGGGTATTGG
TGGTATTGCCGGTGTCGGCACCCCGGCCGCGGCAGCTGCGGCAGCGGCGG
CTGCCAAAGCTGCTAAATACGGTGCCGCGGCGGGTCTGGTGCCAGGAGGT
CCGGGTTTTGGTCCGGGAGTGGTTGGCGTGCCTGGCGCAGGCGTTCCTGG
TGTGGGCGTTCCAGGTGCAGGGATTCCTGTTGTGCCTGGTGCCGGTATTC
CCGGCGCGGCCGTTCCGGGGGTGGTTAGCCCGGAAGCCGCAGCGAAGGCT
GCGGCAAAGGCAGCAAAGTATGGCGCACGCCCAGGAGTCGGCGTGGGTGG
TATCCCGACCTATGGGGTGGGCGCAGGGGGTTTTCCTGGTTTCGGCGTAG
GTGTAGGAGGTATACCGGGCGTGGCCGGTGTACCAGGGGTTGGTGGCGTC
CCTGGTGTTGGCGGTGTGCCAGGTGTTGGTATTTCACCGGAAGCACAGGC
AGCAGCCGCAGCTAAGGCAGCGAAATATGGTGCCGCCGGCGCAGGAGTTT
TAGGTGGGCTGGTTCCGGGCCCGCAGGCAGCTGTGCCGGGGGTTCCAGGC
ACCGGTGGTGTCCCTGGAGTCGGTACGCCCGGCTGCAGCGGCAGCCAAAGC
GGCTGCGAAAGCAGCACAGTTTGGCTTAGTACCGGGTGTGGGAGTTGCCC
CCGGCGTTGGCGTTGCTCCAGGGGTGGGTGTTGCTCCTGGCGTCGGTCTG
GCTCCTGGAGTGGGCGTAGCACCCGGTGTGGGGGTGGCCCCGGGTGTTGG
GGTTGCACCGGGTATCGGTCCGGGCGGTGTCGCAGCAGCAGCTAAAAGCG
CGGCGAAAGTTGCGGCCAAAGCCCAACTGCGCGCCGCCGCGGGCCTCGGT
GCAGGTATTCCGGGGCTGGGTGTCGGAGTTGGAGTCCCGGGTTTGGGCGT
GGGCGCGGGAGTTCCGGGACTGGGAGTGGGTGCCGGAGTTCCTGGCTTTG
GTGCAGGCGCAGATGAAGGTGTTCGTCGTAGCCTGAGTCCGGAACTGCGT
GAAGGTGATCCGAGTAGCAGCCAGCATCTGCCGAGCACCCCGAGCAGCCC
GCGTGTTCCGGGTGCATTAGCTGCAGCAAAAGCCGCCAAGTATGGTGCAG
CCGTGCCGGGCGTCTTAGGTGGTCTGGGCGCCCTGGGTGGTGTAGGCATT
CCGGGAGGTGTTGTGGGTGCAGGACCGGCCGCCGCAGCTGCGGCCGCCAA
AGCAGCTGCAAAAGCGGCCCAGTTTGGTTTAGTGGGCGCCGCAGGTTTAG
GCGGTTTAGGTGTGGGTGGACTGGGTGTACCTGGCGTAGGCGGTCTGGGT
GGAATTCCGCCCGCAGCGGCCGCGAAAGCGGCAAAATATGGCGCGGCAGG
CCTGGGCGGCGTGCTGGGTGGGGCAGGTCAGTTTCCGCTGGGCGGGGTTG
CCGCACGTCCGGGATTTGGTCTGAGCCCGATTTTCCCTGGCGGCGCATGT
CTGGGTAAAGCATGTGGTCGTAAACGTAAAtaa
```

The full length human elastin sequence without the native sequence tag is disclosed in SEQ ID NO: 88.

(SEQ ID NO: 88)
GGVPGAIPGGVPGGVFYPGAGLGALGGGALGPGGKPLKPVPGGLAGAGLG
AGLGAFPAVTFPGALVPGGVADAAAAYKAAKAGAGLGGVPGVGGLGVSAG
AVVPQPGAGVKPGKVPGVGLPGVYPGGVLPGARFPGVGVLPGVPTGAGVK
PKAPGVGGAFAGIPGVGPFGGPQPGVPLGYPIKAPKLPGGYGLPYTTGKL
PYGYGPGGVAGAAGKAGYPTGTGVGPQAAAAAAAKAAAKFGAGAAGVLPG
VGGAGVPGVPGAIPGIGGIAGVGTPAAAAAAAAAAKAAKYGAAAGLVPGG
PGFGPGVVGVPGAGVPGVGVPGAGIPVVPGAGIPGAAVPGVVSPEAAAKA
AAKAAKYGARPGVGVGGIPTYGVGAGGFPGFGVGVGGIPGVAGVPGVGGV
PGVGGVPGVGISPEAQAAAAAKAAKYGAAGAGVLGGLVPGPQAAVPGVPG
TGGVPGVGTPAAAAAKAAAKAAQFGLVPGVGVAPGVGVAPGVGVAPGVGL
APGVGVAPGVGVAPGVGVAPGIGPGGVAAAAKSAAKVAAKAQLRAAAGLG
AGIPGLGVGVGVPGLGVGAGVPGLGVGAGVPGFGAGADEGVRRSLSPELR
EGDPSSSQHLPSTPSSPRVPGALAAAKAAKYGAAVPGVLGGLGALGGVGI
PGGVVGAGPAAAAAAAKAAAKAAQFGLVGAAGLGGLGVGGLGVPGVGGLG
GIPPAAAAKAAKYGAAGLGGVLGGAGQFPLGGVAARPGFGLSPIFPGGAC
LGKACGRKRK

Codon Optimized Elastin with DsbA Secretion Tag

The codon optimized polynucleotide sequence encoding the full length human elastin with a DsbA secretion tag is disclosed in SEQ ID NO: 25. In SEQ ID NO: 25: nucleotides 1-72 encode the DsbA secretion tag encoding amino acids 1-24 of SEQ ID NO: 26; nucleotides 73-2355 encode the amino acids 25-785 of the full length human elastin of SEQ ID NO: 26.

(SEQ ID NO: 25)
ATGAAAAAGATTTGGCTGGCGCTGGCTGGTTTAGTTTTAGCGTTTAGCGC
ATCGGCGGCGCAGTATGAAGATATGGGTGGCGTACCAGGCGCAATTCCTG
GGGGTGTCCCAGGCGGTGTTTTTTATCCGGGCGCCGGTCTTGGCGCACTG
GGTGGCGGTGCACTGGGCCCGGGCGGCAAACCGCTGAAACCGGTACCAGG
TGGTTTAGCAGGCGCCGGCTTAGGCGCAGGTCTGGGAGCATTTCCGGCAG
TTACCTTTCCAGGGGCACTGGTTCCTGGAGGTGTGGCCGATGCAGCCGCG
GCATATAAAGCCGCTAAAGCCGGTGCGGGTTTAGGAGGCGTTCCCAGGTGT
CGGTGGCCTGGGTGTTAGCGCCGGTGCAGTTGTTCCGCAGCCGGGAGCAG
GGGTTAAACCTGGTAAAGTGCCGGGAGTAGGTCTGCCAGGCGTTTATCCT
GGTGGTGTTTTGCCGGGTGCCCGTTTTCCGGGCGTTGGTGTTCTTCCAGG
CGTGCCGACCGGAGCCGGTGTTAAACCGAAAGCCCCCGGTGTTGGAGGTG
CATTTGCAGGCATCCCGGGAGTTGGCCCGTTTGGTGGTCCGCAACCTGGG
GTTCCGTTAGGTTATCCGATTAAAGCACCGAAACTGCCCGGCGGTTATGG
TCTGCCGTACACAACCGGTAAACTGCCGTATGGTTATGGCCCGGGTGGAG
TTGCGGGTGCAGCAGGTAAAGCGGGTTATCCTACCGGAACCGGTGTAGGT
CCGCAGGCCGCTGCTGCCGCCGCCGCAAAAGCAGCGGCTAAATTTGGCGC

-continued
CGGAGCAGCGGGTGTTCTGCCTGGAGTTGGTGGTGCGGGCGTGCCAGGGG
TACCTGGTGCAATTCCGGGTATTGGTGGTATTGCCGGTGTCGGCACCCCG
GCCGCGGCAGCTGCGGCAGCGGCGGCTGCCAAAGCTGCTAAATACGGTGC
CGCGGCGGGTCTGGTGCCAGGAGGTCCGGGTTTTGGTCCGGGAGTGGTTG
GCGTGCCTGGCGCAGGCGTTCCTGGTGTGGGCGTTCCAGGTGCAGGGATT
CCTGTTGTGCCTGGTGCCGGTATTCCCGGCGCGGCCGTTCCGGGGGTGGT
TAGCCCGGAAGCCGCAGCGAAGGCTGCGGCAAAGGCAGCAAAGTATGGCG
CACGCCCAGGAGTCGGCGTGGGTGGTATCCCGACCTATGGGGTGGGCGCA
GGGGGTTTTCCTGGTTTCGGCGTAGGTGTAGGAGGTATACCGGGCGTGGC
CGGTGTACCAGGGGTTGGTGGCGTCCCTGGTGTTGGCGGTGTGCCAGGTG
TTGGTATTTCACCGGAAGCACAGGCAGCAGCCGCAGCTAAGGCAGCGAAA
TATGGTGCCGCCGGCGCAGGAGTTTTAGGTGGGCTGGTTCCGGGCCCGCA
GGCAGCTGTGCCGGGGGTTCCAGGCACCGGTGGTGTCCCTGGAGTCGGTA
CGCCGGCTGCAGCGGCAGCCAAAGCGGCTGCGAAAGCAGCACAGTTTGGC
TTAGTACCGGGTGTGGGAGTTGCCCCCGGCGTTGGCGTTGCTCCAGGGGT
GGGTGTTGCTCCTGGCGTCGGTCTGGCTCCTGGAGTGGGCGTAGCACCCG
GTGTGGGGGTGGCCCCGGGTGTTGGGGTTGCACCGGGTATCGGTCCGGGC
GGTGTCGCAGCAGCAGCTAAAAGCGCGGCGAAAGTTGCGGCCAAAGCCCA
ACTGCGCGCCGCCGCGGGCCTCGGTGCAGGTATTCCGGGGCTGGGTGTCG
GAGTTGGAGTCCCGGGTTTGGGCGTGGGCGCGGGAGTTCCGGGACTGGGA
GTGGGTGCCGGAGTTCCTGGCTTTGGTGCAGGCGCAGATGAAGGTGTTCG
TCGTAGCCTGAGTCCGGAACTGCGTGAAGGTGATCCGAGTAGCAGCCAGC
ATCTGCCGAGCACCCCGAGCAGCCCGCGTGTTCCGGGTGCATTAGCTGCA
GCAAAAGCCGCCAAGTATGGTGCAGCCGTGCCGGGCGTCTTAGGTGGTCT
GGGCGCCCTGGGTGGTGTAGGCATTCCGGGAGGTGTTGTGGGTGCAGGAC
CGGCCGCCGCAGCTGCGGCCGCCAAAGCAGCTGCAAAAGCGGCCCAGTTT
GGTTTAGTGGGCGCCGCAGGTTTAGGCGGTTTAGGTGTGGGTGGACTGGG
TGTACCTGGCGTAGGCGGTCTGGGTGGAATTCCGCCCGCAGCGGCCGCGA
AAGCGGCAAATATGGCGCGGCAGGCCTGGGCGGCGTGCTGGGTGGGGCA
GGTCAGTTTCCGCTGGGCGGGGTTGCCGCACGTCCGGGATTTGGTCTGAG
CCCGATTTTCCCTGGCGGCGCATGTCTGGGTAAAGCATGTGGTCGTAAAC
GTAAAtaa (SEQ ID NO: 26)
MKKIWLALAGLVLAFSASAAQYEDMGGVPGAIPGGVPGGVFYPGAGLGAL
GGGALGPGGKPLKPVPGGLAGAGLGAGLGAFPAVTFPGALVPGGVADAAA
AYKAAKAGAGLGGVPGVGGLGVSAGAVVPQPGAGVKPGKVPGVGLPGVYP
GGVLPGARFPGVGVLPGVPTGAGVKPKAPGVGGAFAGIPGVGPFGGPQPG
VPLGYPIKAPKLPGGYGLPYTTGKLPYGYGPGGVAGAAGKAGYPTGTGVG
PQAAAAAAAKAAAKFGAGAAGVLPGVGGAGVPGVPGAIPGIGGIAGVGTP
AAAAAAAAAAKAAKYGAAAGLVPGGPGFGPGVVGVPGAGVPGVGVPGAGI
PVVPGAGIPGAAVPGVVSPEAAAKAAAKAAKYGARPGVGVGGIPTYGVGA -continued

GGFPGFGVGVGGIPGVAGVPGVGGVPGVGGVPGVGISPEAQAAAAAKAAK

YGAAGAGVLGGLVPGPQAAVPGVPGTGGVPGVGTPAAAAAKAAAKAAQFG

LVPGVGVAPGVGVAPGVGVAPGVGLAPGVGVAPGVGVAPGVGVAPGIGPG

GVAAAAKSAAKVAAKAQLRAAAGLGAGIPGLGVGVGVPGLGVGAGVPGLG

VGAGVPGFGAGADEGVRRSLSPELREGDPSSSQHLPSTPSSPRVPGALAA

AKAAKYGAAVPGVLGGLGALGGVGIPGGVVGAGPAAAAAAAKAAAKAAQF

GLVGAAGLGGLGVGGLGVPGVGGLGGIPPAAAAKAAKYGAAGLGGVLGGA

GQFPLGGVAARPGFGLSPIFPGGACLGKACGRKRK

The polynucleotides of SEQ ID NO: 22 was codon optimized and synthesized by Gen9 DNA, now Ginkgo Bioworks internal synthesis. Overlaps between the pET28 vector and SEQ ID NO: 22 was designed to be between 30 and 40 bp long and added using PCR with the enzyme PRIMESTAR® GXL polymerase (<http://www.clontech.com/US/Products/PCR/GC Rich/PrimeSTAR_GXL_DNA_P olymerase?sitex=10020:22372:US>). The opened pET28a vector and insert DNA (SEQ ID NO: 22) was then assembled together into the final plasmid using SGI GIBSON ASSEMBLY® (<https://us.vwr.com/store/product/17613857/gibson-assembly-hifi-1-step-kit-synthetic-genomics-inc>). Sequence of plasmid was then verified through Sanger sequencing through Eurofins Genomics (<www.eurofinsgenomics.com>).

The transformed cells were cultivated in minimal media and frozen in 1.5 aliquots with glycerol at a ratio of 50:50 of cells to glycerol. One vial of this frozen culture was revived in 50 ml of minimal media overnight at 37° C., 200 rpm. Cells were transferred into 300 ml of minimal media and grown for 6-9 hours to reach an OD600 of 5-10.

A bioreactor was prepared with 2.7 L of minimal media+ glucose and 300 ml of OD600 of 5-10 culture was added to bring the starting volume to 3 L. Cells were grown at 28° C., pH7 with Dissolved Oxygen maintained at 20% saturation using a cascade containing agitation, air and oxygen. pH was controlled using 28% w/w Ammonium hydroxide solution. Fermentation was run in a fed-batch mode using a DO-stat based feeding algorithm once the initial bolus of 40 g/L was depleted around 13 hours. After 24-26 hours of initial growth, the OD600 reached above 100. At this point, 300 mL of 500 g/L sucrose was added and temperature was reduced to 25 C. High density culture was induced for protein production using 1 mM IPTG. Fermentation was continued for another 20-24 hours and cells were harvested using a bench top centrifuge at 9000 rcf, 15 C for 60 minutes. Cell pellet recovered from centrifugation was resuspended in a buffer containing 0.5M NaCl and 0.1M KH2PO4 at pH8 in a weight by weight ratio of 2x buffer to 1x cells.

The fermentations were performed at various temperature ranging from 25° to 28° C. For some fermentations, the temperature of the fermentation was maintained at a constant temperature and immediately upon completion of fermentation (OD600 of 5-10) the elastin was purified. For other fermentations, the temperature of the fermentations is maintained for a desired period of time and when cell densities of OD600 of 5-10 are reached, the temperature is reduced to induce protein production. Typically, the temperature is reduced from 28° C. to 25° C. After the fermentation at 25° C. is continued for 40-60 hours, the elastin is isolated.

The harvested cells were disrupted in a homogenizer at 14,000 psi pressure in 2 passes. Resulting slurry contained the collagen protein along with other proteins.

The supernatant from the homogenized cells was analyzed on an SDS-PAGE gel and a clear band was observed at around 70 kilodaltons corresponding to the expected size of 68 kilodaltons. The purified elastin is analyzed by mass spectrometry.

Full Length Elastin with DsbA Secretion Tag-His Tag-Linker-Thrombin Cleavage Site and GFP Beta-Lactamase Fusion A human elastin with DsbA secretion tag-His tag-Linker-Thrombin cleavage site and GFP Beta-lactamase fusion is disclosed below. The codon-optimized nucleotide sequence encoding this elastin is provided in SEQ ID NO: 27. The amino acid sequence is disclosed in SEQ ID NO: 28. The DsbA secretion tag is encoded by nucleotides 1-72 and encodes amino acids 1-24. The His tag is encoded by nucleotides 73-99 and encodes a 9 histidine tag (SEQ ID NO: 129) of amino acids 25-33. The linker is encoded by nucleotides 100-111 and encodes amino acids 34-37. The thrombin cleavage side is encoded by nucleotides 112-135 and encodes amino acids 38-45. The green fluorescent protein (GFP) with linker is encoded by nucleotides 136-873 and encodes amino acids 46-291. The full-length elastin sequence is encoded by nucleotides 874-3153 and encodes amino acids 292-1051. The Beta-lactamase with linker is encoded by nucleotides 3154-3945 and encodes amino acids 1052-1315.

(SEQ ID NO: 27)
ATGAAAAAGATTTGGCTGGCGCTGGCTGGTTTAGTTTTAGCGTTTAGCGC

ATCGGCGGCGCAGTATGAAGATCACCATCACCACCACCACCATCACCACT

CTGGCTCGAGCCTGGTGCCGCGCGGCAGCCATATGTCTGGCTCGAGCAGT

AAAGGTGAAGAACTGTTCACCGGTGTTGTTCCGATCCTGGTTGAACTGGA

TGGTGATGTTAACGGCCACAAATTCTCTGTTCGTGGTGAAGGTGAAGGTG

ATGCAACCAACGGTAAACTGACCCTGAAATTCATCTGCACTACCGGTAAA

CTGCCGGTTCCATGGCCGACTCTGGTGACTACCCTGACCTATGGTGTTCA

GTGTTTTTCTCGTTACCCGGATCACATGAAGCAGCATGATTTCTTCAAAT

CTGCAATGCCGGAAGGTTATGTACAGGAGCGCACCATTTCTTTCAAAGAC

GATGGCACCTACAAAACCGTGCAGAGGTTAAATTTGAAGGTGATACTCT

GGTGAACCGTATTGAACTGAAAGGCATTGATTTCAAAGAGGACGGCAACA

TCCTGGGCCACAAACTGGAATATAACTTCAACTCCCATAACGTTTACATC

ACCGCAGACAAACAGAAGAACGGTATCAAAGCTAACTTCAAAATTCGCCA

TAACGTTGAAGACGGTAGCGTACAGCTGGCGGACCACTACCAGCAGAACA

CTCCGATCGGTGATGGTCCGGTTCTGCTGCCGGATAACCACTACCTGTCC

ACCCAGTCTaaaCTGTCCAAAGACCCGAACGAAAAGCGCGACCACATGGT

GCTGCTGGAGTTCGTTACTGCAGCAGGTATCACGCACGGCATGGATGAAC

TCTACAAATCTGGCGCGCCGGGCGGTGGCGTACCAGGCGCAATTCCTGGG

GGTGTCCCAGGCGGTGTTTTTTATCCGGGCGCCGGTCTTGGCGCACTGGG

TGGCGGTGCACTGGGCCCGGGCGGCAAACCGCTGAAACCGGTACCAGGTG

GTTTAGCAGGCGCCGGCTTAGGCGCAGGTCTGGGAGCATTTCCGGCAGTT

```
ACCTTTCCAGGGGCACTGGTTCCTGGAGGTGTGGCCGATGCAGCCGCGGC
ATATAAAGCCGCTAAAGCCGGTGCGGGTTTAGGAGGCGTCCCAGGTGTCG
GTGGCCTGGGTGTTAGCGCCGGTGCAGTTGTTCCGCAGCCGGGAGCAGGG
GTTAAACCTGGTAAAGTGCCGGAGTAGGTCTGCCAGGCGTTTATCCTGG
TGGTGTTTTGCCGGGTGCCCGTTTTCCGGGCGTTGGTGTTCTTCCAGGCG
TGCCGACCGGAGCCGGTGTTAAACCGAAAGCCCCCGGTGTTGGAGGTGCA
TTTGCAGGCATCCCGGGAGTTGGCCCGTTTGGTGGTCCGCAACCTGGGGT
TCCGTTAGGTTATCCGATTAAAGCACCGAAACTGCCCGGCGGTTATGGTC
TGCCGTACACAACCGGTAAACTGCCGTATGGTTATGGCCCGGGTGGAGTT
GCGGGTGCAGCAGGTAAAGCGGGTTATCCTACCGGAACCGGTGTAGGTCC
GCAGGCCGCTGCTGCCGCCGCCGCAAAAGCAGCGGCTAAATTTGGCGCCG
GAGCAGCGGGTGTTCTGCCTGGAGTTGGTGGTGCGGGCGTGCCAGGGGTA
CCTGGTGCAATTCCGGGTATTGGTGGTATTGCCGGTGTCGGCACCCCGGC
CGCGGCAGCTGCGGCAGCGGCGGCTGCCAAAGCTGCTAAATACGGTGCCG
CGGCGGGTCTGGTGCCAGGAGGTCCGGGTTTTGGTCCGGGAGTGGTTGGC
GTGCCTGGCGCAGGCGTTCCTGGTGTGGGCGTTCCAGGTGCAGGGATTCC
TGTTGTGCCTGGTGCCGGTATTCCCGGCGGCCGTTCCGGGGGTGGTTA
GCCCGGAAGCCGCAGCGAAGGCTGCGGCAAAGGCAGCAAAGTATGGCGCA
CGCCCAGGAGTCGGCGTGGGTGGTATCCCGACCTATGGGGTGGGCGCAGG
GGGTTTTCCTGGTTTCGGCGTAGGTGTAGGAGGTATACCGGGCGTGGCCG
GTGTACCAGGGGTTGGTGGCGTCCCTGGTGTTGGCGGTGTGCCAGGTGTT
GGTATTTCACCGGAAGCACAGGCAGCAGCCGCAGCTAAGGCAGCGAAATA
TGGTGCCGCCGGCGCAGGAGTTTTAGGTGGGCTGGTTCCGGGCCCGCAGG
CAGCTGTGCCGGGGGTTCCAGGCACCGGTGGTGTCCCTGGAGTCGGTACG
CCGGCTGCAGCGGCAGCCAAAGCGGCTGCGAAAGCAGCACAGTTTGGCTT
AGTACCGGGTGTGGGAGTTGCCCCCGGCGTTGGCGTTGCTCCAGGGGTGG
GTGTTGCTCCTGGCGTCGGTCTGGCTCCTGGAGTGGGCGTAGCACCCGGT
GTGGGGGTGGCCCCGGGTGTTGGGGTTGCACCGGGTATCGGTCCGGGCGG
TGTCGCAGCAGCAGCTAAAAGCGCGGCGAAAGTTGCGGCAAAGCCCAAC
TGCGCGCCGCCGCGGGCCTCGGTGCAGGTATTCCGGGGCTGGGTGTCGGA
GTTGAGTCCCGGGTTTGGGCGTGGGCGCGGGAGTTCCGGGACTGGGAGT
GGGTGCCGGAGTTCCTGGCTTTGGTGCAGGCGCAGATGAAGGTGTTCGTC
GTAGCCTGAGTCCGGAACTGCGTGAAGGTGATCCGAGTAGCAGCCAGCAT
CTGCCGAGCACCCCGAGCAGCCCGCGTGTTCCGGGTGCATTAGCTGCAGC
AAAAGCCGCCAAGTATGGTGCAGCCGTGCCGGGCGTCTTAGGTGGTCTGG
GCGCCCTGGGTGGTGTAGGCATTCCGGGAGGTGTTGTGGGTGCAGGACCG
GCCGCCGCAGCTGCGGCCGCCAAAGCAGCTGCAAAAGCGGCCCAGTTTGG
TTTAGTGGGCGCCGCAGGTTTAGGCGGTTTAGGTGTGGGTGGACTGGGTG
TACCTGGCGTAGGCGGTCTGGGTGGAATTCCGCCCGCAGCGGCCGCGAAA
GCGGCAAATATGGCGCGGCAGGCCTGGGCGGCGTGCTGGGTGGGGCAGG
TCAGTTTCCGCTGGGCGGGGTTGCCGCACGTCCGGGATTTGGTCTGAGCC
CGATTTTCCCTGGCGGCGCATGTCTGGGTAAAGCATGTGGTCGTAAACGT
AAAcacccagaaacgctggtgaaagtaaaagatgctgaagatcagttggg
tgcacgagtgggttacatcgaactggatctcaacagcggtaagatccttg
agagttttcgccccgaagaacgttttccaatgatgagcacttttaaagtt
ctgctatgtggcgcggtattatcccgtattgacgccgggcaagagcaact
cggtcgccgcatacactattctcagaatgacttggttgagtactcaccag
tcacagaaaagcatcttacggatggcatgacagtaagagaattatgcagt
gctgccataaccatgagtgataacactgcggccaacttacttctgacaac
gatcggaggaccgaaggagctaaccgcttttttgcacaacatggggatc
atgtaactcgccttgatcgttgggaaccggagctgaatgaagccatacca
aacgacgagcgtgacaccacgatgcctgtagcaatggcaacaacgttgcg
caaactattaactggcgaactacttactctagcttcccggcaacaattaa
tagactggatggaggcggataaagttgcaggaccacttctgcgctcggcc
cttccggctggctggtttattgctgataaatctggagccggtgagcgtgg
gtctcgcggtatcattgcagcactggggccagatggtaagccctcccgta
tcgtagttatctacacgacggggagtcaggcaactatggatgaacgaaat
agacagatcgctgagataggtgcctcactgattaagcattggtaa (SEQ ID NO: 28)
MKKIWLALAGLVLAFSASAAQYEDHHHHHHHHSGSSLVPRGSHMSGSSS
KGEELFTGVVPILVELDGDVNGHKFSVRGEGEGDATNGKLTLKFICTTGK
LPVPWPTLVTTLTYGVQCFSRYPDHMKQHDFFKSAMPEGYVQERTISFKD
DGTYKTRAEVKFEGDTLVNRIELKGIDFKEDGNILGHKLEYNFNSHNVYI
TADKQKNGIKANFKIRHNVEDGSVQLADHYQQNTPIGDGPVLLPDNHYLS
TQSKLSKDPNEKRDHMVLLEFVTAAGITHGMDELYKSGAPGGGVPGAIPG
GVPGGVFYPGAGLGALGGGALGPGGKPLKPVPGGLAGAGLGAGLGAFPAV
TFPGALVPGGVADAAAAYKAAKAGAGLGGVPGVGGLGVSAGAVVPQPGAG
VKPGKVPGVGLPGVYPGGVLPGARFPGVGVLPGVPTGAVGKPKAPGVGGA
FAGIPGVGPFGGPQPGVPLGYPIKAPKLPGGYGLPYTTGKLPYGYGPGGV
AGAAGKAGYPTGTGVGPQAAAAAAAKAAAKFGAGAAGVLPGVGGAGVPGV
PGAIPGIGGIAGVGTPAAAAAAAAAKKAAKYGAAAGLVPGGPGFGPGVVG
VPGAGVPGVGVPGAGIPVVPGAGIPGAAVPGVVSPEAAAKAAAKAAKYGA
RPGVGVGGIPTYGVGAGGFPGFGVGVGGIPGVAGVPGVGGVPGVGGVPGV
GISPEAQAAAAAKAAKYGAAGAGVLGGLVPGPQAAVPGVPGTGGVPGVGT
PAAAAAKAAAKAAQFGLVPGVGVAPGVGVAPGVGVAPGVGLAPGVGVAPG
VGVAPGVGVAPGIGPGGVAAAAKSAAKVAAKAQLRAAAGLGAGIPGLGVG
VGVPGLGVGAGVPGLGVGAGVPGFGAGADEGVRRSLSPELREGDPSSSQH
LPSTPSSRVPGALAAAKAAKYGAAVPGVLGGLGALGGVGIPGGVVGAGP
AAAAAAAKAAAKAAQFGLVGAAGLGGLGVGGLGVPGVGGLGGIPPAAAAK
AAKYGAAGLGGVLGGAGFPLGGVAARPGFGLSPIFPGGACLGKACGRKR
KHPETLVKVKDAEDQLGARVGYIELDLNSGKILESFRPEERFPMMSTFKV
LLCGAVLSRIDAGQEQLGRRIHYSQNDLVEYSPVTEKHLTDGMTVRELCS
```

AAITMSDNTAANLLLTTIGGPKELTAFLHNMGDHVTRLDRWEPELNEAIP

NDERDTTMPVAMATTLRKLLTGELLTLASRQQLIDWMEADKVAGPLLRSA

LPAGWFIADKSGAGERGSRGIIAALGPDGKPSRIVVIYTTGSQATMDERN

RQIAEIGASLIKHW

Example 5: Production of Truncated Elastin

Truncated human elastin is produced using the expression system as described in Example 4. The full length amino acid sequence lacking the native secretion tag is disclosed in SEQ ID NO: 29.

(SEQ ID NO: 29)
GGVPGAIPGGVPGGVFYPGAGLGALGGGALGPGGKPLKPVPGGLAGAGLG

AGLGAFPAVTFPGALVPGGVADAAAAYKAAKAGAGLGGVPGVGGLGVSAG

AVVPQPGAGVKPGKVPGVGLPGVYPGGVLPGARFPGVGVLPGVPTGAGVK

PKAPGVGGAFAGIPGVGPFGGPQPGVPLGYPIKAPKLPGGYGLPYTTGKL

PYGYGPGGVAGAAGKAGYPTGTGVGPQAAAAAAAKAAAKFGAGAAGVLPG

VGGAGVPGVPGAIPGIGGIAGVGTPAAAAAAAAAKAAKYGAAAGLVPGG

PGFGPGVVGVPGAGVPGVGVPGAGIPVVPGAGIPGAAVPGVVSPEAAAKA

AAKAAKYGARPGVGVGGIPTYGVGAGGFPGFGVGVGGIPGVAGVPGVGGV

PGVGGVPGVGISPEAQAAAAAKAAKYGAAGAGVLGGLVPGPQAAVPGVPG

TGGVPGVGTPAAAAAKAAAKAAQFGLVPGVGVAPGVGVAPGVGVAPGVGL

APGVGVAPGVGVAPGVGVAPGIGPGGVAAAAKSAAKVAAKAQLRAAAGLG

AGIPGLGVGVGVPGLGVGAGVPGLGVGAGVPGFGAGADEGVRRSLSPELR

EGDPSSSQHLPSTPSSPRVPGALAAAKAAKYGAAVPGVLGGLGALGGVGI

PGGVVGAGPAAAAAAAKAAAKAAQFGLVGAAGLGGLGVGGLGVPGVGGLG

GIPPAAAAKAAKYGAAGLGGVLGGAGQFPLGGVAARPGFGLSPIFPGGAC

LGKACGRKRK

The codon optimized polynucleotide sequence encoding the full length human elastin lacking the native secretion tag is disclosed in SEQ ID NO: 30.

(SEQ ID NO: 30)
GGTGGCGTACCAGGCGCAATTCCTGGGGGTGTCCCAGGCGGTGTTTTTTA

TCCGGGCGCCGGTCTTGGCGCACTGGGTGGCGGTGCACTGGGCCCGGGCG

GCAAACCGCTGAAACCGGTACCAGGTGGTTTAGCAGGCGCCGGCTTAGGC

GCAGGTCTGGGAGCATTTCCGGCAGTTACCTTTCCAGGGGCACTGGTTCC

TGGAGGTGTGGCCGATGCAGCCGCGGCATATAAAGCCGCTAAAGCCGGTG

CGGGTTTAGGAGGCGTCCCAGGTGTCGGTGGCCTGGGTGTTAGCGCCGGT

GCAGTTGTTCCGCAGCCGGGAGCAGGGGTTAAACCTGGTAAAGTGCCGGG

AGTAGGTCTGCCAGGCGTTTATCCTGGTGGTGTTTTGCCGGGTGCCCGTT

TTCCGGGCGTTGGTGTTCTTCCAGGCGTGCCGACCGGAGCCGGTGTTAAA

CCGAAAGCCCCCGGTGTTGGAGGTGCATTTGCAGGCATCCCGGGAGTTGG

CCCGTTTGGTGGTCCGCAACCTGGGGTTCCGTTAGGTTATCCGATTAAAG

CACCGAAACTGCCCGGCGGTTATGGTCTGCCGTACACAACCGGTAAACTG

CCGTATGGTTATGGCCCGGGTGGAGTTGCGGGTGCAGCAGGTAAAGCGGG

TTATCCTACCGGAACCGGTGTAGGTCCGCAGGCCGCTGCTGCCGCCGCCG

CAAAAGCAGCGGCTAAATTTGGCGCCGGAGCAGCGGGTGTTCTGCCTGGA

GTTGGTGGTGCGGGCGTGCCAGGGGTACCTGGTGCAATTCCGGGTATTGG

TGGTATTGCCGGTGTCGGCACCCCGGCCGCGGCAGCTGCGGCAGCGGCGG

CTGCCAAAGCTGCTAAATACGGTGCCGCGGCGGGTCTGGTGCCAGGAGGT

CCGGGTTTTGGTCCGGGAGTGGTTGGCGTGCCTGGCGCAGGCGTTCCTGG

TGTGGGCGTTCCAGGTGCAGGGATTCCTGTTGTGCCTGGTGCCGGTATTC

CCGGCGCGGCCGTTCCGGGGGTGGTTAGCCCGGAAGCCGCAGCGAAGGCT

GCGGCAAAGGCAGCAAAGTATGGCGCACGCCCAGGAGTCGGCGTGGGTGG

TATCCCGACCTATGGGGTGGGCGCAGGGGGTTTTCCTGGTTTCGGCGTAG

GTGTAGGAGGTATACCGGGCGTGGCCGGTGTACCAGGGGTTGGTGGCGTC

CCTGGTGTTGGCGGTGTGCCAGGTGTTGGTATTTCACCGGAAGCACAGGC

AGCAGCCGCAGCTAAGGCAGCGAAATATGGTGCCGCCGGCGCAGGAGTTT

TAGGTGGGCTGGTTCCGGGCCCGCAGGCAGCTGTGCCGGGGGTTCCAGGC

ACCGGTGGTGTCCCTGGAGTCGGTACGCCGGCTGCAGCGGCAGCCAAAGC

GGCTGCGAAAGCAGCACAGTTTGGCTTAGTACCGGGTGTGGGAGTTGCCC

CCGGCGTTGGCGTTGCTCCAGGGGTGGGTGTTGCTCCTGGCGTCGGTCTG

GCTCCTGGAGTGGGCGTAGCACCCGGTGTGGGGGTGGCCCCGGGTGTTGG

GGTTGCACCGGGTATCGGTCCGGGCGGTGTCGCAGCAGCAGCTAAAAGCG

CGGCGAAAGTTGCGGCCAAAGCCCAACTGCGCGCCGCCGCGGGCCTCGGT

GCAGGTATTCCGGGGCTGGGTGTCGGAGTTGGAGTCCCGGGTTTGGGCGT

GGGCGCGGGAGTTCCGGGACTGGGAGTGGGTGCCGGAGTTCCTGGCTTTG

GTGCAGGCGCAGATGAAGGTGTTCGTCGTAGCCTGAGTCCGGAACTGCGT

GAAGGTGATCCGAGTAGCAGCCAGCATCTGCCGAGCACCCCGAGCAGCCC

GCGTGTTCCGGGTGCATTAGCTGCAGCAAAAGCCGCCAAGTATGGTGCAG

CCGTGCCGGGCGTCTTAGGTGGTCTGGGCGCCCTGGGTGGTGTAGGCATT

CCGGGAGGTGTTGTGGGTGCAGGACCGGCCGCCGCAGCTGCGGCCGCCAA

AGCAGCTGCAAAAGCGGCCCAGTTTGGTTTAGTGGGCGCCGCAGGTTTAG

GCGGTTTAGGTGTGGGTGGACTGGGTGTACCTGGCGTAGGCGGTCTGGGT

GGAATTCCGCCCtaa

The amino acid sequence of a 60.7 kDa human elastin truncated at the C-terminal is disclosed in SEQ ID NO: 31. The 60.7 kDa truncated elastin has amino acids 706-761 deleted from the full length elastin.

(SEQ ID NO: 31)
GGVPGAIPGGVPGGVFYPGAGLGALGGGALGPGGKPLKPVPGGLAGAGLG

AGLGAFPAVTFPGALVPGGVADAAAAYKAAKAGAGLGGVPGVGGLGVSAG

AVVPQPGAGVKPGKVPGVGLPGVYPGGVLPGARFPGVGVLPGVPTGAGVK

PKAPGVGGAFAGIPGVGPFGGPQPGVPLGYPIKAPKLPGGYGLPYTTGKL

-continued
```
PYGYGPGGVAGAAGKAGYPTGTGVGPQAAAAAAAKAAAKFGAGAAGVLPG

VGGAGVPGVGVPGAIPGIGGIAGVGTPAAAAAAAAAAKAAKYGAAAGLVPGG

PGFGPGVVGVPGAGVPGVGVPGAGIPVVPGAGIPGAAVPGVVSPEAAAKA

AAKAAKYGARPGVGVGGIPTYGVGAGGFPGFGVGVGGIPGVAGVPGVGGV

PGVGGVPGVGISPEAQAAAAAKAAKYGAAGAGVLGGLVPGPQAAVPGVPG

TGGVPGVGTPAAAAAKAAAKAAQFGLVPGVGVAPGVGVAPGVGVAPGVGL

APGVGVAPGVGVAPGVGVAPGIGPGGVAAAAKSAAKVAAKAQLRAAAGLG

AGIPGLGVGVGVPGLGVGAGVPGLGVGAGVPGFGAGADEGVRRSLSPELR

EGDPSSSQHLPSTPSSPRVPGALAAAKAAKYGAAVPGVLGGLGALGGVGI

PGGVVGAGPAAAAAAAKAAAKAAQFGLVGAAGLGGLGVGGLGVPGVGGLG

GIPP
```

The codon optimized polynucleotide sequence encoding the truncated 60.7 kDa human elastin is disclosed in SEQ ID NO: 32.

```
                                         (SEQ ID NO: 32)
GGTGGCGTACCAGGCGCAATTCCTGGGGGTGTCCCAGGCGGTGTTTTTTA

TCCGGGCGCCGGTCTTGGCGCACTGGGTGGCGGTGCACTGGGCCCGGGCG

GCAAACCGCTGAAACCGGTACCAGGTGGTTTAGCAGGCGCCGGCTTAGGC

GCAGGTCTGGGAGCATTTCCGGCAGTTACCTTTCCAGGGGCACTGGTTCC

TGGAGGTGTGGCCGATGCAGCCGCGGCATATAAAGCCGCTAAAGCCGGTG

CGGGTTTAGGAGGCGTCCCAGGTGTCGGTGGCCTGGGTGTTAGCGCCGGT

GCAGTTGTTCCGCAGCCGGGAGCAGGGGTTAAACCTGGTAAAGTGCCGGG

AGTAGGTCTGCCAGGCGTTTATCCTGGTGGTGTTTTGCCGGGTGCCCGTT

TTCCGGGCGTTGGTGTTCTTCCAGGCGTGCCGACCGGAGCCGGTGTTAAA

CCGAAAGCCCCCGGTGTTGGAGGTGCATTTGCAGGCATCCCGGGAGTTGG

CCCGTTTGGTGGTCCGCAACCTGGGGTTCCGTTAGGTTATCCGATTAAAG

CACCGAAACTGCCCGGCGGTTATGGTCTGCCGTACACAACCGGTAAACTG

CCGTATGGTTATGGCCCGGGTGGAGTTGCGGGTGCAGCAGGTAAAGCGGG

TTATCCTACCGGAACCGGTGTAGGTCCGCAGGCCGCTGCTGCCGCCGCCG

CAAAAGCAGCGGCTAAATTTGGCGCCGGAGCAGCGGGTGTTCTGCCTGGA

GTTGGTGGTGCGGGCGTGCCAGGGGTACCTGGTGCAATTCCGGGTATTGG

TGGTATTGCCGGTGTCGGCACCCCGGCCGCGGCAGCTGCGGCAGCGGCG

CTGCCAAAGCTGCTAAATACGGTGCCGCGGCGGGTCTGGTGCCAGGAGGT

CCGGGTTTTGGTCCGGGAGTGGTTGGCGTGCCTGGCGCAGGCGTTCCTGG

TGTGGGCGTTCCAGGTGCAGGGATTCCTGTTGTGCCTGGTGCCGGTATTC

CCGGCGCGGCCGTTCCGGGGGTGGTTAGCCCGGAAGCCGCAGCGAAGGCT

GCGGCAAAGGCAGCAAAGTATGGCGCACGCCCAGGAGTCGGCGTGGGTGG

TATCCCGACCTATGGGGTGGGCGCAGGGGGTTTTCCTGGTTTCGGCGTAG

GTGTAGGAGGTATACCGGGCGTGGCCGGTGTACCAGGGGTTGGTGGCGTC

CCTGGTGTTGGCGGTGTGCCAGGTGTTGGTATTTCACCGGAAGCACAGGC

AGCAGCCGCAGCTAAGGCAGCGAAATATGGTGCCGCCGGCGCAGGAGTTT

TAGGTGGGCTGGTTCCGGGCCCGCAGGCAGCTGTGCCGGGGGTTCCAGGC

ACCGGTGGTGTCCCTGGAGTCGGTACGCCGGCTGCAGCGGCAGCCAAAGC

GGCTGCGAAAGCAGCACAGTTTGGCTTAGTACCGGGTGTGGGAGTTGCCC

CCGGCGTTGGCGTTGCTCCAGGGGTGGGTGTTGCTCCTGGCGTCGGTCTG

GCTCCTGGAGTGGGCGTAGCACCCGGTGTGGGGGTGGCCCCGGGTGTTGG

GGTTGCACCGGGTATCGGTCCGGGCGGTGTCGCAGCAGCAGCTAAAAGCG

CGGCGAAAGTTGCGGCCAAAGCCCAACTGCGCGCCGCCGCGGGCCTCGGT

GCAGGTATTCCGGGGCTGGGTGTCGGAGTTGGAGTCCCGGGTTTGGGCGT

GGGCGCGGGAGTTCCGGGACTGGGAGTGGGTGCCGGAGTTCCTGGCTTTG

GTGCAGGCGCAGATGAAGGTGTTCGTCGTAGCCTGAGTCCGGAACTGCGT

GAAGGTGATCCGAGTAGCAGCCAGCATCTGCCGAGCACCCCGAGCAGCCC

GCGTGTTCCGGGTGCATTAGCTGCAGCAAAAGCCGCCAAGTATGGTGCAG

CCGTGCCGGGCGTCTTAGGTGGTCTGGGCGCCCTGGGTGGTGTAGGCATT

CCGGGAGGTGTTGTGGGTGCAGGACCGGCCGCCGCAGCTGCGGCCGCCAA

AGCAGCTGCAAAAGCGGCCCAGTTTGGTTTAGTGGGCGCCGCAGGTTTAG

GCGGTTTAGGTGTGGGTGGACTGGGTGTACCTGGCGTAGGCGGTCTGGGT

GGAATTCCGCCCtaa
```

The amino acid sequence of a 58.8 kDa human elastin truncated at the N-terminal is disclosed in SEQ ID NO: 33. The 58.8 kDa truncated elastin has amino acids 2-85 deleted from the full length elastin.

```
                                         (SEQ ID NO: 33)
GLGGVPGVGGLGVSAGAVVPQPGAGVKPGKVPGVGLPGVYPGGVLPGARF

PGVGVLPGVPTGAGVKPKAPGVGGAFAGIPGVGPFGGPQPGVPLGYPIKA

PKLPGGYGLPYTTGKLPYGYGPGGVAGAAGKAGYPTGTGVGPQAAAAAAA

KAAAKFGAGAAGVLPGVGGAGVPGVPGAIPGIGGIAGVGTPAAAAAAAAA

AKAAKYGAAAGLVPGGPGFGPGVVGVPGAGVPGVGVPGAGIPVVPGAGIP

GAAVPGVVSPEAAAKAAAKAAKYGARPGVGVGGIPTYGVGAGGFPGFGVG

VGGIPGVAGVPGVGGVPGVGGVPGVGISPEAQAAAAAKAAKYGAAGAGVL

GGLVPGPQAAVPGVPGTGGVPGVGTPAAAAAKAAAKAAQFGLVPGVGVAP

GVGVAPGVGVAPGVGLAPGVGVAPGVGVAPGVGVAPGIGPGGVAAAAKSA

AKVAAKAQLRAAAGLGAGIPGLGVGVGVPGLGVGAGVPGLGVGAGVPGFG

AGADEGVRRSLSPELREGDPSSSQHLPSTPSSPRVPGALAAAKAAKYGAA

VPGVLGGLGALGGVGIPGGVVGAGPAAAAAAAKAAAKAAQFGLVGAAGLG

GLGVGGLGVPGVGGLGGIPPAAAAKAAKYGAAGLGGVLGGAGQFPLGGVA

ARPGFGLSPIFPGGACLGKACGRKRK
```

The codon optimized polynucleotide sequence encoding the 58.8 kDa truncated human elastin is disclosed in SEQ ID NO: 34.

```
                                         (SEQ ID NO: 34)
GGTTTAGGAGGCGTCCCAGGTGTCGGTGGCCTGGGTGTTAGCGCCGGTGC

AGTTGTTCCGCAGCCGGGAGCAGGGGTTAAACCTGGTAAAGTGCCGGGAG
```

-continued
```
TAGGTCTGCCAGGCGTTTATCCTGGTGGTGTTTTGCCGGGTGCCCGTTTT
CCGGGCGTTGGTGTTCTTCCAGGCGTGCCGACCGGAGCCGGTGTTAAACC
GAAAGCCCCGGTGTTGGAGGTGCATTTGCAGGCATCCCGGGAGTTGGCC
CGTTTGGTGGTCCGCAACCTGGGGTTCCGTTAGGTTATCCGATTAAAGCA
CCGAAACTGCCCGGCGGTTATGGTCTGCCGTACACAACCGGTAAACTGCC
GTATGGTTATGGCCCGGGTGGAGTTGCGGGTGCAGCAGGTAAAGCGGGTT
ATCCTACCGGAACCGGTGTAGGTCCGCAGGCCGCTGCTGCCGCCGCCGCA
AAAGCAGCGGCTAAATTTGGCGCCGGAGCAGCGGGTGTTCTGCCTGGAGT
TGGTGGTGCGGGCGTGCCAGGGGTACCTGGTGCAATTCCGGGTATTGGTG
GTATTGCCGGTGTCGGCACCCCGGCCGCGGCAGCTGCGGCAGCGGCGGCT
GCCAAAGCTGCTAAATACGGTGCCGCGGCGGGTCTGGTGCCAGGAGGTCC
GGGTTTTGGTCCGGGAGTGGTTGGCGTGCCTGGCGCAGGCGTTCCTGGTG
TGGGCGTTCCAGGTGCAGGGATTCCTGTTGTGCCTGGTGCCGGTATTCCC
GGCGCGGCCGTTCCGGGGGTGGTTAGCCCGGAAGCCGCAGCGAAGGCTGC
GGCAAAGGCAGCAAAGTATGGCGCACGCCCAGGAGTCGGCGTGGGTGGTA
TCCCGACCTATGGGGTGGGCGCAGGGGGTTTTCCTGGTTTCGGCGTAGGT
GTAGGAGGTATACCGGGCGTGGCCGGTGTACCAGGGGTTGGTGGCGTCCC
TGGTGTTGGCGGTGTGCCAGGTGTTGGTATTTCACCGGAAGCACAGGCAG
CAGCCGCAGCTAAGGCAGCGAAATATGGTGCCGCCGGCGCAGGAGTTTTA
GGTGGGCTGGTTCCGGGCCCGCAGGCAGCTGTGCCGGGGGTTCCAGGCAC
CGGTGGTGTCCCTGGAGTCGGTACGCCGGCTGCAGCGGCAGCCAAAGCGG
CTGCGAAAGCAGCACAGTTTGGCTTAGTACCGGGTGTGGGAGTTGCCCCC
GGCGTTGGCGTTGCTCCAGGGGTGGGTGTTGCTCCTGGCGTCGGTCTGGC
TCCTGGAGTGGGCGTAGCACCCGGTGTGGGGGTGGCCCCGGGTGTTGGGG
TTGCACCGGGTATCGGTCCGGGCGGTGTCGCAGCAGCAGCTAAAAGCGCG
GCGAAAGTTGCGGCCAAAGCCCAACTGCGCGCCGCCGCGGGCCTCGGTGC
AGGTATTCCGGGGCTGGGTGTCGGAGTTGGAGTCCCGGGTTTGGCGTGG
GCGCGGGAGTTCCGGGACTGGGAGTGGGTGCCGGAGTTCCTGGCTTTGGT
GCAGGCGCAGATGAAGGTGTTCGTCGTAGCCTGAGTCCGGAACTGCGTGA
AGGTGATCCGAGTAGCAGCCAGCATCTGCCGAGCACCCCGAGCAGCCCGC
GTGTTCCGGGTGCATTAGCTGCAGCAAAAGCCGCCAAGTATGGTGCAGCC
GTGCCGGGCGTCTTAGGTGGTCTGGGCGCCCTGGGTGGTGTAGGCATTCC
GGGAGGTGTTGTGGGTGCAGGACCGGCCGCCGCAGCTGCGGCCGCCAAAG
CAGCTGCAAAAGCGGCCCAGTTTGGTTTAGTGGGCGCCGCAGGTTTAGGC
GGTTTAGGTGTGGGTGGACTGGGTGTACCTGGCGTAGGCGGTCTGGGTGG
AATTCCGCCCGCAGCGGCCGCGAAAGCGGCAAATATGGCGCGGCAGGCC
TGGGCGGCGTGCTGGGTGGGCAGGTCAGTTTCCGCTGGGCGGGGTTGCC
GCACGTCCGGGATTTGGTCTGAGCCCGATTTTCCCTGGCGGCGCATGTCT
GGGTAAAGCATGTGGTCGTAAACGTAAAtaa
```

The amino acid sequence of a 57 kDa human elastin truncated at the C-terminal is disclosed in SEQ ID NO: 35.

The 57 kDa truncated elastin has amino acids 661-761 deleted from the full length elastin.

```
                                        (SEQ ID NO: 35)
GGVPGAIPGGVPGGVFYPGAGLGALGGGALGPGGKPLKPVPGGLAGAGLG

AGLGAFPAVTFPGALVPGGVADAAAAYKAAKAGAGLGGVPGVGGLGVSAG

AVVPQPGAGVKPGKVPGVGLPGVYPGGVLPGARFPGVGVLPGVPTGAGVK

PKAPGVGGAFAGIPGVGPFGGPQPGVPLGYPIKAPKLPGGYGLPYTTGKL

PYGYGPGGVAGAAGKAGYPTGTGVGPQAAAAAAAKAAAKFGAGAAGVLPG

VGGAGVPGVPGAIPGIGGIAGVGTPAAAAAAAAAKAAKYGAAAGLVPGG

PGFGPGVVGVPGAGVPGVGVPGAGIPVVPGAGIPGAAVPGVVSPEAAAKA

AAKAAKYGARPGVGVGGIPTYGVGAGGFPGFGVGVGGIPGVAGVPGVGGV

PGVGGVPGVGISPEAQAAAAAKAAKYGAAGAGVLGGLVPGPQAAVPGVPG

TGGVPGVGTPAAAAAKAAAKAAQFGLVPGVGVAPGVGVAPGVGVAPGVGL

APGVGVAPGVGVAPGVGVAPGIGPGGVAAAAKSAAKVAAKAQLRAAAGLG

AGIPGLGVGVGVPGLGVGAGVPGLGVGAGVPGFGAGADEGVRRSLSPELR

EGDPSSSQHLPSTPSSPRVPGALAAAKAAKYGAAVPGVLGGLGALGGVGI

PGGVVGAGP
```

The codon optimized polynucleotide sequence encoding the 57 kDa truncated human elastin is disclosed in SEQ ID NO: 36

```
                                        (SEQ ID NO: 36)
GGTGGCGTACCAGGCGCAATTCCTGGGGGTGTCCCAGGCGGTGTTTTTTA

TCCGGGCGCCGGTCTTGGCGCACTGGGTGGCGGTGCACTGGGCCCGGGCG

GCAAACCGCTGAAACCGGTACCAGGTGGTTTAGCAGGCGCCGGCTTAGGC

GCAGGTCTGGGAGCATTTCCGGCAGTTACCTTTCCAGGGGCACTGGTTCC

TGGAGGTGTGGCCGATGCAGCCGCGGCATATAAAGCCGCTAAAGCCGGTG

CGGGTTTAGGAGGCGTCCCAGGTGTCGGTGGCCTGGGTGTTAGCGCCGGT

GCAGTTGTTCCGCAGCCGGGAGCAGGGGTTAAACCTGGTAAAGTGCCGGG

AGTAGGTCTGCCAGGCGTTTATCCTGGTGGTGTTTTGCCGGGTGCCCGTT

TTCCGGGCGTTGGTGTTCTTCCAGGCGTGCCGACCGGAGCCGGTGTTAAA

CCGAAAGCCCCGGTGTTGGAGGTGCATTTGCAGGCATCCCGGGAGTTGG

CCCGTTTGGTGGTCCGCAACCTGGGGTTCCGTTAGGTTATCCGATTAAAG

CACCGAAACTGCCCGGCGGTTATGGTCTGCCGTACACAACCGGTAAACTG

CCGTATGGTTATGGCCCGGGTGGAGTTGCGGGTGCAGCAGGTAAAGCGGG

TTATCCTACCGGAACCGGTGTAGGTCCGCAGGCCGCTGCTGCCGCCGCCG

CAAAAGCAGCGGCTAAATTTGGCGCCGGAGCAGCGGGTGTTCTGCCTGGA

GTTGGTGGTGCGGGCGTGCCAGGGGTACCTGGTGCAATTCCGGGTATTGG

TGGTATTGCCGGTGTCGGCACCCCGGCCGCGGCAGCTGCGGCAGCGGCGG

CTGCCAAAGCTGCTAAATACGGTGCCGCGGCGGGTCTGGTGCCAGGAGGT

CCGGGTTTTGGTCCGGGAGTGGTTGGCGTGCCTGGCGCAGGCGTTCCTGG

TGTGGGCGTTCCAGGTGCAGGGATTCCTGTTGTGCCTGGTGCCGGTATTC

CCGGCGCGGCCGTTCCGGGGGTGGTTAGCCCGGAAGCCGCAGCGAAGGCT
```

```
GCGGCAAAGGCAGCAAAGTATGGCGCACGCCCAGGAGTCGGCGTGGGTGG

TATCCCGACCTATGGGGTGGGCGCAGGGGGTTTTCCTGGTTTCGGCGTAG

GTGTAGGAGGTATACCGGGCGTGGCCGGTGTACCAGGGGTTGGTGGCGTC

CCTGGTGTTGGCGGTGTGCCAGGTGTTGGTATTTCACCGGAAGCACAGGC

AGCAGCCGCAGCTAAGGCAGCGAAATATGGTGCCGCCGGCGCAGGAGTTT

TAGGTGGGCTGGTTCCGGGCCCGCAGGCAGCTGTGCCGGGGGTTCCAGGC

ACCGGTGGTGTCCCTGGAGTCGGTACGCCGGCTGCAGCGGCAGCCAAAGC

GGCTGCGAAAGCAGCACAGTTTGGCTTAGTACCGGGTGTGGGAGTTGCCC

CCGGCGTTGGCGTTGCTCCAGGGGTGGGTGTTGCTCCTGGCGTCGGTCTG

GCTCCTGGAGTGGGCGTAGCACCCGGTGTGGGGGTGGCCCCGGGTGTTGG

GGTTGCACCGGGTATCGGTCCGGGCGGTGTCGCAGCAGCAGCTAAAAGCG

CGGCGAAAGTTGCGGCCAAAGCCCAACTGCGCGCCGCCGCGGGCCTCGGT

GCAGGTATTCCGGGGCTGGGTGTCGGAGTTGGAGTCCCGGGTTTGGGCGT

GGGCGCGGGAGTTCCGGGACTGGGAGTGGGTGCCGGAGTTCCTGGCTTTG

GTGCAGGCGCAGATGAAGGTGTTCGTCGTAGCCTGAGTCCGGAACTGCGT

GAAGGTGATCCGAGTAGCAGCCAGCATCTGCCGAGCACCCCGAGCAGCCC

GCGTGTTCCGGGTGCATTAGCTGCAGCAAAAGCCGCCAAGTATGGTGCAG

CCGTGCCGGGCGTCTTAGGTGGTCTGGGCGCCCTGGGTGGTGTAGGCATT

CCGGGAGGTGTTGTGGGTGCAGGACCGtaa
```

The amino acid sequence of a 53.9 kDa human elastin truncated at the C-terminal is disclosed in SEQ ID NO: 37. The 53.9 kDa truncated elastin has amino acids 624-761 deleted from the full length elastin.

```
                                    (SEQ ID NO: 37)
GGVPGAIPGGVPGGVFYPGAGLGALGGGALGPGGKPLKPVPGGLAGAGLG

AGLGAFPAVTFPGALVPGGVADAAAAYKAAKAGAGLGGVPGVGGLGVSAG

AVVPQPGAGVKPGKVPGVGLPGVYPGGVLPGARFPGVGVLPGVPTGAGVK

PKAPGVGGAFAGIPGVGPFGGPQPGVPLGYPIKAPKLPGGYGLPYTTGKL

PYGYGPGGVAGAAGKAGYPTGTGVGPQAAAAAAAKAAAKFGAGAAGVLPG

VGGAGVPGVPGAIPGIGGIAGVGTPAAAAAAAAAKAAKYGAAAGLVPGG

PGFGPGVVGVPGAGVPGVGVPGAGIPVVPGAGIPGAAVPGVVSPEAAAKA

AAKAAKYGARPGVGVGGIPTYGVGAGGFPGFGVGVGGIPGVAGVPGVGGV

PGVGGVPGVGISPEAQAAAAAKAAKYGAAGAGVLGGLVPGPQAAVPGVPG

TGGVPGVGTPAAAAAKAAAKAAQFGLVPGVGVAPGVGVAPGVGVAPGVGL

APGVGVAPGVGVAPGVGVAPGIGPGGVAAAAKSAAKVAAKAQLRAAAGLG

AGIPGLGVGVGVPGLGVGAGVPGLGVGAGVPGFGAGADEGVRRSLSPELR

EGDPSSSQHLPSTPSSPRVPGA
```

The codon optimized polynucleotide sequence encoding the 53.9 kDa truncated human elastin is disclosed in SEQ ID NO: 38

```
                                    (SEQ ID NO: 38)
GGTGGCGTACCAGGCGCAATTCCTGGGGGTGTCCCAGGCGGTGTTTTTTA

TCCGGGCGCCGGTCTTGGCGCACTGGGTGGCGGTGCACTGGGCCCGGGCG

GCAAACCGCTGAAACCGGTACCAGGTGGTTTAGCAGGCGCCGGCTTAGGC

GCAGGTCTGGGAGCATTTCCGGCAGTTACCTTTCCAGGGGCACTGGTTCC

TGGAGGTGTGGCCGATGCAGCCGCGGCATATAAAGCCGCTAAAGCCGGTG

CGGGTTTAGGAGGCGTCCCAGGTGTCGGTGGCCTGGGTGTTAGCGCCGGT

GCAGTTGTTCCGCAGCCGGGAGCAGGGGTTAAACCTGGTAAAGTGCCGGG

AGTAGGTCTGCCAGGCGTTTATCCTGGTGGTGTTTTGCCGGGTGCCCGTT

TTCCGGGCGTTGGTGTTCTTCCAGGCGTGCCGACCGGAGCCGGTGTTAAA

CCGAAAGCCCCCGGTGTTGGAGGTGCATTTGCAGGCATCCCGGGAGTTGG

CCCGTTTGGTGGTCCGCAACCTGGGGTTCCGTTAGGTTATCCGATTAAAG

CACCGAAACTGCCCGGCGGTTATGGTCTGCCGTACACAACCGGTAAACTG

CCGTATGGTTATGGCCCGGGTGGAGTTGCGGGTGCAGCAGGTAAAGCGGG

TTATCCTACCGGAACCGGTGTAGGTCCGCAGGCCGCTGCTGCCGCCGCCG

CAAAAGCAGCGGCTAAATTTGGCGCCGGAGCAGCGGGTGTTCTGCCTGGA

GTTGGTGGTGCGGGCGTGCCAGGGGTACCTGGTGCAATTCCGGGTATTGG

TGGTATTGCCGGTGTCGGCACCCCGGCCGCGGCAGCTGCGGCAGCGGCGG

CTGCCAAAGCTGCTAAATACGGTGCCGCGGCGGGTCTGGTGCCAGGAGGT

CCGGGTTTTGGTCCGGGAGTGGTTGGCGTGCCTGGCGCAGGCGTTCCTGG

TGTGGGCGTTCCAGGTGCAGGGATTCCTGTTGTGCCTGGTGCCGGTATTC

CCGGCGCGGCCGTTCCGGGGGTGGTTAGCCCGGAAGCCGCAGCGAAGGCT

GCGGCAAAGGCAGCAAAGTATGGCGCACGCCCAGGAGTCGGCGTGGGTGG

TATCCCGACCTATGGGGTGGGCGCAGGGGGTTTTCCTGGTTTCGGCGTAG

GTGTAGGAGGTATACCGGGCGTGGCCGGTGTACCAGGGGTTGGTGGCGTC

CCTGGTGTTGGCGGTGTGCCAGGTGTTGGTATTTCACCGGAAGCACAGGC

AGCAGCCGCAGCTAAGGCAGCGAAATATGGTGCCGCCGGCGCAGGAGTTT

TAGGTGGGCTGGTTCCGGGCCCGCAGGCAGCTGTGCCGGGGGTTCCAGGC

ACCGGTGGTGTCCCTGGAGTCGGTACGCCGGCTGCAGCGGCAGCCAAAGC

GGCTGCGAAAGCAGCACAGTTTGGCTTAGTACCGGGTGTGGGAGTTGCCC

CCGGCGTTGGCGTTGCTCCAGGGGTGGGTGTTGCTCCTGGCGTCGGTCTG

GCTCCTGGAGTGGGCGTAGCACCCGGTGTGGGGGTGGCCCCGGGTGTTGG

GGTTGCACCGGGTATCGGTCCGGGCGGTGTCGCAGCAGCAGCTAAAAGCG

CGGCGAAAGTTGCGGCCAAAGCCCAACTGCGCGCCGCCGCGGGCCTCGGT

GCAGGTATTCCGGGGCTGGGTGTCGGAGTTGGAGTCCCGGGTTTGGGCGT

GGGCGCGGGAGTTCCGGGACTGGGAGTGGGTGCCGGAGTTCCTGGCTTTG

GTGCAGGCGCAGATGAAGGTGTTCGTCGTAGCCTGAGTCCGGAACTGCGT

GAAGGTGATCCGAGTAGCAGCCAGCATCTGCCGAGCACCCCGAGCAGCCC

GCGTGTTCCGGGTGCAtaa
```

The amino acid sequence of a 45.3 kDa human elastin truncated at the C-terminal is disclosed in SEQ ID NO: 39. The 45.3 kDa truncated elastin has amino acids 529-761 deleted from the full length elastin.

(SEQ ID NO: 39)
GGVPGAIPGGVPGGVFYPGAGLGALGGGALGPGGKPLKPVPGGLAGAGLG

AGLGAFPAVTFPGALVPGGVADAAAAYKAAKAGAGLGGVPGVGGLGVSAG

AVVPQPGAGVKPGKVPGVGLPGVYPGGVLPGARFPGVGVLPGVPTGAGVK

PKAPGVGGAFAGIPGVGPFGGPQPGVPLGYPIKAPKLPGGYGLPYTTGKL

PYGYGPGGVAGAAGKAGYPTGTGVGPQAAAAAAAKAAAKFGAGAAGVLPG

VGGAGVPGVPGAIPGIGGIAGVGTPAAAAAAAAAAKAAKYGAAAGLVPGG

PGFGPGVVGVPGAGVPGVGVPGAGIPVVPGAGIPGAAVPGVVSPEAAAKA

AAKAAKYGARPGVGVGGIPTYGVGAGGFPGFGVGVGGIPGVAGVPGVGGV

PGVGGVPGVGVGISPEAQAAAAAKAAKYGAAGAGVLGGLVPGPQAAVPGVPG

TGGVPGVGTPAAAAAKAAAKAAQFGLVPGVGVAPGVGVAPGVGVAPGVGL

APGVGVAPGVGVAPGVGVAPGIGPGGV

The codon optimized polynucleotide sequence encoding the 45.3 kDa truncated human elastin is disclosed in SEQ ID NO: 40

(SEQ ID NO: 40)
GGTGGCGTACCAGGCGCAATTCCTGGGGGTGTCCCAGGCGGTGTTTTTA

TCCGGGCGCCGGTCTTGGCGCACTGGGTGGCGGTGCACTGGGCCCGGGCG

GCAAACCGCTGAAACCGGTACCAGGTGGTTTAGCAGGCGCCGGCTTAGGC

GCAGGTCTGGGAGCATTTCCGGCAGTTACCTTTCCAGGGGCACTGGTTCC

TGGAGGTGTGGCCGATGCAGCCGCGGCATATAAAGCCGCTAAAGCCGGTG

CGGGTTTAGGAGGCGTCCCAGGTGTCGGTGGCCTGGGTGTTAGCGCCGGT

GCAGTTGTTCCGCAGCCGGGAGCAGGGGTTAAACCTGGTAAAGTGCCGGG

AGTAGGTCTGCCAGGCGTTTATCCTGGTGGTGTTTTGCCGGGTGCCCGTT

TTCCGGGCGTTGGTGTTCTTCCAGGCGTGCCGACCGGAGCCGGTGTTAAA

CCGAAAGCCCCCGGTGTTGGAGGTGCATTTGCAGGCATCCCGGGAGTTGG

CCCGTTTGGTGGTCCGCAACCTGGGGTTCCGTTAGGTTATCCGATTAAAG

CACCGAAACTGCCCGGCGGTTATGGTCTGCCGTACACAACCGGTAAACTG

CCGTATGGTTATGGCCCGGGTGGAGTTGCGGGTGCAGCAGGTAAAGCGGG

TTATCCTACCGGAACCGGTGTAGGTCCGCAGGCCGCTGCTGCCGCCGCCG

CAAAAGCAGCGGCTAAATTTGGCGCCGGAGCAGCGGGTGTTCTGCCTGGA

GTTGGTGGTGCGGGCGTGCCAGGGGTACCTGGTGCAATTCCGGGTATTGG

TGGTATTGCCGGTGTCGGCACCCCGGCCGCGGCAGCTGCGGCAGCGGCG

CTGCCAAAGCTGCTAAATACGGTGCCGCGGCGGGTCTGGTGCCAGGAGGT

CCGGGTTTTGGTCCGGGAGTGGTTGGCGTGCCTGGCGCAGGCGTTCCTGG

TGTGGGCGTTCCAGGTGCAGGGATTCCTGTTGTGCCTGGTGCCGGTATTC

CCGGCGCGGCCGTTCCGGGGGTGGTTAGCCCGGAAGCCGCAGCGAAGGCT

GCGGCAAAGGCAGCAAAGTATGGCGCACGCCCAGGAGTCGGCGTGGGTGG

TATCCCGACCTATGGGGTGGGCGCAGGGGGTTTTCCTGGTTTCGGCTAG

GTGTAGGAGGTATACCGGGCGTGGCCGGTGTACCAGGGGTTGGTGGCGTC

CCTGGTGTTGGCGGTGTGCCAGGTGTTGGTATTTCACCGGAAGCACAGGC

AGCAGCCGCAGCTAAGGCAGCGAAATATGGTGCCGCCGGCGCAGGAGTTT

TAGGTGGGCTGGTTCCGGGCCCGCAGGCAGCTGTGCCGGGGGTTCCAGGC

ACCGGTGGTGTCCCTGGAGTCGGTACGCCCGGCTGCAGCGGCAGCCAAAGC

GGCTGCGAAAGCAGCACAGTTTGGCTTAGTACCGGGTGTGGGAGTTGCCC

CCGGCGTTGGCGTTGCTCCAGGGGTGGGTGTTGCTCCTGGCGTCGGTCTG

GCTCCTGGAGTGGGCGTAGCACCCGGTGTGGGGGTGGCCCCGGGTGTTGG

GGTTGCACCGGGTATCGGTCCGGGCGGTGTCtaa

The amino acid sequence of a 44.4 kDa human elastin truncated at the N-terminal is disclosed in SEQ ID NO: 41. The 44.4 kDa truncated elastin has amino acids 2-246 deleted from the full length elastin.

(SEQ ID NO: 41)
GVLPGVGGAGVPGVPGAIPGIGGIAGVGTPAAAAAAAAAAKAAKYGAAAG

LVPGGPGFGPGVVGVPGAGVPGVGVPGAGIPVVPGAGIPGAAVPGVVSPE

AAAKAAAKAAKYGARPGVGVGGIPTYGVGAGGFPGFGVGVGGIPGVAGVP

GVGGVPGVGGVPGVGISPEAQAAAAAKAAKYGAAGAGVLGGLVPGPQAAV

PGVPGTGGVPGVGTPAAAAAKAAAKAAQFGLVPGVGVAPGVGVAPGVGVA

PGVGLAPGVGVAPGVGVAPGVGVAPGIGPGGVAAAAKSAAKVAAKAQLRA

AAGLGAGIPGLGVGVGVPGLGVGAGVPGLGVGAGVPGFGAGADEGVRRSL

SPELREGDPSSSQHLPSTPSSPRVPGALAAAKAAKYGAAVPGVLGGLGAL

GGVGIPGGVVGAGPAAAAAAAKAAAKAAQFGLVGAAGLGGLGVGGLGVPG

VGGLGGIPPAAAAKAAKYGAAGLGGVLGGAGQFPLGGVAARPGFGLSPIF

PGGACLGKACGRKRK

The codon optimized polynucleotide sequence encoding the 44.4 kDa truncated human elastin is disclosed in SEQ ID NO: 42

(SEQ ID NO: 42)
GGTGTTCTGCCTGGAGTTGGTGGTGCGGGCGTGCCAGGGGTACCTGGTGC

AATTCCGGGTATTGGTGGTATTGCCGGTGTCGGCACCCCGGCCGCGGCAG

CTGCGGCAGCGGCGGCTGCCAAAGCTGCTAAATACGGTGCCGCGGCGGGT

CTGGTGCCAGGAGGTCCGGGTTTTGGTCCGGGAGTGGTTGGCGTGCCTGG

CGCAGGCGTTCCTGGTGTGGGCGTTCCAGGTGCAGGGATTCCTGTTGTGC

CTGGTGCCGGTATTCCCGGCGCGGCCGTTCCGGGGGTGGTTAGCCCGGAA

GCCGCAGCGAAGGCTGCGGCAAAGGCAGCAAAGTATGGCGCACGCCCAGG

AGTCGGCGTGGGTGGTATCCCGACCTATGGGGTGGGCGCAGGGGGTTTTC

CTGGTTTCGGCGTAGGTGTAGGAGGTATACCGGGCGTGGCCGGTGTACCA

GGGGTTGGTGGCGTCCCTGGTGTTGGCGGTGTGCCAGGTGTTGGTATTTC

ACCGGAAGCACAGGCAGCAGCCGCAGCTAAGGCAGCGAAATATGGTGCCG

CCGGCGCAGGAGTTTTAGGTGGGCTGGTTCCGGGCCCGCAGGCAGCTGTG

CCGGGGGTTCCAGGCACCGGTGGTGTCCCTGGAGTCGGTACGCCCGGCTGC

AGCGGCAGCCAAAGCGGCTGCGAAAGCAGCACAGTTTGGCTTAGTACCGG

GTGTGGGAGTTGCCCCCGGCGTTGGCGTTGCTCCAGGGGTGGGTGTTGCT

CCTGGCGTCGGTCTGGCTCCTGGAGTGGGCGTAGCACCCGGTGTGGGGGT

```
GGCCCCGGGTGTTGGGGTTGCACCGGGTATCGGTCCGGGCGGTGTCGCAG

CAGCAGCTAAAAGCGCGGCGAAAGTTGCGGCCAAAGCCCAACTGCGCGCC

GCCGCGGGCCTCGGTGCAGGTATTCCGGGGCTGGGTGTCGGAGTTGGAGT

CCCGGGTTTGGGCGTGGGCGCGGGAGTTCCGGGACTGGGAGTGGGTGCCG

GAGTTCCTGGCTTTGGTGCAGGCGCAGATGAAGGTGTTCGTCGTAGCCTG

AGTCCGGAACTGCGTGAAGGTGATCCGAGTAGCAGCCAGCATCTGCCGAG

CACCCCGAGCAGCCCGCGTGTTCCGGGTGCATTAGCTGCAGCAAAAGCCG

CCAAGTATGGTGCAGCCGTGCCGGGCGTCTTAGGTGGTCTGGGCGCCCTG

GGTGGTGTAGGCATTCCGGGAGGTGTTGTGGGTGCAGGACCGGCCGCCGC

AGCTGCGGCCGCCAAAGCAGCTGCAAAAGCGGCCCAGTTTGGTTTAGTGG

GCGCCGCAGGTTTAGGCGGTTTAGGTGTGGGTGGACTGGGTGTACCTGGC

GTAGGCGGTCTGGGTGGAATTCCGCCCGCAGCGGCCGCGAAAGCGGCAAA

ATATGGCGCGGCAGGCCTGGGCGGCGTGCTGGGTGGGGCAGGTCAGTTTC

CGCTGGGCGGGGTTGCCGCACGTCCGGGATTTGGTCTGAGCCCGATTTTC

CCTGGCGGCGCATGTCTGGGTAAAGCATGTGGTCGTAAACGTAAAtaa
```

The amino acid sequence of a 40.4 kDa human elastin truncated at the N-terminal is disclosed in SEQ ID NO: 43. The 40.4 kDa truncated elastin has amino acids 2-295 deleted from the full length elastin.

```
                                          (SEQ ID NO: 43)
GLVPGGPGFGPGVVGVPGAGVPGVGVPGAGIPVVPGAGIPGAAVPGVVSP

EAAAKAAAKAAKYGARPGVGVGGIPTYGVGAGGFPGFGVGVGGIPGVAGV

PGVGGVPGVGGVPGVGISPEAQAAAAAKAAKYGAAGAGVLGGLVPGPQAA

VPGVPGTGGVPGVGTPAAAAAKAAAKAAQFGLVPGVGVAPGVGVAPGVGV

APGVGLAPGVGVAPGVGVAPGVGVAPGIGPGGVAAAAKSAAKVAAKAQLR

AAAGLGAGIPGLGVGVGVPGLGVGAGVPGLGVGAGVPGFGAGADEGVRRS

LSPELREGDPSSSQHLPSTPSSPRVPGALAAAKAAKYGAAVPGVLGGLGA

LGGVGIPGGVVGAGPAAAAAAAKAAAKAAQFGLVGAAGLGGLGVGGLGVP

GVGGLGGIPPAAAAKAAKYGAAGLGGVLGGAGQFPLGGVAARPGFGLSPI

FPGGACLGKACGRKRK
```

The codon optimized polynucleotide sequence encoding the 40.4 kDa truncated human elastin is disclosed in SEQ ID NO: 44

```
                                          (SEQ ID NO: 44)
GGTCTGGTGCCAGGAGGTCCGGGTTTTGGTCCGGGAGTGGTTGGCGTGCC

TGGCGCAGGCGTTCCTGGTGTGGGCGTTCCAGGTGCAGGGATTCCTGTTG

TGCCTGGTGCCGGTATTCCCGGCGCGGCCGTTCCGGGGGTGGTTAGCCCG

GAAGCCGCAGCGAAGGCTGCGGCAAAGGCAGCAAAGTATGGCGCACGCCC

AGGAGTCGGCGTGGGTGGTATCCCGACCTATGGGGTGGGCGCAGGGGGTT

TTCCTGGTTTCGGCGTAGGTGTAGGAGGTATACCGGGCGTGGCCGGTGTA

CCAGGGGTTGGTGGCGTCCCTGGTGTTGGCGGTGTGCCAGGTGTTGGTAT

TTCACCGGAAGCACAGGCAGCAGCCGCAGCTAAGGCAGCGAAATATGGTG

CCGCCGGCGCAGGAGTTTTAGGTGGGCTGGTTCCGGGCCCGCAGGCAGCT

GTGCCGGGGGTTCCAGGCACCGGTGGTGTCCCTGGAGTCGGTACGCCGGC

TGCAGCGGCAGCCAAAGCGGCTGCGAAAGCAGCACAGTTTGGCTTAGTAC

CGGGTGTGGGAGTTGCCCCCGGCGTTGGCGTTGCTCCAGGGGTGGGTGTT

GCTCCTGGCGTCGGTCTGGCTCCTGGAGTGGGCGTAGCACCCGGTGTGGG

GGTGGCCCCGGGTGTTGGGGTTGCACCGGGTATCGGTCCGGGCGGTGTCG

CAGCAGCAGCTAAAAGCGCGGCGAAAGTTGCGGCCAAAGCCCAACTGCGC

GCCGCCGCGGGCCTCGGTGCAGGTATTCCGGGGCTGGGTGTCGGAGTTGG

AGTCCCGGGTTTGGGCGTGGGCGCGGGAGTTCCGGGACTGGGAGTGGGTG

CCGGAGTTCCTGGCTTTGGTGCAGGCGCAGATGAAGGTGTTCGTCGTAGC

CTGAGTCCGGAACTGCGTGAAGGTGATCCGAGTAGCAGCCAGCATCTGCC

GAGCACCCCGAGCAGCCCGCGTGTTCCGGGTGCATTAGCTGCAGCAAAAG

CCGCCAAGTATGGTGCAGCCGTGCCGGGCGTCTTAGGTGGTCTGGGCGCC

CTGGGTGGTGTAGGCATTCCGGGAGGTGTTGTGGGTGCAGGACCGGCCGC

CGCAGCTGCGGCCGCCAAAGCAGCTGCAAAAGCGGCCCAGTTTGGTTTAG

TGGGCGCCGCAGGTTTAGGCGGTTTAGGTGTGGGTGGACTGGGTGTACCT

GGCGTAGGCGGTCTGGGTGGAATTCCGCCCGCAGCGGCCGCGAAAGCGGC

AAAATATGGCGCGGCAGGCCTGGGCGGCGTGCTGGGTGGGGCAGGTCAGT

TTCCGCTGGGCGGGGTTGCCGCACGTCCGGGATTTGGTCTGAGCCCGATT

TTCCCTGGCGGCGCATGTCTGGGTAAAGCATGTGGTCGTAAACGTAAAta a
```

The amino acid sequence of a 39.8 kDa human elastin truncated at the C-terminal is disclosed in SEQ ID NO: 45. The 39.8 kDa truncated elastin has amino acids 462-761 deleted from the full length elastin.

```
                                          (SEQ ID NO: 45)
GGVPGAIPGGVPGGVFYPGAGLGALGGGALGPGGKPLKPVPGGLAGAGLG

AGLGAFPAVTFPGALVPGGVADAAAAYKAAKAGAGLGGVPGVGGLGVSAG

AVVPQPGAGVKPGKVPGVGLPGVYPGGVLPGARFPGVGVLPGVPTGAGVK

PKAPGVGGAFAGIPGVGPFGGPQPGVPLGYPIKAPKLPGGYGLPYTTGKL

PYGYGPGGVAGAAGKAGYPTGTGVGPQAAAAAAAKAAAKFGAGAAGVLPG

VGGAGVPGVPGAIPGIGGIAGVGTPAAAAAAAAAKAAKYGAAAGLVPGG

PGFGPGVVGVPGAGVPGVGVPGAGIPVVPGAGIPGAAVPGVVSPEAAAKA

AAKAAKYGARPGVGVGGIPTYGVGAGGFPGFGVGVGGIPGVAGVPGVGGV

PGVGGVPGVGISPEAQAAAAAKAAKYGAAGAGVLGGLVPGPQAAVPGVPG

TGGVPGVGTP
```

The codon optimized polynucleotide sequence encoding the 39.8 kDa truncated human elastin is disclosed in SEQ ID NO: 46

```
                                          (SEQ ID NO: 46)
GGTGGCGTACCAGGCGCAATTCCTGGGGGTGTCCCAGGCGGTGTTTTTTA

TCCGGGCGCCGGTCTTGGCGCACTGGGTGGCGGTGCACTGGGCCCGGGCG
```

```
GCAAACCGCTGAAACCGGTACCAGGTGGTTTAGCAGGCGCCGGCTTAGGC

GCAGGTCTGGGAGCATTTCCGGCAGTTACCTTTCCAGGGGCACTGGTTCC

TGGAGGTGTGGCCGATGCAGCCGCGGCATATAAAGCCGCTAAAGCCGGTG

CGGGTTTAGGAGGCGTCCCAGGTGTCGGTGGCCTGGGTGTTAGCGCCGGT

GCAGTTGTTCCGCAGCCGGGAGCAGGGGTTAAACCTGGTAAAGTGCCGGG

AGTAGGTCTGCCAGGCGTTTATCCTGGTGGTGTTTTGCCGGGTGCCCGTT

TTCCGGGCGTTGGTGTTCTTCCAGGCGTGCCGACCGGAGCCGGTGTTAAA

CCGAAAGCCCCCGGTGTTGGAGGTGCATTTGCAGGCATCCCGGGAGTTGG

CCCGTTTGGTGGTCCGCAACCTGGGGTTCCGTTAGGTTATCCGATTAAAG

CACCGAAACTGCCCGGCGGTTATGGTCTGCCGTACACAACCGGTAAACTG

CCGTATGGTTATGGCCCGGGTGGAGTTGCGGGTGCAGCAGGTAAAGCGGG

TTATCCTACCGGAACCGGTGTAGGTCCGCAGGCCGCTGCTGCCGCCGCCG

CAAAAGCAGCGGCTAAATTTGGCGCCGGAGCAGCGGGTGTTCTGCCTGGA

GTTGGTGGTGCGGGCGTGCCAGGGGTACCTGGTGCAATTCCGGGTATTGG

TGGTATTGCCGGTGTCGGCACCCCGGCCGCGGCAGCTGCGGCAGCGGCGG

CTGCCAAAGCTGCTAAATACGGTGCCGCGGCGGGTCTGGTGCCAGGAGGT

CCGGGTTTTGGTCCGGGAGTGGTTGGCGTGCCTGGCGCAGGCGTTCCTGG

TGTGGGCGTTCCAGGTGCAGGGATTCCTGTTGTGCCTGGTGCCGGTATTC

CCGGCGCGGCCGTTCCGGGGGTGGTTAGCCCGGAAGCCGCAGCGAAGGCT

GCGGCAAAGGCAGCAAAGTATGGCGCACGCCCAGGAGTCGGCGTGGGTGG

TATCCCGACCTATGGGTGGGCGCAGGGGGTTTTCCTGGTTTCGGCGTAG

GTGTAGGAGGTATACCGGGCGTGGCCGGTGTACCAGGGGTTGGTGGCGTC

CCTGGTGTTGGCGGTGTGCCAGGTGTTGGTATTTCACCGGAAGCACAGGC

AGCAGCCGCAGCTAAGGCAGCGAAATATGGTGCCGCCGGCGCAGGAGTTT

TAGGTGGGCTGGTTCCGGGCCCGCAGGCAGCTGTGCCGGGGGTTCCAGGC

ACCGGTGGTGTCCCTGGAGTCGGTACGCCGtaa
```

The amino acid sequence of a 36.1 kDa human elastin truncated at the C-terminal is disclosed in SEQ ID NO: 47. The 36.1 kDa truncated elastin has amino acids 418-761 deleted from the full length elastin.

```
                                            (SEQ ID NO: 47)
GGVPGAIPGGVPGGVFYPGAGLGALGGGALGPGGKPLKPVPGGLAGAGLG

AGLGAFPAVTFPGALVPGGVADAAAAYKAAKAGAGLGGVPGVGGLGVSAG

AVVPQPGAGVKPGKVPGVGLPGVYPGGVLPGARFPGVGVLPGVPTGAGVK

PKAPGVGGAFAGIPGVGPFGGPQPGVPLGYPIKAPKLPGGYGLPYTTGKL

PYGYGPGGVAGAAGKAGYPTGTGVGPQAAAAAAAKAAAKFGAGAAGVLPG

VGGAGVPGVPGAIPGIGGIAGVGTPAAAAAAAAAKAAKYGAAAGLVPGG

PGFGPGVVGVPGAGVPGVGVPGAGIPVVPGAGIPGAAVPGVVSPEAAAKA

AAKAAKYGARPGVGVGGIPTYGVGAGGFPGFGVGVGGIPGVAGVPGVGGV

PGVGGVPGVGISPEAQ
```

The codon optimized polynucleotide sequence encoding the 36.1 kDa truncated elastin is disclosed in SEQ ID NO: 48

```
                                            (SEQ ID NO: 48)
GGTGGCGTACCAGGCGCAATTCCTGGGGGTGTCCCAGGCGGTGTTTTTA

TCCGGGCGCCGGTCTTGGCGCACTGGGTGGCGGTGCACTGGGCCCGGGCG

GCAAACCGCTGAAACCGGTACCAGGTGGTTTAGCAGGCGCCGGCTTAGGC

GCAGGTCTGGGAGCATTTCCGGCAGTTACCTTTCCAGGGGCACTGGTTCC

TGGAGGTGTGGCCGATGCAGCCGCGGCATATAAAGCCGCTAAAGCCGGTG

CGGGTTTAGGAGGCGTCCCAGGTGTCGGTGGCCTGGGTGTTAGCGCCGGT

GCAGTTGTTCCGCAGCCGGGAGCAGGGGTTAAACCTGGTAAAGTGCCGGG

AGTAGGTCTGCCAGGCGTTTATCCTGGTGGTGTTTTGCCGGGTGCCCGTT

TTCCGGGCGTTGGTGTTCTTCCAGGCGTGCCGACCGGAGCCGGTGTTAAA

CCGAAAGCCCCCGGTGTTGGAGGTGCATTTGCAGGCATCCCGGGAGTTGG

CCCGTTTGGTGGTCCGCAACCTGGGGTTCCGTTAGGTTATCCGATTAAAG

CACCGAAACTGCCCGGCGGTTATGGTCTGCCGTACACAACCGGTAAACTG

CCGTATGGTTATGGCCCGGGTGGAGTTGCGGGTGCAGCAGGTAAAGCGGG

TTATCCTACCGGAACCGGTGTAGGTCCGCAGGCCGCTGCTGCCGCCGCCG

CAAAAGCAGCGGCTAAATTTGGCGCCGGAGCAGCGGGTGTTCTGCCTGGA

GTTGGTGGTGCGGGCGTGCCAGGGGTACCTGGTGCAATTCCGGGTATTGG

TGGTATTGCCGGTGTCGGCACCCCGGCCGCGGCAGCTGCGGCAGCGGCGG

CTGCCAAAGCTGCTAAATACGGTGCCGCGGCGGGTCTGGTGCCAGGAGGT

CCGGGTTTTGGTCCGGGAGTGGTTGGCGTGCCTGGCGCAGGCGTTCCTGG

TGTGGGCGTTCCAGGTGCAGGGATTCCTGTTGTGCCTGGTGCCGGTATTC

CCGGCGCGGCCGTTCCGGGGGTGGTTAGCCCGGAAGCCGCAGCGAAGGCT

GCGGCAAAGGCAGCAAAGTATGGCGCACGCCCAGGAGTCGGCGTGGGTGG

TATCCCGACCTATGGGTGGGCGCAGGGGGTTTTCCTGGTTTCGGCGTAG

GTGTAGGAGGTATACCGGGCGTGGCCGGTGTACCAGGGGTTGGTGGCGTC

CCTGGTGTTGGCGGTGTGCCAGGTGTTGGTATTTCACCGGAAGCACAGta a
```

The amino acid sequence of a 34.9 kDa human elastin truncated at the N-terminal is disclosed in SEQ ID NO: 49. The 34.9 kDa truncated elastin has amino acids 2-360 deleted from the full length elastin.

```
                                            (SEQ ID NO: 49)
RPGVGVGGIPTYGVGAGGFPGFGVGVGGIPGVAGVPGVGGVPGVGGVPGVG

ISPEAQAAAAAKAAKYGAAGAGVLGGLVPGPQAAVPGVPGTGGVPGVGTPA

AAAAKAAAKAAQFGLVPGVGVAPGVGVAPGVGVAPGVGLAPGVGVAPGVGV

APGVGVAPGIGPGGVAAAAKSAAKVAAKAQLRAAAGLGAGIPGLGVGVGVP

GLGVGAGVPGLGVGAGVPGFGAGADEGVRRSLSPELREGDPSSSQHLPSTP

SSPRVPGALAAAKAAKYGAAVPGVLGGLGALGGVGIPGGVVGAGPAAAAAA

AKAAAKAAQFGLVGAAGLGGLGVGGLGVPGVGGLGGIPPAAAAKAAKYGAA

GLGGVLGGAGQFPLGGVAARPGFGLSPIFPGGACLGKACGRKRK
```

The codon optimized polynucleotide sequence encoding the 34.9 kDa truncated human elastin is disclosed in SEQ ID NO: 50

(SEQ ID NO: 50)
CGCCCAGGAGTCGGCGTGGGTGGTATCCCGACCTATGGGGTGGGCGCAGGG

GGTTTTCCTGGTTTCGGCGTAGGTGTAGGAGGTATACCGGGCGTGGCCGGT

GTACCAGGGGTTGGTGGCGTCCCTGGTGTTGGCGGTGTGCCAGGTGTTGGT

ATTTCACCGGAAGCACAGGCAGCAGCCGCAGCTAAGGCAGCGAAATATGGT

GCCGCCGGCGCAGGAGTTTTAGGTGGGCTGGTTCCGGGCCCGCAGGCAGCT

GTGCCGGGGGTTCCAGGCACCGGTGGTGTCCCTGGAGTCGGTACGCCGGCT

GCAGCGGCAGCCAAAGCGGCTGCGAAAGCAGCACAGTTTGGCTTAGTACCG

GGTGTGGGAGTTGCCCCCGGCGTTGGCGTTGCTCCAGGGGTGGGTGTTGCT

CCTGGCGTCGGTCTGGCTCCTGGAGTGGGCGTAGCACCCGGTGTGGGGGTG

GCCCCGGGTGTTGGGGTTGCACCGGGTATCGGTCCGGCGGTGTCGCAGCA

GCAGCTAAAAGCGCGGCGAAAGTTGCGGCCAAAGCCCAACTGCGCGCCGCC

GCGGGCCTCGGTGCAGGTATTCCGGGGCTGGGTGTCGGAGTTGGAGTCCCG

GGTTTGGGCGTGGGCGCGGGAGTTCCGGGACTGGGAGTGGGTGCCGGAGTT

CCTGGCTTTGGTGCAGGCGCAGATGAAGGTGTTCGTCGTAGCCTGAGTCCG

GAACTGCGTGAAGGTGATCCGAGTAGCAGCCAGCATCTGCCGAGCACCCCG

AGCAGCCCGCGTGTTCCGGGTGCATTAGCTGCAGCAAAAGCCGCTCAAGTAT

GGTGCAGCCGTGCCGGGCGTCTTAGGTGGTCTGGGCGCCCTGGGTGGTGTA

GGCATTCCGGGAGGTGTTGTGGGTGCAGGACCGGCCGCCGCAGCTGCGGCC

GCCAAAGCAGCTGCAAAAGCGGCCCAGTTTGGTTTAGTGGGCGCCGCAGGT

TTAGGCGGTTTAGGTGTGGGTGGACTGGGTGTACCTGGCGTAGGCGGTCTG

GGTGGAATTCCGCCCGCAGCGGCCGCGAAAGCGGCAAAATATGGCGCGGCA

GGCCTGGGCGGCGTGCTGGGTGGGGCAGGTCAGTTTCCGCTGGGCGGGGTT

GCCGCACGTCCGGGATTTGGTCTGAGCCCGATTTTCCCTGGCGGCGCATGT

CTGGGTAAAGCATGTGGTCGTAAACGTAAAtaa

The amino acid sequence of a 32 kDa human elastin truncated at the C-terminal is disclosed in SEQ ID NO: 51. The 32 kDa truncated elastin has amino acids 373-761 deleted from the full length elastin.

(SEQ ID NO: 51)
GGVPGAIPGGVPGGVFYPGAGLGALGGGALGPGGKPLKPVPGGLAGAGLGA

GLGAFPAVTFPGALVPGGVADAAAAYKAAKAGAGLGGVPGVGGLGVSAGAV

VPQPGAGVKPGKVPGVGLPGVYPGGVLPGARFPGVGVLPGVPTGAGVKPKA

PGVGGAFAGIPGVGPFGGPQPGVPLGYPIKAPKLPGGYGLPYTTGKLPYGY

GPGGVAGAAGKAGYPTGTGVGPQAAAAAAAKAAAKFGAGAAGVLPGVGGAG

VPGVPGAIPGIGGIAGVGTPAAAAAAAAAAKAAKYGAAAGLVPGGPGFGPG

VVGVPGAGVPGVGVPGAGIPVVPGAGIPGAAVPGVVSPEAAAKAAAKAAKY

GARPGVGVGGIPTY

The codon optimized polynucleotide sequence encoding the 32 kDa truncated human elastin is disclosed in SEQ ID NO: 52

(SEQ ID NO: 52)
GGTGGCGTACCAGGCGCAATTCCTGGGGGTGTCCCAGGCGGTGTTTTTTAT

CCGGGCGCCGGTCTTGGCGCACTGGGTGGCGGTGCACTGGGCCCGGGCGGC

AAACCGCTGAAACCGGTACCAGGTGGTTTAGCAGGCGCCGGCTTAGGCGCA

GGTCTGGGAGCATTTCCGGCAGTTACCTTTCCAGGGGCACTGGTTCCTGGA

GGTGTGGCCGATGCAGCCGCGGCATATAAAGCCGCTAAAGCCGGTGCGGGT

TTAGGAGGCGTCCCAGGTGTCGGTGGCCTGGGTGTTAGCGCCGGTGCAGTT

GTTCCGCAGCCGGGAGCAGGGGTTAAACCTGGTAAAGTGCCGGGAGTAGGT

CTGCCAGGCGTTTATCCTGGTGGTGTTTTGCCGGGTGCCCGTTTTCCGGGC

GTTGGTGTTCTTCCAGGCGTGCCGACCGGAGCCGGTGTTAAACCGAAAGCC

CCCGGTGTTGGAGGTGCATTTGCAGGCATCCCGGGAGTTGGCCCGTTTGGT

GGTCCGCAACCTGGGGTTCCGTTAGGTTATCCGATTAAAGCACCGAAACTG

CCCGGCGGTTATGGTCTGCCGTACACAACCGGTAAACTGCCGTATGGTTAT

GGCCCGGGTGGAGTTGCGGGTGCAGCAGGTAAAGCGGGTTATCCTACCGGA

ACCGGTGTAGGTCCGCAGGCCGCTGCTGCCGCCGCCGCAAAAGCAGCGGCT

AAATTTGGCGCCGGAGCAGCGGGTGTTCTGCCTGGAGTTGGTGGTGCGGGC

GTGCCAGGGGTACCTGGTGCAATTCCGGGTATTGGTGGTATTGCCGGTGTC

GGCACCCCGGCCGCGGCAGCTGCGGCAGCGGCGGCTGCCAAAGCTGCTAAA

TACGGTGCCGCGGCGGGTCTGGTGCCAGGAGGTCCGGGTTTTGGTCCGGGA

GTGGTTGGCGTGCCTGGCGCAGGCGTTCCTGGTGTGGGCGTTCCAGGTGCA

GGGATTCCTGTTGTGCCTGGTGCCGGTATTCCCGGCGCGGCCGTTCCGGGG

GTGGTTAGCCCGGAAGCCGCAGCGAAGGCTGCGGCAAAGGCAGCAAAGTAT

GGCGCACGCCCAGGAGTCGGCGTGGGTGGTATCCCGACCTATtaa

The amino acid sequence of a 29.9 kDa human elastin truncated at the C-terminal is disclosed in SEQ ID NO: 53. The 60.7 kDa truncated elastin has amino acids 347-761 deleted from the full length elastin.

(SEQ ID NO: 53)
GGVPGAIPGGVPGGVFYPGAGLGALGGGALGPGGKPLKPVPGGLAGAGLGA

GLGAFPAVTFPGALVPGGVADAAAAYKAAKAGAGLGGVPGVGGLGVSAGAV

VPQPGAGVKPGKVPGVGLPGVYPGGVLPGARFPGVGVLPGVPTGAGVKPKA

PGVGGAFAGIPGVGPFGGPQPGVPLGYPIKAPKLPGGYGLPYTTGKLPYGY

GPGGVAGAAGKAGYPTGTGVGPQAAAAAAAKAAAKFGAGAAGVLPGVGGAG

VPGVPGAIPGIGGIAGVGTPAAAAAAAAAAKAAKYGAAAGLVPGGPGFGPG

VVGVPGAGVPGVGVPGAGIPVVPGAGIPGAAVPGVVSPE

The codon optimized polynucleotide sequence encoding the 29.9 kDa truncated human elastin is disclosed in SEQ ID NO: 54

(SEQ ID NO: 54)
GGTGGCGTACCAGGCGCAATTCCTGGGGGTGTCCCAGGCGGTGTTTTTTAT

CCGGGCGCCGGTCTTGGCGCACTGGGTGGCGGTGCACTGGGCCCGGGCGGC

AAACCGCTGAAACCGGTACCAGGTGGTTTAGCAGGCGCCGGCTTAGGCGCA

GGTCTGGGAGCATTTCCGGCAGTTACCTTTCCAGGGGCACTGGTTCCTGGA

-continued

```
GGTGTGGCCGATGCAGCCGCGGCATATAAAGCCGCTAAAGCCGGTGCGGGT
TTAGGAGGCGTCCCAGGTGTCGGTGGCCTGGGTGTTAGCGCCGGTGCAGTT
GTTCCGCAGCCGGGAGCAGGGGTTAAACCTGGTAAAGTGCCGGGAGTAGGT
CTGCCAGGCGTTTATCCTGGTGGTGTTTTGCCGGGTGCCCGTTTTCCGGGC
GTTGGTGTTCTTCCAGGCGTGCCGACCGGAGCCGGTGTTAAACCGAAAGCC
CCCGGTGTTGGAGGTGCATTTGCAGGCATCCCGGGAGTTGGCCCGTTTGGT
GGTCCGCAACCTGGGGTTCCGTTAGGTTATCCGATTAAAGCACCGAAACTG
CCCGGCGGTTATGGTCTGCCGTACACAACCGGTAAACTGCCGTATGGTTAT
GGCCCGGGTGGAGTTGCGGGTGCAGCAGGTAAAGCGGGTTATCCTACCGGA
ACCGGTGTAGGTCCGCAGGCCGCTGCTGCCGCCGCCGCAAAAGCAGCGGCT
AAATTTGGCGCCGGAGCAGCGGGTGTTCTGCCTGGAGTTGGTGGTGCGGGC
GTGCCAGGGGTACCTGGTGCAATTCCGGGTATTGGTGGTATTGCCGGTGTC
GGCACCCCGGCCGCGGCAGCTGCGGCAGCGGCGGCTGCCAAAGCTGCTAAA
TACGGTGCCGCGGCGGGTCTGGTGCCAGGAGGTCCGGGTTTTGGTCCGGGA
GTGGTTGGCGTGCCTGGCGCAGGCGTTCCTGGTGTGGGCGTTCCAGGTGCA
GGGATTCCTGTTGTGCCTGGTGCCGGTATTCCCGGCGCGGCCGTTCCGGGG
GTGGTTAGCCCGGAAtaa
```

The amino acid sequence of a 29.4 kDa human elastin truncated at the N-terminal is disclosed in SEQ ID NO: 55. The 29.4 kDa truncated elastin has amino acids 2-425 deleted from the full length elastin.

(SEQ ID NO: 55)
KYGAAGAGVLGGLVPGPQAAVPGVPGTGGVPGVGTPAAAAKAAAKAAQFG

LVPGVGVAPGVGVAPGVGVAPGVGLAPGVGVAPGVGVAPGVGVAPGIGPGG

VAAAAKSAAKVAAKAQLRAAAGLGAGIPGLGVGVGVPGLGVGAGVPGLGVG

AGVPGFGAGADEGVRRSLSPELREGDPSSSQHLPSTPSSPRVPGALAAAKA

AKYGAAVPGVLGGLGALGGVGIPGGVVGAGPAAAAAAAKAAAKAAQFGLVG

AAGLGGLGVGGLGVPGVGGLGGIPPAAAAKAAKYGAAGLGGVLGGAGQFPL

GGVAARPGFGLSPIFPGGACLGKACGRKRK

The codon optimized polynucleotide sequence encoding the 29.4 kDa truncated human elastin is disclosed in SEQ ID NO: 56

(SEQ ID NO: 56)
AAATATGGTGCCGCCGGCGCAGGAGTTTTAGGTGGGCTGGTTCCGGGCCCG

CAGGCAGCTGTGCCGGGGGTTCCAGGCACCGGTGGTGTCCCTGGAGTCGGT

ACGCCGGCTGCAGCGGCAGCCAAAGCGGCTGCGAAAGCAGCACAGTTTGGC

TTAGTACCGGGTGTGGGAGTTGCCCCGGCGTTGGCGTTGCTCCAGGGGTG

GGTGTTGCTCCTGGCGTCGGTCTGGCTCCTGGAGTGGGCGTAGCACCCGGT

GTGGGGGTGGCCCCGGGTGTTGGGGTTGCACCGGGTATCGGTCCGGGCGGT

GTCGCAGCAGCAGCTAAAGCGCGGCGAAAGTTGCGGCCAAAGCCCAACTG

CGCGCCGCCGCGGGCCTCGGTGCAGGTATTCCGGGGCTGGGTGTCGGAGTT

GGAGTCCCGGGTTTGGGCGTGGGCGCGGGAGTTCCGGGACTGGGAGTGGGT
```
GCCGGAGTTCCTGGCTTTGGTGCAGGCGCAGATGAAGGTGTTCGTCGTAGC

CTGAGTCCGGAACTGCGTGAAGGTGATCCGAGTAGCAGCCAGCATCTGCCG

AGCACCCCGAGCAGCCCGCGTGTTCCGGGTGCATTAGCTGCAGCAAAAGCC

GCCAAGTATGGTGCAGCCGTGCCGGGCGTCTTAGGTGGTCTGGGCGCCCTG

GGTGGTGTAGGCATTCCGGGAGGTGTTGTGGGTGCAGGACCGGCCGCCGCA

GCTGCGGCCGCAAAGCAGCTGCAAAAGCGGCCCAGTTTGGTTTAGTGGGC

GCCGCAGGTTTAGGCGGTTTAGGTGTGGGTGGACTGGGTGTACCTGGCGTA

GGCGGTCTGGGTGGAATTCCGCCCGCAGCGGCCGCGAAAGCGGCAAAATAT

GGCGCGGCAGGCCTGGGCGGCGTGCTGGGTGGGGCAGGTCAGTTTCCGCTG

GGCGGGGTTGCCGCACGTCCGGGATTTGGTCTGAGCCCGATTTTCCCTGGC

GGCGCATGTCTGGGTAAAGCATGTGGTCGTAAACGTAAAtaa
```

The amino acid sequence of a 25.3 kDa human elastin truncated at the N-terminal is disclosed in SEQ ID NO: 57. The 25.3 kDa truncated elastin has amino acids 2-473 deleted from the full length elastin.

(SEQ ID NO: 57)
QFGLVPGVGVAPGVGVAPGVGVAPGVGLAPGVGVAPGVGVAPGVGVAPGIG

PGGVAAAAKSAAKVAAKAQLRAAAGLGAGIPGLGVGVGVPGLGVGAGVPGL

GVGAGVPGFGAGADEGVRRSLSPELREGDPSSSQHLPSTPSSPRVPGALAA

AKAAKYGAAVPGVLGGLGALGGVGIPGGVVGAGPAAAAAAAKAAAKAAQFG

LVGAAGLGGLGVGGLGVPGVGGLGGIPPAAAAKAAKYGAAGLGGVLGGAGQ

FPLGGVAARPGFGLSPIFPGGACLGKACGRKRK

The codon optimized polynucleotide sequence encoding the 25.3 kDa truncated human elastin is disclosed in SEQ ID NO: 58

(SEQ ID NO: 58)
CAGTTTGGCTTAGTACCGGGTGTGGGAGTTGCCCCCGGCGTTGGCGTTGCT

CCAGGGGTGGGTGTTGCTCCTGGCGTCGGTCTGGCTCCTGGAGTGGGCGTA

GCACCCGGTGTGGGGGTGGCCCCGGGTGTTGGGGTTGCACCGGGTATCGGT

CCGGGCGGTGTCGCAGCAGCAGCTAAAAGCGCGGCGAAAGTTGCGGCCAAA

GCCCAACTGCGCGCCGCCGCGGGCCTCGGTGCAGGTATTCCGGGGCTGGGT

GTCGGAGTTGGAGTCCCGGGTTTGGGCGTGGGCGCGGGAGTTCCGGGACTG

GGAGTGGGTGCCGGAGTTCCTGGCTTTGGTGCAGGCGCAGATGAAGGTGTT

CGTCGTAGCCTGAGTCCGGAACTGCGTGAAGGTGATCCGAGTAGCAGCCAG

CATCTGCCGAGCACCCCGAGCAGCCCGCGTGTTCCGGGTGCATTAGCTGCA

GCAAAAGCCGCCAAGTATGGTGCAGCCGTGCCGGGCGTCTTAGGTGGTCTG

GGCGCCCTGGGTGGTGTAGGCATTCCGGGAGGTGTTGTGGGTGCAGGACCG

GCCGCCGCAGCTGCGGCCGCAAAGCAGCTGCAAAAGCGGCCCAGTTTGGT

TTAGTGGGCGCCGCAGGTTTAGGCGGTTTAGGTGTGGGTGGACTGGGTGTA

CCTGGCGTAGGCGGTCTGGGTGGAATTCCGCCCGCAGCGGCCGCGAAAGCG

GCAAAATATGGCGCGGCAGGCCTGGGCGGCGTGCTGGGTGGGGCAGGTCAG

TTTCCGCTGGGCGGGGTTGCCGCACGTCCGGGATTTGGTCTGAGCCCGATT
```

The amino acid sequence of a 24.1 kDa human elastin truncated at the C-terminal is disclosed in SEQ ID NO: 59. The 24.1 kDa truncated elastin has amino acids 277-761 deleted from the full length elastin.

(SEQ ID NO: 59)
GGVPGAIPGGVPGGVFYPGAGLGALGGGALGPGGKPLKPVPGGLAGAGLGA

GLGAFPAVTFPGALVPGGVADAAAAYKAAKAGAGLGGVPGVGGLGVSAGAV

VPQPGAGVKPGKVPGVGLPGVYPGGVLPGARFPGVGVLPGVPTGAGVKPKA

PGVGGAFAGIPGVGPFGGPQPGVPLGYPIKAPKLPGGYGLPYTTGKLPYGY

GPGGVAGAAGKAGYPTGTGVGPQAAAAAAAKAAAKFGAGAAGVLPGVGGAG

VPGVPGAIPGIGGIAGVGTP

The codon optimized polynucleotide sequence encoding the 24.1 kDa truncated human elastin is disclosed in SEQ ID NO: 60

(SEQ ID NO: 60)
GGTGGCGTACCAGGCGCAATTCCTGGGGTGTCCCAGGCGGTGTTTTTAT

CCGGGCGCCGGTCTTGGCGCACTGGGTGGCGGTGCACTGGGCCCGGGCGGC

AAACCGCTGAAACCGGTACCAGGTGGTTTAGCAGGCGCCGGCTTAGGCGCA

GGTCTGGGAGCATTTCCGGCAGTTACCTTTCCAGGGGCACTGGTTCCTGGA

GGTGTGGCCGATGCAGCCGCGGCATATAAAGCCGCTAAAGCCGGTGCGGGT

TTAGGAGGCGTCCCAGGTGTCGGTGGCCTGGGTGTTAGCGCCGGTGCAGTT

GTTCCGCAGCCGGGAGCAGGGGTTAAACCTGGTAAAGTGCCGGGAGTAGGT

CTGCCAGGCGTTTATCCTGGTGGTGTTTTGCCGGGTGCCCGTTTTCCGGGC

GTTGGTGTTCTTCCAGGCGTGCCGACCGGAGCCGGTGTTAAACCGAAAGCC

CCCGGTGTTGGAGGTGCATTTGCAGGCATCCCGGGAGTTGGCCCGTTTGGT

GGTCCGCAACCTGGGGTTCCGTTAGGTTATCCGATTAAAGCACCGAAACTG

CCCGGCGGTTATGGTCTGCCGTACACAACCGGTAAACTGCCGTATGGTTAT

GGCCCGGGTGGAGTTGCGGGTGCAGCAGGTAAAGCGGGTTATCCTACCGGA

ACCGGTGTAGGTCCGCAGGCCGCTGCTGCCGCCGCCGCAAAAGCAGCGGCT

AAATTTGGCGCCGGAGCAGCGGGTGTTCTGCCTGGAGTTGGTGGTGCGGGC

GTGCCAGGGGTACCTGGTGCAATTCCGGGTATTGGTGGTATTGCCGGTGTC

GGCACCCCGtaa

The amino acid sequence of a 20.3 kDa human elastin truncated at the C-terminal is disclosed in SEQ ID NO: 61. The 20.3 kDa truncated elastin has amino acids 229-761 deleted from the full length elastin.

(SEQ ID NO: 61)
GGVPGAIPGGVPGGVFYPGAGLGALGGGALGPGGKPLKPVPGGLAGAGLGA

GLGAFPAVTFPGALVPGGVADAAAAYKAAKAGAGLGGVPGVGGLGVSAGAV

VPQPGAGVKPGKVPGVGLPGVYPGGVLPGARFPGVGVLPGVPTGAGVKPKA

PGVGGAFAGIPGVGPFGGPQPGVPLGYPIKAPKLPGGYGLPYTTGKLPYGY

GPGGVAGAAGKAGYPTGTGVGPQ

The codon optimized polynucleotide sequence encoding the 20.3 kDa truncated human elastin is disclosed in SEQ ID NO: 62

(SEQ ID NO: 62)
GGTGGCGTACCAGGCGCAATTCCTGGGGTGTCCCAGGCGGTGTTTTTAT

CCGGGCGCCGGTCTTGGCGCACTGGGTGGCGGTGCACTGGGCCCGGGCGGC

AAACCGCTGAAACCGGTACCAGGTGGTTTAGCAGGCGCCGGCTTAGGCGCA

GGTCTGGGAGCATTTCCGGCAGTTACCTTTCCAGGGGCACTGGTTCCTGGA

GGTGTGGCCGATGCAGCCGCGGCATATAAAGCCGCTAAAGCCGGTGCGGGT

TTAGGAGGCGTCCCAGGTGTCGGTGGCCTGGGTGTTAGCGCCGGTGCAGTT

GTTCCGCAGCCGGGAGCAGGGGTTAAACCTGGTAAAGTGCCGGGAGTAGGT

CTGCCAGGCGTTTATCCTGGTGGTGTTTTGCCGGGTGCCCGTTTTCCGGGC

GTTGGTGTTCTTCCAGGCGTGCCGACCGGAGCCGGTGTTAAACCGAAAGCC

CCCGGTGTTGGAGGTGCATTTGCAGGCATCCCGGGAGTTGGCCCGTTTGGT

GGTCCGCAACCTGGGGTTCCGTTAGGTTATCCGATTAAAGCACCGAAACTG

CCCGGCGGTTATGGTCTGCCGTACACAACCGGTAAACTGCCGTATGGTTAT

GGCCCGGGTGGAGTTGCGGGTGCAGCAGGTAAAGCGGGTTATCCTACCGGA

ACCGGTGTAGGTCCGCAGtaa

The amino acid sequence of a19.6 kDa human elastin truncated at the N-terminal is disclosed in SEQ ID NO: 63. The 19.6 kDa truncated elastin has amino acids 2-542 deleted from the full length elastin.

(SEQ ID NO: 63)
QLRAAAGLGAGIPGLGVGVGVPGLGVGAGVPGLGVGAGVPGFGAGADEGVR

RSLSPELREGDPSSSQHLPSTPSSPRVPGALAAAKAAKYGAAVPGVLGGLG

ALGGVGIPGGVVGAGPAAAAAAAKAAAKAAQFGLVGAAGLGGLGVGGLGVP

GVGGLGGIPPAAAAKAAKYGAAGLGGVLGGAGQFPLGGVAARPGFGLSPIF

PGGACLGKACGRKRK

The codon optimized polynucleotide sequence encoding the 19.6 kDa truncated human elastin is disclosed in SEQ ID NO: 64

(SEQ ID NO: 64)
CAACTGCGCGCCGCCGCGGGCCTCGGTGCAGGTATTCCGGGGCTGGGT

GTCGGAGTTGGAGTCCCGGGTTTGGGCGTGGGCGCGGGAGTTCCGGGA

CTGGGAGTGGGTGCCGGAGTTCCTGGCTTTGGTGCAGGCGCAGATGAA

GGTGTTCGTCGTAGCCTGAGTCCGGAACTGCGTGAAGGTGATCCGAGT

AGCAGCCAGCATCTGCCGAGCACCCCGAGCAGCCCGCGTGTTCCGGGT

GCATTAGCTGCAGCAAAAGCCGCCAAGTATGGTGCAGCCGTGCCGGGC

GTCTTAGGTGGTCTGGGCGCCCTGGGTGGTGTAGGCATTCCGGGAGGT

GTTGTGGGTGCAGGACCGGCCGCCGCAGCTGCGGCCGCCAAAGCAGCT

GCAAAAGCGGCCCAGTTTGGTTTAGTGGGCGCCGCAGGTTTAGGCGGT

TTAGGTGTGGGTGGACTGGGTGTACCTGGCGTAGGCGGTCTGGGTGGA

ATTCCGCCCGCAGCGGCCGCGAAAGCGGCAAAATATGGCGCGGCAGGC

CTGGGCGGCGTGCTGGGTGGGGCAGGTCAGTTTCCGCTGGGCGGGGTT

GCCGCACGTCCGGGATTTGGTCTGAGCCCGATTTTCCCTGGCGGCGCA

TGTCTGGGTAAAGCATGTGGTCGTAAACGTAAAtaa

The amino acid sequence of a 11 kDa human elastin truncated at the N-terminal is disclosed in SEQ ID NO: 65. The 11 kDa truncated elastin has amino acids 2-635 deleted from the full length elastin.

(SEQ ID NO: 65)
VPGVLGGLGALGGVGIPGGVVGAGPAAAAAAAKAAAKAAQFGLVGAAG

LGGLGVGGLGVPGVGGLGGIPPAAAAKAAKYGAAGLGGVLGGAGQFPL

GGVAARPGFGLSPIFPGGACLGKACGRKRK

The codon optimized polynucleotide sequence encoding the 11 kDa truncated human elastin is disclosed in SEQ ID NO: 66

(SEQ ID NO: 66)
GTGCCGGGCGTCTTAGGTGGTCTGGGCGCCCTGGGTGGTGTAGGCATT

CCGGGAGGTGTTGTGGGTGCAGGACCGGCCGCCGCAGCTGCGGCCGCC

AAAGCAGCTGCAAAAGCGGCCCAGTTTGGTTTAGTGGGCGCCGCAGGT

TTAGGCGGTTTAGGTGTGGGTGGACTGGGTGTACCTGGCGTAGGCGGT

CTGGGTGGAATTCCGCCCGCAGCGGCCGCGAAAGCGGCAAAATATGGC

GCGGCAGGCCTGGGCGGCGTGCTGGGTGGGGCAGGTCAGTTTCCGCTG

GGCGGGGTTGCCGCACGTCCGGGATTTGGTCTGAGCCCGATTTTCCCT

GGCGGCGCATGTCTGGGTAAAGCATGTGGTCGTAAACGTAAAtaa

The amino acid sequence of a 7.9 kDa human elastin truncated at the N-terminal is disclosed in SEQ ID NO: 67. The 7.9 kDa truncated elastin has amino acids 2-674 deleted from the full length elastin.

(SEQ ID NO: 67)
QFGLVGAAGLGGLGVGGLGVPGVGGLGGIPPAAAAKAAKYGAAGLGGV

LGGAGQFPLGGVAARPGFGLSPIFPGGACLGKACGRKRK

The codon optimized polynucleotide sequence encoding the 7.9 kDa truncated human elastin is disclosed in SEQ ID NO: 68

(SEQ ID NO: 68)
CAGTTTGGTTTAGTGGGCGCCGCAGGTTTAGGCGGTTTAGGTGTGGGT

GGACTGGGTGTACCTGGCGTAGGCGGTCTGGGTGGAATTCCGCCCGCA

GCGGCCGCGAAAGCGGCAAAATATGGCGCGGCAGGCCTGGGCGGCGTG

CTGGGTGGGGCAGGTCAGTTTCCGCTGGGCGGGGTTGCCGCACGTCCG

GGATTTGGTCTGAGCCCGATTTTCCCTGGCGGCGCATGTCTGGGTAAA

GCATGTGGTCGTAAACGTAAAtaa

The amino acid sequence of a 6.3 kDa human elastin truncated at the C-terminal is disclosed in SEQ ID NO: 69. The 6.3 kDa truncated elastin has amino acids 74-761 deleted from the full length elastin.

(SEQ ID NO: 69)
GGVPGAIPGGVPGGVFYPGAGLGALGGGALGPGGKPLKPVPGGLAGAG

LGAGLGAFPAVTFPGALVPGGVAD

The codon optimized polynucleotide sequence encoding the 6.3 kDa truncated human elastin is disclosed in SEQ ID NO: 70:

(SEQ ID NO: 70)
GGTGGCGTACCAGGCGCAATTCCTGGGGGTGTCCCAGGCGGTGTTTTT

TATCCGGGCGCCGGTCTTGGCGCACTGGGTGGCGGTGCACTGGGCCCG

GGCGGCAAACCGCTGAAACCGGTACCAGGTGGTTTAGCAGGCGCCGGC

TTAGGCGCAGGTCTGGGGAGCATTTCCGGCAGTTACCTTTCCAGGGGCA

CTGGTTCCTGGAGGTGTGGCCGATtaa

The amino acid sequence of a 4.3 kDa human elastin truncated at the N-terminal is disclosed in SEQ ID NO: 71. The 4.3 kDa truncated elastin has amino acids 2-717 deleted from the full length elastin.

(SEQ ID NO: 71)
GLGGVLGGAGQFPLGGVAARPGFGLSPIFPGGACLGKACGRKRK

The codon optimized polynucleotide sequence encoding the 4.3 kDa truncated human elastin is disclosed in SEQ ID NO: 72

(SEQ ID NO: 72)
GGCCTGGGCGGCGTGCTGGGTGGGGCAGGTCAGTTTCCGCTGGGCGGG

GTTGCCGCACGTCCGGGATTTGGTCTGAGCCCGATTTTCCCTGGCGGC

GCATGTCTGGGTAAAGCATGTGGTCGTAAACGTAAAtaa

Truncated Human Elastin 1 with DsbA Secretion and FLAG Tag

The amino acid sequence of truncated human elastin 1 with DsbA secretion and FLAG tag is disclosed in SEQ ID NO: 98. The DsbA secretion tag is encoded by nucleotides 1-57 of SEQ ID NO: 99 and the amino acid sequences are amino acids 1-19 of SEQ ID NO: 98. The elastin nucleotide sequences are nucleotides 58-657 of SEQ ID NO: 99 and the amino acid sequences are amino acids 20-219 of SEQ ID NO: 98. The FLAG nucleotide sequences are nucleotides 658-684 of SEQ ID NO: 99 and the amino acid sequences are amino acids 220-228 of SEQ ID NO: 98.

(SEQ ID NO: 98)
MKKIWLALAGLVLAFSASAGGVPGAIPGGVPGGVFYPGAGLGALGGGA

LGPGGKPLKPVPGGLAGAGLGAGLGAFPAVTFPGALVPGGVADAAAAY

KAAKAGAGLGGVPGVGGLGVSAGAVVPQPGAGVKPGKVPGVGLPGVYP

GGVLPGARFPGVGVLPGVPTGAGVKPKAPGVGGAFAGIPGVGPFGGPQ

PGVPLGYPIKAPKLPGGYGLPYTTGKLGDYKDDDDK

The nucleic acid sequence of truncated human elastin 1 with DsbA secretion and FLAG tag is disclosed in SEQ ID NO: 99.

(SEQ ID NO: 99)
ATGAAAAAGATTTGGCTGGCGCTGGCTGGTTTAGTTTTAGCGTTTAGC

GCATCGGCGGGTGGCGTACCAGGCGCAATTCCTGGGGGTGTCCCAGGC

GGTGTTTTTTATCCGGGCGCCGGTCTTGGCGCACTGGGTGGCGGTGCA

CTGGGCCCGGGCGGCAAACCGCTGAAACCGGTACCAGGTGGTTTAGCA

GGCGCCGGCTTAGGCGCAGGTCTGGGAGCATTTCCGGCAGTTACCTTT

CCAGGGGCACTGGTTCCTGGAGGTGTGGCCGATGCAGCCGCGGCATAT

AAAGCCGCTAAAGCCGGTGCGGGTTTAGGAGGCGTCCCAGGTGTCGGT

GGCCTGGGTGTTAGCGCCGGTGCAGTTGTTCCGCAGCCGGGAGCAGGG

GTTAAACCTGGTAAAGTGCCGGGAGTAGGTCTGCCAGGCGTTTATCCT

GGTGGTGTTTTGCCGGGTGCCCGTTTTCCGGGCGTTGGTGTTCTTCCA

GGCGTGCCGACCGGAGCCGGTGTTAAACCGAAAGCCCCCGGTGTTGGA

GGTGCATTTGCAGGCATCCCGGGAGTTGGCCCGTTTGGTGGTCCGCAA

CCTGGGGTTCCGTTAGGTTATCCGATTAAAGCACCGAAACTGCCCGGC

GGTTATGGTCTGCCGTACACAACCGGTAAACTGGGTGACTACAAAGAC

GACGACGACAAAtaa

The polynucleotide of SEQ ID NO: 99 was subcloned into vector pET28a, expressed host *E. coli* cells and the truncated elastin was purified as described herein. The purified elastin produced a clear band on SDS-PAGE and an anti-FLAG western was observed at around 25 kilodaltons. There were no existing bands that appear at that location on the gel in the absence of expression of this protein.

Truncated Human Elastin 2 with DsbA Secretion and FLAG Tag

The amino acid sequence of truncated human elastin type 2 with DsbA secretion and FLAG tag is disclosed in SEQ ID NO: 100. The DsbA secretion tag is encoded by nucleotides 1-57 of SEQ ID NO: 101 and the amino acid sequences are amino acids 1-19 of SEQ ID NO: 100. The elastin nucleotide sequences are nucleotides 58-657 of SEQ ID NO: 101 and the amino acid sequences are amino acids 20-219 of SEQ ID NO: 100. The FLAG nucleotide sequences are nucleotides 658-684 of SEQ ID NO: 101 and the amino acid sequences are amino acids 220-228 of SEQ ID NO: 100.

(SEQ ID NO: 100)
MKKIWLALAGLVLAFSASAPYGYGPGGVAGAAGKAGYPTGTGVGPQAA

AAAAAKAAAKFGAGAAGVLPGVGGAGVPGVPGAIPGIGGIAGVGTPAA

AAAAAAAKAAKYGAAAGLVPGGPGFGPGVVGVPGAGVPGVGVPGAGI

PVVPGAGIPGAAVPGVVSPEAAAKAAAKAAKYGARPGVGVGGIPTYGV

GAGGFPGFGVGVGGIPGVAGVPGVGGVGDYKDDDDK

The nucleic acid sequence of truncated human elastin 2 with DsbA secretion and FLAG tag is disclosed in SEQ ID NO: 101.

(SEQ ID NO: 101)
ATGAAAAAGATTTGGCTGGCGCTGGCTGGTTTAGTTTTAGCGTTTAGC

GCATCGGCGCCGTATGGTTATGGCCCGGGTGGAGTTGCGGGTGCAGCA

GGTAAAGCGGGTTATCCTACCGGAACCGGTGTAGGTCCGCAGGCCGCT

GCTGCCGCCGCCGCAAAAGCAGCGGCTAAATTTGGCGCCGGAGCAGCG

GGTGTTCTGCCTGGAGTTGGTGGTGCGGGCGTGCCAGGGGTACCTGGT

GCAATTCCGGGTATTGGTGGTATTGCCGGTGTCGGCACCCCGGCCGCG

GCAGCTGCGGCAGCGGCGGCTGCCAAAGCTGCTAAATACGGTGCCGCG

GCGGGTCTGGTGCCAGGAGGTCCGGGTTTTGGTCCGGGAGTGGTTGGC

GTGCCTGGCGCAGGCGTTCCTGGTGTGGGCGTTCCAGGTGCAGGGATT

CCTGTTGTGCCTGGTGCCGGTATTCCCGGCGCGGCCGTTCCGGGGGTG

GTTAGCCCGGAAGCCGCAGCGAAGGCTGCGGCAAAGGCAGCAAAGTAT

GGCGCACGCCCAGGAGTCGGCGTGGGTGGTATCCCGACCTATGGGGTG

GGCGCAGGGGGTTTTCCTGGTTTCGGCGTAGGTGTAGGAGGTATACCG

GGCGTGGCCGGTGTACCAGGGGTTGGTGGCGTCGGTGACTACAAAGAC

GACGACGACAAAtaa

The polynucleotide of SEQ ID NO: 101 was subcloned into vector pET28a, expressed host *E. coli* cells and the truncated elastin was purified as described herein. The purified elastin produced a clear band on SDS-PAGE and an anti-FLAG western was observed at around 25 kilodaltons. There were no existing bands that appear at that location on the gel in the absence of expression of this protein.

Example 6: Effect of Truncated Collagen on Fibroblast Cell Viability, Procollagen Synthesis, and Elastin Synthesis A human fibroblast cell culture was used to assess the ability of the truncated jellyfish collagen molecule of Example 2 to determine its effect on procollagen, and elastin synthesis. The human fibroblast cell culture was also used to determine the increased viability of the human fibroblast cells after exposure to the truncated jellyfish collagen.

A stock solution of 2% w/w truncated collagen was prepared from the histidine tagged truncated collagen of example 3. Aliquots from the 2% stock truncated collagen solution were then used in the experiments described below.

Preparation of Fibroblasts

Fibroblasts were seeded into the individual wells of a 24-well plate in 0.5 ml of Fibroblast Growth Media (FGM) and incubated overnight at 37±2° C. and 5±1% $CO_2$. On the following day the media was removed via aspiration to eliminate any non-adherent cells and replaced with 0.5 ml of fresh FGM. The cells were grown until confluent, with a media change every 48 to 72 hours. Upon reaching confluency the cells were treated for 24 hours with DMEM supplemented with 1.5% FBS to wash out any effects from the growth factors included in the normal culture media. After the 24-hour wash out period the cells were treated with the truncated jellyfish collagen at specified concentrations dissolved in FGM with 1.5% FBS. Transforming Growth Factor Beta (TGF-β) (20 ng/ml) was used as a positive control for collagen and elastin synthesis. Untreated cells (negative controls) just received DMEM with 1.5% FBS. The cells were incubated for 48 hours and at the end of the incubation period cell culture medium was collected and either stored frozen (−75° C.) or assayed immediately. Materials were tested in triplicate.

MTT Assay

The MTT (3-(4,5-Dimethylthiazol-2-yl)-2,5-diphenyltetrazolium bromide, a tetrazole) assay is a colorimetric assay used to determine the metabolic activity of cells. Changes in cell number were assessed via an MTT assay. When cells are exposed to MTT, reduction of MTT by mitochondria in viable cells results in the formation of insoluble purple formazin crystals that are extracted from the cells with isopropanol and quantified spectrophotometrically. Non-living cells cannot reduce MTT and therefore cannot produce the purple formazin crystals. The intensity of the purple color is directly proportional to the number of living cells (metabolically active cells). The intensity of the purple color is directly proportional to the metabolic activity of the cells and is inversely proportional to the toxicity of the test material.

After the 2-day incubation discussed above, the cell culture medium was removed (see above) and the fibroblasts were washed twice with PBS to remove any remaining jellyfish glycogen molecules. After the final wash, 500 µl of DMEM supplemented with 0.5 mg/ml MTT was added to each well and the cells were incubated for 1 hour at 37±2° C. and 5±1% $CO_2$. After the incubation, the DMEM/MTT solution was removed and the cells were washed again once with PBS and then 0.5 ml of isopropyl alcohol was added to the well to extract the purple formazin crystals. Two hundred microliters of the isopropyl extracts was transferred to a 96-well plate and the plate was read at 540 nm using isopropyl alcohol as a blank.

The mean MTT absorbance value for the negative control cells was calculated and used to represent 100% cell viability. The individual MTT absorbance values from the cells undergoing the various treatments were then divided by the mean value for the negative control cells and expressed as a percent to determine the change in cell viability caused by each treatment.

In Tables 1, 2 and 3 of this example, the experiments were performed by using the designated aliquots of the 2% stock truncated collagen solution in the assays. For example, in the samples that tested the "10% Collagen Solution," an aliquot of the 2% truncated collagens in an amount sufficient to provide 10% of the assay volume was used. For a total assay volume of 1.0 ml, 100 µl of the 2% stock truncated collagen solution was used. In Tables 1, 2 and 3, "10% Collagen Solution" is 0.2% collagen, "5% Collagen Solution" is 0.1% collagen, "1% Collagen Solution" is 0.02% collagen, "0.5% Collagen Solution" is 0.01% collagen, "0.1% Collagen Solution" is 0.002% collagen, "0.05% Collagen Solution" is 0.001% collagen, "0.01% Collagen Solution" is 0.0002% collagen, "0.005% Collagen Solution" is 0.0001% collagen.

The results for the MTT assay are presented in Table 3. The values are presented as the mean percent viability±the deviation from the mean.

TABLE 3

| MTT Assay | |
|---|---|
| Untreated | 100 ± 6.1 |
| 20 ng/ml TGF-B | 110 ± 2.9 |
| 10% Collagen Solution | 131 ± 7.8* |
| 5% Collagen Solution | 140 ± 8.3* |
| 1% Collagen Solution | 116 ± 0.9 |
| 0.5% Collagen Solution | 105 ± 4.8 |
| 0.1% Collagen Solution | 102 ± 1.1 |
| 0.05% Collagen Solution | 106 ± 3.4 |
| 0.01% Collagen Solution | 112 ± 1.9 |
| 0.005% Collagen Solution | 103 ± 3.9 |

*Denotes values that are significantly different from the Untreated group ($p < 0.05$).

The histidine tagged truncated jellyfish collagen showed protective effect by increasing the cell viability of human fibroblast cells.

Procollagen Synthesis

Fibroblasts are the main source of the extracellular matrix peptides, including the structural proteins collagen and elastin. Procollagen is a large peptide synthesized by fibroblasts in the dermal layer of the skin and is the precursor for collagen. As the peptide is processed to form a mature collagen protein, the propeptide portion is cleaved off (type I C-peptide). Both the mature collagen protein and the type I C-peptide fragment are then released into the extracellular environment. As collagen is synthesized the type I C-peptide fragment accumulates into the tissue culture medium. Since there is a 1:1 stoichiometric ratio between the two parts of the procollagen peptide, assaying for type I C-peptide will reflect the amount of collagen synthesized. Type 1 C-peptide can be assayed via an ELISA based method.

A series of type I C-peptide standards was prepared ranging from 0 ng/ml to 640 ng/ml. Next, an ELISA microplate was prepared by removing any unneeded strips from the plate frame followed by the addition of 100 µl of peroxidase-labeled anti procollagen type I-C peptide antibody to each well used in the assay. Twenty (20) µl of either sample (collected tissue culture media) or standard was then added to appropriate wells and the microplate was covered and allowed to incubate for 3±0.25 hours at 37° C. After the incubation the wells were aspirated and washed three times with 400 µl of wash buffer. After the last wash was removed 100 µl of peroxidase substrate solution (hydrogen peroxide+ tetramethylbenzidine as a chromagen) was added to each well and the plate was incubated for 15±5 minutes at room temperature. After the incubation 100 µl of stop solution (1 N sulfuric acid) was added to each well and the plate was read using a microplate reader at 450 nm.

To quantify the amount of each substance present, a standard curve was generated using known concentrations of each substance. A regression analysis was performed to establish the line that best fits these data points. Absorbance values for the test materials and untreated samples were used to estimate the amount of each substance present in each sample.

The results for the ELISA assays are presented in Table 4.

TABLE 4

Type I Collagen Assay.
The values presented are mean concentration
(ng/ml) ± the deviation from the mean.

| Treatment | Type I C-Peptide (ng/ml) |
|---|---|
| Untreated | 1718 ± 94 |
| 20 ng/ml TGF-B | 3028 ± 332* |
| 10% Collagen Solution | 1940 ± 100 |
| 5% Collagen Solution | 2394 ± 125* |
| 1% Collagen Solution | 1773 ± 183 |
| 0.5% Collagen Solution | 1127 ± 19* |
| 0.1% Collagen Solution | 1158 ± 10* |
| 0.05% Collagen Solution | 1416 ± 64 |
| 0.01% Collagen Solution | 1835 ± 404 |
| 0.005% Collagen Solution | 1551 ± 149 |

*Denotes values that are significantly different from the Untreated group ($p < 0.05$).

The truncated histidine tagged jellyfish collagen was observed to have a biphasic effect on collagen synthesis. At the 1%, 5% and the 10% levels, collagen synthesis increased. At the 5% concentration truncated jellyfish collagen significantly increased collagen synthesis with a p-value of less than 0.05.

Elastin Synthesis

Elastin is the main component of a network of elastic fibers that give tissues their ability to recoil after a transient stretch. This protein is released by fibroblasts (soluble elastin) into the extracellular space where it is then cross-linked to other elastin proteins to form an extensive network of fibers and sheets (insoluble elastin). Soluble elastin can be readily measured from cell culture medium via an ELISA based method.

Soluble α-elastin was dissolved in 0.1 M sodium carbonate (pH 9.0) at a concentration of 1.25 μg/ml. 150 μl of this solution was then applied to the wells of a 96-well maxisorp Nunc plate and the plate was incubated overnight at 4° C. On the following day the wells were saturated with PBS containing 0.25% BSA and 0.05% TWEEN® 20. The plate was then incubated with this blocking solution for 1 hour at 37° C. and then washed two times with PBS containing 0.05% TWEEN® 20.

A set of α-elastin standards was generated ranging from 0 to 100 ng/ml. 180 μl of either standard or truncated jellyfish collagen was then transferred to a 650 μl microcentrifuge tube. An anti-elastin antibody solution was prepared (the antibody was diluted 1:100 in PBS containing 0.25% BSA and 0.05% TWEEN® 20) and 20 μl of the solution was added to the tube. The tubes were then incubated overnight at 4±2° C. On the following day, 150 μl was transferred from each tube to the 96-well elastin ELISA plate, and the plate was incubated for 1 hour at room temperature. The plate was then washed 3 times with PBS containing 0.05% TWEEN® 20. After washing, 200 μl of a solution containing a peroxidase linked secondary antibody diluted in PBS containing 0.25% BSA and 0.05% TWEEN® 20 was added, and the plate was incubated for 1 hour at room temperature. After washing the plate three times, 200 μl of a substrate solution was added and the plate was incubated for 10 to 30 minutes in the dark at room temperature. After this final incubation the plate was read at 460 nm using a plate reader.

TABLE 5

The values are also presented as mean concentration (ng/ml) ± deviation from the mean.

| Treatment | Elastin (ng/ml) |
| --- | --- |
| Untreated | 79 ± 19 |
| 20 ng/ml TGFB1 | 243 ± 35* |
| 10% Collagen Solution | 68 ± 18 |
| 5% Collagen Solution | 99 ± 13 |
| 1% Collagen Solution | 126 ± 21 |
| 0.5% Collagen Solution | 145 ± 21* |
| 0.1% Collagen Solution | 76 ± 14 |
| 0.05% Collagen Solution | 58 ± 6 |
| 0.01% Collagen Solution | 53 ± 5 |
| 0.005% Collagen Solution | 56 ± 24 |

*Denotes values that are significantly different from the Untreated group ($p < 0.05$).

Truncated his-tagged jellyfish collagen significantly increased elastin production when it was used at the 0.5% concentration as shown in Table 5.

Example 7: Effect of Truncated Collagen on Keratinocyte Proliferation and UVB Protection A human keratinocyte cell culture model was used to assess the ability of the test materials to exert an effect on cell proliferation. In addition, the impact of the test materials on the cell viability after an exposure to UVB was also assessed.

A stock solution of 2% w/w truncated collagen was prepared from the truncated collagen of example 1. Aliquots from the 2% stock truncated collagen solution was then used in the experiments described below.

This study was conducted in two parts. In the first part cultured keratinocytes were incubated with the test materials for 48 hours, after which changes in the number of viable cells were assessed using an MTT assay. In the second part of the study cultured keratinocytes were irradiated with UVB and then treated with the test materials for 48 hours. At the end of the 48 hour period the number of viable cells was again assessed via an MTT assay.

Changes in cell number of viable cells can be determined using an MTT (3-(4,5-Dimethylthiazol-2-yl)-2,5-diphenyltetrazolium bromide, a tetrazole) assay. The MTT assay is a colorimetric analysis of the metabolic activity of the cell, which is a reflection of the number of viable cells. Reduction of MTT by mitochondria in viable cells results in the formation of insoluble purple formazin crystals that are extracted from the cells with isopropanol and quantified spectrophotometrically. The intensity of the purple color is directly proportional to the number of metabolically active cells.

Proliferation Assay

For the proliferation assay the keratinocytes were seeded into 96-well plates using without growth factors and incubated for 24 hours at 37±2° C. and 5±1% CO2. After this initial incubation the media was replaced with media supplemented with the test materials. Normal media (with growth factors) was used as a positive control. After the addition of the test materials the cells were cultured for 48 hours as described above. At the end of the incubation period changes in the number of viable cells was determined using an MTT assay.

UVB Protection Assay

For the UVB protection assay the keratinocytes were seeded into 96-well plates using normal media and incubated for 24 hours at 37±2° C. and 5±1% CO2. After this initial incubation the media was replaced with 100 μl of phosphate buffered saline (PBS) and the cells were exposed to UVB (40 mJ/cm2). After the UVB exposure, the PBS was replaced with fresh media supplemented with the test materials (ascorbic acid at 100 μg/ml served as the positive control) and the cells were cultured for 48 hours at 37±2° C. and 5±1% CO2. At the end of the 48 hour incubation cell viability was determined using an MTT assay.

MTT Assay

After the 48-hour incubation the cell culture medium was removed and replaced with 200 μl of culture media supplemented with 0.5 mg/ml MTT. The well plates were incubated for 1 hour at 37±2° C. and 5±1% CO2. After the incubation, the MTT solution was removed and the cells were washed once with phosphate buffered saline and then 200 μl of isopropyl alcohol was added to the well to extract the purple formazin crystals. The 96-well plate was read at 540 nm using isopropyl alcohol as a blank.

The mean absorbance value for the cells not treated with test materials (proliferation assay: Untreated Group) or not exposed to UVB (UVB protection assay: Non-UVB Exposed Group) was calculated and used to represent 100% cell viability. The individual absorbance values from the cells undergoing the various treatments were then divided by the mean absorbance value representing 100% cell viability and expressed as a percent to determine the change in cell viability caused by each treatment.

The results for the Proliferation assay using the his-tagged truncated jellyfish collagen are presented in Table 6. The results for the UVB Protection assay using the his-tagged truncated jellyfish collagen are presented in Table 7. The values for both assays are presented as mean viability±standard deviation.

TABLE 6.

Proliferation Assay

| | |
|---|---|
| Untreated | 100 ± 3.4 |
| Positive Control (Growth Factors) | 139 ± 3.8* |
| 10% Collagen Solution | 103 ± 9.4 |
| 5% Collagen Solution | 97 ± 7.3 |
| 1% Collagen Solution | 94 ± 5.0 |
| 0.5% Collagen Solution | 93 ± 7.0 |
| 0.1% Collagen Solution | 95 ± 2.5 |
| 0.05% Collagen Solution | 99 ± 6.0 |
| 0.01% Collagen Solution | 96 ± 6.4 |
| 0.005% Collagen Solution | 96 ± 2.8 |

*Denotes values which are significantly different from the Untreated Group (p < 0.05)

TABLE 7

UVB Protection Assay

| | |
|---|---|
| Non-UVB Exposed | 100 ± 1.7* |
| Untreated | 77 ± 1.8 |
| 100 ug/ml Trolox | 92 ± 2.0* |
| 10% Collagen Solution | 76 ± 8.6 |
| 5% Collagen Solution | 92 ± 3.9* |
| 1% Collagen Solution | 91 ± 2.9* |
| 0.5% Collagen Solution | 100 ± 4.5* |
| 0.1% Collagen Solution | 86 ± 4.8 |
| 0.05% Collagen Solution | 91 ± 1.6* |
| 0.01% Collagen Solution | 83 ± 7.5 |
| 0.005% Collagen Solution | 82 ± 4.7 |

*Denotes values which are significantly different from the Untreated Group (p < 0.05)

For the proliferation assay the Untreated group was used to represent 100% cell viability. Values above 100% reflect an increase in the number of viable cells and hence are indicative of cell proliferation. In this study, the test material was not observed to promote cell proliferation.

In addition, the keratinocyte proliferation assay was performed using the truncated collagen of SEQ ID NO: 91. A 1% and 0.5% collagen solution of a 5% stock solution was prepared according to Example 8 and tested. The truncated collagen of SEQ ID NO: 91 had keratinocyte cell viability assay values of 102±2.9 and 102±2.0, respectively. The observed values were statistically significant (p<0.05).

In addition to its effects on cell proliferation, the test material was also screened to determine if it had an impact on cell recovery after UVB exposure. In this study, exposure to UVB was observed to result in a significant reduction in the number of viable cells 48 hours post exposure. However, treatment with the test material prevented this decrease in cell viability. The effect was evident within a concentration range between 0.05% and 5% of the test material, with an optimal effect at a concentration of 0.05%. Within this range of concentrations cell viability was significantly greater than the untreated group (with the lone exception of the 0.01% concentration), demonstrating that the material has UVB protective effect. Since this material was added after the UVB exposure it could be acting to reduce the damaging effects of the UVB irradiation, or it could be helping the damaged cells to recover at a faster rate. With respect to the latter, then truncated collagen is beneficial when applied topically to the skin and has a regenerative effect on skin cells damaged by UVB.

In addition, the UVB protection assay was performed using the truncated collagen of SEQ ID NO: 91. A 1% and 0.5% collagen solution of SEQ ID NO: 91 had keratinocyte cell viability assay values of 80±4.6 and 78±2.5, respectively. The observed values were statistically significant (p<0.05).

Example 8: Effect of Truncated Collagen on Thymine Dimer Formation

Upon exposure to ultraviolet radiation the thymine dimer (TT dimer) content in DNA present in cells increases. Increases in TT dimer formation are correlated with skin damage and certain types of cell proliferative diseases including skin cancer.

The polynucleotide of SEQ ID NO: 11 was expressed in the expression system of Example 1 and purified as described in this example. The encoded polypeptide includes the DsbA secretion tag. As the polypeptide is processed through the secretion pathway, the DsbA tag, amino acids 1-24 of SEQ ID NO: 12 is cleaved by the host cell. The truncated collagen without the DsbA secretion tag is provided in SEQ ID NO: 91.

The truncated collagen of SEQ ID NO: 91 was tested to determine if it could reduce TT dimer formation is human epidermal keratinocytes. For this study, the cells were exposed to UVB (25 mJ/cm2). Following the exposures cells were treated with the test materials or Trolox (100 ug/ml) and incubated overnight. On the following day cellular DNA was extracted and assayed for thymine dimer content using an ELISA based method.

Human keratinocytes were seeded into 12-well plates using normal media and incubated for 24 hours at 37±2° C. and 5±1% CO2. After this initial incubation the media was replaced with 100 µl of phosphate buffered saline (PBS) and the cells were exposed to UVB (25 mJ/cm2). After the UVB exposure, the PBS was replaced with fresh media supplemented with the test materials or Trolox (100 µg/ml, this served as the positive control) and the cells were cultured overnight at 37±2° C. and 5±1% CO2. At the end of the incubation cellular DNA was extracted.

After the overnight incubation the cell culture media was removed from the wells and replaced with 200 µl of PBS and 20 µl of Proteinase K. After swirling the plate to mix the PBS and Proteinase K, 200 µl of buffer AL was added to each well. After again swirling the plate to mix the reagents, the plates were incubated for 10 minutes at 55±2° C. After cooling the plate to room temperature, the DNA was precipitated by the addition of 200 µl of 100% ethanol. The precipitated DNA mixtures were then transferred to DNEASY® Spin Columns in 2 ml collection tubes and centrifuged at 8,000 RPM for 1 minute. The flow through and collection tubes were discarded, and 500 µl of Wash Buffer One was added to the spin column and the column was placed into a new collection tube and centrifuged at 8,000 RPM for 1 minute. The flow through and collection tube were again discarded, and 500 µl of Wash Buffer Two was added to the spin column and the column was placed into a new collection tube and centrifuged at 14,000 RPM for 3 minutes. The spin column was then placed into a new 1.5 ml centrifuge tube and 110 µl of ultrapure water was added to the column. The column was incubated for 1 minute at room temperature and then centrifuged at 8,000 RPM for 1 minute.

Extracted DNA was quantified via a fluorometric assay. A 2 µl aliquot of the DNA sample was mixed with 100 µl TE buffer in a 96-well plate. A series of DNA standards was also transferred to wells in a 96-well plate (in duplicate). Finally, 100 µl of dilute CYQUANT® Green dye was added to each well and the fluorescence intensity of each well was determined using an excitation wavelength of 480 nm and an emission wavelength of 520 nm.

Thymine Dimer Detection was determined using an OXISELECT™ UV-Induced DNA Damage ELISA Kit)

Aliquots of genomic DNA samples or standards were converted to single stranded DNA by incubating the samples at 95° C. for 10 minutes and then chilled on ice. 100 μl or each sample or standard was transferred to a DNA binding ELISA plate and incubated overnight at 4° C. On the following day the wells were rinsed once with 100 μl of PBS and then blocked with 150 μl of Assay Diluent for one hour at room temperature. After removing the Assay Diluent, 100 μl of anti-CPD antibody was added to each well and the plate was incubated for one hour at room temperature. After this incubation, the plate was washed three times with 250 μl of wash buffer per well, and then 150 μl of Blocking Reagent was added to the plate. The plate will be blocked again for one hour at room temperature, and then washed three times as described before. 100 μl of Secondary Antibody was then added to each well and the plate was incubated for 1 hour at room temperature. After washing the plate again, 100 μl of substrate was added to each well and the plate was incubated for 5-20 minutes to allow for color generation in the plate. The color generation reaction was stopped by the addition of 100 μl of stop solution and the plate was read at 460 nm using a plate reader.

To quantify the amount of DNA present, a standard curve was generated using known concentrations of DNA and their respective fluorescence intensity (measured in RFUs or relative fluorescence units). A regression analysis was performed to establish the line that best fits these data points. The Relative Fluorescence Units (RFU) for each unknown sample was then used to estimate the amount of DNA.

Figure 5:
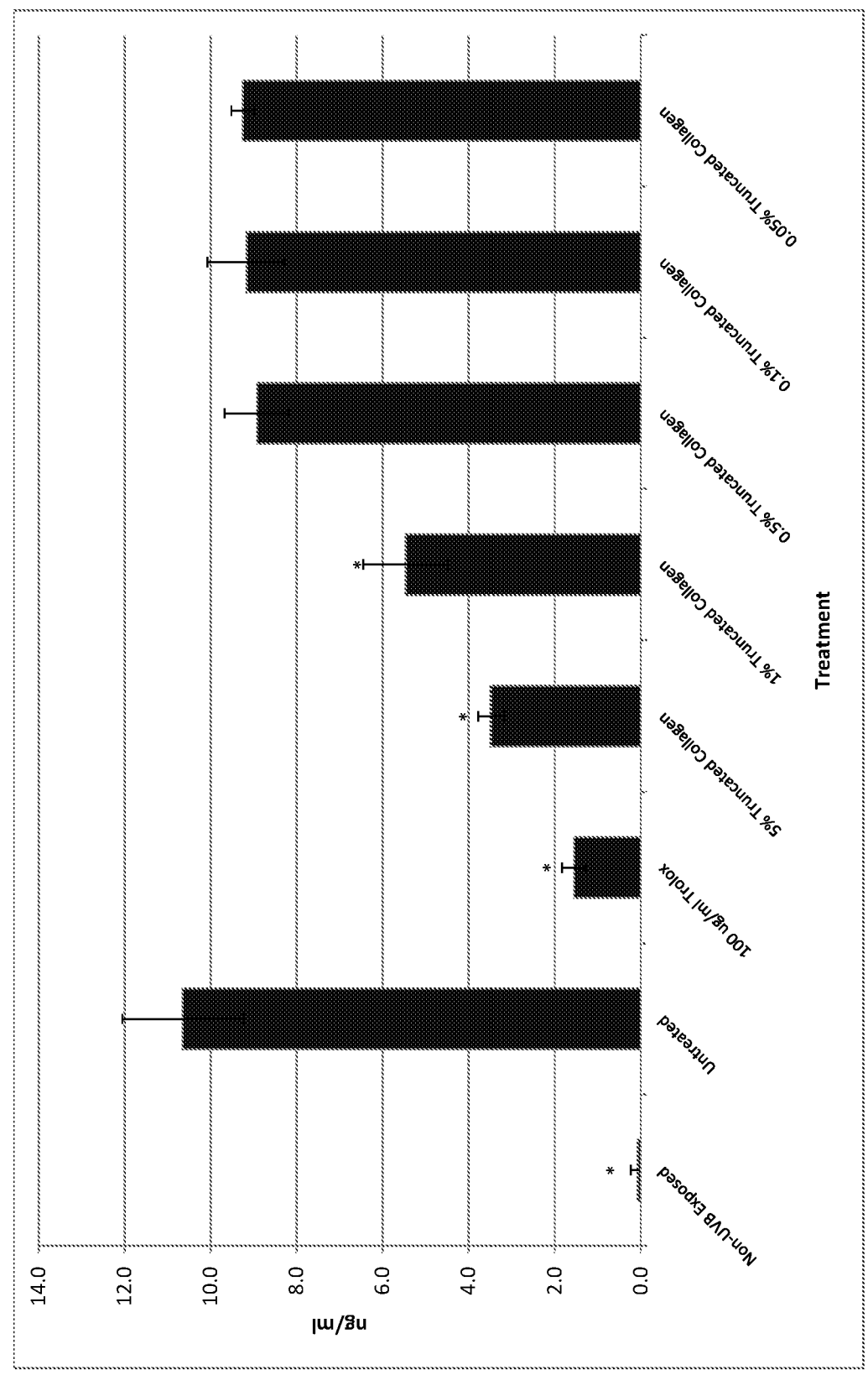
FIG. 5 illustrates the reduction in TT dimer formation by treatment of human keratinocytes with truncated collagen.

A series of DNA standards with known amounts of thymine dimer content were used to generate a standard curve. This standard curve was used to determine the amount of DNA damage in the sample DNA. Means for each treatment group were calculated and compared using an ANOVA. In table 8 and FIG. 5, a standard 5% collagen solution (5 g truncated collagen in 95 ml deionized water was further diluted with phosphate buffered saline (PBS) to the indicated percent solution.

TABLE 8

Thymine Dimer Assay

| Treatment | Thymine Dimer, ng/ml |
| --- | --- |
| Non-UVB Exposed | 0.1 ± 0.2* |
| Untreated | 10.7 ± 1.4* |
| 100 μg/ml Trolox | 1.6 ± 0.3* |
| 5% Truncated Collagen | 3.5 ± 0.3* |
| 1% Truncated Collagen | 5.5 ± 1.0* |
| 0.5% Truncated Collagen | 8.9 ± 0.8 |
| 0.1% Truncated Collagen | 9.2 ± 0.9 |
| 0.05% Truncated Collagen | 9.2 ± 0.3 |

*Denotes values which are statistically significantly different from untreated with P < 0.05

Table 8 shows that the 5% and the 1% truncated collagen solution reduced TT dimer formation with statistical significance (p<0.05). The data is presented graphically in FIG. 5.

The experiment was repeated with a different lot of truncated collagen (SEQ ID NO: 91). The amount of TT dimer in ng/ml in non-UVB exposed cells was 1.3±1.2, untreated cells was 18.1±0.4, 100 μg/ml Trolox treated cells was 7.9±0.3, 5% collagen was 13.1±0.2, and 1% collagen was 17.4±0.7. The reduction in TT dimer formation for non-UVB exposed cells, Trolox treated cells, 5% collagen treated cells and 1% collagen treated cells was statistically significant compared to untreated cells (p<0.05).

Example 9: Human Collagens

Truncated Human Collagen Type 21 Alpha 1

A truncated human collagen type 21 alpha 1 without a His tag, linker, and thrombin cleavage site is disclosed below. The codon-optimized nucleotide sequence encoding this collagen and the amino acid sequence are disclosed below. In SEQ ID NOs: 73 and 74, the DsbA secretion tag is encoded by nucleotides 1-72 and encodes amino acids 1-24. In SEQ ID NOs: 73 and 74, the truncated collagen sequence is encoded by nucleotides 73-633 and encodes amino acids 25-211.

The codon-optimized nucleotide sequence encoding this collagen is provided in SEQ ID NO: 73.

(SEQ ID NO: 73)
ATGAAAAAGATTTGGCTGGCGCTGGCTGGTTTAGTTTTAGCGTTTAGC

GCATCGGCGGCGCAGTATGAAGATGCAGGTTTTCCGGGTCTGCCTGGT

CCGGCAGGCGAACCGGGTCGTCATGGTAAAGATGGTCTGATGGGTAGT

CCGGGTTTTAAAGGTGAAGCAGGTTCACCGGGTGCACCTGGTCAGGAT

GGCACCCGTGGTGAACCGGGTATTCCGGGATTTCCGGGTAATCGTGGC

CTGATGGGTCAGAAAGGTGAAATTGGTCCGCCTGGTCAGCAGGGTAAA

AAAGGCGCACCGGGTATGCCAGGACTGATGGGTTCAAATGGCAGTCCG

GGTCAGCCAGGCACACCGGGTTCAAAAGGTAGCAAAGGCGAACCTGGT

ATTCAGGGTATGCCTGGTGCAAGCGGTCTGAAAGGCGAGCCAGGTGCC

ACCGGTTCTCCGGGTGAACCAGGTTATATGGGTCTGCCAGGTATCCAA

GGCAAAAAAGGTGATAAAGGTAATCAGGGCGAAAAAGGCATTCAGGGC

CAGAAAGGCGAAAATGGCCGTCAGGGTATTCCAGGCCAGCAGGGCATC

CAGGGTCATCATGGTGCAAAAGGTGAACGTGGTGAAAAGGGCGAACCA

GGTGTTCGTtaa

The amino acid sequence is disclosed in SEQ ID NO: 74.

(SEQ ID NO: 74)
MKKIWLALAGLVLAFSASAAQYEDAGFPGLPGPAGEPGRHGKDGLMGS

PGFKGEAGSPGAPGQDGTRGEPGIPGFPGNRGLMGQKGEIGPPGQQGK

KGAPGMPGLMGSNGSPGQPGTPGSKGSKGEPGIQGMPGASGLKGEPGA

TGSPGEPGYMGLPGIQGKKGDKGNQGEKGIQGQKGENGRQGIPGQQGI

QGHHGAKGERGEKGEPGVR

The codon-optimized nucleotide sequence encoding the truncated human collagen type 21 alpha 1 without the DsbA secretion tag collagen is provided in SEQ ID NO: 75.

(SEQ ID NO: 75)
TGCAGGTTTTCCGGGTCTGCCTGGTCCGGCAGGCGAACCGGGTCGTCAT

GGTAAAGATGGTCTGATGGGTAGTCCGGGTTTTAAAGGTGAAGCAGGTT

CACCGGGTGCACCTGGTCAGGATGGCACCCGTGGTGAACCGGGTATTCC

GGGATTTCCGGGTAATCGTGGCCTGATGGGTCAGAAAGGTGAAATTGGT

```
-continued
CCGCCTGGTCAGCAGGGTAAAAAAGGCGCACCGGGTATGCCAGGACTGA

TGGGTTCAAATGGCAGTCCGGGTCAGCCAGGCACACCGGGTTCAAAAGG

TAGCAAAGGCGAACCTGGTATTCAGGGTATGCCTGGTGCAAGCGGTCTG

AAAGGCGAGCCAGGTGCCACCGGTTCTCCGGGTGAACCAGGTTATATGG

GTCTGCCAGGTATCCAAGGCAAAAAAGGTGATAAAGGTAATCAGGGCGA

AAAAGGCATTCAGGGCCAGAAAGGCGAAAATGGCCGTCAGGGTATTCCA

GGCCAGCAGGGCATCCAGGGTCATCATGGTGCAAAAGGTGAACGTGGTG

AAAAGGGCGAACCAGGTGTTCGTtaa
```

The amino acid sequence of truncated human collagen type 21 alpha 1 without the DsbA secretion tag is disclosed in SEQ ID NO: 76.

```
                                    (SEQ ID NO: 76)
AGFPGLPGPAGEPGRHGKDGLMGSPGFKGEAGSPGAPGQDGTRGEPGIP

GFPGNRGLMGQKGEIGPPGQQGKKGAPGMPGLMGSNGSPGQPGTPGSKG

SKGEPGIQGMPGASGLKGEPGATGSPGEPGYMGLPGIQGKKGDKGNQGE

KGIQGQKGENGRQGIPGQQGIQGHHGAKGERGEKGEPGVR
```

Truncated Human Collagen Type 1 Alpha 2 (1)

A truncated human collagen type 1 alpha 2 without a His tag, linker, and thrombin cleavage site is disclosed below. The codon-optimized nucleotide sequence and the amino acid sequences are disclosed below. In SEQ ID NOs: 78 and 79, The DsbA secretion tag is encoded by nucleotides 1-72 and encodes amino acids 1-24. The truncated collagen sequence is encoded by nucleotides 73-636 and encodes amino acids 25-212.

The codon-optimized nucleotide sequence encoding this collagen is provided in SEQ ID NO: 77.

```
                                    (SEQ ID NO: 77)
ATGAAAAAGATTTGGCTGGCGCTGGCTGGTTTAGTTTTAGCGTTTAGCG

CATCGGCGGCGCAGTATGAAGATATGGGTCCGCCTGGTAGCCGTGGTGC

AAGTGGTCCGGCAGGCGTTCGTGGTCCGAATGGTGATGCAGGTCGTCCG

GGTGAACCGGGTCTGATGGGTCCTCGTGGTCTGCCTGGTTCACCGGGTA

ATATTGGTCCTGCAGGTAAAGAAGGTCCGGTTGGTCTGCCAGGTATTGA

TGGCCGTCCGGGTCCGATTGGTCCAGCCGGTGCACGTGGTGAACCTGGC

AATATTGGTTTTCCGGGTCCTAAAGGTCCGACCGGTGATCCGGGTAAAA

ATGGTGATAAAGGTCATGCAGGTCTGGCAGGCGCACGCGGTGCACCTGG

TCCGGATGGTAATAATGGTGCACAGGGTCCACCGGGTCCGCAGGGTGTT

CAAGGTGGTAAAGGCGAACAGGGTCCTGCCGGTCCTCCGGGTTTTCAGG

GACTGCCTGGTCCGAGCGGTCCTGCGGGTGAAGTTGGTAAACCTGGTGA

ACGCGGTCTGCATGGTGAATTTGGCCTGCCTGGGCCTGCAGGTCCGCGT

GGCGAACGTGGTCCGCCAGGTGAAAGCGGTGCAGCAGGTCCGACAGGTt aa
```

The amino acid sequence is disclosed in SEQ ID NO: 78.

```
                                    (SEQ ID NO: 78)
MKKIWLALAGLVLAFSASAAQYEDMGPPGSRGASGPAGVRGPNGDAGRP

GEPGLMGPRGLPGSPGNIGPAGKEGPVGLPGIDGRPGPIGPAGARGEPG

NIGFPGPKGPTGDPGKNGDKGHAGLAGARGAPGPDGNNGAQGPPGPQGV

QGGKGEQGPAGPPGFQGLPGPSGPAGEVGKPGERGLHGEFGLPGPAGPR

GERGPPGESGAAGPTG
```

The nucleic acid sequence of truncated human collagen type 1 alpha 2(1) without the DsbA secretion tag is disclosed in SEQ ID NO: 79.

```
                                    (SEQ ID NO: 79)
ATGGGTCCGCCTGGTAGCCGTGGTGCAAGTGGTCCGGCAGGCGTTCGTG

GTCCGAATGGTGATGCAGGTCGTCCGGGTGAACCGGGTCTGATGGGTCC

TCGTGGTCTGCCTGGTTCACCGGGTAATATTGGTCCTGCAGGTAAAGAA

GGTCCGGTTGGTCTGCCAGGTATTGATGGCCGTCCGGGTCCGATTGGTC

CAGCCGGTGCACGTGGTGAACCTGGCAATATTGGTTTTCCGGGTCCTAA

AGGTCCGACCGGTGATCCGGGTAAAAATGGTGATAAAGGTCATGCAGGT

CTGGCAGGCGCACGCGGTGCACCTGGTCCGGATGGTAATAATGGTGCAC

AGGGTCCACCGGGTCCGCAGGGTGTTCAAGGTGGTAAAGGCGAACAGGG

TCCTGCCGGTCCTCCGGGTTTTCAGGGACTGCCTGGTCCGAGCGGTCCT

GCGGGTGAAGTTGGTAAACCTGGTGAACGCGGTCTGCATGGTGAATTTG

GCCTGCCTGGGCCTGCAGGTCCGCGTGGCGAACGTGGTCCGCCAGGTGA

AAGCGGTGCAGCAGGTCCGACAGGTtaa
```

The amino acid sequence of truncated human collagen type 1 alpha 2(1) without the DsbA secretion tag is disclosed in SEQ ID NO: 80.

```
                                    (SEQ ID NO: 80)
MGPPGSRGASGPAGVRGPNGDAGRPGEPGLMGPRGLPGSPGNIGPAGKE

GPVGLPGIDGRPGPIGPAGARGEPGNIGFPGPKGPTGDPGKNGDKGHAG

LAGARGAPGPDGNNGAQGPPGPQGVQGGKGEQGPAGPPGFQGLPGPSGP

AGEVGKPGERGLHGEFGLPGPAGPRGERGPPGESGAAGPTG
```

Truncated Human Collagen Type 1 Alpha 2 (2)

A truncated human collagen type 1 alpha 2 without a His tag, linker, and thrombin cleavage site is disclosed below. The codon-optimized nucleotide sequence and the amino acid sequences are disclosed below. in SEQ ID NO: 82 and 83, the DsbA secretion tag is encoded by nucleotides 1-72 and encodes amino acids 1-24. The truncated collagen sequence is encoded by nucleotides 73-609 and encodes amino acids 25-203.

The codon-optimized nucleotide sequence encoding this collagen is provided in SEQ ID NO: 81.

```
                                    (SEQ ID NO: 81)
ATGAAAAAGATTTGGCTGGCGCTGGCTGGTTTAGTTTTAGCGTTTAGCG

CATCGGCGGCGCAGTATGAAGATGGTTTTCAGGGTCCTGCCGGTGAACC
```

-continued
GGGTGAACCTGGTCAGACAGGTCCGGCAGGCGCACGTGGTCCTGCAGGT

CCTCCTGGTAAAGCCGGTGAAGATGGTCATCCGGGTAAACCGGGTCGTC

CTGGTGAACGTGGTGTTGTTGGTCCGCAGGGTGCCCGTGGTTTTCCGGG

TACTCCGGGTCTGCCAGGTTTTAAAGGTATTCGTGGTCATAATGGTCTG

GATGGTCTGAAAGGTCAGCCTGGTGCACCGGGTGTTAAAGGTGAACCAG

GTGCTCCGGGTGAAAATGGCACACCGGGTCAGACCGGTGCGCGTGGTCT

GCCTGGCGAACGCGGTCGTGTTGGTGCACCTGGTCCAGCCGGTGCACGC

GGTAGTGATGGTAGCGTTGGTCCGGTTGGTCCAGCGGGTCCGATTGGTA

GCGCAGGTCCACCGGGTTTTCCAGGCGCACCGGGTCCGAAAGGTGAAAT

TGGTGCAGTTGGTAATGCAGGCCCTGCCGGTCCAGCAGGACCGCGTGGT

GAAGTTGGCCTGCCTGGTCTGtaa

The amino acid sequence is disclosed in SEQ ID NO: 82.

(SEQ ID NO: 82)
MKKIWLALAGLVLAFSASAAQYEDGFQGPAGEPGEPGQTGPAGARGPAG

PPGKAGEDGHPGKPGRPGERGVVGPQGARGFPGTPGLPGFKGIRGHNGL

DGLKGQPGAPGVKGEPGAPGENGTPGQTGARGLPGERGRVGAPGPAGAR

GSDGSVGPVGPAGPIGSAGPPGFPGAPGPKGEIGAVGNAGPAGPAGPRG

EVGLPGL

The nucleic acid sequence of truncated human collagen type 1 alpha 2(2) without the DsbA secretion tag is disclosed in SEQ ID NO: 83.

(SEQ ID NO: 83)
GGTTTTCAGGGTCCTGCCGGTGAACCGGGTGAACCTGGTCAGACAGGTC

CGGCAGGCGCACGTGGTCCTGCAGGTCCTCCTGGTAAAGCCGGTGAAGA

TGGTCATCCGGGTAAACCGGGTCGTCCTGGTGAACGTGGTGTTGTTGGT

CCGCAGGGTGCCCGTGGTTTTCCGGGTACTCCGGGTCTGCCAGGTTTTA

AAGGTATTCGTGGTCATAATGGTCTGGATGGTCTGAAAGGTCAGCCTGG

TGCACCGGGTGTTAAAGGTGAACCAGGTGCTCCGGGTGAAAATGGCACA

CCGGGTCAGACCGGTGCGCGTGGTCTGCCTGGCGAACGCGGTCGTGTTG

GTGCACCTGGTCCAGCCGGTGCACGCGGTAGTGATGGTAGCGTTGGTCC

GGTTGGTCCAGCGGGTCCGATTGGTAGCGCAGGTCCACCGGGTTTTCCA

GGCGCACCGGGTCCGAAAGGTGAAATTGGTGCAGTTGGTAATGCAGGCC

CTGCCGGTCCAGCAGGACCGCGTGGTGAAGTTGGCCTGCCTGGTCTGta a

The amino acid sequence of truncated human collagen type 1 alpha 2(2) without the DsbA secretion tag is disclosed in SEQ ID NO: 84.

(SEQ ID NO: 84)
GFQGPAGEPGEPGQTGPAGARGPAGPPGKAGEDGHPGKPGRPGERGVVG

PQGARGFPGTPGLPGFKGIRGHNGLDGLKGQPGAPGVKGEPGAPGENGT

PGQTGARGLPGERGRVGAPGPAGARGSDGSVGPVGPAGPIGSAGPPGFP

GAPGPKGEIGAVGNAGPAGPAGPRGEVGLPGL

The polynucleotides of SEQ ID NO: 73, 77 or 81 were subcloned in vector pET28a as described herein to prepare a transformation vector. Host cells were transformed with the vector the polynucleotides were expressed as described in Example 2.

After the fermentation was completed, the truncated human collagen was purified from the fermentation broth using the procedures disclosed in Example 3. The purified truncated human collagens were analyzed using SDS-PAGE and HPLC as disclosed in Example 3.

All three truncated human collagens ran at the expected molecular weights in the SDS-PAGE analysis. In analyzing the truncated human collagens using HPLC, a standard curve using the jellyfish collagen of Example 3 was utilized. The retention times of the human collagens were slightly different than the jellyfish collagen. The retention time of SEQ ID NO: 76 was 5.645 minutes, the retention time of SEQ ID NO: 80 was 5.631 minutes, and SEQ ID NO: 84 ran at two peaks and the retention times were 5.531 and 5.7 minutes.

Truncated Human Collagen Type 1 Alpha 2 Truncation 5 with DsbA Secretion and FLAG Tag The amino acid sequence of truncated human collagen type 1 alpha 2 truncation 5 with DsbA secretion and FLAG tag is disclosed in SEQ ID NO: 92. The DsbA secretion tag is encoded by nucleotides 1-57 of SEQ ID NO: 93 and the amino acid sequences are amino acids 1-19 of SEQ ID NO: 92. The collagen nucleotide sequences are nucleotides 58-657 of SEQ ID NO: 93 and the amino acid sequences are amino acids 20-219 of SEQ ID NO: 92. The FLAG nucleotide sequences are nucleotides 658-684 of SEQ ID NO: 93 and the amino acid sequences are amino acids 220-228.

(SEQ ID NO: 92)
MKKIWLALAGLVLAFSASAGDQGPVGRTGEVGAVGPPGFAGEKGPSGEA

GTAGPPGTPGPQGLLGAPGILGLPGSRGERGLPGVAGAVGEPGPLGIAG

PPGARGPPGAVGSPGVNGAPGEAGRDGNPGNDGPPGRDGQPGHKGERGY

PGNIGPVGAAGAPGPHGPVGPAGKHGNRGETGPSGPVGPAGAVGPRGPS

GPQGIRGDKGEPGEKGPRGLPGLGDYKDDDDK

The nucleic acid sequence of truncated human collagen type 1 alpha 2 truncation 5 with DsbA secretion and FLAG tag is disclosed in SEQ ID NO: 93.

(SEQ ID NO: 93)
ATGAAAAAGATTTGGCTGGCGCTGGCTGGTTTAGTTTTAGCGTTTAGCG

CATCGGCGGGTGATCAGGGTCCGGTTGGTCGTACCGGTGAAGTTGGTGC

AGTCGGGCCGCCGGGTTTTGCGGGTGAAAAAGGCCCGTCAGGTGAAGC

AGGCACCGCTGGCCCTCCTGGCACGCCTGGCCCACAGGGTTTACTGGGC

GCACCTGGAATTCTGGGACTGCCGGGCAGCCGTGGAGAACGCGGTTTAC

CAGGTGTTGCCGGTGCCGTTGGTGAACCTGGTCCACTGGGCATTGCAGG

GCCGCCTGGCGCACGGGGACCGCCTGGTGCTGTTGGTAGTCCGGGTGTG

AATGGTGCTCCGGGTGAAGCCGGTCGTGACGGTAATCCGGGAAATGACG

GCCCGCCAGGCCGCGATGGTCAGCCGGGTCATAAAGGTGAGCGTGGTTA

CCCAGGTAATATTGGTCCAGTCGGTGCCGCCGGTGCGCCGGGTCCTCAT

GGCCCTGTCGGTCCAGCCGGTAAACATGGTAATCGCGGTGAGACAGGTC

-continued
CGTCAGGACCAGTGGGCCCTGCTGGCGCAGTCGGTCCGCGCGGGCCGAG

TGGCCCTCAGGGTATTCGTGGCGATAAAGGGGAACCGGGCGAAAAAGGG

CCGCGGGGTCTGCCAGGCCTGGGTGACTACAAAGACGACGACGACAAAt aa

The polynucleotide of SEQ ID NO: 93 was subcloned into vector pET28a, expressed host *E. coli* cells and the truncated collagen was purified as described herein. The purified collagen produced a clear band on SDS-PAGE and an anti-FLAG western was observed at around 100 kilodaltons. There were no existing bands that appear at that location on the gel in the absence of expression of this protein.

Truncated Human Collagen Type 1 Alpha 2 Truncation 6 with DsbA Secretion and FLAG Tag The amino acid sequence of truncated human collagen type 1 alpha 2 truncation 6 with DsbA secretion and FLAG tag is disclosed in SEQ ID NO: 94. The DsbA secretion tag is encoded by nucleotides 1-57 of SEQ ID NO: 95 and the amino acid sequences are amino acids 1-19 of SEQ ID NO: 94. The collagen nucleotide sequences are nucleotides 58-657 of SEQ ID NO: 95 and the amino acid sequences are amino acids 20-219 of SEQ ID NO: 94. The FLAG nucleotide sequences are nucleotides 658-684 of SEQ ID NO: 95 and the amino acid sequences are amino acids 220-228 of SEQ ID NO: 94.

(SEQ ID NO: 94)
MKKIWLALAGLVLAFSASAKGHNGLQGLPGIAGHHGDQGAPGSVGPAGP

RGPAGPSGPAGKDGRTGHPGTVGPAGIRGPQGHQGPAGPPGPPGPPGPP

GVSGGGYDFGYDGDFYRADQPRSAPSLRPKDYEVDATLKSLNNQIETLL

TPEGSRKNPARTCRDLRLSHPEWSSGYYWIDPNQGCTMDAIKVYCDFST

GETCIRAQPENIPAKNWYRSSKDGYKDDDDK

The nucleic acid sequence of truncated human collagen type 1 alpha 2 truncation 6 with DsbA secretion and FLAG tag is disclosed in SEQ ID NO: 95.

(SEQ ID NO: 95)
ATGAAAAAGATTTGGCTGGCGCTGGCTGGTTTAGTTTTAGCGTTTAGCG

CATCGGCGAAAGGTCACAATGGACTGCAAGGCCTGCCAGGTATTGCAGG

TCATCATGGTGATCAAGGTGCCCCGGGAAGCGTTGGTCCGGCGGGCCG

AGAGGCCCTGCGGGACCTTCAGGTCCGGCAGGCAAAGATGGTCGGACAG

GCCATCCGGGCACCGTTGGCCCTGCAGGAATTCGTGGACCGCAGGGTCA

TCAGGGACCTGCTGGTCCGCCAGGTCCCCCGGGCCCTCCGGGACCACCG

GGTGTTAGTGGTGGTGGTTATGATTTTGGCTATGATGGTGATTTTATC

GTGCAGATCAGCCGCGTAGCGCACCGAGCCTGCGTCCTAAAGATTATGA

AGTTGATGCAACCCTGAAAAGCCTGAATAATCAGATTGAAACACTGCTG

ACACCGGAAGGTAGCCGTAAAAATCCGGCCCGTACCTGTCGTGATCTGC

GTCTGAGCCACCCGGAATGGAGCAGCGGTTATTATTGGATTGATCCGAA

-continued
TCAAGGTTGTACCATGGATGCAATTAAAGTTTATTGTGATTTTAGCACA

GGTGAAACATGTATCCGTGCACAGCCGGAAAATATTCCGGCCAAAAATT

GGTATCGTAGTAGCAAAGATGGTGACTACAAAGACGACGACGACAAAta a

The polynucleotide of SEQ ID NO: 94 was subcloned into vector pET28a, expressed host *E. coli* cells and the truncated collagen was purified as described herein. The purified collagen produced a clear band on SDS-PAGE and an anti-FLAG western was observed at around 25 kilodaltons. There were no existing bands that appear at that location on the gel in the absence of expression of this protein.

Truncated Human Collagen Type 1 Alpha 2 Truncation 7 with DsbA Secretion and FLAG Tag The amino acid sequence of truncated human collagen type 1 alpha 2 truncation 7 with DsbA secretion and FLAG tag is disclosed in SEQ ID NO: 96. The DsbA secretion tag is encoded by nucleotides 1-57 of SEQ ID NO: 97 and the amino acid sequences are amino acids 1-19 of SEQ ID NO: 96. The collagen nucleotide sequences are nucleotides 58-759 of SEQ ID NO: 96 and the amino acid sequences are amino acids 20-253 of SEQ ID NO: 96. The FLAG nucleotide sequences are nucleotides 760-786 of SEQ ID NO: 97 and the amino acid sequences are amino acids 254-262 of SEQ ID NO: 96.

(SEQ ID NO: 96)
MKKIWLALAGLVLAFSASAYEVDATLKSLNNQIETLLTPEGSRKNPART

CRDLRLSHPEWSSGYYWIDPNQGCTMDAIKVYCDFSTGETCIRAQPENI

PAKNWYRSSKDKKHVWLGETINAGSQFEYNVEGVTSKEMATQLAFMRLL

ANYASQNITYHCKNSIAYMDEETGNLKKAVILQGSNDVELVAEGNSRFT

YTVLVDGCSKKTNEWGKTIIEYKTNKPSRLPFLDIAPLDIGGADQEFFV

DIGPVCFKGDYKDDDDK

The nucleic acid sequence of truncated human collagen type 1 alpha 2 truncation 7 with DsbA secretion and FLAG tag is disclosed in SEQ ID NO: 97.

(SEQ ID NO: 97)
TGAAAAAGATTTGGCTGGCGCTGGCTGGTTTAGTTTTAGCGTTTAGCGCA

TCGGCGTATGAAGTTGATGCAACCCTGAAAAGCCTGAATAATCAGATTGA

AACACTGCTGACACCGGAAGGTAGCCGTAAAAATCCGGCCCGTACCTGTC

GTGATCTGCGTCTGAGCCACCCGGAATGGAGCAGCGGTTATTATTGGATT

GATCCGAATCAAGGTTGTACCATGGATGCAATTAAAGTTTATTGTGATTT

TAGCACAGGTGAAACATGTATCCGTGCACAGCCGGAAAATATTCCGGCCA

AAAATTGGTATCGTAGTAGCAAAGATAAAAAACATGTGTGGCTGGGTGAA

ACCATTAATGCAGGTAGCCAGTTTGAATACAATGTTGAAGGTGTTACCAG

CAAAGAAATGGCAACACAGCTGGCATTTATGCGTCTGCTGGCAAATTATG

CAAGCCAGAATATTACATATCATTGTAAAAATAGCATTGCATATATGGAT

GAAGAAACCGGTAATCTGAAAAAAGCAGTTATTCTGCAGGGTAGCAATGA

TGTTGAACTGGTTGCCGAAGGTAATAGCCGTTTTACATATACCGTTCTGG

TTGATGGTTGTAGCAAAAAAACCAATGAATGGGGTAAAACCATCATTGAA

-continued

TATAAAACCAACAAACCGAGCCGTCTGCCGTTTCTGGATATCGCTCCGCT

GGATATTGGTGGTGCCGATCAGGAATTTTTTGTCGATATCGGTCCTGTGT

GTTTTAAAGGTGACTACAAAGACGACGACGACAAAtaa

The polynucleotide of SEQ ID NO: 97 was subcloned into vector pET28a, expressed host *E. coli* cells and the truncated collagen was purified as described herein. The purified collagen produced a clear band on SDS-PAGE and an anti-FLAG western was observed at around 30 kilodaltons. There were no existing bands that appear at that location on the gel in the absence of expression of this protein.

Example 10: Protective Effect of Truncated Human Collagen on Fibroblasts

The effect of truncated human collagen on fibroblast cell viability, procollagen synthesis, and elastin Synthesis is determined according to the methods of Example 6.

The effect of truncated human collagen on Keratinocyte proliferation and UVB protection is determined according to the methods of Example 7.

The effect of truncated collagen on thymine dimer formation after exposure to UV radiation is determined according to the methods of Example 8.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Example 11: Effect of Truncated Collagen on Inflammatory Cytokines

Keratinocytes and dermal fibroblasts play an important role in the immune response of the skin. In response to irritating chemicals or UV radiation (pro-inflammatory/pro-irriation stimuli), keratinocytes can release a vast array of cytokines. These cytokines are thought to help engage immune cells to the site of inflammation. Cytokines released by the keratinocytes include TNFα, IL-1α, IL-1β, IL-3, IL-6, IL-7, IL-8, IL-10, IL-18, and IL-1RA.

The testing model used for this study was the MatTek EPIDERM®. This skin model consists of normal human-derived epidermal keratinocytes that have been cultured to form a multilayered, highly differentiated model of the human epidermis. Ultrastructural analysis has revealed the presence of keratohyalin granules, tonofilament bundles, desmosomes, and a multi-layered stratum corneum containing intercellular lamellar lipid layers arranged in patterns characteristic of in vivo epidermis. Markers of mature epidermis specific differentiation such as pro-filaggrin, the K1/K10 cytokeratin pair, involucrin, and type I epidermal transglutaminase have been localized in this model. The MatTek EPIDERM® is also mitotically and metabolically active.

The MatTek EPIDERMA® tissues were used to assess the ability of various test materials to inhibit the release of the inflammatory mediator IL-1α. Test materials were compared to an over the counter topical hydrocortisone preparation (positive control) as well as to untreated tissues (negative control 1) and untreated, non-inflamed tissues (negative control 2). This test was also used to assess the viability of the tissues after exposure to the test materials.

IL-1α, IL-6 and IL-8 are synthesized and stored in keratinocytes and have been identified as a mediators of skin irritation and inflammation. Release of these cytokines can be directly measured in tissue culture media via a colorimetric based enzyme linked immunosorbent assay (ELISA). Briefly, antibodies covalently linked to a solid support will bind IL-1α, IL-6 or IL-8 present in spent culture media samples. A second antibody that is covalently attached to an acetylcholinesterase enzyme will in turn detect the specific bound cytokines. Upon addition of an appropriate color substrate the acetylcholinesterase enzyme will generate a colored end product that can be measured spectrophotometrically.

MatTek EPIDERM® Tissues were purchased from MatTek corporation and were stored at 4° C. until used. Prior to use, the tissues to be used were removed from the agarose-shipping tray and placed into a 6-well plate containing 0.9 ml of hydrocortisone free assay medium (37±2° C.). The tissues were allowed to incubate overnight at 37±2° C. and 5±1% CO2. After this initial incubation, the assay medium was replaced with 0.9 ml of fresh hydrocortisone free medium (37±2° C.). Three tissues were prepared for each test material.

An inflammatory response in the tissues was initiated via UV irradiation (UVB). A UV lamp was used to give a 300 mJ/cm$^2$ dose of UVB radiation to the tissues. Immediately after the application of the inflammatory stimuli 50 μl or mg of test material was applied directly onto the surface of the tissue. An over the counter hydrocortisone cream was used as a positive control. For a negative control tissues were exposed to the inflammatory stimuli but were not treated with any type of anti-inflammatory material. One additional set of tissues was left without exposure to the inflammatory stimuli to provide a baseline measurement for the cytokines. The tissues were incubated at 37±2° C. and 5±1% CO2 for 24 hours after exposure to the inflammatory stimuli. After the 24-hour incubation the cell culture medium was collect and stored at −75° C. until analyzed for cytokines.

The ELISA plates were prepared by diluting the appropriate capture antibody in PBS. Next, 100 μl of the diluted capture antibody was added to the wells of a 96-well ELISA plate and the plate was incubated overnight at room temperature. On the following day the plate was washed three times with 300 μl wash buffer (0.05% TWEEN® 20 in PBS) and then blocked by adding 300 μl of blocking buffer (1% BSA in PBS) to each well. The plate was incubated with the blocking buffer for at least one hour. After the incubation the blocking buffer was removed and the plate was washed three times as described above.

A series of standards was prepared and 100 μl of each of these standards was dispensed into two wells (duplicates) in the appropriate 96-well plate. Subsequently, 100 μl of each sample was added to additional wells and the plate was incubated for two hours at room temperature. After the incubation the plate was washed three times as described above. Once the last wash was removed, 100 μl of a biotin conjugated detection antibody was added. After incubating the plate for two hours at room temperature the plate was washed again as described above. 100 μl of HRP-streptavidin was then added to each well and the plate was incubated for 20 minutes at room temperature. Once the last wash was removed, 100 μl of substrate solution (hydrogen peroxide+ tetramethylbenzidine as a chromagen) was added to each well. Once a sufficient level of color development had occurred, 50 µl of stop solution (2N sulfuric acid) was added to each well and the plate was read at 460 nm.

After the 24 hour incubation, the tissues were rinsed twice with at least 100 µl of phosphate buffered saline to remove the test material and then transferred to a 6-well plate containing 1.0 ml of assay medium supplemented with MTT (1 mg/ml) and allowed to incubate for 3±0.25 hours at 37±2° C. and 5±1% CO2. After the incubation, the tissues were rinsed at least twice with 100 µl of phosphate buffered saline, blotted dry, and then placed into a 24-well plate containing 2 ml of isopropanol per well. The 24-well plate was covered and allowed to incubate at room temperature for at least 2 hours on a rocking platform to extract the reduced MTT from the tissues. After the extraction, a 200 µl sample of the isopropanol/MTT mixture was transferred to a 96-well plate and the absorbance of the sample was read at 540 nm with a plate reader using 200 µl of isopropanol as the blank. The MTT assay is described in Example 6 herein. The cell viability results of the MTT assay were similar to the results obtained in Example 6

The results of the IL-1a assay are shown in Table 9 below. A 2% stock solution of the jellyfish collagen of SEQ ID NO: 91 is Sample 4 and Sample 3 is a 2% stock solution of the truncated jellyfish collagen of SEQ ID NO: 10. In Table 9 below, the indicated percentage is the percent dilution of the stock solution used for the test. For example, the 1% Sample 4 treatment is a 1% solution of the 2% stock truncated collagen solution. The untreated cells produced 18.2 pg/ml of Il-1a. Upon treatment with truncated collagen, all samples showed decreases in Il-1a production. The 1% Sample 4 treatment reduced IL-1A production to 13.4 pg/ml, which is significant with a p value of less than 0.05. The decrease in IL-1a production indicates that the truncated collagen has anti-inflammatory effects.

TABLE 9

Il-1a Assay

| Treatment | Il-1a pg/ml |
|---|---|
| Non-UVB Exposed | 4.9 ± 2.1 |
| Untreated | 18.2 ± 1.4 |
| 1% Hydrocortisone | 6.7 ± 0.6 |
| 5% Sample 4 | 18.1 ± 1.1 |
| 1% Sample 4 | 13.4 ± 0.9* |
| 0.5% Sample 4 | 15.7 ± 0.7 |
| 0.1% Sample 4 | 13.9 ± 1.7* |
| 5% Sample 3 | 15.8 ± 2.0 |

Denotes values that are significantly different from Untreated (p < 0.05)

Example 11: Urban Dust Protection by Truncated Collagen

A keratinocyte cell culture model was used to assess the ability of truncated collagens to exert a protective effect by promoting cell survival after exposure to urban dust.

Human epidermal keratinocytes were pretreated with the test materials and then exposed to urban dust. At the end of the treatment period changes in cell viability were then determined via an MTT assay.

Keratinocytes were seeded into the individual wells of a 96 well plate in 100 µl of medium and incubated overnight at 37±2° C. and 5±1% CO2 On the following day the media was removed via aspiration to eliminate any non-adherent cells and replaced with 100 µL of fresh medium. The cells were grown until confluent, with a media change every 48 to 72 hours.

Pretreatment with Test Material Followed by Urban Dust Treatment

Test materials were prepared at 2× their final desired concentrations in cell culture media. Urban dust (NIST 1649B from Sigma Chemicals) was also prepared at 2× solutions. For the pretreatment, 50 µl of 2× test material was combined with 50 µl of culture media and the cells were incubated for 24 hours. At the end of the pretreatment period the test material containing culture media was removed and replaced with 50 µl of 2× urban dust and 50 µl of media. Another set of cells was treated with media alone (non-dust exposed) and used as a reference control to represent 100% cell viability. The cells were then incubated for 24 hours and then subjected to an MTT assay to determine changes in cell viability.

At the end of the treatment period, the cell culture medium was removed and the cells were washed with PBS. After the wash, 100 µl of cell culture media supplemented with 0.5 mg/ml MTT was added to each well and the cells were incubated for 30 minutes at 37+2° C. and 5+1% CO2. After the incubation, the media/MTT solution was removed and the cells were washed again once with PBS and then 100 µl of isopropyl alcohol was added to the wells to extract the purple formazin crystals. The 96-well plate was then read at 540 nm using isopropyl alcohol as a blank.

The mean MTT absorbance value for the non-dust exposed cells was calculated and used to represent 100% value for cell number. The individual MTT values from the cells undergoing the various treatments was then divided by the mean value for the non-dust exposed cells and expressed as a percent to determine the change in cell number caused by each treatment.

The MTT results for the pretreatment with the test material then dust treatments are presented in Table 10. Table 10 shows that as the cells were treated with increasing amounts of collagen, cell viability increased upon pretreatment with truncated collagen and subsequent exposure to urban dust. These results show that truncated collagen protects against the decline in cell viability associated with urban dust exposure.

TABLE 10

MTT Assay, Truncated Collagen Pretreatment

| Treatment | Viability (% Non-Dust Exposed) 4 mg/ml Urban Dust | Viability (% Non-Dust Exposed) 2 mg/ml Urban Dust |
|---|---|---|
| Non-Dust Exposed | 100 ± 4.4* | 100 ± 1.8 |
| Untreated | 59 ± 3.8 | 70 ± 0.9 |
| 0.1% Collagen | 61 ± 4.7 | 72 ± 3.5 |
| 0.5% Collagen | 59 ± 2.2 | 73 ± 2.2 |
| 1% Collagen | 58 ± 0.5 | 74 ± 2.6 |
| 5% Collagen | 66 ± 1.0 | 83 ± 6.5* |

*Denotes values that are significantly different from untreated group (p < 0.05)

Example 12: Truncated *Chondrosia reniformis* (Kidney Sponge) Collagen

Truncated *Chondrosia reniformis* (Kidney Sponge) Fibrillar Collagen 1 with DsbA Secretion and FLAG Tag The amino acid sequence of truncated *Chondrosia reniformis* fibrillar collagen 1 with DsbA secretion and FLAG tag is disclosed in SEQ ID NO: 102. The DsbA secretion tag is encoded by nucleotides 1-57 of SEQ ID NO: 103 and the amino acid sequences are amino acids 1-19 of SEQ ID NO:

102. The fibrillary collagen nucleotide sequences are nucleotides 58-792 of SEQ ID NO: 103 and the amino acid sequences are amino acids 20-264 of SEQ ID NO: 102. The FLAG nucleotide sequences are nucleotides 793-819 of SEQ ID NO: 103 and the amino acid sequences are amino acids 265-273 of SEQ ID NO: 102.

(SEQ ID NO: 102)
MKKIWLALAGLVLAFSASAPVGRRGPKGSRGDPGDGGAAGPKGPEGVDGL

IGEPGQPGPIGAEGSSGLEGFLGDKGSKGARGGPGNRGRPGQDGVPGQDG

RAGEKGEGGETGDRGQQGLRGKVGDPGLVGDLGAQGPQGSQGLVGPPGIP

GEPGSGGEPGDQGPRGPEGPQGSPGVRGGRGERGTPGAVGPKGPPGKNGA

DGPRGLPGASGPPGSPGNQGPEGSRGADGNNGFPGDDGENGLVGIPGEPG

PKGARGTRGELGKTGDYKDDDDK

The nucleic acid sequence of truncated *Chondrosia reniformis* fibrillar collagen 1 with DsbA secretion and FLAG tag is disclosed in SEQ ID NO: 103.

(SEQ ID NO: 103)
ATGAAAAAGATTTGGCTGGCGCTGGCTGGTTTAGTTTTAGCGTTTAGCGC

ATCGGCGCCGGTTGGTCGTCGTGGTCCGAAAGGTAGCCGTGGTGATCCTG

GTGATGGTGGTGCAGCAGGTCCTAAAGGTCCGGAAGGTGTTGATGGTCTG

ATTGGTGAACCGGGTCAGCCTGGTCCGATTGGCGCAGAAGGTAGCAGCGG

TCTGGAAGGTTTTCTGGGTGATAAAGGTAGCAAAGGTGCACGTGGTGGTC

CGGGTAATCGCGGTCGTCCTGGTCAGGATGGTGTTCCGGGTCAAGATGGT

CGTGCCGGTGAAAAAGGTGAAGGTGGTGAAACCGGTGATCGCGGTCAGCA

GGGTCTGCGTGGTAAAGTTGGTGATCCAGGTCTGGTGGGTGATCTGGGTG

CACAGGGTCCGCAGGGTAGCCAAGGTCTGGTTGGTCCGCCTGGTATTCCG

GGTGAACCTGGTAGCGGTGGCGAACCGGGTGATCAGGGTCCTCGCGGTCC

AGAAGGTCCTCAGGGTTCACCGGGTGTTCGCGGTGGTCGTGGTAACGTG

GTACACCGGGTGCAGTTGGACCGAAAGGTCCGCCAGGTAAAAATGGTGCA

GATGGTCCGCGTGGTCTGCCTGGTGCAAGCGGTCCTCCGGGTAGTCCTGG

TAACCAGGGTCCTGAAGGTTCTCGTGGTGCCGATGGTAATAATGGTTTTC

CAGGTGATGATGGTGAAAATGGCCTGGTTGGTATCCCTGGCGAACCAGGT

CCAAAAGGCGCACGCGGTACACGCGGTGAACTGGGTAAAACCGGTGACTA

CAAAGACGACGACGACAAAtaa

The polynucleotide of SEQ ID NO: 103 was subcloned into vector pET28a, expressed host *E. coli* cells and the truncated *Chondrosia reniformis* fibrillar collagen 1was purified as described herein. The purified fibrillar collagen produced a clear band on SDS-PAGE and an anti-FLAG western was observed at around 40 kilodaltons. There were no existing bands that appear at that location on the gel in the absence of expression of this protein.

Truncated *Chondrosia reniformis* (Kidney Sponge) Fibrillar Collagen 2 with DsbA Secretion and FLAG Tag The amino acid sequence of truncated *Chondrosia reniformis* fibrillar collagen 2 with DsbA secretion and FLAG tag is disclosed in SEQ ID NO: 104. The DsbA secretion tag is encoded by nucleotides 1-57 of SEQ ID NO: 105 and the amino acid sequences are amino acids 1-19 of SEQ ID NO: 104. The fibrillary collagen nucleotide sequences are nucleotides 58-1323 of SEQ ID NO: 105 and the amino acid sequences are amino acids 20-441 of SEQ ID NO: 104. The FLAG nucleotide sequences are nucleotides 1324-1350 of SEQ ID NO: 105 and the amino acid sequences are amino acids 442-450 of SEQ ID NO: 105.

(SEQ ID NO: 104)
MKKIWLALAGLVLAFSASAGRGGPAGLQGAAGNPGDPGDRGQAGEIGLPG

TEGQRGQGGSRGDDGIGGQSGTDGDPGNDGVAGIRGARGEPGATGPEGAA

GQKGDRGRFGEQGRPGNDGPPGRRGRVGNLGETGAEGDEGTRGYTGDRGP

EGAIGISGVTGNPGPQGIKGPPGDTGHPGRQGPSGPQGPPGIPGTDGLTI

HNLIKPPSQFFDATSSSDPLTDAVVESILKSFQYAELEIDLTKKPDGTMK

YPAISCDDLHKDYPQLPSGNYTLDPNGGCKNDAFETYCEFNNSVKMCLTP

KIPTLLPMGTYKYYVNSEGYYSPNDFGLNLRFFEYYGSVTQLKFLQTKAT

RVTQTIRVLCKNYDPLHKQPVFIGMNDETVMDEPRMEENQCQYFNGLSAH

VELELSSNDPSYLPIYEMRLYLGRKTNEELGIELGDLCFEYGDYKDDDDK

The nucleic acid sequence of truncated *Chondrosia reniformis* fibrillar collagen 2 with DsbA secretion and FLAG tag is disclosed in SEQ ID NO: 105.

(SEQ ID NO: 105)
ATGAAAAAGATTTGGCTGGCGCTGGCTGGTTTAGTTTTAGCGTTTAGCGC

ATCGGCGGGTCGTGGCGGTCCGGCAGGTCTGCAGGGTGCTGCAGGTAATC

CTGGCGACCCTGGCGATCGTGGTCAGGCAGGCGAATTGGTCTGCCAGGC

ACCGAAGGTCAGCGTGGTCAAGGTGGTTCACGTGGTGATGACGGTATTGG

TGGTCAGAGCGGCACCGATGGCGATCCGGGTAACGATGGTGTTGCAGGTA

TTCGTGGTGCACGCGGAGAACCTGGTGCCACCGGACCTGAAGGTGCAGCC

GGTCAGAAAGGTGATCGTGGCCGTTTTGGCGAACAGGGTCGTCCGGGAAA

TGATGGTCCACCGGGTCGCCGTGGCCGTGTGGGCAATCTGGGTGAAACAG

GTGCCGAAGGTGATGAAGGCACCCGTGGTTATACAGGTGACCGTGGACCG

GAAGGCGCAATTGGTATTAGCGGTGTGACCGGTAATCCGGGTCCACAGGG

CATTAAAGGCCCTCCGGGTGATACGGGTCATCCGGGTCGTCAGGGACCGA

GCGGTCCGCAAGGACCACCGGGTATTCCAGGTACAGATGGCCTGACCATT

CATAATCTGATTAAACCGCCTAGCCAGTTTTTTGATGCAACCAGCAGCAG

CGATCCGCTGACCGATGCAGTTGTTGAAAGCATTCTGAAATCTTTTCAGT

ATGCCGAGCTGGAAATTGACCTGACCAAAAAACCGGATGGCACCATGAAA

TATCCGGCAATTAGCTGTGATGATCTGCACAAAGATTATCCGCAGCTGCC

GAGCGGTAATTATACCCTGGATCCGAATGGTGGTTGTAAAAATGATGCCT

TTGAAACCTATTGCGAGTTCAACAATAGCGTGAAAATGTGTCTGACCCCG

AAAATTCCGACACTGCTGCCGATGGGCACCTATAAATACTATGTTAATAG

CGAGGGTTACTACAGCCCGAATGATTTTGGTCTGAATCTGCGCTTTTTG

AGTATTATGGTAGCGTTACCCAGCTGAAATTTCTGCAGACCAAAGCAACC

CGTGTTACCCAGACCATTCGTGTTCTGTGTAAAAACTATGATCCGCTGCA

TAAACAGCCGGTTTTTATTGGTATGAATGACGAAACCGTTATGGATGAAC

CGCGTATGGAAGAAAATCAGTGCCAGTATTTTAACGGTCTGAGCGCACAT

```
-continued
GTTGAACTGGAACTGAGCAGCAATGATCCGAGCTATCTGCCGATTTATGA

AATGCGTCTGTATCTGGGTCGTAAAACCAATGAAGAACTGGGCATTGAAC

TGGGCGATCTGTGTTTTGAATATGGTGACTACAAAGACGACGACGACAAA taa
```

The polynucleotide of SEQ ID NO: 105 was subcloned into vector pET28a, expressed host *E. coli* cells and the truncated *Chondrosia reniformis* fibrillar collagen 2 was purified as described herein. The purified fibrillary collagen produced a clear band on SDS-PAGE and an anti-FLAG western was observed at around 55 kilodaltons. There were no existing bands that appear at that location on the gel in the absence of expression of this protein.

Truncated *Chondrosia reniformis* (Kidney Sponge) Non-Fibrillar Collagen 1 with DsbA Secretion and FLAG Tag The amino acid sequence of truncated *Chondrosia reniformis* non-fibrillar collagen 1 with DsbA secretion and FLAG tag is disclosed in SEQ ID NO: 106. The DsbA secretion tag is encoded by nucleotides 1-57 of SEQ ID NO: 107 and the amino acid sequences are amino acids 1-19 of SEQ ID NO: 106. The non-fibrillar collagen nucleotide sequences are nucleotides 58-831 of SEQ ID NO: 107 and the amino acid sequences are amino acids 20-277 of SEQ ID NO: 106. The FLAG nucleotide sequences are nucleotides 832-858 of SEQ ID NO: 107 and the amino acid sequences are amino acids 278-286 of SEQ ID NO: 106.

```
                                         (SEQ ID NO: 106)
MKKIWLALAGLVLAFSASAEKTSSKVALMTVLVVITGALIIEGTSITRGS

THVNRGLRKRQTSEDNCEAVKVGLPGRDGREGPPGPPGPAGRDGRDAVCS

NQTTGLGAKGDRGPPGTPGFPGEVGRPGPPGADGIPGPQGERGAVGPGGK

PGPRGEVGTPGADGADGATGATGVQGPDGAKGEKGASGTAGLKGEKGDTC

IPDSNSTLGMPGTPGAGGSKGQKGESGIVGPKGERGEIGTPGHPGFRGAD

GEPGHKGVPGRAGAQGDRGDPGDDGLTGDYKDDDDK
```

The nucleic acid sequence of truncated *Chondrosia reniformis* non-fibrillar collagen 1 with DsbA secretion and FLAG tag is disclosed in SEQ ID NO: 107.

```
                                         (SEQ ID NO: 107)
ATGAAAAAGATTTGGCTGGCGCTGGCTGGTTTAGTTTTAGCGTTTAGCGC

ATCGGCGGAAAAAACCAGCAGCAAAGTTGCACTGATGACCGTTCTGGTTG

TTATTACCGGTGCACTGATTATTGAAGGCACCAGCATTACCCGTGGTAGC

ACCCATGTTAATCGTGGTCTGCGTAAACGTCAGACCAGCGAAGATAATTG

TGAAGCAGTTAAAGTTGGTCTGCCAGGTCGTGATGGTCGTGAAGGTCCTC

CGGGTCCGCCTGGTCCGGCTGGCAGAGATGGCCGTGATGCAGTTTGTAGC

AATCAGACCACCGGTCTGGGTGCAAAAGGTGATCGTGGTCCGCCAGGTAC

ACCGGGTTTTCCGGGTGAAGTTGGCCGTCCGGGTCCACCGGGTGCAGATG

GTATTCCGGGTCCTCAGGGTGAACGTGGTGCAGTTGGTCCTGGTGGTAAA

CCTGGTCCGCGTGGTGAAGTGGGCACCCCTGGTGCCGATGGCGCAGATGG

TGCAACCGGTGCGACCGGTGTTCAGGGTCCTGATGGTGCCAAAGGCGAAA

AAGGTGCAAGCGGCACCGCAGGTCTGAAAGGTGAGAAAGGCGATACCTGT
```

```
-continued
ATTCCGGATAGCAATAGCACCCTGGGTATGCCTGGTACACCAGGTGCCGG

TGGTAGCAAAGGCCAGAAAGGTGAAAGTGGTATTGTTGGTCCGAAAGGCG

AACGCGGTGAAATTGGCACACCGGGTCATCCTGGTTTTCGTGGTGCGGAT

GGTGAACCAGGTCATAAAGGTGTTCCGGGTCGTGCCGGTGCGCAGGGTGA

TCGCGGTGATCCGGGTGATGATGGTCTGACCGGTGACTACAAAGACGACG

ACGACAAAtaa
```

The polynucleotide of SEQ ID NO: 107 was subcloned into vector pET28a, expressed host *E. coli* cells and the truncated *Chondrosia reniformis* non-fibrillar collagen 1 was purified as described herein. The purified non-fibrillar collagen produced a clear band on SDS-PAGE and an anti-FLAG western was observed at around 30 kilodaltons. There were no existing bands that appear at that location on the gel in the absence of expression of this protein.

Truncated *Chondrosia reniformis* (Kidney Sponge) Non Fibrillar Collagen 2 with DsbA Secretion and FLAG Tag The amino acid sequence of truncated *Chondrosia reniformis* non-fibrillar collagen 2 with DsbA secretion and FLAG tag is disclosed in SEQ ID NO: 108. The DsbA secretion tag is encoded by nucleotides 1-57 of SEQ ID NO: 109 and the amino acid sequences are amino acids 1-19 of SEQ ID NO: 108. The non-fibrillar collagen nucleotide sequences are nucleotides 58-1509 of SEQ ID NO: 109 and the amino acid sequences are amino acids 20-503 of SEQ ID NO: 108. The FLAG nucleotide sequences are nucleotides 1510-1536 of SEQ ID NO: 109 and the amino acid sequences are amino acids 504-512 of SEQ ID NO: 108.

```
                                         (SEQ ID NO: 108)
MKKIWLALAGLVLAFSASAGFPGAPGADGAPGQKGELGAVGPQGTPGLSG

PSGPTGPPGPKGVRGAPGSSGAKGDAGNPGDDGPVGPQGVPGVDGSPGQK

GETGRVGPRGHDGINGTPGEDGATGFPGPDGAKGEKGTSGTAGLKGEKGD

TCIPDSNSTLGMPGTPGAGWSKGQKGESGIVGPKGEKGEIGTPGPPGFRG

ADGEPGQRGEPGRAGAQGERGAPGNNGRDGFPGDPGADGAPGQKGELGAI

GHPGFSGPSGPSGPTGPPGPKGVRGAQGRPGDRGSPGDVGPIGAPGPPGA

DGVPGLTGVQGRDGPKGESASSGAVYVRWGRTTCPSGADVVYSGRAAGAK

YDHSGGTSDHHCLPNNPQYLSEDDTNALGAQLYGVEYEIRDRSSPYNSLD

QSDMPCVVCNANGRSQLLMVPARYTCPTGWSREYYGYMMSEGKAKNREGR

KTTICMDFSAEAVPGSGANTNPSPGIMMRANCNGLACPPYQSNTPLTCAV

CTKGDYKDDDDK
```

The nucleic acid sequence of truncated *Chondrosia reniformis* non-fibrillar collagen 2 with DsbA secretion and FLAG tag is disclosed in SEQ ID NO: 109.

```
                                         (SEQ ID NO: 109)
ATGAAAAAGATTTGGCTGGCGCTGGCTGGTTTAGTTTTAGCGTTTAGCGC

ATCGGCGGGTTTTCCTGGCGCTCCGGGTGCCGACGGTGCTCCGGGTCAAA

AAGGTGAACTGGGTGCCGTGGGTCCGCAGGGCACTCCGGGTCTGAGTGGT

CCTAGTGGTCCGACCGGTCCACCAGGTCCAAAAGGCGTGCGTGGTGCACC

GGGTAGCAGCGGAGCCAAAGGTGATGCAGGTAACCCTGGTGATGACGGTC
```

-continued
CGGTTGGTCCACAGGGCGTTCCAGGTGTTGATGGTAGCCCTGGCCAAAAG

GGTGAAACCGGTCGTGTGGGTCCTCGTGGTCATGATGGTATTAATGGCAC

CCCAGGTGAAGATGGTGCGACAGGCTTTCCAGGTCCGGATGGCGCAAAGG

GTGAGAAGGGCACCAGCGGTACAGCTGGCCTGAAGGGCGAAAAGGGCGAT

ACATGCATCCCGGATTCAAATTCAACACTGGGCATGCCAGGTACGCCTGG

CGCAGGTTGGAGTAAAGGACAAAAAGGCGAATCAGGCATTGTGGGACCTA

AAGGCGAGAAGGGTGAGATTGGTACTCCGGGACCGCCAGGCTTTCGCGGT

GCAGACGGCGAACCGGGTCAGCGTGGCGAACCTGGTCGTGCAGGCGCACA

AGGTGAACGCGGAGCCCCTGGTAATAATGGACGTGATGGCTTTCCTGGTG

ATCCAGGTGCAGATGGCGCACCTGGCCAGAAAGGCGAACTGGGAGCAATT

GGTCATCCGGGATTTAGCGGTCCGTCAGGTCCGAGCGGACCGACAGGTCC

TCCTGGACCGAAAGGTGTACGTGGCGCACAGGGTCGTCCTGGCGATCGTG

GCAGTCCAGGTGATGTGGGTCCGATTGGTGCACCTGGTCCTCCAGGTGCG

GACGGCGTGCCTGGTTTAACAGGTGTGCAGGGTCGCGACGGTCCTAAAGG

TGAATCAGCAAGCAGCGGTGCAGTTTATGTTCGTTGGGGTCGTACCACCT

GTCCTAGCGGAGCAGATGTTGTTTATAGCGGTCGCGCAGCCGGTGCAAAA

TATGATCATTCAGGTGGCACCTCAGATCATCATTGTCTGCCGAATAATCC

GCAGTATCTGAGCGAAGATGATACCAATGCACTGGGTGCACAGCTGTATG

GTGTGGAATATGAAATTCGTGATCGTAGCAGCCCGTATAATAGCCTGGAT

CAGAGCGATATGCCGTGTGTTGTTTGTAATGCAAATGGTCGTAGCCAGCT

GCTGATGGTTCCGGCACGTTATACATGCCCGACCGGTTGGAGCCGTGAAT

ATTATGGTTATATGATGAGCGAAGGCAAAGCCAAAAATCGCGAAGGTCGT

AAAACCACCATTTGTATGGATTTTAGCGCAGAAGCAGTTCCTGGTAGCGG

TGCAAATACCAATCCGAGTCCGGGTATTATGATGCGTGCAAATTGTAATG

GTCTGGCATGTCCGCCTTATCAGAGCAATACACCGCTGACCTGTGCCGTT

TGTACCAAAGGTGACTACAAAGACGACGACGACAAAtaa

The polynucleotide of SEQ ID NO: 109 was subcloned into vector pET28a, expressed host *E. coli* cells and the truncated *Chondrosia reniformis* non-fibrillar collagen 2 was purified as described herein. The purified fibrillary collagen produced a clear band on SDS-PAGE and an anti-FLAG western was observed at around 60 kilodaltons. There were no existing bands that appear at that location on the gel in the absence of expression of this protein.

Example 13: Truncated *Rhincodon typus* (Whale Shark) Collagen

Truncated *Rhincodon typus* (Whale Shark) Collagen Type 1 Alpha 1 Truncation 1 with DsbA Secretion and FLAG Tag The amino acid sequence of truncated *Rhincodon typus* collagen type1 truncation 1 with DsbA secretion and FLAG tag is disclosed in SEQ ID NO: 110. The DsbA secretion tag is encoded by nucleotides 1-57 of SEQ ID NO: 111 and the amino acid sequences are amino acids 1-19 of SEQ ID NO: 110. The collagen nucleotide sequences are nucleotides 58-630 of SEQ ID NO: 111 and the amino acid sequences are amino acids 20-210 of SEQ ID NO: 110. The FLAG nucleotide sequences are nucleotides 631-657 of SEQ ID NO: 111 and the amino acid sequences are amino acids 211-219 of SEQ ID NO: 110.

(SEQ ID NO: 110)
MKKIWLALAGLVLAFSASAGPAGAKGPSGDIGRPGESGSPGARGHSGQPG

RTGIAGNQGLPGTAGEEGRTGPPGPAGLRGQAGMMGFPGPKGAAGLPGKP

GDRGNVGLAGPRGAPGKDGEVGAQGPPGVAGPTGPRGETGLAGSVGFQGM

PGPSGAAGEPGKPGNQGLRGDAGSPGMIGPRGERGLPGERGASGAQGLLG

PRGTSGAPGLGDYKDDDDK

The nucleic acid sequence of truncated *Rhincodon typus* collagen type1 truncation 1 with DsbA secretion and FLAG tag is disclosed in SEQ ID NO: 111.

(SEQ ID NO: 111)
ATGAAAAAGATTTGGCTGGCGCTGGCTGGTTTAGTTTTAGCGTTTAGCGC

ATCGGCGGGTCCGGCAGGCGCAAAAGGTCCGAGCGGTGATATTGGTCGTC

CGGGTGAAAGCGGTAGTCCGGGTGCACGTGGTCATAGCGGTCAGCCTGGT

CGTACCGGTATTGCAGGTAATCAGGGTCTGCCTGGTACAGCCGGTGAAGA

AGGTCGCACCGGTCCGCCAGGTCCTGCAGGTCTGCGTGGTCAGGCAGGTA

TGATGGGTTTTCCGGGTCCGAAAGGTGCAGCGGGTCTGCCAGGCAAACCG

GGTGATCGTGGTAATGTTGGTCTGGCTGGTCCGCGTGGTGCACCGGGTAA

AGATGGTGAAGTTGGTGCACAGGGTCCTCCGGGTGTTGCAGGTCCGACCG

GTCCTCGTGGTGAAACCGGTCTGGCAGGTAGCGTTGGTTTTCAGGGTATG

CCAGGTCCGTCAGGTGCAGCAGGCGAACCTGGTAAACCGGGTAACCAGGG

CCTGCGTGGTGATGCCGGTTCACCGGGTATGATTGGTCCACGCGGTGAAC

GTGGCCTGCCTGGCGAACGTGGTGCAAGCGGTGCACAAGGTCTGCTGGGT

CCACGTGGCACCTCAGGCGCACCAGGTCTGGGTGACTACAAAGACGACGA

CGACAAAtaa

The polynucleotide of SEQ ID NO: 111 was subcloned into vector pET28a, expressed host *E. coli* cells and the truncated *Rhincodon typus* collagen type1 truncation 1 was purified as described herein. The purified collagen produced a clear band on SDS-PAGE and an anti-FLAG western was observed at around 25 kilodaltons. There were no existing bands that appear at that location on the gel in the absence of expression of this protein.

Truncated *Rhincodon typus* (Whale Shark) Collagen Type 6 Alpha 1 Truncation 2 with DsbA Secretion and FLAG Tag The amino acid sequence of truncated *Rhincodon typus* collagen type 6 truncation 2 with DsbA secretion and FLAG tag is disclosed in SEQ ID NO: 112. The DsbA secretion tag is encoded by nucleotides 1-57 of SEQ ID NO: 113 and the amino acid sequences are amino acids 1-19 of SEQ ID NO: 112. The collagen nucleotide sequences are nucleotides 58-684 of SEQ ID NO: 113 and the amino acid sequences are amino acids 20-228 of SEQ ID NO: 112. The FLAG nucleotide sequences are nucleotides 685-711 of SEQ ID NO: 113 and the amino acid sequences are amino acids 229-237 of SEQ ID NO: 112.

(SEQ ID NO: 112)
MKKIWLALAGLVLAFSASAQGIPGSAGKEGGKGDPGPLGSPGKPGPDGLR

GFAGARGLPGAAGPPGLKGAEGPMGAPGLTGSTGERGPNGPAGAIGLPGR

PGGPGPPGPVGEKGDPGDKGLPGPAGDDGVQGAMGLPGPIGSQGPPGDYG

-continued

DKGELGKPGQKGSKGDKGESGPPGPIGIQGPIGHPGPIGSDGSPGLRGYL

GMRGQKGDDGIRGLPGSAGPVGLQGLPGGDYKDDDDK

The nucleic acid sequence of truncated *Rhincodon typus* collagen type 6 truncation 2 with DsbA secretion and FLAG tag is disclosed in SEQ ID NO: 113.

(SEQ ID NO: 113)
ATGAAAAAGATTTGGCTGGCGCTGGCTGGTTTAGTTTTAGCGTTTAGCGC

ATCGGCGCAGGGTATTCCGGGTAGCGCAGGTAAAGAAGGTGGTAAAGGCG

ATCCGGGTCCGCTGGGTTCACCGGGTAAACCGGGTCCTGATGGTCTGCGT

GGTTTTGCCGGTGCACGTGGTCTGCCTGGTGCAGCAGGTCCGCCTGGTCT

GAAAGGTGCCGAAGGTCCGATGGGTGCTCCGGGTCTGACCGGTAGCACCG

GTGAACGCGGTCCGAATGGTCCGGCAGGCGCAATTGGTCTGCCAGGTCGT

CCTGGTGGTCCGGGTCCTCCTGGTCCGGTTGGTGAAAAAGGTGATCCTGG

TGATAAAGGCCTGCCTGGTCCTGCCGGTGATGATGGTGTTCAGGGTGCCA

TGGGCTTACCGGGTCCGATTGGTAGCCAGGGTCCTCCGGGTGATTATGGC

GATAAAGGTGAACTGGGTAAACCTGGCCAGAAAGGTAGCAAAGGTGACAA

AGGCGAAAGCGGTCCGCCAGGTCCGATCGGCATTCAGGGTCCTATTGGTC

ATCCAGGTCCAATTGGTTCAGATGGCTCACCGGGACTGCGTGGCTATCTG

GGTATGCGTGGACAGAAAGGTGATGACGGTATTCGTGGCCTGCCAGGTAG

TGCAGGTCCGGTGGGTCTGCAGGGACTGCCTGGTGGTGACTACAAAGACG

ACGACGACAAAtaa

The polynucleotide of SEQ ID NO: 113 was subcloned into vector pET28a, expressed host *E. coli* cells and the truncated *Rhincodon typus* collagen type 6 truncation 2 was purified as described herein. The purified collagen produced a clear band on SDS-PAGE and an anti-FLAG western was observed at around 35 kilodaltons. There were no existing bands that appear at that location on the gel in the absence of expression of this protein.

Truncated *Rhincodon typus* (Whale Shark) Collagen Type 6 Alpha 1 Truncation 3 with DsbA Secretion and FLAG Tag The amino acid sequence of truncated *Rhincodon typus* collagen type 6 alpha 1 truncation 3 with DsbA secretion and FLAG tag is disclosed in SEQ ID NO: 114. The DsbA secretion tag is encoded by nucleotides 1-57 of SEQ ID NO: 115 and the amino acid sequences are amino acids 1-19 of SEQ ID NO: 114. The collagen nucleotide sequences are nucleotides 58-735 of SEQ ID NO: 115 and the amino acid sequences are amino acids 20-245 of SEQ ID NO: 114. The FLAG nucleotide sequences are nucleotides 736-762 of SEQ ID NO: 115 and the amino acid sequences are amino acids 246-254 of SEQ ID NO: 114.

(SEQ ID NO: 114)
MKKIWLALAGLVLAFSASAKGETGEAGDPGTPGEPGIAGPKGDVGDKGDA

GPPGAAGPAGVKGPPGEDGAKGDVGPAGFPGDPGPTGEPGVPGMDGGVGE

KGSLGDPGLTGPRGASGEPGPPGSPGKRGPPGPAGPEGREGLKGSKGSPG

QEGPVGRTGPIGPQGSPGNVGPKGLRGIPGPTGEQGLLGPPGQAGPPGPM

GPPGMPGLRGAQGLKGDKGHVGLIGLIGPPGEMGEKGDQGLPGIQGDYKD

DDDK

The nucleic acid sequence of truncated *Rhincodon typus* collagen type 6 alpha 1 truncation 3 with DsbA secretion and FLAG tag is disclosed in SEQ ID NO: 115.

(SEQ ID NO: 115)
ATGAAAAAGATTTGGCTGGCGCTGGCTGGTTTAGTTTTAGCGTTTAGCGC

ATCGGCGAAAGGTGAAACCGGTGAAGCGGGTGATCCGGGTACACCGGGTG

AACCTGGTATTGCAGGTCCGAAAGGTGATGTTGGTGATAAAGGTGACGCA

GGTCCGCCTGGTGCAGCAGGTCCGGCAGGCGTTAAAGGTCCTCCGGGTGA

AGATGGTGCAAAAGGCGACGTTGGTCCTGCAGGTTTTCCTGGCGATCCGG

GTCCGACTGGTGAACCGGGTGTGCCAGGTATGGATGGTGGTGTGGGTGAA

AAAGGTAGCCTGGGTGATCCTGGTCTGACCGGTCCGCGTGGCGCAAGTGG

TGAACCAGGTCCACCGGGTAGTCCGGGTAAACGTGGTCCTCCTGGACCGG

CTGGTCCGGAAGGTCGTGAAGGTCTGAAAGGTAGCAAAGGTTCACCGGGT

CAAGAAGGTCCGGTTGGTCGTACCGGTCCGATTGGTCCGCAGGGCTCACC

GGGTAATGTTGGTCCTAAAGGTCTGCGTGGTATTCCGGGTCCTACAGGCG

AACAGGGTCTGCTGGGTCCGCCAGGCCAAGCAGGTCCTCCAGGTCCTATG

GGTCCACCTGGTATGCCTGGCCTGCGTGGTGCCCAGGGCCTGAAAGGCGA

TAAAGGCCATGTTGGTCTGATTGGCCTGATTGGTCCACCAGGTGAAATGG

GAGAAAAAGGCGATCAGGGCCTGCCTGGTATTCAGGGTGACTACAAAGAC

GACGACGACAAAtaa

The polynucleotide of SEQ ID NO: 115 was subcloned into vector pET28a, expressed host *E. coli* cells and the truncated *Rhincodon typus* collagen type1 truncation 1 was purified as described herein. The purified collagen produced a clear band on SDS-PAGE and an anti-FLAG western was observed at around 25 kilodaltons. There were no existing bands that appear at that location on the gel in the absence of expression of this protein.

SEQUENCE LISTING

<160> NUMBER OF SEQ ID NOS: 153

<210> SEQ ID NO 1
<211> LENGTH: 429
<212> TYPE: PRT
<213> ORGANISM: Podocoryna carnea

<400> SEQUENCE: 1

Gly Pro Gln Gly Val Val Gly Ala Asp Gly Lys Asp Gly Thr Pro Gly

-continued

```
 1               5                  10                 15
Glu Lys Gly Glu Gln Gly Arg Thr Gly Ala Ala Gly Lys Gln Gly Ser
             20                  25                  30
Pro Gly Ala Asp Gly Ala Arg Gly Pro Leu Gly Ser Ile Gly Gln Gln
             35                  40                  45
Gly Ala Arg Gly Glu Pro Gly Asp Pro Gly Ser Pro Gly Leu Arg Gly
             50                  55                  60
Asp Thr Gly Leu Ala Gly Val Lys Gly Val Ala Gly Pro Ser Gly Arg
 65                  70                  75                  80
Pro Gly Gln Pro Gly Ala Asn Gly Leu Pro Gly Val Asn Gly Arg Gly
             85                  90                  95
Gly Leu Arg Gly Lys Pro Gly Ala Lys Gly Ile Ala Gly Ser Asp Gly
            100                 105                 110
Glu Ala Gly Glu Ser Gly Ala Pro Gly Gln Ser Gly Pro Thr Gly Pro
            115                 120                 125
Arg Gly Gln Arg Gly Pro Ser Gly Glu Asp Gly Asn Pro Gly Leu Gln
            130                 135                 140
Gly Leu Pro Gly Ser Asp Gly Glu Pro Gly Glu Gly Gln Pro Gly
145                 150                 155                 160
Arg Ser Gly Gln Pro Gly Gln Gln Gly Pro Arg Gly Ser Pro Gly Glu
            165                 170                 175
Val Gly Pro Arg Gly Ser Lys Gly Pro Ser Gly Asp Arg Gly Asp Arg
            180                 185                 190
Gly Glu Arg Gly Val Pro Gly Gln Thr Gly Ser Ala Gly Asn Val Gly
            195                 200                 205
Glu Asp Gly Glu Gln Gly Gly Lys Gly Val Asp Gly Ala Ser Gly Pro
            210                 215                 220
Ser Gly Ala Leu Gly Ala Arg Gly Pro Pro Gly Ser Arg Gly Asp Thr
225                 230                 235                 240
Gly Ala Val Gly Pro Pro Gly Pro Thr Gly Arg Ser Gly Leu Pro Gly
            245                 250                 255
Asn Ala Gly Gln Lys Gly Pro Ser Gly Glu Pro Gly Ser Pro Gly Lys
            260                 265                 270
Ala Gly Ser Ala Gly Glu Gln Gly Pro Pro Gly Lys Asp Gly Ser Asn
            275                 280                 285
Gly Glu Pro Gly Ser Pro Gly Lys Glu Gly Arg Gly Leu Ala Gly
            290                 295                 300
Pro Pro Gly Pro Asp Gly Arg Arg Gly Glu Thr Gly Ser Pro Gly Ile
305                 310                 315                 320
Ala Gly Ala Leu Gly Lys Pro Gly Leu Glu Gly Pro Lys Gly Tyr Pro
            325                 330                 335
Gly Leu Arg Gly Arg Asp Gly Thr Asn Gly Lys Arg Gly Glu Gln Gly
            340                 345                 350
Glu Thr Gly Pro Asp Gly Val Arg Gly Ile Pro Gly Asn Asp Gly Gln
            355                 360                 365
Ser Gly Lys Pro Gly Ile Asp Gly Ile Asp Gly Thr Asn Gly Gln Pro
            370                 375                 380
Gly Glu Ala Gly Tyr Gln Gly Arg Gly Thr Arg Gly Gln Leu Gly
385                 390                 395                 400
Glu Thr Gly Asp Val Gly Gln Asn Gly Asp Arg Gly Ala Pro Gly Pro
            405                 410                 415
Asp Gly Ser Lys Gly Ser Ala Gly Arg Pro Gly Leu Arg
            420                 425
```

<210> SEQ ID NO 2
<211> LENGTH: 1289
<212> TYPE: DNA
<213> ORGANISM: Podocoryna carnea

<400> SEQUENCE: 2

| | | | | | |
|---|---|---|---|---|---|
| ggaccacaag | gtgttgtagg | agctgatggc | aaagatggaa | caccgggaga | gaaaggtgag | 60 |
| caaggacgaa | ccggagctgc | aggaaaacag | ggaagccctg | gagcagatgg | agcaagaggc | 120 |
| cctcttggat | caattggaca | caaggtgct | cgtggagaac | ctggtgatcc | aggatctccc | 180 |
| ggcttaagag | gagatactgg | attggctgga | gtcaaaggag | tagcaggacc | atctggtcga | 240 |
| cctggacaac | ccggtgcaaa | tggattacct | ggtgtgaatg | gcagaggcgg | tttgagaggc | 300 |
| aaacctggtg | ctaaaggaat | tgctggcagt | gatggagaag | cggagaatc | tggcgcacct | 360 |
| ggacagtccg | gacctaccgg | tccacgtggt | caacgaggac | caagtggtga | ggatggtaat | 420 |
| cctggattac | agggattgcc | tggttctgat | ggagagcccg | gagaggaagg | acaacctgga | 480 |
| agatctggtc | aaccaggaca | gcaaggacca | cgtggttccc | ctggagaggt | aggaccaaga | 540 |
| ggatctaaag | gtccatcagg | agatcgtggt | gacaggggag | agagaggtgt | tcctggacaa | 600 |
| acaggttcgg | ctggaaatgt | aggagaagat | ggagagcaag | gaggcaaagg | tgtcgatgga | 660 |
| gcgagtggac | caagtggagc | tcttggtgct | cgtggtcccc | caggaagtag | aggtgacacc | 720 |
| ggggcagtgg | gacctcccgg | acctactggg | cgatctggtt | tacctggaaa | cgcaggacaa | 780 |
| aagggaccaa | gtggtgaacc | aggtagtcca | ggaaaagcag | gatcagctgg | tgaacagggt | 840 |
| cctcctggta | agacggatc | aaatggtgaa | cctggatctc | ctggcaaaga | gggtgaacgt | 900 |
| ggtcttgctg | gtccaccagg | tccagatggc | agacgtggtg | aaacgggatc | tccaggtatc | 960 |
| gctggtgctc | ttggtaaacc | aggtttggaa | ggacctaaag | gttatccagg | attaagagga | 1020 |
| agagatggaa | ccaatggcaa | acgaggagaa | caaggagaaa | ctggtcctga | tggagtcaga | 1080 |
| ggtattcctg | gaaatgatgg | acaatctggc | aaaccaggta | ttgatggtat | tgacggaaca | 1140 |
| aatggtcaac | aggtgaggc | tggataccaa | ggtggtagag | gtacacgtgg | tcagttaggt | 1200 |
| gaaactggtg | atgtcggaca | gaatggagat | cgaggagctc | ctggtcctga | tggatctaaa | 1260 |
| ggttctgctg | gtagaccagg | acttcgtgg | | | | 1289 |

<210> SEQ ID NO 3
<211> LENGTH: 1425
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

| | | | | | |
|---|---|---|---|---|---|
| atgaaaaaga | tttggctggc | gctggctggt | ttagttttag | cgtttagcgc | atcggcggcg | 60 |
| cagtatgaag | atcaccatca | ccaccaccac | catcaccact | ctggctcgag | cctggtgccg | 120 |
| cgcggcagcc | atatgggtcc | gcagggtgtt | gttggtgcag | atggtaaaga | cggtaccccg | 180 |
| ggtgaaaaag | gagaacaggg | acgtacaggt | gcagcaggta | acagggcag | cccgggtgcc | 240 |
| gatggtgccc | gtggcccgct | gggtagcatt | ggtcagcagg | gtgcaagagg | cgaaccgggc | 300 |
| gatccgggta | gtccgggcct | gcgtggtgat | acgggtctgg | ccggtgttaa | aggcgttgca | 360 |
| ggtccttcag | gtcgtccagg | tcaaccgggt | gcaaatggtc | tgccgggtgt | taatggtcgt | 420 |
| ggcggtctgc | gtggcaaacc | gggagcaaaa | ggtattgcag | gtagcgatgg | agaagccggt | 480 |

```
gaaagcggtg ccccgggtca gagtggtccg accggtccgc gcggtcagcg tggtccgtct      540
ggtgaagatg gcaatccggg tctgcagggt ctgcctggta gtgatggcga accaggtgaa      600
gaaggtcagc cgggtcgttc aggccagccg ggccagcagg gccgcgtgg tagcccgggc       660 gaagttggcc cgcggggtag taaaggtcct agtggcgatc gcggtgatcg tggtgaacgc      720
ggtgttcctg gtcagaccgg tagcgcaggt aatgttggcg aagatggtga acagggtggc      780
aaaggtgttg atggtgcaag cggtccgagc ggtgcactgg gtgcacgtgg tcctccgggc      840
agccgtggtg acaccggtgc agttggtccg cctggcccga ccggccgtag tggcttaccg      900
ggtaatgcag gtcagaaagg tccgtcaggt gaacctggca gccctggtaa agcaggtagt      960
gccggtgagc agggtccgcc gggcaaagat ggtagtaatg gtgagccggg tagccctggc     1020
aaagaaggtg aacgtggtct ggcaggaccg ccgggtcctg atggtcgccg cggtgaaacg     1080
ggttcaccgg gtattgccgg tgccctgggt aaaccaggtc tggaaggtcc gaaaggttat     1140
cctggtctgc gcggtcgtga tggtaccaat ggcaaacgtg gcgaacaggg cgaaaccggt     1200
ccagatggtg ttcgtggtat tccgggtaac gatggtcaga gcggtaaacc gggcattgat     1260
ggtattgatg gcaccaatgg tcagcctggc gaagcaggtt atcagggtgg tcgcggtacc     1320
cgtggtcagc tgggtgaaac aggtgatgtt ggtcagaatg gtgatcgcgg cgcaccgggt     1380
ccggatggta gcaaaggtag cgccggtcgt ccgggtttac gttaa                     1425

<210> SEQ ID NO 4
<211> LENGTH: 1425
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
atgaaaaaga tttggctggc gctggctggt ttagttttag cgtttagcgc atcggcggcg       60
cagtatgaag atcaccatca ccaccaccac catcaccact ctggctcgag cctggtgccg      120
cgcggcagcc atatgggtcc gcagggtgtt gttggtgcag atggtaaaga cggtaccccg      180
ggtgaaaaag gtgaacaggg tcgtaccggt gcagcaggta acagggcag cccgggtgcc      240 gatggtgccc gtgccccgct gggtagcatt ggtcagcagg gtgcacgtgg cgaaccgggc      300
gatccgggta gcccgggcct gcgtggtgat acgggtctgg ccggtgttaa aggcgttgca      360
ggtccttctg gtcgtccagg tcaaccgggt gcaaatggtc tgccgggtgt taatggtcgt      420
ggcggtctgc gtggcaaacc gggtgcaaaa ggtattgcag gtagcgatgg cgaagccggt      480
gaaagcggtg ccccgggtca gagcggtccg accggtccgc gcggtcagcg tggtccgtct      540
ggtgaagatg gcaatccggg tctgcagggt ctgcctggta gcgatggcga accaggtgaa      600
gaaggtcagc cgggtcgttc tggccagccg ggccagcagg gccgcgtgg tagcccgggc       660 gaagttggcc cgcgcggttc taaaggtcct agcggcgatc gcggtgatcg tggtgaacgc      720
ggtgttcctg gtcagaccgg tagcgcaggt aatgttggcg aagatggtga acagggtggc      780
aaaggtgttg atggtgcaag cggtccgagc ggtgcactgg gtgcacgtgg tcctccgggc      840
agccgtggtg acaccggtgc agttggtccg cctggcccga ccggccgtag cggcctgccg      900
ggtaatgcag gtcagaaagg tccgtctggt gaacctggca gccctggtaa agcaggtagc      960
gccggtgagc agggtccgcc gggcaaagat ggtagcaatg gtgagccggg tagccctggc     1020
aaagaaggtg aacgtggtct ggcaggtccg ccgggtcctg atggtcgccg cggtgaaacg     1080
```

```
ggttctccgg gtattgccgg tgccctgggt aaaccaggtc tggaaggtcc gaaaggttat    1140
cctggtctgc gcggtcgtga tggtaccaat ggcaaacgtg gcaacaggg cgaaaccggt     1200 ccagatggtg ttcgtggtat tccgggtaac gatggtcaga gcggtaaacc gggcattgat   1260
ggtattgatg gcaccaatgg tcagcctggc gaagcaggtt atcagggtgg tcgcggtacc   1320
cgtggtcagc tgggtgaaac cggtgatgtt ggtcagaatg gtgatcgcgg cgcaccgggt   1380
ccggatggta gcaaaggtag cgccggtcgt ccgggtctgc gttaa                   1425
```

<210> SEQ ID NO 5
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Met Lys Lys Ile Trp Leu Ala Leu Ala Gly Leu Val Leu Ala Phe Ser
1               5                   10                  15

Ala Ser Ala Ala Gln Tyr Glu Asp His His His His His His
            20                  25                  30

His Ser Gly Ser Ser Leu Val Pro Arg Gly Ser His Met Gly Pro Gln
        35                  40                  45

Gly Val Val Gly Ala Asp Gly Lys Asp Gly Thr Pro Gly Glu Lys Gly
    50                  55                  60

Glu Gln Gly Arg Thr Gly Ala Ala Gly Lys Gln Gly Ser Pro Gly Ala
65                  70                  75                  80

Asp Gly Ala Arg Gly Pro Leu Gly Ser Ile Gly Gln Gln Gly Ala Arg
                85                  90                  95

Gly Glu Pro Gly Asp Pro Gly Ser Pro Gly Leu Arg Gly Asp Thr Gly
            100                 105                 110

Leu Ala Gly Val Lys Gly Val Ala Gly Pro Ser Gly Arg Pro Gly Gln
        115                 120                 125

Pro Gly Ala Asn Gly Leu Pro Gly Val Asn Gly Arg Gly Gly Leu Arg
    130                 135                 140

Gly Lys Pro Gly Ala Lys Gly Ile Ala Gly Ser Asp Gly Glu Ala Gly
145                 150                 155                 160

Glu Ser Gly Ala Pro Gly Gln Ser Gly Pro Thr Gly Pro Arg Gly Gln
                165                 170                 175

Arg Gly Pro Ser Gly Glu Asp Gly Asn Pro Gly Leu Gln Gly Leu Pro
            180                 185                 190

Gly Ser Asp Gly Glu Pro Gly Glu Gly Gln Pro Gly Arg Ser Gly
        195                 200                 205

Gln Pro Gly Gln Gln Gly Pro Arg Gly Ser Pro Gly Glu Val Gly Pro
    210                 215                 220

Arg Gly Ser Lys Gly Pro Ser Gly Asp Arg Gly Asp Arg Gly Glu Arg
225                 230                 235                 240

Gly Val Pro Gly Gln Thr Gly Ser Ala Gly Asn Val Gly Glu Asp Gly
                245                 250                 255

Glu Gln Gly Gly Lys Gly Val Asp Gly Ala Ser Gly Pro Ser Gly Ala
            260                 265                 270

Leu Gly Ala Arg Gly Pro Pro Gly Ser Arg Gly Asp Thr Gly Ala Val
        275                 280                 285

Gly Pro Pro Gly Pro Thr Gly Arg Ser Gly Leu Pro Gly Asn Ala Gly
```

```
                290                 295                 300

Gln Lys Gly Pro Ser Gly Glu Pro Ser Pro Gly Lys Ala Gly Ser
305                 310                 315                 320

Ala Gly Glu Gln Gly Pro Pro Gly Lys Asp Gly Ser Asn Gly Glu Pro
            325                 330                 335

Gly Ser Pro Gly Lys Glu Gly Glu Arg Gly Leu Ala Gly Pro Pro Gly
            340                 345                 350

Pro Asp Gly Arg Arg Gly Glu Thr Gly Ser Pro Gly Ile Ala Gly Ala
        355                 360                 365

Leu Gly Lys Pro Gly Leu Glu Gly Pro Lys Gly Tyr Pro Gly Leu Arg
    370                 375                 380

Gly Arg Asp Gly Thr Asn Gly Lys Arg Gly Glu Gln Gly Glu Thr Gly
385                 390                 395                 400

Pro Asp Gly Val Arg Gly Ile Pro Gly Asn Asp Gly Gln Ser Gly Lys
            405                 410                 415

Pro Gly Ile Asp Gly Ile Asp Gly Thr Asn Gly Gln Pro Gly Glu Ala
            420                 425                 430

Gly Tyr Gln Gly Gly Arg Gly Thr Arg Gly Gln Leu Gly Glu Thr Gly
        435                 440                 445

Asp Val Gly Gln Asn Gly Asp Arg Gly Ala Pro Gly Pro Asp Gly Ser
    450                 455                 460

Lys Gly Ser Ala Gly Arg Pro Gly Leu Arg
465                 470

<210> SEQ ID NO 6
<211> LENGTH: 1362
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
atgaaaaaga tttggctggc gctggctggt ttagttttag cgtttagcgc atcggcggcg     60
cagtatgaag atggtccgca gggtgttgtt ggtgcagatg gtaaagacgg taccccgggt    120
gaaaaaggag aacagggacg tacaggtgca gcaggtaaac agggcagccc gggtgccgat    180
ggtgcccgtg gcccgctggg tagcattggt cagcagggtg caagaggcga accgggcgat    240
ccgggtagtc cgggcctgcg tggtgatacg ggtctggccg gtgttaaagg cgttgcaggt    300
ccttcaggtc gtccaggtca accgggtgca aatggtctgc cgggtgttaa tggtcgtggc    360
ggtctgcgtg gcaaaccggg agcaaaaggt attgcaggta gcgatggaga agccggtgaa    420
agcggtgccc cgggtcagag tggtccgacc ggtccgcgcg gtcagcgtgg tccgtctggt    480
gaagatggca atccgggtct gcagggtctg cctggtagtg atggcgaacc aggtgaagaa    540
ggtcagccgg tcgttcagg ccagccgggc cagcagggcc gcgtggtag cccgggcgaa    600 gttggcccgc ggggtagtaa aggtcctagt ggcgatcgcg gtgatcgtgg tgaacgcggt    660
gttcctggtc agaccggtag cgcaggtaat gttggcgaag atggtgaaca gggtggcaaa    720
ggtgttgatg gtgcaagcgg tccgagcggt gcactgggtg cacgtggtcc tccgggcagc    780
cgtggtgaca ccggtgcagt tggtccgcct ggcccgaccg ccgtagtgg cttaccgggt    840 aatgcaggtc agaaaggtcc gtcaggtgaa cctggcagcc ctggtaaagc aggtagtgcc    900
ggtgagcagg gtccgccggg caagatggt agtaatggtg agccgggtag ccctggcaaa    960
gaaggtgaac gtggtctggc aggaccgccg ggtcctgatg gtcgccgcgg tgaaacgggt   1020
```

```
tcaccgggta ttgccggtgc cctgggtaaa ccaggtctgg aaggtccgaa aggttatcct    1080
ggtctgcgcg gtcgtgatgg taccaatggc aaacgtggcg aacagggcga aaccggtcca    1140
gatggtgttc gtggtattcc gggtaacgat ggtcagagcg gtaaaccggg cattgatggt    1200
attgatggca ccaatggtca gcctggcgaa gcaggttatc agggtggtcg cggtacccgt    1260
ggtcagctgg gtgaaacagg tgatgttggt cagaatggtg atcgcggcgc accgggtccg    1320
gatggtagca aaggtagcgc cggtcgtccg ggtttacgtt aa                      1362
```

<210> SEQ ID NO 7
<211> LENGTH: 1362
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
atgaaaaaga tttggctggc gctggctggt ttagttttag cgtttagcgc atcggcggcg     60
cagtatgaag atggtccgca gggtgttgtt ggtgcagatg gtaaagacgg taccccgggt    120
gaaaaaggtg aacagggtcg taccggtgca gcaggtaaac agggcagccc gggtgccgat    180
ggtgcccgtg gcccgctggg tagcattggt cagcagggtg cacgtggcga accgggcgat    240
ccgggtagcc cgggcctgcg tggtgatacg ggtctggccg gtgttaaagg cgttgcaggt    300
ccttctggtc gtccaggtca accgggtgca aatggtctgc cgggtgttaa tggtcgtggc    360
ggtctgcgtg gcaaaccggg tgcaaaaggt attgcaggta gcgatggcga agccggtgaa    420
agcggtgccc cgggtcagag cggtccgacc ggtccgcgcg gtcagcgtgg tccgtctggt    480
gaagatggca atccgggtct gcagggtctg cctggtagcg atggcgaacc aggtgaagaa    540
ggtcagccgg gtcgttctgg ccagccgggc cagcagggcc gcgtggtag  cccgggcgaa   600 gttgccccgc gcggttctaa aggtcctagc ggcgatcgcg gtgatcgtgg tgaacgcggt    660
gttcctggtc agaccggtag cgcaggtaat gttggcgaag atggtgaaca gggtggcaaa    720
ggtgttgatg gtcaagcgg tccgagcggt gcactgggtg cacgtggtcc tccgggcagc    780
cgtggtgaca ccggtgcagt tggtccgcct ggcccgaccg gccgtagcgg cctgccgggt    840
aatgcaggtc agaaaggtcc gtctggtgaa cctggcagcc ctggtaaagc aggtagcgcc    900
ggtgagcagg gtccgccggg caaagatggt agcaatggtg agccgggtag ccctggcaaa    960
gaaggtgaac gtggtctggc aggtccgccg ggtcctgatg gtcgccgcgg tgaaacgggt   1020
tctccgggta ttgccggtgc cctgggtaaa ccaggtctgg aaggtccgaa aggttatcct   1080
ggtctgcgcg gtcgtgatgg taccaatggc aaacgtggcg aacagggcga aaccggtcca   1140
gatggtgttc gtggtattcc gggtaacgat ggtcagagcg gtaaaccggg cattgatggt   1200
attgatggca ccaatggtca gcctggcgaa gcaggttatc agggtggtcg cggtacccgt   1260
ggtcagctgg gtgaaaccgg tgatgttggt cagaatggtg atcgcggcgc accgggtccg   1320
gatggtagca aaggtagcgc cggtcgtccg ggtctgcgtt aa                      1362
```

<210> SEQ ID NO 8
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 8

Met Lys Lys Ile Trp Leu Ala Leu Ala Gly Leu Val Leu Ala Phe Ser
1               5                   10                  15

Ala Ser Ala Ala Gln Tyr Glu Asp Gly Pro Gln Gly Val Val Gly Ala
            20                  25                  30

Asp Gly Lys Asp Gly Thr Pro Gly Glu Lys Gly Glu Gln Gly Arg Thr
        35                  40                  45

Gly Ala Ala Gly Lys Gln Gly Ser Pro Gly Ala Asp Gly Ala Arg Gly
    50                  55                  60

Pro Leu Gly Ser Ile Gly Gln Gln Gly Ala Arg Gly Glu Pro Gly Asp
65                  70                  75                  80

Pro Gly Ser Pro Gly Leu Arg Gly Asp Thr Gly Leu Ala Gly Val Lys
                85                  90                  95

Gly Val Ala Gly Pro Ser Gly Arg Pro Gly Gln Pro Gly Ala Asn Gly
            100                 105                 110

Leu Pro Gly Val Asn Gly Arg Gly Leu Arg Gly Lys Pro Gly Ala
        115                 120                 125

Lys Gly Ile Ala Gly Ser Asp Gly Glu Ala Gly Glu Ser Gly Ala Pro
    130                 135                 140

Gly Gln Ser Gly Pro Thr Gly Pro Arg Gly Gln Arg Gly Pro Ser Gly
145                 150                 155                 160

Glu Asp Gly Asn Pro Gly Leu Gln Gly Leu Pro Gly Ser Asp Gly Glu
                165                 170                 175

Pro Gly Glu Glu Gly Gln Pro Gly Arg Ser Gly Gln Pro Gly Gln Gln
            180                 185                 190

Gly Pro Arg Gly Ser Pro Gly Glu Val Gly Pro Arg Gly Ser Lys Gly
        195                 200                 205

Pro Ser Gly Asp Arg Gly Asp Arg Gly Glu Arg Gly Val Pro Gly Gln
    210                 215                 220

Thr Gly Ser Ala Gly Asn Val Gly Glu Asp Gly Glu Gln Gly Gly Lys
225                 230                 235                 240

Gly Val Asp Gly Ala Ser Gly Pro Ser Gly Ala Leu Gly Ala Arg Gly
                245                 250                 255

Pro Pro Gly Ser Arg Gly Asp Thr Gly Ala Val Gly Pro Pro Gly Pro
            260                 265                 270

Thr Gly Arg Ser Gly Leu Pro Gly Asn Ala Gly Gln Lys Gly Pro Ser
        275                 280                 285

Gly Glu Pro Gly Ser Pro Gly Lys Ala Gly Ser Ala Gly Glu Gln Gly
    290                 295                 300

Pro Pro Gly Lys Asp Gly Ser Asn Gly Glu Pro Gly Ser Pro Gly Lys
305                 310                 315                 320

Glu Gly Glu Arg Gly Leu Ala Gly Pro Gly Pro Asp Gly Arg Arg
                325                 330                 335

Gly Glu Thr Gly Ser Pro Gly Ile Ala Gly Ala Leu Gly Lys Pro Gly
            340                 345                 350

Leu Glu Gly Pro Lys Gly Tyr Pro Gly Leu Arg Gly Arg Asp Gly Thr
        355                 360                 365

Asn Gly Lys Arg Gly Glu Gln Gly Glu Thr Gly Pro Asp Gly Val Arg
    370                 375                 380

Gly Ile Pro Gly Asn Asp Gly Gln Ser Gly Lys Pro Gly Ile Asp Gly
385                 390                 395                 400

Ile Asp Gly Thr Asn Gly Gln Pro Gly Glu Ala Gly Tyr Gln Gly Gly
                405                 410                 415
```

```
Arg Gly Thr Arg Gly Gln Leu Gly Glu Thr Gly Asp Val Gly Gln Asn
                420                 425                 430

Gly Asp Arg Gly Ala Pro Gly Pro Asp Gly Ser Lys Gly Ser Ala Gly
            435                 440                 445

Arg Pro Gly Leu Arg
    450

<210> SEQ ID NO 9
<211> LENGTH: 825
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
atgaaaaaga tttggctggc gctggctggt ttagttttag cgtttagcgc atcggcggcg      60
cagtatgaag atcaccatca ccaccaccac catcaccact ctggctcgag cctggtgccg     120
cgcggcagcc atatgggtcc gcagggtgtt gttggtgcag atggtaaaga cggtaccccg     180
ggtgaaaaag gagaacaggg acgtacaggt gcagcaggta acagggcag cccgggtgcc      240 gatggtgccc gtggcccgct gggtagcatt ggtcagcagg gtgcaagagg cgaaccgggc     300
gatccgggta gtccgggcct gcgtggtgat acgggtctgg ccggtgttaa aggcgttgca     360
ggtccttcag gtcgtccagg tcaaccgggt gcaaatggtc tgccgggtgt taatggtcgt     420
ggcggtctgg aacgtggtct ggcaggaccg ccgggtcctg atggtcgccg cggtgaaacg     480
ggttcaccgg gtattgccgg tgccctgggt aaaccaggtc tggaaggtcc gaaaggttat     540
cctggtctgc gcggtcgtga tggtaccaat ggcaaacgtg gcaacagggc gaaaccggt      600 ccagatggtg ttcgtggtat tccgggtaac gatggtcaga gcggtaaacc gggcattgat     660
ggtattgatg caccaatgg tcagcctggc gaagcaggtt atcagggtgg tcgcggtacc     720
cgtggtcagc tgggtgaaac aggtgatgtt ggtcagaatg gtgatcgcgg cgcaccgggt     780
ccggatggta gcaaaggtag cgccggtcgt ccgggtttac gttaa                     825

<210> SEQ ID NO 10
<211> LENGTH: 274
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Lys Lys Ile Trp Leu Ala Leu Ala Gly Leu Val Leu Ala Phe Ser
1               5                   10                  15

Ala Ser Ala Ala Gln Tyr Glu Asp His His His His His His His His
            20                  25                  30

His Ser Gly Ser Ser Leu Val Pro Arg Gly Ser His Met Gly Pro Gln
        35                  40                  45

Gly Val Val Gly Ala Asp Gly Lys Asp Gly Thr Pro Gly Glu Lys Gly
    50                  55                  60

Glu Gln Gly Arg Thr Gly Ala Ala Gly Lys Gln Gly Ser Pro Gly Ala
65                  70                  75                  80

Asp Gly Ala Arg Gly Pro Leu Gly Ser Ile Gly Gln Gln Gly Ala Arg
                85                  90                  95

Gly Glu Pro Gly Asp Pro Gly Ser Pro Gly Leu Arg Gly Asp Thr Gly
```

```
            100                 105                 110
Leu Ala Gly Val Lys Gly Val Ala Gly Pro Ser Gly Arg Pro Gly Gln
        115                 120                 125

Pro Gly Ala Asn Gly Leu Pro Gly Val Asn Gly Arg Gly Gly Leu Glu
    130                 135                 140

Arg Gly Leu Ala Gly Pro Gly Pro Asp Gly Arg Arg Gly Glu Thr
145                 150                 155                 160

Gly Ser Pro Gly Ile Ala Gly Ala Leu Gly Lys Pro Gly Leu Glu Gly
                165                 170                 175

Pro Lys Gly Tyr Pro Gly Leu Arg Gly Arg Asp Gly Thr Asn Gly Lys
            180                 185                 190

Arg Gly Glu Gln Gly Glu Thr Gly Pro Asp Gly Val Arg Gly Ile Pro
        195                 200                 205

Gly Asn Asp Gly Gln Ser Gly Lys Pro Gly Ile Asp Gly Ile Asp Gly
    210                 215                 220

Thr Asn Gly Gln Pro Gly Glu Ala Gly Tyr Gln Gly Arg Gly Thr
225                 230                 235                 240

Arg Gly Gln Leu Gly Glu Thr Gly Asp Val Gly Gln Asn Gly Asp Arg
                245                 250                 255

Gly Ala Pro Gly Pro Asp Gly Ser Lys Gly Ser Ala Gly Arg Pro Gly
            260                 265                 270

Leu Arg

<210> SEQ ID NO 11
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
atgaaaaaga tttggctggc gctggctggt ttagttttag cgtttagcgc atcggcggcg      60
cagtatgaag atggtccgca gggtgttgtt ggtgcagatg gtaaagacgg taccccgggt     120
aatgcaggtc agaaaggtcc gtcaggtgaa cctggcagcc tggtaaagc aggtagtgcc      180 ggtgagcagg gtccgccggg caaagatggt agtaatggtg agccgggtag ccctggcaaa     240
gaaggtgaac gtggtctggc aggaccgccg ggtcctgatg tcgccgcgg tgaaacgggt      300 tcaccgggta ttgccggtgc cctgggtaaa ccaggtctgg aaggtccgaa aggttatcct     360
ggtctgcgcg gtcgtgatgg taccaatggc aaacgtggcg aacagggcga accggtcca    420 gatggtgttc gtggtattcc gggtaacgat ggtcagagcg gtaaaccggg cattgatggt    480
attgatggca ccaatggtca gcctggcgaa gcaggttatc agggtggtcg cggtacccgt    540
ggtcagctgg gtgaaacagg tgatgttggt cagaatggtg atcgcggcgc accgggtccg    600
gatggtagca aggtagcgc cggtcgtccg ggtttacgtt aa                         642

<210> SEQ ID NO 12
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Lys Lys Ile Trp Leu Ala Leu Ala Gly Leu Val Leu Ala Phe Ser
```

```
              1               5                  10                 15
Ala Ser Ala Ala Gln Tyr Glu Asp Gly Pro Gln Gly Val Val Gly Ala
                 20                  25                 30

Asp Gly Lys Asp Gly Thr Pro Gly Asn Ala Gly Gln Lys Gly Pro Ser
             35                  40                 45

Gly Glu Pro Gly Ser Pro Gly Lys Ala Gly Ser Ala Gly Glu Gln Gly
         50                  55                 60

Pro Pro Gly Lys Asp Gly Ser Asn Gly Glu Pro Gly Ser Pro Gly Lys
65                   70                  75                  80

Glu Gly Glu Arg Gly Leu Ala Gly Pro Pro Gly Pro Asp Gly Arg Arg
                 85                  90                 95

Gly Glu Thr Gly Ser Pro Gly Ile Ala Gly Ala Leu Gly Lys Pro Gly
                100                 105                110

Leu Glu Gly Pro Lys Gly Tyr Pro Gly Leu Arg Gly Arg Asp Gly Thr
            115                 120                 125

Asn Gly Lys Arg Gly Glu Gln Gly Glu Thr Gly Pro Asp Gly Val Arg
            130                 135                 140

Gly Ile Pro Gly Asn Asp Gly Gln Ser Gly Lys Pro Gly Ile Asp Gly
145                 150                 155                 160

Ile Asp Gly Thr Asn Gly Gln Pro Gly Glu Ala Gly Tyr Gln Gly Gly
                165                 170                 175

Arg Gly Thr Arg Gly Gln Leu Gly Glu Thr Gly Asp Val Gly Gln Asn
            180                 185                 190

Gly Asp Arg Gly Ala Pro Gly Pro Asp Gly Ser Lys Gly Ser Ala Gly
            195                 200                 205

Arg Pro Gly Leu Arg
            210

<210> SEQ ID NO 13
<211> LENGTH: 696
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
atgaaaaaga tttggctggc gctggctggt ttagttttag cgtttagcgc atcggcggcg      60
cagtatgaag atggtgaaaa aggtgaaaag ggcgagaaag gtgagaaagg cgaaaagggt     120 gaaaaggtc cgcagggtgt tgttggtgca gatggtaaag acggtacccc gggtaatgca      180
ggtcagaaag gtccgtcagg tgaacctggc agccctggta aagcaggtag tgccggtgag     240
cagggtccgc cgggcaaaga tggtagtaat ggtgagccgg gtagccctgg caaagaaggt     300
gaacgtggtc tggcaggacc gccgggtcct gatggtcgcc gcggtgaaac gggttcaccg     360
ggtattgccg gtgccctggg taaaccaggt ctggaaggtc cgaaaggtta tcctggtctg     420
cgcggtcgtg atggtaccaa tggcaaacgt ggcgaacagg gcgaaaccgg tccagatggt     480
gttcgtggta ttccgggtaa cgatggtcag agcggtaaac cgggcattga tggtattgat     540
ggcaccaatg gtcagcctgg cgaagcaggt tatcagggtg gtcgcggtac ccgtggtcag     600
ctgggtgaaa caggtgatgt tggtcagaat ggtgatcgcg gcgcaccggg tccggatggt     660
agcaaaggta cgccggtcg tccgggttta cgttaa                                696

<210> SEQ ID NO 14
<211> LENGTH: 231
```

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 14

Met Lys Lys Ile Trp Leu Ala Leu Ala Gly Leu Val Leu Ala Phe Ser
1               5                   10                  15

Ala Ser Ala Ala Gln Tyr Glu Asp Gly Glu Lys Gly Glu Lys Gly Glu
            20                  25                  30

Lys Gly Glu Lys Gly Glu Lys Gly Glu Lys Gly Pro Gln Val Val
        35                  40                  45

Gly Ala Asp Gly Lys Asp Gly Thr Pro Gly Asn Ala Gly Gln Lys Gly
    50                  55                  60

Pro Ser Gly Glu Pro Gly Ser Pro Gly Lys Ala Gly Ser Ala Gly Glu
65                  70                  75                  80

Gln Gly Pro Pro Gly Lys Asp Gly Ser Asn Gly Glu Pro Gly Ser Pro
                85                  90                  95

Gly Lys Glu Gly Glu Arg Gly Leu Ala Gly Pro Pro Gly Pro Asp Gly
            100                 105                 110

Arg Arg Gly Glu Thr Gly Ser Pro Gly Ile Ala Gly Ala Leu Gly Lys
        115                 120                 125

Pro Gly Leu Glu Gly Pro Lys Gly Tyr Pro Gly Leu Arg Gly Arg Asp
    130                 135                 140

Gly Thr Asn Gly Lys Arg Gly Glu Gln Gly Glu Thr Gly Pro Asp Gly
145                 150                 155                 160

Val Arg Gly Ile Pro Gly Asn Asp Gly Gln Ser Gly Lys Pro Gly Ile
                165                 170                 175

Asp Gly Ile Asp Gly Thr Asn Gly Gln Pro Gly Glu Ala Gly Tyr Gln
            180                 185                 190

Gly Gly Arg Gly Thr Arg Gly Gln Leu Gly Glu Thr Gly Asp Val Gly
        195                 200                 205

Gln Asn Gly Asp Arg Gly Ala Pro Gly Pro Asp Gly Ser Lys Gly Ser
    210                 215                 220

Ala Gly Arg Pro Gly Leu Arg
225                 230

<210> SEQ ID NO 15
<211> LENGTH: 696
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15
atgaaaaaga tttggctggc gctggctggt ttagttttag cgtttagcgc atcggcggcg      60
cagtatgaag atggtgataa aggtgataag ggcgacaaag gtgacaaagg cgataagggt    120
gataaaggtc cgcagggtgt tgttggtgca gatggtaaag acggtacccc gggtaatgca    180
ggtcagaaag gtccgtcagg tgaacctggc agccctggta aagcaggtag tgccggtgag    240
cagggtccgc cgggcaaaga tggtagtaat ggtgagccgg gtagccctgg caaagaaggt    300
gaacgtggtc tggcaggacc gccgggtcct gatggtcgcc gcggtgaaac gggttcaccg    360
ggtattgccg gtgccctggg taaaccaggt ctggaaggtc cgaaaggtta tcctggtctg    420
cgcggtcgtg atggtaccaa tggcaaacgt ggcgaacagg gcgaaaccgg tccagatggt    480

```
gttcgtggta ttccgggtaa cgatggtcag agcggtaaac cgggcattga tggtattgat      540
ggcaccaatg gtcagcctgg cgaagcaggt tatcagggtg gtcgcggtac ccgtggtcag      600
ctgggtgaaa caggtgatgt tggtcagaat ggtgatcgcg gcgcaccggg tccggatggt      660
agcaaaggta gcgccggtcg tccgggttta cgttaa                                696
```

```
<210> SEQ ID NO 16
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16
```

```
Met Lys Lys Ile Trp Leu Ala Leu Ala Gly Leu Val Leu Ala Phe Ser
1               5                   10                  15

Ala Ser Ala Ala Gln Tyr Glu Asp Gly Asp Lys Gly Asp Lys Gly Asp
            20                  25                  30

Lys Gly Asp Lys Gly Asp Lys Gly Asp Lys Gly Pro Gln Gly Val Val
        35                  40                  45

Gly Ala Asp Gly Lys Asp Gly Thr Pro Gly Asn Ala Gly Gln Lys Gly
    50                  55                  60

Pro Ser Gly Glu Pro Gly Ser Pro Gly Lys Ala Gly Ser Ala Gly Glu
65                  70                  75                  80

Gln Gly Pro Pro Gly Lys Asp Gly Ser Asn Gly Glu Pro Gly Ser Pro
                85                  90                  95

Gly Lys Glu Gly Glu Arg Gly Leu Ala Gly Pro Pro Gly Pro Asp Gly
            100                 105                 110

Arg Arg Gly Glu Thr Gly Ser Pro Gly Ile Ala Gly Ala Leu Gly Lys
        115                 120                 125

Pro Gly Leu Glu Gly Pro Lys Gly Tyr Pro Gly Leu Arg Gly Arg Asp
    130                 135                 140

Gly Thr Asn Gly Lys Arg Gly Glu Gln Gly Glu Thr Gly Pro Asp Gly
145                 150                 155                 160

Val Arg Gly Ile Pro Gly Asn Asp Gly Gln Ser Gly Lys Pro Gly Ile
                165                 170                 175

Asp Gly Ile Asp Gly Thr Asn Gly Gln Pro Gly Glu Ala Gly Tyr Gln
            180                 185                 190

Gly Gly Arg Gly Thr Arg Gly Gln Leu Gly Glu Thr Gly Asp Val Gly
        195                 200                 205

Gln Asn Gly Asp Arg Gly Ala Pro Gly Pro Asp Gly Ser Lys Gly Ser
    210                 215                 220

Ala Gly Arg Pro Gly Leu Arg
225                 230
```

```
<210> SEQ ID NO 17
<211> LENGTH: 2232
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
```

```
atgaaaaaga tttggctggc gctggctggt ttagttttag cgtttagcgc atcggcggcg      60
cagtatgaag atcaccatca ccaccaccac catcaccact ctggctcgag cctggtgccg     120
```

```
cgcggcagcc atatgtctgg ctcgagcagt aaaggtgaag aactgttcac cggtgttgtt      180
ccgatcctgg ttgaactgga tggtgatgtt aacggccaca aattctctgt tcgtggtgaa      240
ggtgaaggtg atgcaaccaa cggtaaactg accctgaaat tcatctgcac taccggtaaa      300
ctgccggttc catggccgac tctggtgact accctgacct atggtgttca gtgtttttct      360
cgttacccgg atcacatgaa gcagcatgat ttcttcaaat ctgcaatgcc ggaaggttat      420
gtacaggagc gcaccatttc tttcaaagac gatggcacct acaaaacccg tgcagaggtt      480
aaatttgaag gtgatactct ggtgaaccgt attgaactga aaggcattga tttcaaagag      540
gacggcaaca tcctgggcca caaactggaa tataacttca actcccataa cgtttacatc      600
accgcagaca acagaagaac ggtatcaaa gctaacttca aaattcgcca taacgttgaa       660
gacggtagcg tacagctggc ggaccactac cagcagaaca ctccgatcgg tgatggtccg      720
gttctgctgc cggataacca ctacctgtcc acccagtcta aactgtccaa agacccgaac      780
gaaaagcgcg accacatggt gctgctggag ttcgttactg cagcaggtat cacgcacggc      840
atggatgaac tctacaaatc tggcgcgccg ggcggtccgc agggtgttgt tggtgcagat      900
ggtaaagacg gtaccccggg taatgcaggt cagaaaggtc cgtcaggtga acctggcagc      960
cctggtaaag caggtagtgc cggtgagcag ggtccgccgg gcaaagatgg tagtaatggt     1020
gagccgggta gccctggcaa agaaggtgaa cgtggtctgg caggaccgcc gggtcctgat     1080
ggtcgccgcg gtgaaacggg ttcaccgggt attgccggtg ccctgggtaa accaggtctg     1140
gaaggtccga aaggttatcc tggtctgcgc ggtcgtgatg gtaccaatgg caaacgtggc     1200
gaacagggcg aaaccggtcc agatggtgtt cgtggtattc cgggtaacga tggtcagagc     1260
ggtaaaccgg gcattgatgg tattgatggc accaatggtc agcctggcga agcaggttat     1320
cagggtggtc gcggtacccg tggtcagctg ggtgaaacag gtgatgttgg tcagaatggt     1380
gatcgcggcg caccgggtcc ggatggtagc aaaggtagcg ccggtcgtcc gggtttacgt     1440
cacccagaaa cgctggtgaa agtaaaagat gctgaagatc agttgggtgc acgagtgggt     1500
tacatcgaac tggatctcaa cagcggtaag atccttgaga gttttcgccc gaagaacgt      1560 tttccaatga tgagcacttt taaagttctg ctatgtggcg cggtattatc ccgtattgac     1620
gccgggcaag agcaactcgg tcgccgcata cactattctc agaatgactt ggttgagtac     1680
tcaccagtca cagaaaagca tcttacggat ggcatgacag taagagaatt atgcagtgct     1740
gccataacca tgagtgataa cactgcggcc aacttacttc tgacaacgat cggaggaccg     1800
aaggagctaa ccgcttttt gcacaacatg ggggatcatg taactcgcct tgatcgttgg     1860
gaaccggagc tgaatgaagc cataccaaac gacgagcgtg acaccacgat gcctgtagca     1920
atggcaacaa cgttgcgcaa actattaact ggcgaactac ttactctagc ttcccggcaa     1980
caattaatag actggatgga ggcggataaa gttgcaggac cacttctgcg ctcggccctt     2040
ccggctggct ggtttattgc tgataaatct ggagccggtg agcgtgggtc tcgcggtatc     2100
attgcagcac tggggccaga tggtaagccc tcccgtatcg tagttatcta cacgacgggg     2160
agtcaggcaa ctatggatga acgaaataga cagatcgctg agataggtgc ctcactgatt     2220
aagcattggt aa                                                         2232

<210> SEQ ID NO 18
<211> LENGTH: 743
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 18

Met Lys Lys Ile Trp Leu Ala Leu Ala Gly Leu Val Leu Ala Phe Ser
1               5                   10                  15

Ala Ser Ala Ala Gln Tyr Glu Asp His His His His His His
            20                  25                  30

His Ser Gly Ser Ser Leu Val Pro Arg Gly Ser His Met Ser Gly Ser
        35                  40                  45

Ser Ser Lys Gly Glu Glu Leu Phe Thr Gly Val Val Pro Ile Leu Val
    50                  55                  60

Glu Leu Asp Gly Asp Val Asn Gly His Lys Phe Ser Val Arg Gly Glu
65                  70                  75                  80

Gly Glu Gly Asp Ala Thr Asn Gly Lys Leu Thr Leu Lys Phe Ile Cys
                85                  90                  95

Thr Thr Gly Lys Leu Pro Val Pro Trp Pro Thr Leu Val Thr Thr Leu
            100                 105                 110

Thr Tyr Gly Val Gln Cys Phe Ser Arg Tyr Pro Asp His Met Lys Gln
        115                 120                 125

His Asp Phe Phe Lys Ser Ala Met Pro Glu Gly Tyr Val Gln Glu Arg
    130                 135                 140

Thr Ile Ser Phe Lys Asp Asp Gly Thr Tyr Lys Thr Arg Ala Glu Val
145                 150                 155                 160

Lys Phe Glu Gly Asp Thr Leu Val Asn Arg Ile Glu Leu Lys Gly Ile
                165                 170                 175

Asp Phe Lys Glu Asp Gly Asn Ile Leu Gly His Lys Leu Glu Tyr Asn
            180                 185                 190

Phe Asn Ser His Asn Val Tyr Ile Thr Ala Asp Lys Gln Lys Asn Gly
        195                 200                 205

Ile Lys Ala Asn Phe Lys Ile Arg His Asn Val Glu Asp Gly Ser Val
    210                 215                 220

Gln Leu Ala Asp His Tyr Gln Gln Asn Thr Pro Ile Gly Asp Gly Pro
225                 230                 235                 240

Val Leu Leu Pro Asp Asn His Tyr Leu Ser Thr Gln Ser Lys Leu Ser
                245                 250                 255

Lys Asp Pro Asn Glu Lys Arg Asp His Met Val Leu Leu Glu Phe Val
            260                 265                 270

Thr Ala Ala Gly Ile Thr His Gly Met Asp Glu Leu Tyr Lys Ser Gly
        275                 280                 285

Ala Pro Gly Gly Pro Gln Gly Val Val Gly Ala Asp Gly Lys Asp Gly
    290                 295                 300

Thr Pro Gly Asn Ala Gly Gln Lys Gly Pro Ser Gly Glu Pro Gly Ser
305                 310                 315                 320

Pro Gly Lys Ala Gly Ser Ala Gly Glu Gln Gly Pro Gly Lys Asp
                325                 330                 335

Gly Ser Asn Gly Glu Pro Gly Ser Pro Gly Lys Glu Gly Glu Arg Gly
            340                 345                 350

Leu Ala Gly Pro Pro Gly Pro Asp Gly Arg Gly Glu Thr Gly Ser
        355                 360                 365

Pro Gly Ile Ala Gly Ala Leu Gly Lys Pro Gly Leu Glu Gly Pro Lys
    370                 375                 380

Gly Tyr Pro Gly Leu Arg Gly Arg Asp Gly Thr Asn Gly Lys Arg Gly
385                 390                 395                 400

Glu Gln Gly Glu Thr Gly Pro Asp Gly Val Arg Gly Ile Pro Gly Asn
            405                 410                 415

Asp Gly Gln Ser Gly Lys Pro Gly Ile Asp Gly Ile Asp Gly Thr Asn
            420                 425                 430

Gly Gln Pro Gly Glu Ala Gly Tyr Gln Gly Gly Arg Gly Thr Arg Gly
            435                 440                 445

Gln Leu Gly Glu Thr Gly Asp Val Gly Gln Asn Gly Asp Arg Gly Ala
        450                 455                 460

Pro Gly Pro Asp Gly Ser Lys Gly Ser Ala Gly Arg Pro Gly Leu Arg
465                 470                 475                 480

His Pro Glu Thr Leu Val Lys Val Lys Asp Ala Glu Asp Gln Leu Gly
                485                 490                 495

Ala Arg Val Gly Tyr Ile Glu Leu Asp Leu Asn Ser Gly Lys Ile Leu
            500                 505                 510

Glu Ser Phe Arg Pro Glu Glu Arg Phe Pro Met Met Ser Thr Phe Lys
            515                 520                 525

Val Leu Leu Cys Gly Ala Val Leu Ser Arg Ile Asp Ala Gly Gln Glu
            530                 535                 540

Gln Leu Gly Arg Arg Ile His Tyr Ser Gln Asn Asp Leu Val Glu Tyr
545                 550                 555                 560

Ser Pro Val Thr Glu Lys His Leu Thr Asp Gly Met Thr Val Arg Glu
                565                 570                 575

Leu Cys Ser Ala Ala Ile Thr Met Ser Asp Asn Thr Ala Ala Asn Leu
            580                 585                 590

Leu Leu Thr Thr Ile Gly Gly Pro Lys Glu Leu Thr Ala Phe Leu His
            595                 600                 605

Asn Met Gly Asp His Val Thr Arg Leu Asp Arg Trp Glu Pro Glu Leu
            610                 615                 620

Asn Glu Ala Ile Pro Asn Asp Glu Arg Asp Thr Thr Met Pro Val Ala
625                 630                 635                 640

Met Ala Thr Thr Leu Arg Lys Leu Leu Thr Gly Glu Leu Leu Thr Leu
                645                 650                 655

Ala Ser Arg Gln Gln Leu Ile Asp Trp Met Glu Ala Asp Lys Val Ala
            660                 665                 670

Gly Pro Leu Leu Arg Ser Ala Leu Pro Ala Gly Trp Phe Ile Ala Asp
            675                 680                 685

Lys Ser Gly Ala Gly Glu Arg Gly Ser Arg Gly Ile Ile Ala Ala Leu
            690                 695                 700

Gly Pro Asp Gly Lys Pro Ser Arg Ile Val Val Ile Tyr Thr Thr Gly
705                 710                 715                 720

Ser Gln Ala Thr Met Asp Glu Arg Asn Arg Gln Ile Ala Glu Ile Gly
                725                 730                 735

Ala Ser Leu Ile Lys His Trp
            740

<210> SEQ ID NO 19
<211> LENGTH: 2232
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
atgaaaaaga tttggctggc gctggctggt ttagttttag cgtttagcgc atcggcggcg    60

```
cagtatgaag atcaccatca ccaccaccac catcaccact ctggctcgag cctggtgccg    120
cgcggcagcc atatgtctgg ctcgagcagt aaaggtgaag aactgttcac cggtgttgtt    180
ccgatcctgg ttgaactgga tggtgatgtt aacggccaca aattctctgt tcgtggtgaa    240
ggtgaaggtg atgcaaccaa cggtaaactg accctgaaat tcatctgcac taccggtaaa    300
ctgccggttc catggccgac tctggtgact accctgacct atggtgttca gtgttttcct    360
cgttacccgg atcacatgaa gcagcatgat ttcttcaaat ctgcaatgcc ggaaggttat    420
gtacaggagc gcaccatttc tttcaaagac gatggcacct acaaaacccg tgcagaggtt    480
aaatttgaag tgatactct ggtgaaccgt attgaactga aaggcattga tttcaaagag    540
gacggcaaca tcctgggcca caaactggaa tataacttca actcccataa cgtttacatc    600
accgcagaca aacagaagaa cggtatcaaa gctaacttca aaattcgcca taacgttgaa    660
gacggtagcg tacagctggc ggaccactac cagcagaaca ctccgatcgg tgatggtccg    720
gttctgctgc cggataacca ctacctgtcc acccagtcta aactgtccaa agacccgaac    780
gaaaagcgcg accacatggt gctgctggag ttcgttactg cagcaggtat cacgcacggc    840
atggatgaac tctacaaatc tggcgcgccg ggcggtccgc agggtgttgt tggtgcagat    900
ggtaaagacg gtaccccggg taatgcaggt cagaaaggtc cgtcaggtga acctggcagc    960
cctggtaaag caggtagtgc cggtgagcag ggtccgccgg gcaaagatgg tagtaatggt   1020
gagccgggta gccctggcaa agaaggtgaa cgtggtctgg caggaccgcc gggtcctgat   1080
ggtcgccgcg gtgaaacggg ttcaccgggt attgccggtg ccctgggtaa accaggtctg   1140
gaaggtccga aaggttatcc tggtctgcgc ggtcgtgatg gtaccaatgg caaacgtggc   1200
gaacagggcg aaaccggtcc agatggtgtt cgtggtattc cgggtaacga tggtcagagc   1260
ggtaaaccgg gcattgatgg tattgatggc accaatggtc agcctggcga agcaggttat   1320
cagggtggtc gcgtacccg tggtcagctg ggtgaaacag gtgatgttgg tcagaatggt   1380
gatcgcggcg caccgggtcc ggatggtagc aaaggtagcg ccggtcgtcc gggtttacgt   1440
cacccagaaa cgctggtgaa agtaaaagat gctgaagatc agttgggtgc acgagtgggt   1500
tacatcgaac tggatctcaa cagcggtaag atccttgaga gttttcgccc cgaagaacgt   1560
tttccaatga tgagcacttt taaagttctg ctatgtggcg cggtattatc ccgtattgac   1620
gccgggcaag agcaactcgg tcgccgcata cactattctc agaatgactt ggttgagtac   1680
tcaccagtca cagaaaagca tcttacggat ggcatgacag taagagaatt atgcagtgct   1740
gccataacca tgagtgataa cactgcggcc aacttacttc tgacaacgat cggaggaccg   1800
aaggagctaa ccgctttttt gcacaacatg ggggatcatg taactcgcct tgatcgttgg   1860
gaaccggagc tgaatgaagc cataccaaac gacgagcgtg acaccacgat gcctgtagca   1920
atggcaacaa cgttgcgcaa actattaact ggcgaactac ttactctagc ttcccggcaa   1980
caattaatag actggatgga ggcggataaa gttgcaggac cacttctgcg ctcggccctt   2040
ccggctggct ggtttattgc tgataaatct ggagccggtg agcgtgggtc tcgcggtatc   2100
attgcagcac tggggccaga tggtaagccc tcccgtatcg tagttatcta cacgacgggg   2160
agtcaggcaa ctatggatga acgaaataga cagatcgctg atataggtgc ctcactgatt   2220
aagcattggt aa                                                        2232

<210> SEQ ID NO 20
<211> LENGTH: 743
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 20

```
Met Lys Lys Ile Trp Leu Ala Leu Ala Gly Leu Val Leu Ala Phe Ser
1               5                   10                  15

Ala Ser Ala Ala Gln Tyr Glu Asp His His His His His His His His
            20                  25                  30

His Ser Gly Ser Ser Leu Val Pro Arg Gly Ser His Met Ser Gly Ser
        35                  40                  45

Ser Ser Lys Gly Glu Glu Leu Phe Thr Gly Val Val Pro Ile Leu Val
    50                  55                  60

Glu Leu Asp Gly Asp Val Asn Gly His Lys Phe Ser Val Arg Gly Glu
65                  70                  75                  80

Gly Glu Gly Asp Ala Thr Asn Gly Lys Leu Thr Leu Lys Phe Ile Cys
                85                  90                  95

Thr Thr Gly Lys Leu Pro Val Pro Trp Pro Thr Leu Val Thr Thr Leu
            100                 105                 110

Thr Tyr Gly Val Gln Cys Phe Ser Arg Tyr Pro Asp His Met Lys Gln
        115                 120                 125

His Asp Phe Phe Lys Ser Ala Met Pro Glu Gly Tyr Val Gln Glu Arg
    130                 135                 140

Thr Ile Ser Phe Lys Asp Asp Gly Thr Tyr Lys Thr Arg Ala Glu Val
145                 150                 155                 160

Lys Phe Glu Gly Asp Thr Leu Val Asn Arg Ile Glu Leu Lys Gly Ile
                165                 170                 175

Asp Phe Lys Glu Asp Gly Asn Ile Leu Gly His Lys Leu Glu Tyr Asn
            180                 185                 190

Phe Asn Ser His Asn Val Tyr Ile Thr Ala Asp Lys Gln Lys Asn Gly
        195                 200                 205

Ile Lys Ala Asn Phe Lys Ile Arg His Asn Val Glu Asp Gly Ser Val
    210                 215                 220

Gln Leu Ala Asp His Tyr Gln Gln Asn Thr Pro Ile Gly Asp Gly Pro
225                 230                 235                 240

Val Leu Leu Pro Asp Asn His Tyr Leu Ser Thr Gln Ser Lys Leu Ser
                245                 250                 255

Lys Asp Pro Asn Glu Lys Arg Asp His Met Val Leu Leu Glu Phe Val
            260                 265                 270

Thr Ala Ala Gly Ile Thr His Gly Met Asp Glu Leu Tyr Lys Ser Gly
        275                 280                 285

Ala Pro Gly Gly Pro Gln Gly Val Val Gly Ala Asp Gly Lys Asp Gly
    290                 295                 300

Thr Pro Gly Asn Ala Gly Gln Lys Gly Pro Ser Gly Glu Pro Gly Ser
305                 310                 315                 320

Pro Gly Lys Ala Gly Ser Ala Gly Glu Gln Gly Pro Gly Lys Asp
                325                 330                 335

Gly Ser Asn Gly Glu Pro Gly Ser Pro Gly Lys Glu Gly Glu Arg Gly
            340                 345                 350

Leu Ala Gly Pro Pro Gly Pro Asp Gly Arg Arg Gly Glu Thr Gly Ser
        355                 360                 365

Pro Gly Ile Ala Gly Ala Leu Gly Lys Pro Gly Leu Glu Gly Pro Lys
    370                 375                 380
```

```
Gly Tyr Pro Gly Leu Arg Gly Arg Asp Gly Thr Asn Gly Lys Arg Gly
385                 390                 395                 400

Glu Gln Gly Glu Thr Gly Pro Asp Gly Val Arg Gly Ile Pro Gly Asn
            405                 410                 415

Asp Gly Gln Ser Gly Lys Pro Gly Ile Asp Gly Ile Asp Gly Thr Asn
        420                 425                 430

Gly Gln Pro Gly Glu Ala Gly Tyr Gln Gly Gly Arg Gly Thr Arg Gly
    435                 440                 445

Gln Leu Gly Glu Thr Gly Asp Val Gly Gln Asn Gly Asp Arg Gly Ala
450                 455                 460

Pro Gly Pro Asp Gly Ser Lys Gly Ser Ala Gly Arg Pro Gly Leu Arg
465                 470                 475                 480

His Pro Glu Thr Leu Val Lys Val Lys Asp Ala Glu Asp Gln Leu Gly
            485                 490                 495

Ala Arg Val Gly Tyr Ile Glu Leu Asp Leu Asn Ser Gly Lys Ile Leu
        500                 505                 510

Glu Ser Phe Arg Pro Glu Glu Arg Phe Pro Met Met Ser Thr Phe Lys
    515                 520                 525

Val Leu Leu Cys Gly Ala Val Leu Ser Arg Ile Asp Ala Gly Gln Glu
530                 535                 540

Gln Leu Gly Arg Arg Ile His Tyr Ser Gln Asn Asp Leu Val Glu Tyr
545                 550                 555                 560

Ser Pro Val Thr Glu Lys His Leu Thr Asp Gly Met Thr Val Arg Glu
            565                 570                 575

Leu Cys Ser Ala Ala Ile Thr Met Ser Asp Asn Thr Ala Ala Asn Leu
        580                 585                 590

Leu Leu Thr Thr Ile Gly Gly Pro Lys Glu Leu Thr Ala Phe Leu His
    595                 600                 605

Asn Met Gly Asp His Val Thr Arg Leu Asp Arg Trp Glu Pro Glu Leu
610                 615                 620

Asn Glu Ala Ile Pro Asn Asp Glu Arg Asp Thr Thr Met Pro Val Ala
625                 630                 635                 640

Met Ala Thr Thr Leu Arg Lys Leu Leu Thr Gly Glu Leu Leu Thr Leu
            645                 650                 655

Ala Ser Arg Gln Gln Leu Ile Asp Trp Met Glu Ala Asp Lys Val Ala
        660                 665                 670

Gly Pro Leu Leu Arg Ser Ala Leu Pro Ala Gly Trp Phe Ile Ala Asp
    675                 680                 685

Lys Ser Gly Ala Gly Glu Arg Gly Ser Arg Gly Ile Ile Ala Ala Leu
690                 695                 700

Gly Pro Asp Gly Lys Pro Ser Arg Ile Val Val Ile Tyr Thr Thr Gly
705                 710                 715                 720

Ser Gln Ala Thr Met Asp Glu Arg Asn Arg Gln Ile Ala Glu Ile Gly
            725                 730                 735

Ala Ser Leu Ile Lys His Trp
        740

<210> SEQ ID NO 21
<211> LENGTH: 786
<212> TYPE: PRT
<213> ORGANISM: Homo sapiens

<400> SEQUENCE: 21

Met Ala Gly Leu Thr Ala Ala Ala Pro Arg Pro Gly Val Leu Leu Leu
1               5                   10                  15
```

```
Leu Leu Ser Ile Leu His Pro Ser Arg Pro Gly Gly Val Pro Gly Ala
         20                  25                  30

Ile Pro Gly Gly Val Pro Gly Val Phe Tyr Pro Gly Ala Gly Leu
         35                  40                  45

Gly Ala Leu Gly Gly Ala Leu Gly Pro Gly Lys Pro Leu Lys
 50                  55                  60

Pro Val Pro Gly Gly Leu Ala Gly Ala Gly Leu Gly Ala Gly Leu Gly
 65                  70                  75                  80

Ala Phe Pro Ala Val Thr Phe Pro Gly Ala Leu Val Pro Gly Val
                 85                  90                  95

Ala Asp Ala Ala Ala Tyr Lys Ala Ala Lys Ala Gly Ala Gly Leu
             100                 105                 110

Gly Gly Val Pro Gly Val Gly Gly Leu Gly Val Ser Ala Gly Ala Val
         115                 120                 125

Val Pro Gln Pro Gly Ala Gly Val Lys Pro Gly Lys Val Pro Gly Val
 130                 135                 140

Gly Leu Pro Gly Val Tyr Pro Gly Gly Val Leu Pro Gly Ala Arg Phe
 145                 150                 155                 160

Pro Gly Val Gly Val Leu Pro Gly Val Pro Thr Gly Ala Gly Val Lys
                 165                 170                 175

Pro Lys Ala Pro Gly Val Gly Gly Ala Phe Ala Gly Ile Pro Gly Val
             180                 185                 190

Gly Pro Phe Gly Gly Pro Gln Pro Gly Val Pro Leu Gly Tyr Pro Ile
         195                 200                 205

Lys Ala Pro Lys Leu Pro Gly Gly Tyr Gly Leu Pro Tyr Thr Thr Gly
 210                 215                 220

Lys Leu Pro Tyr Gly Tyr Gly Pro Gly Gly Val Ala Gly Ala Ala Gly
 225                 230                 235                 240

Lys Ala Gly Tyr Pro Thr Gly Thr Gly Val Gly Pro Gln Ala Ala Ala
                 245                 250                 255

Ala Ala Ala Ala Lys Ala Ala Lys Phe Gly Ala Gly Ala Ala Gly
             260                 265                 270

Val Leu Pro Gly Val Gly Gly Ala Gly Val Pro Gly Val Pro Gly Ala
         275                 280                 285

Ile Pro Gly Ile Gly Gly Ile Ala Gly Val Gly Thr Pro Ala Ala Ala
         290                 295                 300

Ala Ala Ala Ala Ala Ala Lys Ala Ala Lys Tyr Gly Ala Ala Ala
 305                 310                 315                 320

Gly Leu Val Pro Gly Gly Pro Gly Phe Gly Pro Gly Val Val Gly Val
                 325                 330                 335

Pro Gly Ala Gly Val Pro Gly Val Gly Val Pro Gly Ala Gly Ile Pro
             340                 345                 350

Val Val Pro Gly Ala Gly Ile Pro Gly Ala Ala Val Pro Gly Val Val
         355                 360                 365

Ser Pro Glu Ala Ala Ala Lys Ala Ala Lys Ala Ala Lys Tyr Gly
             370                 375                 380

Ala Arg Pro Gly Val Gly Val Gly Gly Ile Pro Thr Tyr Gly Val Gly
 385                 390                 395                 400

Ala Gly Gly Phe Pro Gly Phe Gly Val Gly Val Gly Ile Pro Gly
                 405                 410                 415

Val Ala Gly Val Pro Gly Val Gly Val Pro Gly Val Gly Gly Val
             420                 425                 430
```

| | | | | | | | | | | |
|---|---|---|---|---|---|---|---|---|---|---|
| Pro | Gly | Val | Gly | Ile | Ser | Pro | Glu | Ala | Gln | Ala | Ala | Ala | Ala | Ala | Lys |
| | | | 435 | | | | 440 | | | | 445 | | | | |

Pro Gly Val Gly Ile Ser Pro Glu Ala Gln Ala Ala Ala Ala Ala Lys
                435                 440                 445
Ala Ala Lys Tyr Gly Ala Ala Gly Ala Gly Val Leu Gly Gly Leu Val
    450                 455                 460
Pro Gly Pro Gln Ala Ala Val Pro Gly Val Pro Gly Thr Gly Val
465                 470                 475                 480
Pro Gly Val Gly Thr Pro Ala Ala Ala Lys Ala Ala Ala Lys
                485                 490                 495
Ala Ala Gln Phe Gly Leu Val Pro Gly Val Gly Val Ala Pro Gly Val
            500                 505                 510
Gly Val Ala Pro Gly Val Gly Val Ala Pro Gly Val Gly Leu Ala Pro
            515                 520                 525
Gly Val Gly Val Ala Pro Gly Val Gly Val Ala Pro Gly Val Gly Val
            530                 535                 540
Ala Pro Gly Ile Gly Pro Gly Val Ala Ala Ala Lys Ser Ala
545                 550                 555                 560
Ala Lys Val Ala Ala Lys Ala Gln Leu Arg Ala Ala Gly Leu Gly
                565                 570                 575
Ala Gly Ile Pro Gly Leu Gly Val Gly Val Gly Val Pro Gly Leu Gly
                580                 585                 590
Val Gly Ala Gly Val Pro Gly Leu Gly Val Gly Ala Gly Val Pro Gly
            595                 600                 605
Phe Gly Ala Gly Ala Asp Glu Gly Val Arg Arg Ser Leu Ser Pro Glu
            610                 615                 620
Leu Arg Glu Gly Asp Pro Ser Ser Ser Gln His Leu Pro Ser Thr Pro
625                 630                 635                 640
Ser Ser Pro Arg Val Pro Gly Ala Leu Ala Ala Ala Lys Ala Ala Lys
                645                 650                 655
Tyr Gly Ala Ala Val Pro Gly Val Leu Gly Gly Leu Gly Ala Leu Gly
                660                 665                 670
Gly Val Gly Ile Pro Gly Gly Val Val Gly Ala Gly Pro Ala Ala Ala
            675                 680                 685
Ala Ala Ala Ala Lys Ala Ala Lys Ala Ala Gln Phe Gly Leu Val
690                 695                 700
Gly Ala Ala Gly Leu Gly Gly Leu Gly Val Gly Gly Leu Gly Val Pro
705                 710                 715                 720
Gly Val Gly Gly Leu Gly Gly Ile Pro Pro Ala Ala Ala Lys Ala
                725                 730                 735
Ala Lys Tyr Gly Ala Ala Gly Leu Gly Gly Val Leu Gly Gly Ala Gly
                740                 745                 750
Gln Phe Pro Leu Gly Gly Val Ala Ala Arg Pro Gly Phe Gly Leu Ser
                755                 760                 765
Pro Ile Phe Pro Gly Gly Ala Cys Leu Gly Lys Ala Cys Gly Arg Lys
                770                 775                 780
Arg Lys
785

<210> SEQ ID NO 22
<211> LENGTH: 2361
<212> TYPE: DNA
<213> ORGANISM: Homo sapiens

<400> SEQUENCE: 22
atggcgggtc tgacggcggc ggccccgcgg cccggagtcc tcctgctcct gctgtccatc    60

```
ctccacccct ctcggcctgg aggggtccct ggggccattc ctggtggagt tcctggagga    120
gtcttttatc caggggctgg tctcggagcc cttggaggag gagcgctggg gcctggaggc    180
aaacctctta agccagttcc cggagggctt gcgggtgctg gccttggggc agggctcggc    240
gccttccccg cagttacctt tccgggggct ctggtgcctg gtggagtggc tgacgctgct    300
gcagcctata aagctgctaa ggctggcgct gggcttggtg gtgtcccagg agttggtggc    360
ttaggagtgt ctgcaggtgc ggtggttcct cagcctggag ccggagtgaa gcctgggaaa    420
gtgccgggtg tggggctgcc aggtgtatac ccaggtggcg tgctcccagg agctcggttc    480
cccggtgtgg gggtgctccc tggagttccc actggagcag gagttaagcc caaggctcca    540
ggtgtaggtg gagcttttgc tggaatccca ggagttggac cctttggggg accgcaacct    600
ggagtcccac tggggtatcc catcaaggcc cccaagctgc ctggtggcta tggactgccc    660
tacaccacag ggaaactgcc ctatggctat gggcccggag gagtggctgg tgcagcgggc    720
aaggctggtt acccaacagg gacagggggtt ggccccagg cagcagcagc agcggcagct    780
aaagcagcag caaagttcgg tgctggagca gccgagtcc tccctggtgt tggaggggct    840
ggtgttcctg gcgtgcctgg ggcaattcct ggaattggag gcatcgcagg cgttgggact    900
ccagctgcag ctgcagctgc agcagcagcc gctaaggcag ccaagtatgg agctgctgca    960
ggcttagtgc ctggtgggcc aggctttggc ccgggagtag ttggtgtccc aggagctggc   1020
gttccaggtg ttggtgtccc aggagctggg attccagttg tcccaggtgc tgggatccca   1080
ggtgctgcgg ttccaggggt tgtgtcacca gaagcagctg ctaaggcagc tgcaaaggca   1140
gccaaatacg gggccaggcc cggagtcgga gttgaggca ttcctactta cggggttgga   1200
gctgggggct ttcccggctt tggtgtcgga gtcggaggta tccctggagt cgcaggtgtc   1260
cctggtgtcg gaggtgttcc cggagtcgga ggtgtcccgg agttggcat ttcccccgaa   1320 gctcaggcag cagctgccgc caaggctgcc aagtacggtg ctgcaggagc aggagtgctg   1380
ggtgggctag tgccaggtcc ccaggcgca gtcccaggtg tgccgggcac gggaggagtg   1440
ccaggagtgg ggaccccagc agctgcagct gctaaagcag ccgccaaagc cgcccagttt   1500 ggggttagttc ctggtgtcgg cgtggctcct ggagttggcg tggctcctgg tgtcggtgtg   1560
gctcctggag ttggcttggc tcctggagtt ggcgtggctc ctggagttgg tgtggctcct   1620
ggcgttggcg tggctcccgg cattggccct ggtggagttg cagctgcagc aaaatccgct   1680
gccaaggtgg ctgccaaagc ccagctccga gctgcagctg gcttggtgc tggcatccct   1740 ggacttggag ttggtgtcgg cgtccctgga cttggagttg gtgctggtgt tcctggactt   1800
ggagttggtg ctggtgttcc tggcttcggg gcaggtgcag atgagggagt taggcggagc   1860
ctgtcccctg agctcaggga aggagatccc tcctcctctc agcacctccc cagcaccccc   1920
tcatcaccca gggtacctgg agccctggct gccgctaaag cagccaaata tggagcagca   1980
gtgcctgggg tccttggagg gctcggggct ctcggtggag taggcatccc aggcggtgtg   2040
gtgggagccg acccgccgc cgccgctgcc gcagccaaag ctgctgccaa agccgcccag   2100
tttggcctag tggagccgc tgggctcgga ggactcggag tcggagggct ggagttcca   2160 ggtgttgggg gccttggagg tatacctcca gctgcagccg ctaaagcagc taaatacggt   2220
gctgctggcc ttggaggtgt cctaggggggt gccgggcagt cccacttgg aggagtggca   2280 gcaagacctg gcttcggatt gtctcccatt ttcccaggtg gggcctgcct ggggaaagct   2340
tgtggccgga agagaaaatg a                                             2361
```

<210> SEQ ID NO 23
<211> LENGTH: 2418
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 23

| | | | | | |
|---|---|---|---|---|---|
| atgaaaaaga | tttggctggc | gctggctggt | ttagttttag | cgtttagcgc | atcggcggcg | 60 |
| cagtatgaag | atcaccatca | ccaccaccac | catcaccact | ctggctcgag | cctggtgccg | 120 |
| cgcggcagcc | atatgggtgg | cgtaccaggc | gcaattcctg | ggggtgtccc | aggcggtgtt | 180 |
| ttttatccgg | gcgccggtct | ggcgcactg | ggtggcggtg | cactgggccc | gggcggcaaa | 240 |
| ccgctgaaac | cggtaccagg | tggtttagca | ggcgccggct | taggcgcagg | tctgggagca | 300 |
| tttccggcag | ttaccttttcc | aggggcactg | gttcctggag | gtgtggccga | tgcagccgcg | 360 |
| gcatataaag | ccgctaaagc | cggtgcgggt | ttaggaggcg | tcccaggtgt | cggtggcctg | 420 |
| ggtgttagcg | ccggtgcagt | tgttccgcag | ccgggagcag | gggttaaacc | tggtaaagtg | 480 |
| ccgggagtag | gtctgccagg | cgtttatcct | ggtggtgttt | gccgggtgc | ccgttttccg | 540 |
| ggcgttggtg | ttcttccagg | cgtgccgacc | ggagccggtt | taaaccgaa | agccccggt | 600 |
| gttggaggtg | catttgcagg | catcccggga | gttggcccgt | ttggtggtcc | gcaacctggg | 660 |
| gttccgttag | gttatccgat | taaagcaccg | aaactgcccg | cgcggttatgg | tctgccgtac | 720 |
| acaaccggta | aactgccgta | tggttatggc | ccgggtggag | ttgcgggtgc | agcaggtaaa | 780 |
| gcgggttatc | ctaccggaac | cggtgtaggt | ccgcaggccg | ctgctgccgc | cgccgcaaaa | 840 |
| gcagcggcta | aatttggcgc | cggagcagcg | ggtgttctgc | ctggagttgg | tggtgcgggc | 900 |
| gtgccagggg | tacctggtgc | aattccgggt | attggtggta | ttgccggtgt | cggcaccccg | 960 |
| gccgcggcag | ctgcggcagc | ggcggctgcc | aaagctgcta | atacggtgc | cgcggcgggt | 1020 |
| ctggtgccag | gaggtccggg | ttttggtccg | ggagtggttg | gcgtgcctgg | cgcaggcgtt | 1080 |
| cctggtgtgg | gcgttccagg | tgcagggatt | cctgttgtgc | ctggtgccgg | tattcccggc | 1140 |
| gcggccgttc | cggggggtggt | tagcccggaa | gccgcagcga | aggctgcggc | aaaggcagca | 1200 |
| aagtatggcg | cacgcccagg | agtcggcgtg | ggtggtatcc | cgacctatgg | ggtgggcgca | 1260 |
| ggggggttttc | ctggtttcgg | cgtaggtgta | ggaggtatac | cgggcgtggc | cggtgtacca | 1320 |
| ggggggttggtg | gcgtccctgg | tgttggcggt | gtgccaggtg | ttggtatttc | accggaagca | 1380 |
| caggcagcag | ccgcagctaa | ggcagcgaaa | tatggtgccg | ccggcgcagg | agttttaggt | 1440 |
| gggctggttc | cgggcccgca | ggcagctgtg | ccggggggttc | caggcaccgg | tggtgtccct | 1500 |
| ggagtcggta | cgccggctgc | agcggcagcc | aaagcggctg | cgaaagcagc | acagtttggc | 1560 |
| ttagtaccgg | gtgtgggagt | tgccccccggc | gttggcgttg | ctccagggggt | gggtgttgct | 1620 |
| cctggcgtcg | gtctggctcc | tggagtgggc | gtagcacccg | gtgtggggt | ggccccgggt | 1680 |
| gttggggttg | caccgggtat | cggtccggc | ggtgtcgcag | cagcagctaa | aagcgcggcg | 1740 |
| aaagttgcgg | ccaaagccca | actgcgcgcc | gccgcgggcc | tcggtgcagg | tattccgggg | 1800 |
| ctgggtgtcg | gagttggagt | cccgggtttg | ggcgtgggcg | cggagttcc | gggactggga | 1860 |
| gtgggtgccg | gagttcctgg | ctttggtgca | ggcgcagatg | aaggtgttcg | tcgtagcctg | 1920 |
| agtccggaac | tgcgtgaagg | tgatccgagt | agcagccagc | atctgccgag | caccccgagc | 1980 |
| agcccgcgtg | ttccgggtgc | attagctgca | gcaaaagccg | ccaagtatgg | tgcagccgtg | 2040 |
| ccgggcgtct | taggtggtct | gggcgccctg | ggtggtgtag | gcattccggg | aggtgttgtg | 2100 |

```
ggtgcaggac cggccgccgc agctgcggcc gccaaagcag ctgcaaaagc ggcccagttt    2160
ggtttagtgg gcgccgcagg tttaggcggt ttaggtgtgg gtggactggg tgtacctggc    2220
gtaggcggtc tgggtggaat tccgcccgca gcggccgcga aagcggcaaa atatggcgcg    2280
gcaggcctgg gcggcgtgct gggtggggca ggtcagtttc cgctgggcgg ggttgccgca    2340
cgtccgggat ttggtctgag cccgattttc cctggcggcg catgtctggg taaagcatgt    2400
ggtcgtaaac gtaaataa                                                  2418
```

<210> SEQ ID NO 24
<211> LENGTH: 805
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

```
Met Lys Lys Ile Trp Leu Ala Leu Ala Gly Leu Val Leu Ala Phe Ser
1               5                   10                  15

Ala Ser Ala Ala Gln Tyr Glu Asp His His His His His His His
            20                  25                  30

His Ser Gly Ser Ser Leu Val Pro Arg Gly Ser His Met Gly Gly Val
        35                  40                  45

Pro Gly Ala Ile Pro Gly Gly Val Pro Gly Gly Val Phe Tyr Pro Gly
    50                  55                  60

Ala Gly Leu Gly Ala Leu Gly Gly Gly Ala Leu Gly Pro Gly Gly Lys
65                  70                  75                  80

Pro Leu Lys Pro Val Pro Gly Gly Leu Ala Gly Ala Gly Leu Gly Ala
                85                  90                  95

Gly Leu Gly Ala Phe Pro Ala Val Thr Phe Pro Gly Ala Leu Val Pro
            100                 105                 110

Gly Gly Val Ala Asp Ala Ala Ala Ala Tyr Lys Ala Ala Lys Ala Gly
        115                 120                 125

Ala Gly Leu Gly Gly Val Pro Gly Val Gly Gly Leu Gly Val Ser Ala
    130                 135                 140

Gly Ala Val Val Pro Gln Pro Gly Ala Gly Val Lys Pro Gly Lys Val
145                 150                 155                 160

Pro Gly Val Gly Leu Pro Gly Val Tyr Pro Gly Gly Val Leu Pro Gly
                165                 170                 175

Ala Arg Phe Pro Gly Val Gly Val Leu Pro Gly Val Pro Thr Gly Ala
            180                 185                 190

Gly Val Lys Pro Lys Ala Pro Gly Val Gly Gly Ala Phe Ala Gly Ile
        195                 200                 205

Pro Gly Val Gly Pro Phe Gly Gly Pro Gln Pro Gly Val Pro Leu Gly
    210                 215                 220

Tyr Pro Ile Lys Ala Pro Lys Leu Pro Gly Gly Tyr Gly Leu Pro Tyr
225                 230                 235                 240

Thr Thr Gly Lys Leu Pro Tyr Gly Tyr Gly Pro Gly Gly Val Ala Gly
                245                 250                 255

Ala Ala Gly Lys Ala Gly Tyr Pro Thr Gly Thr Gly Val Gly Pro Gln
            260                 265                 270

Ala Ala Ala Ala Ala Ala Ala Lys Ala Ala Lys Phe Gly Ala Gly
        275                 280                 285

Ala Ala Gly Val Leu Pro Gly Val Gly Gly Ala Gly Val Pro Gly Val
```

```
                290                 295                 300
Pro Gly Ala Ile Pro Gly Ile Gly Gly Ile Ala Gly Val Gly Thr Pro
305                 310                 315                 320

Ala Ala Ala Ala Ala Ala Ala Ala Lys Ala Ala Lys Tyr Gly
            325                 330                 335

Ala Ala Ala Gly Leu Val Pro Gly Gly Pro Gly Phe Gly Pro Gly Val
            340                 345                 350

Val Gly Val Pro Gly Ala Gly Val Pro Gly Val Gly Val Pro Gly Ala
            355                 360                 365

Gly Ile Pro Val Val Pro Gly Ala Gly Ile Pro Gly Ala Ala Val Pro
    370                 375                 380

Gly Val Val Ser Pro Glu Ala Ala Lys Ala Ala Lys Ala Ala
385                 390                 395                 400

Lys Tyr Gly Ala Arg Pro Gly Val Gly Val Gly Gly Ile Pro Thr Tyr
                405                 410                 415

Gly Val Gly Ala Gly Gly Phe Pro Gly Phe Gly Val Gly Val Gly Gly
            420                 425                 430

Ile Pro Gly Val Ala Gly Val Pro Gly Val Gly Val Pro Gly Val
    435                 440                 445

Gly Gly Val Pro Gly Val Gly Ile Ser Pro Glu Ala Gln Ala Ala Ala
    450                 455                 460

Ala Ala Lys Ala Ala Lys Tyr Gly Ala Ala Gly Ala Gly Val Leu Gly
465                 470                 475                 480

Gly Leu Val Pro Gly Pro Gln Ala Ala Val Pro Gly Val Pro Gly Thr
            485                 490                 495

Gly Gly Val Pro Gly Val Gly Thr Pro Ala Ala Ala Ala Lys Ala
    500                 505                 510

Ala Ala Lys Ala Ala Gln Phe Gly Leu Val Pro Gly Val Gly Val Ala
            515                 520                 525

Pro Gly Val Gly Val Ala Pro Gly Val Gly Val Ala Pro Gly Val Gly
    530                 535                 540

Leu Ala Pro Gly Val Gly Val Ala Pro Gly Val Gly Val Ala Pro Gly
545                 550                 555                 560

Val Gly Val Ala Pro Gly Ile Gly Pro Gly Gly Val Ala Ala Ala
            565                 570                 575

Lys Ser Ala Ala Lys Val Ala Ala Lys Ala Gln Leu Arg Ala Ala
            580                 585                 590

Gly Leu Gly Ala Gly Ile Pro Gly Leu Gly Val Gly Val Gly Val Pro
    595                 600                 605

Gly Leu Gly Val Gly Ala Gly Val Pro Gly Leu Gly Val Gly Ala Gly
    610                 615                 620

Val Pro Gly Phe Gly Ala Gly Ala Asp Glu Gly Val Arg Arg Ser Leu
625                 630                 635                 640

Ser Pro Glu Leu Arg Glu Gly Asp Pro Ser Ser Gln His Leu Pro
            645                 650                 655

Ser Thr Pro Ser Ser Pro Arg Val Pro Gly Ala Leu Ala Ala Ala Lys
            660                 665                 670

Ala Ala Lys Tyr Gly Ala Ala Val Pro Gly Val Leu Gly Gly Leu Gly
            675                 680                 685

Ala Leu Gly Gly Val Gly Ile Pro Gly Gly Val Val Gly Ala Gly Pro
    690                 695                 700

Ala Ala Ala Ala Ala Ala Ala Lys Ala Ala Ala Lys Ala Ala Gln Phe
705                 710                 715                 720
```

```
Gly Leu Val Gly Ala Ala Gly Leu Gly Gly Leu Gly Val Gly Gly Leu
                725                 730                 735

Gly Val Pro Gly Val Gly Gly Leu Gly Gly Ile Pro Pro Ala Ala Ala
            740                 745                 750

Ala Lys Ala Ala Lys Tyr Gly Ala Ala Gly Leu Gly Gly Val Leu Gly
        755                 760                 765

Gly Ala Gly Gln Phe Pro Leu Gly Gly Val Ala Arg Pro Gly Phe
    770                 775                 780

Gly Leu Ser Pro Ile Phe Pro Gly Gly Ala Cys Leu Gly Lys Ala Cys
785                 790                 795                 800

Gly Arg Lys Arg Lys
            805

<210> SEQ ID NO 25
<211> LENGTH: 2358
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
atgaaaaaga tttggctggc gctggctggt ttagttttag cgtttagcgc atcggcggcg     60
cagtatgaag atatgggtgg cgtaccaggc gcaattcctg ggggtgtccc aggcggtgtt   120
ttttatccgg gcgccggtct ggcgcactg ggtggcggtg cactgggccc gggcggcaaa    180
ccgctgaaac cggtaccagg tggtttagca ggcgccggct taggcgcagg tctgggagca   240
tttccggcag ttacctttcc aggggcactg gttcctggag gtgtggccga tgcagccgcg   300
gcatataaag ccgctaaagc cggtgcgggt ttaggaggcg tcccaggtgt cggtggcctg   360
ggtgttagcg ccggtgcagt tgttccgcag ccgggagcag gggttaaacc tggtaaagtg   420
ccgggagtag gtctgccagg cgtttatcct ggtggtgttt tgccgggtgc ccgttttccg   480
ggcgttggtg ttcttccagg cgtgccgacc ggagccggtg ttaaaccgaa agccccggt    540 gttgaaggtg catttgcagg catcccggga gttggcccgt tggtggtcc gcaacctggg    600 gttccgttag gttatccgat taaagcaccg aaactgcccg gcggttatgg tctgccgtac   660
acaaccggta aactgccgta tggttatggc cgggtggag ttgcgggtgc agcaggtaaa    720
gcgggttatc ctaccggaac cggtgtaggt ccgcaggccg ctgctgccgc cgccgcaaaa   780
gcagcggcta aatttggcgc cggagcagcg ggtgttctgc ctggagttgg tggtgcgggc   840
gtgccagggg tacctggtgc aattccgggt attggtggta ttgccggtgt cggcaccccg   900
gccgcggcag ctgcggcagc ggcggctgcc aaagctgcta atacggtgc cgcggcgggt    960 ctggtgccag gaggtccggg ttttggtccg ggagtggttg gcgtgcctgg cgcaggcgtt  1020
cctggtgtgg gcgttccagg tgcagggatt cctgttgtgc ctggtgccgg tattcccggc  1080
gcggccgttc cggggtggt tagcccggaa ccgcagcga aggctgcggc aaaggcagca    1140
aagtatggcg cacgcccagg agtcggcgtg gtgggtatcc gacctatgg gtgggcgca    1200 gggggttttc ctggtttcgg cgtaggtgta ggaggtatac cggcgtggc cggtgtacca   1260 ggggttggtg gcgtccctgg tgttggcggt gtgccaggtg ttggtatttc accggaagca  1320
caggcagcag ccgcagctaa ggcagcgaaa tatggtgccg ccggcgcagg agttttaggt  1380
gggctggttc cggccccgca ggcagctgtg ccggggggttc caggcaccgg tggtgtccct  1440
ggagtcggta cgccggctgc agcggcagcc aaagcggctg cgaaagcagc acagtttggc  1500
```

```
ttagtaccgg gtgtgggagt tgcccccggc gttggcgttg ctccaggggt gggtgttgct   1560
cctggcgtcg gtctggctcc tggagtgggc gtagcacccg tgtgggggt ggccccgggt    1620 gttggggttg caccgggtat cggtccgggc ggtgtcgcag cagcagctaa aagcgcggcg   1680
aaagttgcgg ccaaagccca actgcgcgcc gccgcgggcc tcggtgcagg tattccgggg   1740
ctgggtgtcg gagttggagt cccgggtttg ggcgtgggcg cgggagttcc gggactggga   1800
gtgggtgccg gagttcctgg ctttggtgca ggcgcagatg aaggtgttcg tcgtagcctg   1860
agtccggaac tgcgtgaagg tgatccgagt agcagccagc atctgccgag caccccgagc   1920
agcccgcgtg ttccgggtgc attagctgca gcaaaagccg ccaagtatgg tgcagccgtg   1980
ccgggcgtct taggtggtct gggcgccctg ggtggtgtag gcattccggg aggtgttgtg   2040
ggtgcaggac cggccgccgc agctgcggcc gccaaagcag ctgcaaaagc ggcccagttt   2100
ggtttagtgg gcgccgcagg tttaggcggt ttaggtgtgg gtggactggg tgtacctggc   2160
gtaggcggtc tgggtggaat tccgcccgca gcggccgcga aagcggcaaa atatggcgcg   2220
gcaggcctgg gcggcgtgct gggtggggca ggtcagtttc gctgggcgg ggttgccgca    2280 cgtccgggat ttggtctgag cccgattttc cctggcggcg catgtctggg taaagcatgt   2340
ggtcgtaaac gtaaataa                                                 2358
```

<210> SEQ ID NO 26
<211> LENGTH: 785
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Met Lys Lys Ile Trp Leu Ala Leu Ala Gly Leu Val Leu Ala Phe Ser
1               5                   10                  15

Ala Ser Ala Ala Gln Tyr Glu Asp Met Gly Gly Val Pro Gly Ala Ile
            20                  25                  30

Pro Gly Gly Val Pro Gly Gly Val Phe Tyr Pro Gly Ala Gly Leu Gly
        35                  40                  45

Ala Leu Gly Gly Gly Ala Leu Gly Pro Gly Gly Lys Pro Leu Lys Pro
    50                  55                  60

Val Pro Gly Gly Leu Ala Gly Ala Gly Leu Gly Ala Gly Leu Gly Ala
65                  70                  75                  80

Phe Pro Ala Val Thr Phe Pro Gly Ala Leu Val Pro Gly Gly Val Ala
                85                  90                  95

Asp Ala Ala Ala Ala Tyr Lys Ala Ala Lys Ala Gly Ala Gly Leu Gly
            100                 105                 110

Gly Val Pro Gly Val Gly Gly Leu Gly Val Ser Ala Gly Ala Val Val
        115                 120                 125

Pro Gln Pro Gly Ala Gly Val Lys Pro Gly Lys Val Pro Gly Val Gly
    130                 135                 140

Leu Pro Gly Val Tyr Pro Gly Gly Val Leu Pro Gly Ala Arg Phe Pro
145                 150                 155                 160

Gly Val Gly Val Leu Pro Gly Val Pro Thr Gly Ala Gly Val Lys Pro
                165                 170                 175

Lys Ala Pro Gly Val Gly Gly Ala Phe Ala Gly Ile Pro Gly Val Gly
            180                 185                 190

Pro Phe Gly Gly Pro Gln Pro Gly Val Pro Leu Gly Tyr Pro Ile Lys
```

-continued

```
                195                 200                 205
Ala Pro Lys Leu Pro Gly Gly Tyr Gly Leu Pro Tyr Thr Thr Gly Lys
210                 215                 220

Leu Pro Tyr Gly Tyr Gly Pro Gly Gly Val Ala Gly Ala Ala Gly Lys
225                 230                 235                 240

Ala Gly Tyr Pro Thr Gly Thr Gly Val Gly Pro Gln Ala Ala Ala Ala
                245                 250                 255

Ala Ala Ala Lys Ala Ala Ala Lys Phe Gly Ala Gly Ala Ala Gly Val
            260                 265                 270

Leu Pro Gly Val Gly Gly Ala Gly Val Pro Gly Val Pro Gly Ala Ile
        275                 280                 285

Pro Gly Ile Gly Gly Ile Ala Gly Val Gly Thr Pro Ala Ala Ala Ala
    290                 295                 300

Ala Ala Ala Ala Ala Ala Lys Ala Ala Lys Tyr Gly Ala Ala Ala Gly
305                 310                 315                 320

Leu Val Pro Gly Gly Pro Gly Phe Gly Pro Gly Val Val Gly Val Pro
                325                 330                 335

Gly Ala Gly Val Pro Gly Val Gly Val Pro Gly Ala Gly Ile Pro Val
            340                 345                 350

Val Pro Gly Ala Gly Ile Pro Gly Ala Ala Val Pro Gly Val Val Ser
        355                 360                 365

Pro Glu Ala Ala Lys Ala Ala Lys Ala Ala Lys Tyr Gly Ala
    370                 375                 380

Arg Pro Gly Val Gly Val Gly Gly Ile Pro Thr Tyr Gly Val Gly Ala
385                 390                 395                 400

Gly Gly Phe Pro Gly Phe Gly Val Gly Val Gly Gly Ile Pro Gly Val
                405                 410                 415

Ala Gly Val Pro Gly Val Gly Gly Val Pro Gly Val Gly Val Pro
            420                 425                 430

Gly Val Gly Ile Ser Pro Glu Ala Gln Ala Ala Ala Ala Lys Ala
        435                 440                 445

Ala Lys Tyr Gly Ala Ala Gly Ala Gly Val Leu Gly Gly Leu Val Pro
    450                 455                 460

Gly Pro Gln Ala Ala Val Pro Gly Val Pro Gly Thr Gly Gly Val Pro
465                 470                 475                 480

Gly Val Gly Thr Pro Ala Ala Ala Ala Lys Ala Ala Ala Lys Ala
                485                 490                 495

Ala Gln Phe Gly Leu Val Pro Gly Val Gly Val Ala Pro Gly Val Gly
            500                 505                 510

Val Ala Pro Gly Val Gly Val Ala Pro Gly Val Gly Leu Ala Pro Gly
        515                 520                 525

Val Gly Val Ala Pro Gly Val Gly Val Ala Pro Gly Val Gly Val Ala
    530                 535                 540

Pro Gly Ile Gly Pro Gly Gly Val Ala Ala Ala Lys Ser Ala Ala
545                 550                 555                 560

Lys Val Ala Ala Lys Ala Gln Leu Arg Ala Ala Ala Gly Leu Gly Ala
                565                 570                 575

Gly Ile Pro Gly Leu Gly Val Gly Val Gly Val Pro Gly Leu Gly Val
            580                 585                 590

Gly Ala Gly Val Pro Gly Leu Gly Val Gly Ala Gly Val Pro Gly Phe
        595                 600                 605

Gly Ala Gly Ala Asp Glu Gly Val Arg Arg Ser Leu Ser Pro Glu Leu
    610                 615                 620
```

```
Arg Glu Gly Asp Pro Ser Ser Gln His Leu Pro Ser Thr Pro Ser
625                 630                 635                 640

Ser Pro Arg Val Pro Gly Ala Leu Ala Ala Ala Lys Ala Ala Lys Tyr
            645                 650                 655

Gly Ala Ala Val Pro Gly Val Leu Gly Gly Leu Gly Ala Leu Gly Gly
                660                 665                 670

Val Gly Ile Pro Gly Gly Val Val Gly Ala Gly Pro Ala Ala Ala
        675                 680                 685

Ala Ala Ala Lys Ala Ala Ala Lys Ala Ala Gln Phe Gly Leu Val Gly
690                 695                 700

Ala Ala Gly Leu Gly Gly Leu Gly Val Gly Gly Leu Gly Val Pro Gly
705                 710                 715                 720

Val Gly Gly Leu Gly Gly Ile Pro Pro Ala Ala Ala Lys Ala Ala
                725                 730                 735

Lys Tyr Gly Ala Ala Gly Leu Gly Gly Val Leu Gly Gly Ala Gly Gln
            740                 745                 750

Phe Pro Leu Gly Gly Val Ala Ala Arg Pro Gly Phe Gly Leu Ser Pro
            755                 760                 765

Ile Phe Pro Gly Gly Ala Cys Leu Gly Lys Ala Cys Gly Arg Lys Arg
    770                 775                 780

Lys
785

<210> SEQ ID NO 27
<211> LENGTH: 3945
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
atgaaaaaga tttggctggc gctggctggt ttagttttag cgtttagcgc atcggcggcg        60
cagtatgaag atcaccatca ccaccaccac catcaccact ctggctcgag cctggtgccg       120
cgcggcagcc atatgtctgg ctcgagcagt aaaggtgaag aactgttcac cggtgttgtt       180
ccgatcctgg ttgaactgga tggtgatgtt aacggccaca aattctctgt tcgtggtgaa       240
ggtgaaggtg atgcaaccaa cggtaaactg accctgaaat tcatctgcac taccggtaaa       300
ctgccggttc catggccgac tctggtgact accctgacct atggtgttca gtgttttctc       360
cgttacccgg atcacatgaa gcagcatgat ttcttcaaat ctgcaatgcc ggaaggttat       420
gtacaggagc gcaccatttc tttcaaagac gatggcacct acaaaacccg tgcagaggtt       480
aaatttgaag tgatactctg gtgaaccgta ttgaactgaa aggcattgat ttcaaagag        540 gacggcaaca tcctgggcca caactggaat ataacttca actcccataa cgtttacatc        600
accgcagaca aacagaagaa cggtatcaaa gctaacttca aaattcgcca taacgttgaa       660
gacggtagcg tacagctggc ggaccactac cagcagaaca ctccgatcgg tgatggtccg       720
gttctgctgc cggataacca ctacctgtcc acccagtcta aactgtccaa agacccgaac       780
gaaaagcgcg accacatggt gctgctggag ttcgttactg cagcaggtat cacgcacggc       840
atggatgaac tctacaaatc tggcgcgccg ggcggtggcg taccaggcgc aattcctggg       900
ggtgtcccag gcggtgtttt ttatccgggc gccggtcttg cgcactgggt ggcggtgca        960 ctgggcccgg gcggcaaacc gctgaaaccg gtaccaggtg gtttagcagg cgccggctta      1020
```

```
ggcgcaggtc tgggagcatt tccggcagtt acctttccag gggcactggt tcctggaggt    1080
gtggccgatg cagccgcggc atataaagcc gctaaagccg gtgcgggttt aggaggcgtc    1140
ccaggtgtcg gtggcctggg tgttagcgcc ggtgcagttg ttccgcagcc gggagcaggg    1200
gttaaacctg gtaaagtgcc gggagtaggg ctgccaggcg tttatcctgg tggtgttttg    1260
ccgggtgccc gttttccggg cgttggtgtt cttccaggcg tgccgaccgg agccggtgtt    1320
aaaccgaaag cccccggtgt tggaggtgca tttgcaggca tcccgggagt tggcccgttt    1380
ggtggtccgc aacctggggt tccgttaggt tatccgatta agcaccgaa actgcccggc     1440 ggttatggtc tgccgtacac aaccggtaaa ctgccgtatg gttatggccc gggtggagtt    1500
gcgggtgcag caggtaaagc gggttatcct accggaaccg gtgtaggtcc gcaggccgct    1560
gctgccgccg ccgcaaaagc agcggctaaa tttggcgccg gagcagcggg tgttctgcct    1620
ggagttggtg gtgcgggcgt gccaggggta cctggtgcaa ttccgggtat tggtggtatt    1680
gccggtgtcg gcaccccggc cgcggcagct gcggcagcgg cggctgccaa agctgctaaa    1740
tacggtgccg cggcgggtct ggtgccagga ggtccgggtt ttggtccggg agtggttggc    1800
gtgcctggcg caggcgttcc tggtgtgggc gttccaggtg cagggattcc tgttgtgcct    1860
ggtgccggta ttcccggcgc ggccgttccg ggggtggtta gcccggaagc cgcagcgaag    1920
gctgcggcaa aggcagcaaa gtatggcgca cgcccaggag tcggcgtggg tggtatcccg    1980
acctatgggg tgggcgcagg gggttttcct ggtttcggcg taggtgtagg aggtataccg    2040
ggcgtggccg gtgtaccagg ggttggtggc gtccctggtg ttggcggtgt gccaggtgtt    2100
ggtatttcac cggaagcaca ggcagcagcc gcagctaagg cagcgaaata tggtgccgcc    2160
ggcgcaggag ttttaggtgg gctggttccg ggcccgcagg cagctgtgcc gggggttcca    2220
ggcaccggtg gtgtccctgg agtcggtacg ccggctgcag cggcagccaa agcggctgcg    2280
aaagcagcac agtttggctt agtaccgggt gtgggagttg ccccggcgt tggcgttgct     2340 ccaggggtgg gtgttgctcc tggcgtcggt ctggctcctg gagtgggcgt agcacccggt    2400
gtgggggtgg ccccgggtgt tggggttgca ccgggtatcg gtccgggcgg tgtcgcagca    2460
gcagctaaaa gcgcggcgaa aagttgcggcc aaagcccaac tgcgcgccgc cgcgggcctc    2520
ggtgcaggta ttccggggct gggtgtcgga gttggagtcc cgggtttggg cgtgggcgcg    2580
ggagttccgg gactgggagt gggtgccgga gttcctggct ttggtgcagg cgcagatgaa    2640
ggtgttcgtc gtagcctgag tccggaactg cgtgaaggtg atccgagtag cagccagcat    2700
ctgccgagca ccccgagcag cccgcgtgtt ccgggtgcat tagctgcagc aaaagccgcc    2760
aagtatggtg cagccgtgcc gggcgtctta ggtggtctgg gcgccctggg tggtgtaggc    2820
attccgggag gtgttgtggg tgcaggaccg gccgccgcag ctgcggccgc caaagcagct    2880
gcaaaagcgg cccagtttgg tttagtgggc gccgcaggtt taggcggttt aggtgtgggt    2940
ggactgggtg tacctggcgt aggcggtctg ggtggaattc cgcccgcagc ggccgcgaaa    3000
gcggcaaaat atggcgcggc aggcctgggc ggcgtgctgg gtgggggcagg tcagtttccg    3060 ctgggcgggg ttgccgcacg tccgggattt ggtctgagcc cgattttccc tggcggcgca    3120
tgtctgggta agcatgtgg tcgtaaacgt aaacacccag aaacgctggt gaaagtaaaa    3180
gatgctgaag atcagttggg tgcacgagtg ggttacatcg aactggatct caacagcggt    3240
aagatccttg agagttttcg ccccgaagaa cgttttccaa tgatgagcac ttttaaagtt    3300
ctgctatgtg gcgcggtatt atcccgtatt gacgccgggc aagagcaact cggtcgccgc    3360
atacactatt ctcagaatga cttggttgag tactcaccag tcacagaaaa gcatcttacg    3420
```

```
gatggcatga cagtaagaga attatgcagt gctgccataa ccatgagtga taacactgcg   3480
gccaacttac ttctgacaac gatcggagga ccgaaggagc taaccgcttt tttgcacaac   3540
atgggggatc atgtaactcg ccttgatcgt tgggaaccgg agctgaatga agccatacca   3600
aacgacgagc gtgacaccac gatgcctgta gcaatggcaa caacgttgcg caaactatta   3660
actggcgaac tacttactct agcttcccgg caacaattaa tagactggat ggaggcggat   3720
aaagttgcag gaccacttct cgctcggcc cttccggctg ctggtttat tgctgataaa    3780 tctggagccg gtgagcgtgg gtctcgcggt atcattgcag cactggggcc agatggtaag   3840
ccctcccgta tcgtagttat ctacacgacg gggagtcagg caactatgga tgaacgaaat   3900
agacagatcg ctgagatagg tgcctcactg attaagcatt ggtaa                  3945
```

<210> SEQ ID NO 28
<211> LENGTH: 1314
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Met Lys Lys Ile Trp Leu Ala Leu Ala Gly Leu Val Leu Ala Phe Ser
1               5                   10                  15

Ala Ser Ala Ala Gln Tyr Glu Asp His His His His His His
            20                  25                  30

His Ser Gly Ser Ser Leu Val Pro Arg Gly Ser His Met Ser Gly Ser
        35                  40                  45

Ser Ser Lys Gly Glu Glu Leu Phe Thr Gly Val Val Pro Ile Leu Val
    50                  55                  60

Glu Leu Asp Gly Asp Val Asn Gly His Lys Phe Ser Val Arg Gly Glu
65                  70                  75                  80

Gly Glu Gly Asp Ala Thr Asn Gly Lys Leu Thr Leu Lys Phe Ile Cys
                85                  90                  95

Thr Thr Gly Lys Leu Pro Val Pro Trp Pro Thr Leu Val Thr Thr Leu
            100                 105                 110

Thr Tyr Gly Val Gln Cys Phe Ser Arg Tyr Pro Asp His Met Lys Gln
        115                 120                 125

His Asp Phe Phe Lys Ser Ala Met Pro Glu Gly Tyr Val Gln Glu Arg
    130                 135                 140

Thr Ile Ser Phe Lys Asp Asp Gly Thr Tyr Lys Thr Arg Ala Glu Val
145                 150                 155                 160

Lys Phe Glu Gly Asp Thr Leu Val Asn Arg Ile Glu Leu Lys Gly Ile
                165                 170                 175

Asp Phe Lys Glu Asp Gly Asn Ile Leu Gly His Lys Leu Glu Tyr Asn
            180                 185                 190

Phe Asn Ser His Asn Val Tyr Ile Thr Ala Asp Lys Gln Lys Asn Gly
        195                 200                 205

Ile Lys Ala Asn Phe Lys Ile Arg His Asn Val Glu Asp Gly Ser Val
    210                 215                 220

Gln Leu Ala Asp His Tyr Gln Gln Asn Thr Pro Ile Gly Asp Gly Pro
225                 230                 235                 240

Val Leu Leu Pro Asp Asn His Tyr Leu Ser Thr Gln Ser Lys Leu Ser
                245                 250                 255

Lys Asp Pro Asn Glu Lys Arg Asp His Met Val Leu Leu Glu Phe Val
```

-continued

```
            260                 265                 270
Thr Ala Ala Gly Ile Thr His Gly Met Asp Glu Leu Tyr Lys Ser Gly
            275                 280                 285

Ala Pro Gly Gly Gly Val Pro Gly Ala Ile Pro Gly Gly Val Pro Gly
            290                 295                 300

Gly Val Phe Tyr Pro Gly Ala Gly Leu Gly Ala Leu Gly Gly Gly Ala
305                 310                 315                 320

Leu Gly Pro Gly Lys Pro Leu Lys Pro Val Pro Gly Gly Leu Ala
            325                 330                 335

Gly Ala Gly Leu Gly Ala Gly Leu Gly Ala Phe Pro Ala Val Thr Phe
            340                 345                 350

Pro Gly Ala Leu Val Pro Gly Val Ala Asp Ala Ala Ala Ala Tyr
            355                 360                 365

Lys Ala Ala Lys Ala Gly Ala Gly Leu Gly Gly Val Pro Gly Val Gly
            370                 375                 380

Gly Leu Gly Val Ser Ala Gly Ala Val Val Pro Gln Pro Gly Ala Gly
385                 390                 395                 400

Val Lys Pro Gly Lys Val Pro Gly Val Gly Leu Pro Gly Val Tyr Pro
            405                 410                 415

Gly Gly Val Leu Pro Gly Ala Arg Phe Pro Gly Val Gly Val Leu Pro
            420                 425                 430

Gly Val Pro Thr Gly Ala Gly Val Lys Pro Lys Ala Pro Gly Val Gly
            435                 440                 445

Gly Ala Phe Ala Gly Ile Pro Gly Val Gly Pro Phe Gly Gly Pro Gln
450                 455                 460

Pro Gly Val Pro Leu Gly Tyr Pro Ile Lys Ala Pro Lys Leu Pro Gly
465                 470                 475                 480

Gly Tyr Gly Leu Pro Tyr Thr Thr Gly Lys Leu Pro Tyr Gly Tyr Gly
            485                 490                 495

Pro Gly Gly Val Ala Gly Ala Ala Gly Lys Ala Gly Tyr Pro Thr Gly
            500                 505                 510

Thr Gly Val Gly Pro Gln Ala Ala Ala Ala Ala Lys Ala Ala
            515                 520                 525

Ala Lys Phe Gly Ala Gly Ala Ala Gly Val Leu Pro Gly Val Gly Gly
            530                 535                 540

Ala Gly Val Pro Gly Val Pro Gly Ala Ile Pro Gly Ile Gly Gly Ile
545                 550                 555                 560

Ala Gly Val Gly Thr Pro Ala Ala Ala Ala Ala Ala Ala Ala
            565                 570                 575

Lys Ala Ala Lys Tyr Gly Ala Ala Gly Leu Val Pro Gly Gly Pro
            580                 585                 590

Gly Phe Gly Pro Gly Val Val Gly Val Pro Gly Ala Gly Val Pro Gly
            595                 600                 605

Val Gly Val Pro Gly Ala Gly Ile Pro Val Val Pro Gly Ala Gly Ile
            610                 615                 620

Pro Gly Ala Ala Val Pro Gly Val Val Ser Pro Glu Ala Ala Lys
625                 630                 635                 640

Ala Ala Ala Lys Ala Ala Lys Tyr Gly Ala Arg Pro Gly Val Gly Val
            645                 650                 655

Gly Gly Ile Pro Thr Tyr Gly Val Gly Ala Gly Gly Phe Pro Gly Phe
            660                 665                 670

Gly Val Gly Val Gly Gly Ile Pro Gly Val Ala Gly Val Pro Gly Val
            675                 680                 685
```

-continued

```
Gly Gly Val Pro Gly Val Gly Val Pro Gly Val Gly Ile Ser Pro
    690             695             700

Glu Ala Gln Ala Ala Ala Ala Lys Ala Ala Lys Tyr Gly Ala Ala
705             710             715             720

Gly Ala Gly Val Leu Gly Gly Leu Val Pro Gly Gln Ala Ala Val
            725             730             735

Pro Gly Val Pro Gly Thr Gly Gly Val Pro Gly Val Gly Thr Pro Ala
                740             745             750

Ala Ala Ala Ala Lys Ala Ala Ala Lys Ala Ala Gln Phe Gly Leu Val
            755             760             765

Pro Gly Val Gly Val Ala Pro Gly Val Gly Val Ala Pro Gly Val Gly
    770             775             780

Val Ala Pro Gly Val Gly Leu Ala Pro Gly Val Gly Val Ala Pro Gly
785             790             795             800

Val Gly Val Ala Pro Gly Val Gly Val Ala Pro Gly Ile Gly Pro Gly
            805             810             815

Gly Val Ala Ala Ala Lys Ser Ala Ala Lys Val Ala Ala Lys Ala
        820             825             830

Gln Leu Arg Ala Ala Gly Leu Gly Ala Gly Ile Pro Gly Leu Gly
        835             840             845

Val Gly Val Gly Val Pro Gly Leu Gly Val Gly Ala Gly Val Pro Gly
850             855             860

Leu Gly Val Gly Ala Gly Val Pro Gly Phe Gly Ala Gly Ala Asp Glu
865             870             875             880

Gly Val Arg Arg Ser Leu Ser Pro Glu Leu Arg Glu Gly Asp Pro Ser
            885             890             895

Ser Ser Gln His Leu Pro Ser Thr Pro Ser Ser Pro Arg Val Pro Gly
        900             905             910

Ala Leu Ala Ala Ala Lys Ala Ala Lys Tyr Gly Ala Ala Val Pro Gly
            915             920             925

Val Leu Gly Gly Leu Gly Ala Leu Gly Gly Val Gly Ile Pro Gly Gly
    930             935             940

Val Val Gly Ala Gly Pro Ala Ala Ala Ala Ala Ala Lys Ala Ala
945             950             955             960

Ala Lys Ala Ala Gln Phe Gly Leu Val Gly Ala Ala Gly Leu Gly Gly
            965             970             975

Leu Gly Val Gly Gly Leu Gly Val Pro Gly Val Gly Gly Leu Gly Gly
            980             985             990

Ile Pro Pro Ala Ala Ala Ala Lys Ala Ala Lys Tyr Gly Ala Ala Gly
            995             1000            1005

Leu Gly Gly Val Leu Gly Gly Ala Gly Gln Phe Pro Leu Gly Gly
        1010            1015            1020

Val Ala Ala Arg Pro Gly Phe Gly Leu Ser Pro Ile Phe Pro Gly
        1025            1030            1035

Gly Ala Cys Leu Gly Lys Ala Cys Gly Arg Lys Arg Lys His Pro
        1040            1045            1050

Glu Thr Leu Val Lys Val Lys Asp Ala Glu Asp Gln Leu Gly Ala
        1055            1060            1065

Arg Val Gly Tyr Ile Glu Leu Asp Leu Asn Ser Gly Lys Ile Leu
        1070            1075            1080

Glu Ser Phe Arg Pro Glu Glu Arg Phe Pro Met Met Ser Thr Phe
        1085            1090            1095
```

```
Lys Val Leu Leu Cys Gly Ala Val Leu Ser Arg Ile Asp Ala Gly
    1100            1105            1110

Gln Glu Gln Leu Gly Arg Arg Ile His Tyr Ser Gln Asn Asp Leu
    1115            1120            1125

Val Glu Tyr Ser Pro Val Thr Glu Lys His Leu Thr Asp Gly Met
    1130            1135            1140

Thr Val Arg Glu Leu Cys Ser Ala Ala Ile Thr Met Ser Asp Asn
    1145            1150            1155

Thr Ala Ala Asn Leu Leu Leu Thr Thr Ile Gly Gly Pro Lys Glu
    1160            1165            1170

Leu Thr Ala Phe Leu His Asn Met Gly Asp His Val Thr Arg Leu
    1175            1180            1185

Asp Arg Trp Glu Pro Glu Leu Asn Glu Ala Ile Pro Asn Asp Glu
    1190            1195            1200

Arg Asp Thr Thr Met Pro Val Ala Met Ala Thr Thr Leu Arg Lys
    1205            1210            1215

Leu Leu Thr Gly Glu Leu Leu Thr Leu Ala Ser Arg Gln Gln Leu
    1220            1225            1230

Ile Asp Trp Met Glu Ala Asp Lys Val Ala Gly Pro Leu Leu Arg
    1235            1240            1245

Ser Ala Leu Pro Ala Gly Trp Phe Ile Ala Asp Lys Ser Gly Ala
    1250            1255            1260

Gly Glu Arg Gly Ser Arg Gly Ile Ile Ala Ala Leu Gly Pro Asp
    1265            1270            1275

Gly Lys Pro Ser Arg Ile Val Val Ile Tyr Thr Thr Gly Ser Gln
    1280            1285            1290

Ala Thr Met Asp Glu Arg Asn Arg Gln Ile Ala Glu Ile Gly Ala
    1295            1300            1305

Ser Leu Ile Lys His Trp
    1310

<210> SEQ ID NO 29
<211> LENGTH: 760
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gly Gly Val Pro Gly Ala Ile Pro Gly Gly Val Pro Gly Gly Val Phe
1               5                   10                  15

Tyr Pro Gly Ala Gly Leu Gly Ala Leu Gly Gly Gly Ala Leu Gly Pro
                20                  25                  30

Gly Gly Lys Pro Leu Lys Pro Val Pro Gly Gly Leu Ala Gly Ala Gly
            35                  40                  45

Leu Gly Ala Gly Leu Gly Ala Phe Pro Ala Val Thr Phe Pro Gly Ala
        50                  55                  60

Leu Val Pro Gly Gly Val Ala Asp Ala Ala Ala Tyr Lys Ala Ala
65                  70                  75                  80

Lys Ala Gly Ala Gly Leu Gly Gly Val Pro Gly Val Gly Gly Leu Gly
                85                  90                  95

Val Ser Ala Gly Ala Val Val Pro Gln Pro Gly Ala Gly Val Lys Pro
                100                 105                 110

Gly Lys Val Pro Gly Val Gly Leu Pro Gly Val Tyr Pro Gly Gly Val
            115                 120                 125
```

```
Leu Pro Gly Ala Arg Phe Pro Gly Val Gly Val Leu Pro Gly Val Pro
    130                 135                 140
Thr Gly Ala Gly Val Lys Pro Lys Ala Pro Gly Val Gly Gly Ala Phe
145                 150                 155                 160
Ala Gly Ile Pro Gly Val Gly Pro Phe Gly Gly Pro Gln Pro Gly Val
            165                 170                 175
Pro Leu Gly Tyr Pro Ile Lys Ala Pro Lys Leu Pro Gly Gly Tyr Gly
            180                 185                 190
Leu Pro Tyr Thr Thr Gly Lys Leu Pro Tyr Gly Tyr Gly Pro Gly Gly
        195                 200                 205
Val Ala Gly Ala Ala Gly Lys Ala Gly Tyr Pro Thr Gly Thr Gly Val
    210                 215                 220
Gly Pro Gln Ala Ala Ala Ala Ala Ala Lys Ala Ala Ala Lys Phe
225                 230                 235                 240
Gly Ala Gly Ala Ala Gly Val Leu Pro Gly Val Gly Gly Ala Gly Val
                245                 250                 255
Pro Gly Val Pro Gly Ala Ile Pro Gly Ile Gly Gly Ile Ala Gly Val
            260                 265                 270
Gly Thr Pro Ala Ala Ala Ala Ala Ala Ala Ala Ala Ala Lys Ala Ala
        275                 280                 285
Lys Tyr Gly Ala Ala Ala Gly Leu Val Pro Gly Gly Pro Gly Phe Gly
    290                 295                 300
Pro Gly Val Val Gly Val Pro Gly Ala Gly Val Pro Gly Val Gly Val
305                 310                 315                 320
Pro Gly Ala Gly Ile Pro Val Val Pro Gly Ala Gly Ile Pro Gly Ala
                325                 330                 335
Ala Val Pro Gly Val Val Ser Pro Glu Ala Ala Lys Ala Ala Ala
            340                 345                 350
Lys Ala Ala Lys Tyr Gly Ala Arg Pro Gly Val Gly Val Gly Gly Ile
    355                 360                 365
Pro Thr Tyr Gly Val Gly Ala Gly Gly Phe Pro Gly Phe Gly Val Gly
    370                 375                 380
Val Gly Gly Ile Pro Gly Val Ala Gly Val Pro Gly Val Gly Gly Val
385                 390                 395                 400
Pro Gly Val Gly Gly Val Pro Gly Val Gly Ile Ser Pro Glu Ala Gln
            405                 410                 415
Ala Ala Ala Ala Ala Lys Ala Ala Lys Tyr Gly Ala Ala Gly Ala Gly
                420                 425                 430
Val Leu Gly Gly Leu Val Pro Gly Pro Gln Ala Ala Val Pro Gly Val
    435                 440                 445
Pro Gly Thr Gly Gly Val Pro Gly Val Gly Thr Pro Ala Ala Ala Ala
    450                 455                 460
Ala Lys Ala Ala Ala Lys Ala Ala Gln Phe Gly Leu Val Pro Gly Val
465                 470                 475                 480
Gly Val Ala Pro Gly Val Gly Val Ala Pro Gly Val Gly Val Ala Pro
                485                 490                 495
Gly Val Gly Leu Ala Pro Gly Val Gly Val Ala Pro Gly Val Gly Val
            500                 505                 510
Ala Pro Gly Val Gly Val Ala Pro Gly Ile Gly Pro Gly Gly Val Ala
        515                 520                 525
Ala Ala Ala Lys Ser Ala Ala Lys Val Ala Ala Lys Ala Gln Leu Arg
    530                 535                 540
```

| | | | | | | | | | | | | | | | |
|---|---|---|---|---|---|---|---|---|---|---|---|---|---|---|---|
|Ala|Ala|Ala|Gly|Leu|Gly|Ala|Gly|Ile|Pro|Gly|Leu|Gly|Val|Gly|Val|
|545| | | |550| | | |555| | | |560| | | |
|Gly|Val|Pro|Gly|Leu|Gly|Val|Gly|Ala|Gly|Val|Pro|Gly|Leu|Gly|Val|
| | | |565| | | |570| | | |575| | | | |
|Gly|Ala|Gly|Val|Pro|Gly|Phe|Gly|Ala|Gly|Ala|Asp|Glu|Gly|Val|Arg|
| | |580| | | |585| | | |590| | | | | |
|Arg|Ser|Leu|Ser|Pro|Glu|Leu|Arg|Glu|Gly|Asp|Pro|Ser|Ser|Ser|Gln|
| |595| | | |600| | | |605| | | | | | |
|His|Leu|Pro|Ser|Thr|Pro|Ser|Ser|Pro|Arg|Val|Pro|Gly|Ala|Leu|Ala|
|610| | | |615| | | |620| | | | | | | |
|Ala|Ala|Lys|Ala|Ala|Lys|Tyr|Gly|Ala|Ala|Val|Pro|Gly|Val|Leu|Gly|
|625| | | |630| | | |635| | | |640| | | |
|Gly|Leu|Gly|Ala|Leu|Gly|Gly|Val|Gly|Ile|Pro|Gly|Gly|Val|Val|Gly|
| | | |645| | | |650| | | |655| | | | |
|Ala|Gly|Pro|Ala|Ala|Ala|Ala|Ala|Ala|Lys|Ala|Ala|Ala|Lys|Ala|
| | |660| | | |665| | | |670| | | | | |
|Ala|Gln|Phe|Gly|Leu|Val|Gly|Ala|Ala|Gly|Leu|Gly|Gly|Leu|Gly|Val|
| |675| | | |680| | | |685| | | | | | |
|Gly|Gly|Leu|Gly|Val|Pro|Gly|Val|Gly|Gly|Leu|Gly|Gly|Ile|Pro|Pro|
|690| | | |695| | | |700| | | | | | | |
|Ala|Ala|Ala|Ala|Lys|Ala|Ala|Lys|Tyr|Gly|Ala|Ala|Gly|Leu|Gly|Gly|
|705| | | |710| | | |715| | | |720| | | |
|Val|Leu|Gly|Gly|Ala|Gly|Gln|Phe|Pro|Leu|Gly|Gly|Val|Ala|Ala|Arg|
| | | |725| | | |730| | | |735| | | | |
|Pro|Gly|Phe|Gly|Leu|Ser|Pro|Ile|Phe|Pro|Gly|Gly|Ala|Cys|Leu|Gly|
| | |740| | | |745| | | |750| | | | | |
|Lys|Ala|Cys|Gly|Arg|Lys|Arg|Lys|
| |755| | | |760| | | |

<210> SEQ ID NO 30
<211> LENGTH: 2115
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 30

```
ggtggcgtac caggcgcaat tcctgggggt gtcccaggcg gtgtttttta tccgggcgcc      60
ggtcttggcg cactgggtgg cggtgcactg ggcccgggcg gcaaaccgct gaaaccggta     120
ccaggtggtt tagcaggcgc cggcttaggc gcaggtctgg gagcatttcc ggcagttacc     180
tttccagggg cactggttcc tggaggtgtg gccgatgcag ccgcggcata taaagccgct     240
aaagccggtg cgggtttagg aggcgtccca ggtgtcggtg gcctgggtgt tagcgccggt     300
gcagttgttc cgcagccggg agcaggggtt aaacctggta agtgccgggg agtaggtctg     360
ccaggcgttt atcctggtgg tgttttgccg ggtgcccgtt ttccgggcgt tggtgttctt     420
ccaggcgtgc cgaccggagc cggtgttaaa ccgaaagccc ccggtgttgg aggtgcattt     480
gcaggcatcc cggagttggg cccgtttggt ggtccgcaac ctggggttcc gttaggttat     540
ccgattaaag caccgaaact gcccggcggt tatggtctgc cgtacacaac cggtaaactg     600
ccgtatggtt atggcccggg tggagttgcg ggtgcagcag gtaaagcggg ttatcctacc     660
ggaaccggtg taggtccgca ggccgctgct ccgccgccg caaaagcagc ggctaaattt     720
ggcgccggag cagcgggtgt tctgcctgga gttggtggtg cgggcgtgcc aggggtacct     780
```

-continued

| | |
|---|---|
| ggtgcaattc cgggtattgg tggtattgcc ggtgtcggca ccccggccgc ggcagctgcg | 840 |
| gcagcggcgg ctgccaaagc tgctaaatac ggtgccgcgg cgggtctggt gccaggaggt | 900 |
| ccgggttttg gtccgggagt ggttggcgtg cctggcgcag gcgttcctgg tgtgggcgtt | 960 |
| ccaggtgcag ggattcctgt tgtgcctggt gccggtattc ccggcgcggc cgttccgggg | 1020 |
| gtggttagcc cggaagccgc agcgaaggct gcggcaaagg cagcaaagta tggcgcacgc | 1080 |
| ccaggagtcg gcgtgggtgg tatcccgacc tatggggtgg gcgcagggg ttttcctggt | 1140 |
| ttcggcgtag gtgtaggagg tataccgggc gtggccggtg taccagggt tggtggcgtc | 1200 |
| cctggtgttg gcggtgtgcc aggtgttggt atttcaccgg aagcacaggc agcagccgca | 1260 |
| gctaaggcag cgaaatatgg tgccgccggc gcaggagttt aggtgggct ggttccgggc | 1320 |
| ccgcaggcag ctgtgccggg ggttccaggc accggtggtg tccctggagt cggtacgccg | 1380 |
| gctgcagcgg cagccaaagc ggctgcgaaa gcagcacagt ttggcttagt accgggtgtg | 1440 |
| ggagttgccc ccggcgttgg cgttgctcca ggggtgggtg ttgctcctgg cgtcggtctg | 1500 |
| gctcctggag tgggcgtagc accggtgtg ggggtggccc cgggtgttgg ggttgcaccg | 1560 |
| ggtatcggtc cgggcggtgt cgcagcagca gctaaaagcg cggcgaaagt tgcggccaaa | 1620 |
| gcccaactgc gcgccgccgc gggcctcggt gcaggtattc cggggctggg tgtcggagtt | 1680 |
| ggagtcccgg gtttgggcgt gggcgcggga gttccgggac tgggagtggg tgccggagtt | 1740 |
| cctggctttg gtgcaggcgc agatgaaggt gttcgtcgta gcctgagtcc ggaactgcgt | 1800 |
| gaaggtgatc cgagtagcag ccagcatctg ccgagcaccc cgagcagccc gcgtgttccg | 1860 |
| ggtgcattag ctgcagcaaa agccgccaag tatggtgcag ccgtgccggg cgtcttaggt | 1920 |
| ggtctgggcg ccctgggtgg tgtaggcatt ccgggaggtg ttgtgggtgc aggaccggcc | 1980 |
| gccgcagctg cggccgccaa agcagctgca aaagcggccc agtttggttt agtgggcgcc | 2040 |
| gcaggtttag gcggtttagg tgtgggtgga ctgggtgtac ctggcgtagg cggtctgggt | 2100 |
| ggaattccgc cctaa | 2115 |

<210> SEQ ID NO 31
<211> LENGTH: 704
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gly Gly Val Pro Gly Ala Ile Pro Gly Gly Val Pro Gly Gly Val Phe
1               5                   10                  15

Tyr Pro Gly Ala Gly Leu Gly Ala Leu Gly Gly Gly Ala Leu Gly Pro
            20                  25                  30

Gly Gly Lys Pro Leu Lys Pro Val Pro Gly Gly Leu Ala Gly Ala Gly
        35                  40                  45

Leu Gly Ala Gly Leu Gly Ala Phe Pro Ala Val Thr Phe Pro Gly Ala
    50                  55                  60

Leu Val Pro Gly Gly Val Ala Asp Ala Ala Ala Tyr Lys Ala Ala
65                  70                  75                  80

Lys Ala Gly Ala Gly Leu Gly Gly Val Pro Gly Val Gly Gly Leu Gly
                85                  90                  95

Val Ser Ala Gly Ala Val Val Pro Gln Pro Gly Ala Gly Val Lys Pro
            100                 105                 110

Gly Lys Val Pro Gly Val Gly Leu Pro Gly Val Tyr Pro Gly Gly Val

```
            115                 120                 125
Leu Pro Gly Ala Arg Phe Pro Gly Val Gly Val Leu Pro Gly Val Pro
            130                 135                 140
Thr Gly Ala Gly Val Lys Pro Lys Ala Pro Gly Val Gly Gly Ala Phe
145                 150                 155                 160
Ala Gly Ile Pro Gly Val Gly Pro Phe Gly Pro Gln Pro Gly Val
                    165                 170                 175
Pro Leu Gly Tyr Pro Ile Lys Ala Pro Lys Leu Pro Gly Gly Tyr Gly
                180                 185                 190
Leu Pro Tyr Thr Thr Gly Lys Leu Pro Tyr Gly Tyr Gly Pro Gly Gly
                195                 200                 205
Val Ala Gly Ala Ala Gly Lys Ala Gly Tyr Pro Thr Gly Thr Gly Val
                210                 215                 220
Gly Pro Gln Ala Ala Ala Ala Ala Ala Lys Ala Ala Ala Lys Phe
225                 230                 235                 240
Gly Ala Gly Ala Ala Gly Val Leu Pro Gly Val Gly Ala Gly Val
                    245                 250                 255
Pro Gly Val Pro Gly Ala Ile Pro Gly Ile Gly Gly Ile Ala Gly Val
                260                 265                 270
Gly Thr Pro Ala Ala Ala Ala Ala Ala Ala Ala Ala Lys Ala Ala
                275                 280                 285
Lys Tyr Gly Ala Ala Ala Gly Leu Val Pro Gly Gly Pro Gly Phe Gly
290                 295                 300
Pro Gly Val Val Gly Val Pro Gly Ala Gly Val Pro Gly Val Gly Val
305                 310                 315                 320
Pro Gly Ala Gly Ile Pro Val Val Pro Gly Ala Gly Ile Pro Gly Ala
                325                 330                 335
Ala Val Pro Gly Val Val Ser Pro Glu Ala Ala Lys Ala Ala Ala
                340                 345                 350
Lys Ala Ala Lys Tyr Gly Ala Arg Pro Gly Val Gly Val Gly Gly Ile
                355                 360                 365
Pro Thr Tyr Gly Val Gly Ala Gly Gly Phe Pro Gly Phe Gly Val Gly
370                 375                 380
Val Gly Gly Ile Pro Gly Val Ala Gly Val Pro Gly Val Gly Gly Val
385                 390                 395                 400
Pro Gly Val Gly Gly Val Pro Gly Val Gly Ile Ser Pro Glu Ala Gln
                    405                 410                 415
Ala Ala Ala Ala Ala Lys Ala Ala Lys Tyr Gly Ala Ala Gly Ala Gly
                    420                 425                 430
Val Leu Gly Gly Leu Val Pro Gly Pro Gln Ala Ala Val Pro Gly Val
                435                 440                 445
Pro Gly Thr Gly Gly Val Pro Gly Val Gly Thr Pro Ala Ala Ala Ala
                450                 455                 460
Ala Lys Ala Ala Ala Lys Ala Ala Gln Phe Gly Leu Val Pro Gly Val
465                 470                 475                 480
Gly Val Ala Pro Gly Val Gly Val Ala Pro Gly Val Gly Val Ala Pro
                    485                 490                 495
Gly Val Gly Leu Ala Pro Gly Val Gly Val Ala Pro Gly Val Gly Val
                500                 505                 510
Ala Pro Gly Val Gly Val Ala Pro Gly Ile Gly Pro Gly Gly Val Ala
                515                 520                 525
Ala Ala Ala Lys Ser Ala Ala Lys Val Ala Ala Lys Ala Gln Leu Arg
                530                 535                 540
```

Ala Ala Ala Gly Leu Gly Ala Gly Ile Pro Gly Leu Gly Val Gly Val
545                 550                 555                 560

Gly Val Pro Gly Leu Gly Val Gly Ala Gly Val Pro Gly Leu Gly Val
                565                 570                 575

Gly Ala Gly Val Pro Gly Phe Gly Ala Gly Ala Asp Glu Gly Val Arg
            580                 585                 590

Arg Ser Leu Ser Pro Glu Leu Arg Glu Gly Asp Pro Ser Ser Ser Gln
        595                 600                 605

His Leu Pro Ser Thr Pro Ser Ser Pro Arg Val Pro Gly Ala Leu Ala
    610                 615                 620

Ala Ala Lys Ala Ala Lys Tyr Gly Ala Ala Val Pro Gly Val Leu Gly
625                 630                 635                 640

Gly Leu Gly Ala Leu Gly Gly Val Gly Ile Pro Gly Gly Val Val Gly
                645                 650                 655

Ala Gly Pro Ala Ala Ala Ala Ala Ala Lys Ala Ala Ala Lys Ala
            660                 665                 670

Ala Gln Phe Gly Leu Val Gly Ala Ala Gly Leu Gly Gly Leu Gly Val
        675                 680                 685

Gly Gly Leu Gly Val Pro Gly Val Gly Gly Leu Gly Gly Ile Pro Pro
    690                 695                 700

<210> SEQ ID NO 32
<211> LENGTH: 2115
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
ggtggcgtac caggcgcaat tcctgggggt gtcccaggcg gtgttttta tccgggcgcc      60
ggtcttggcg cactgggtgg cggtgcactg ggcccgggcg gcaaaccgct gaaaccggta     120
ccaggtggtt tagcaggcgc cggcttaggc gcaggtctgg gagcatttcc ggcagttacc     180
tttccagggg cactggttcc tggaggtgtg gccgatgcag ccgcggcata taaagccgct     240
aaagccggtg cgggtttagg aggcgtccca ggtgtcggtg gcctgggtgt tagcgccggt     300
gcagttgttc cgcagccggg agcagggggtt aaacctggta aagtgccggg agtaggtctg     360
ccaggcgttt atcctggtgg tgttttgccg ggtgcccgtt ttccgggcgt tggtgttctt     420
ccaggcgtgc cgaccggagc cggtgttaaa ccgaaagccc ccggtgttgg aggtgcattt     480
gcaggcatcc cgggagttgg cccgtttggt ggtccgcaac ctggggttcc gttaggttat     540
ccgattaaag caccgaaact gcccggcggt tatggtctgc cgtacacaac cggtaaactg     600
ccgtatggtt atggcccggg tggagttgcg ggtgcagcag gtaaagcggg ttatcctacc     660
ggaaccggtg taggtccgca ggccgctgct gccgccgccg caaaagcagc ggctaaattt     720
ggcgccggag cagcgggtgt tctgcctgga gttggtggtg cggggcgtgcc aggggtacct     780
ggtgcaattc cgggtattgg tggtattgcc ggtgtcggca cccggccgc ggcagctgcg     840
gcagcggcgg ctgccaaagc tgctaaatac ggtgccgcgg cggtctggt gccaggaggt     900
ccgggtttg gtccgggagt ggttggcgtg cctggcgcag gcgttcctgg tgtgggcgtt     960
ccaggtgcag ggattcctgt tgtgcctggt gccggtattc cggcgcggc cgttccgggg    1020
gtggttagcc cggaagccgc agcgaaggct gcggcaaagg cagcaaagta tggcgcacgc    1080
ccaggagtcg gcgtgggtgg tatcccgacc tatggggtgg gcgcaggggg ttttcctggt    1140

```
ttcggcgtag gtgtaggagg tataccgggc gtggccggtg taccaggggt tggtggcgtc    1200
cctggtgttg gcggtgtgcc aggtgttggt atttcaccgg aagcacaggc agcagccgca    1260
gctaaggcag cgaaatatgg tgccgccggc gcaggagttt taggtgggct ggttccgggc    1320
ccgcaggcag ctgtgccggg ggttccaggc accggtggtg tccctggagt cggtacgccg    1380
gctgcagcgg cagccaaagc ggctgcgaaa gcagcacagt ttggcttagt accgggtgtg    1440
ggagttgccc ccggcgttgg cgttgctcca ggggtgggtg ttgctcctgg cgtcggtctg    1500
gctcctggag tgggcgtagc acccggtgtg ggggtggccc cgggtgttgg ggttgcaccg    1560
ggtatcggtc cgggcggtgt cgcagcagca gctaaaagcg cggcgaaagt tgcggccaaa    1620
gcccaactgc gcgccgccgc gggcctcggt gcaggtattc cggggctggg tgtcggagtt    1680
ggagtcccgg gtttgggcgt gggcgcggga gttccgggac tgggagtggg tgccggagtt    1740
cctggctttg gtgcaggcgc agatgaaggt gttcgtcgta gcctgagtcc ggaactgcgt    1800
gaaggtgatc cgagtagcag ccagcatctg ccgagcaccc cgagcagccc gcgtgttccg    1860
ggtgcattag ctgcagcaaa agccgccaag tatggtgcag ccgtgccggg cgtcttaggt    1920
ggtctgggcg ccctgggtgg tgtaggcatt ccgggaggtg ttgtgggtgc aggaccggcc    1980
gccgcagctg cggccgccaa agcagctgca aaagcggccc agtttggtttt agtgggcgcc    2040 gcaggtttag gcggtttagg tgtgggtgga ctgggtgtac ctggcgtagg cggtctgggt    2100
ggaattccgc cctaa                                                    2115

<210> SEQ ID NO 33
<211> LENGTH: 676
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gly Leu Gly Gly Val Pro Gly Val Gly Leu Gly Val Ser Ala Gly
1               5                   10                  15

Ala Val Val Pro Gln Pro Gly Ala Gly Val Lys Pro Gly Lys Val Pro
            20                  25                  30

Gly Val Gly Leu Pro Gly Val Tyr Pro Gly Gly Val Leu Pro Gly Ala
        35                  40                  45

Arg Phe Pro Gly Val Gly Val Leu Pro Gly Val Pro Thr Gly Ala Gly
    50                  55                  60

Val Lys Pro Lys Ala Pro Gly Val Gly Gly Ala Phe Ala Gly Ile Pro
65                  70                  75                  80

Gly Val Gly Pro Phe Gly Gly Pro Gln Pro Gly Val Pro Leu Gly Tyr
                85                  90                  95

Pro Ile Lys Ala Pro Lys Leu Pro Gly Gly Tyr Gly Leu Pro Tyr Thr
            100                 105                 110

Thr Gly Lys Leu Pro Tyr Gly Tyr Gly Pro Gly Gly Val Ala Gly Ala
        115                 120                 125

Ala Gly Lys Ala Gly Tyr Pro Thr Gly Thr Gly Val Gly Pro Gln Ala
    130                 135                 140

Ala Ala Ala Ala Ala Ala Lys Ala Ala Ala Lys Phe Gly Ala Gly Ala
145                 150                 155                 160

Ala Gly Val Leu Pro Gly Val Gly Gly Ala Gly Val Pro Gly Val Pro
                165                 170                 175
```

-continued

```
Gly Ala Ile Pro Gly Ile Gly Gly Ile Ala Gly Val Gly Thr Pro Ala
            180                 185                 190
Ala Ala Ala Ala Ala Ala Ala Ala Lys Ala Ala Lys Tyr Gly Ala
    195                 200                 205
Ala Ala Gly Leu Val Pro Gly Gly Pro Gly Phe Gly Pro Gly Val Val
    210                 215                 220
Gly Val Pro Gly Ala Gly Val Pro Gly Val Gly Val Pro Gly Ala Gly
225                 230                 235                 240
Ile Pro Val Val Pro Gly Ala Gly Ile Pro Gly Ala Ala Val Pro Gly
                245                 250                 255
Val Val Ser Pro Glu Ala Ala Lys Ala Ala Lys Ala Ala Lys
            260                 265                 270
Tyr Gly Ala Arg Pro Gly Val Gly Val Gly Gly Ile Pro Thr Tyr Gly
    275                 280                 285
Val Gly Ala Gly Gly Phe Pro Gly Phe Gly Val Gly Val Gly Gly Ile
    290                 295                 300
Pro Gly Val Ala Gly Val Pro Gly Val Gly Val Pro Gly Val Gly
305                 310                 315                 320
Gly Val Pro Gly Val Gly Ile Ser Pro Glu Ala Gln Ala Ala Ala
                325                 330                 335
Ala Lys Ala Ala Lys Tyr Gly Ala Ala Gly Ala Gly Val Leu Gly Gly
    340                 345                 350
Leu Val Pro Gly Pro Gln Ala Ala Val Pro Gly Val Pro Gly Thr Gly
    355                 360                 365
Gly Val Pro Gly Val Gly Thr Pro Ala Ala Ala Ala Lys Ala Ala
    370                 375                 380
Ala Lys Ala Ala Gln Phe Gly Leu Val Pro Gly Val Gly Val Ala Pro
385                 390                 395                 400
Gly Val Gly Val Ala Pro Gly Val Gly Val Ala Pro Gly Val Gly Leu
                405                 410                 415
Ala Pro Gly Val Gly Val Ala Pro Gly Val Gly Val Ala Pro Gly Val
                420                 425                 430
Gly Val Ala Pro Gly Ile Gly Pro Gly Gly Val Ala Ala Ala Lys
            435                 440                 445
Ser Ala Ala Lys Val Ala Ala Lys Ala Gln Leu Arg Ala Ala Gly
    450                 455                 460
Leu Gly Ala Gly Ile Pro Gly Leu Gly Val Gly Val Gly Val Pro Gly
465                 470                 475                 480
Leu Gly Val Gly Ala Gly Val Pro Gly Leu Gly Val Gly Ala Gly Val
                485                 490                 495
Pro Gly Phe Gly Ala Gly Ala Asp Glu Gly Val Arg Arg Ser Leu Ser
                500                 505                 510
Pro Glu Leu Arg Glu Gly Asp Pro Ser Ser Ser Gln His Leu Pro Ser
            515                 520                 525
Thr Pro Ser Ser Pro Arg Val Pro Gly Ala Leu Ala Ala Ala Lys Ala
    530                 535                 540
Ala Lys Tyr Gly Ala Ala Val Pro Gly Val Leu Gly Gly Leu Gly Ala
545                 550                 555                 560
Leu Gly Gly Val Gly Ile Pro Gly Gly Val Gly Ala Gly Pro Ala
                565                 570                 575
Ala Ala Ala Ala Ala Lys Ala Ala Ala Lys Ala Ala Gln Phe Gly
            580                 585                 590
Leu Val Gly Ala Ala Gly Leu Gly Gly Leu Gly Val Gly Gly Leu Gly
```

```
                595                 600                 605
Val Pro Gly Val Gly Leu Gly Gly Ile Pro Ala Ala Ala Ala
    610                 615                 620

Lys Ala Ala Lys Tyr Gly Ala Ala Gly Leu Gly Gly Val Leu Gly Gly
625                 630                 635                 640

Ala Gly Gln Phe Pro Leu Gly Gly Val Ala Ala Arg Pro Gly Phe Gly
                645                 650                 655

Leu Ser Pro Ile Phe Pro Gly Gly Ala Cys Leu Gly Lys Ala Cys Gly
            660                 665                 670

Arg Lys Arg Lys
        675

<210> SEQ ID NO 34
<211> LENGTH: 2031
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
ggtttaggag gcgtcccagg tgtcggtggc ctgggtgtta gcgccggtgc agttgttccg      60
cagccgggag caggggttaa acctggtaaa gtgccgggag taggtctgcc aggcgtttat     120
cctggtggtg ttttgccggg tgcccgtttt ccgggcgttg tgttcttcc aggcgtgccg      180 accggagccg gtgttaaacc gaaagccccc ggtgttggag gtgcatttgc aggcatcccg     240
ggagttggcc cgtttggtgg tccgcaacct ggggttccgt taggttatcc gattaaagca     300
ccgaaactgc ccggcggtta tggtctgccg tacacaaccg gtaaactgcc gtatggttat     360
ggcccgggtg gagttgcggg tgcagcaggt aaagcgggtt atcctaccgg aaccggtgta     420
ggtccgcagg ccgctgctgc cgccgccgca aaagcagcgg ctaaatttgg cgccggagca     480
gcgggtgttc tgcctggagt tggtggtgcg ggcgtgccag gggtacctgg tgcaattccg     540
ggtattggtg gtattgccgg tgtcggcacc ccggccgcgg cagctgcggc agcggcggct     600
gccaaagctg ctaaatacgg tgccgcgcg gtctggtgc aggaggtcc gggttttggt       660 ccgggagtgg ttggcgtgcc tggcgcaggc gttcctggtg tgggcgttcc aggtgcaggg     720
attcctgttg tgcctggtgc cggtattccc ggcgcggccg ttccgggggt ggttagcccg     780
gaagccgcag cgaaggctgc ggcaaaggca gcaaagtatg gcgcacgccc aggagtcggc     840
gtgggtggta tcccgaccta tggggtgggc gcaggggggtt ttcctggttt cggcgtaggt     900
gtaggaggta taccgggcgt ggccggtgta ccaggggttg gtggcgtccc tggtgttggc     960
ggtgtgccag gtgttggtat ttcaccggaa gcacaggcag cagccgcagc taaggcagcg    1020
aaatatggtg ccgccggcgc aggagttttta ggtgggctgg ttccgggccc gcaggcagct    1080
gtgccggggg ttccaggcac cggtggtgtc cctggagtcg gtacgccggc tgcagcggca    1140
gccaaagcgg ctgcgaaagc agcacagttt ggcttagtac cgggtgtggg agttgccccc    1200
ggcgttggcg ttgctccagg ggtgggtgtt gctcctggcg tcggtctggc tcctggagtg    1260
ggcgtagcac ccggtgtggg ggtggccccg gtgttgggg ttgcaccggg tatcggtccg    1320 gcggtgtcg cagcagcagc taaaagcgcg gcgaaagttg cggccaaagc ccaactgcgc    1380
gccgccgcgg gcctcggtgc aggtattccg gggctgggtg tcggagttgg agtcccgggt    1440
ttgggcgtgg gcgcgggagt tccgggactg ggagtgggtg ccggagttcc tggctttggt    1500
gcaggcgcag atgaaggtgt tcgtcgtagc ctgagtccgg aactgcgtga aggtgatccg    1560
```

-continued

```
agtagcagcc agcatctgcc gagcacccccg agcagcccgc gtgttccggg tgcattagct    1620
gcagcaaaag ccgccaagta tggtgcagcc gtgccgggcg tcttaggtgg tctgggcgcc    1680
ctgggtggtg taggcattcc gggaggtgtt gtgggtgcag accggccgc cgcagctgcg     1740 gccgccaaaa cagctgcaaa agcggcccag tttggtttag tgggcgccgc aggtttaggc    1800
ggtttaggtg tgggtggact gggtgtacct ggcgtaggcg gtctgggtgg aattccgccc    1860
gcagcggccg cgaaagcggc aaaatatggc gcggcaggcc tgggcggcgt gctgggtggg    1920
gcaggtcagt ttccgctggg cggggttgcc gcacgtccgg gatttggtct gagcccgatt    1980
ttccctggcg gcgcatgtct gggtaaagca tgtggtcgta aacgtaaata a             2031
```

<210> SEQ ID NO 35
<211> LENGTH: 659
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 35

```
Gly Gly Val Pro Gly Ala Ile Pro Gly Gly Val Pro Gly Gly Val Phe
1               5                   10                  15

Tyr Pro Gly Ala Gly Leu Gly Ala Leu Gly Gly Ala Leu Gly Pro
            20                  25                  30

Gly Gly Lys Pro Leu Lys Pro Val Pro Gly Gly Leu Ala Ala Gly
            35                  40                  45

Leu Gly Ala Gly Leu Gly Ala Phe Pro Ala Val Thr Phe Pro Gly Ala
50                  55                  60

Leu Val Pro Gly Gly Val Ala Asp Ala Ala Ala Tyr Lys Ala Ala
65                  70                  75                  80

Lys Ala Gly Ala Gly Leu Gly Val Pro Gly Val Gly Gly Leu Gly
            85                  90                  95

Val Ser Ala Gly Ala Val Pro Gln Pro Gly Ala Gly Val Lys Pro
            100                 105                 110

Gly Lys Val Pro Gly Val Gly Leu Pro Gly Val Tyr Pro Gly Gly Val
            115                 120                 125

Leu Pro Gly Ala Arg Phe Pro Gly Val Gly Val Leu Pro Gly Val Pro
130                 135                 140

Thr Gly Ala Gly Val Lys Pro Lys Ala Pro Gly Val Gly Gly Ala Phe
145                 150                 155                 160

Ala Gly Ile Pro Gly Val Gly Pro Phe Gly Pro Gln Pro Gly Val
            165                 170                 175

Pro Leu Gly Tyr Pro Ile Lys Ala Pro Lys Leu Pro Gly Gly Tyr Gly
            180                 185                 190

Leu Pro Tyr Thr Thr Gly Lys Leu Pro Tyr Gly Tyr Gly Pro Gly Gly
            195                 200                 205

Val Ala Gly Ala Ala Gly Lys Ala Gly Tyr Pro Thr Gly Thr Gly Val
            210                 215                 220

Gly Pro Gln Ala Ala Ala Ala Ala Ala Lys Ala Ala Lys Phe
225                 230                 235                 240

Gly Ala Gly Ala Ala Gly Val Leu Pro Gly Val Gly Gly Ala Gly Val
                245                 250                 255

Pro Gly Val Pro Gly Ala Ile Pro Gly Ile Gly Gly Ile Ala Gly Val
            260                 265                 270
```

```
Gly Thr Pro Ala Ala Ala Ala Ala Ala Ala Ala Lys Ala Ala
            275                 280                 285

Lys Tyr Gly Ala Ala Gly Leu Val Pro Gly Pro Gly Phe Gly
        290                 295                 300

Pro Gly Val Val Gly Val Pro Gly Ala Gly Val Pro Gly Val Gly Val
305                 310                 315                 320

Pro Gly Ala Gly Ile Pro Val Val Pro Gly Ala Gly Ile Pro Gly Ala
                325                 330                 335

Ala Val Pro Gly Val Val Ser Pro Glu Ala Ala Lys Ala Ala
            340                 345                 350

Lys Ala Ala Lys Tyr Gly Ala Arg Pro Gly Val Gly Val Gly Gly Ile
355                 360                 365

Pro Thr Tyr Gly Val Gly Ala Gly Gly Phe Pro Gly Phe Gly Val Gly
        370                 375                 380

Val Gly Gly Ile Pro Gly Val Ala Gly Val Pro Gly Val Gly Val
385                 390                 395                 400

Pro Gly Val Gly Gly Val Pro Gly Val Gly Ile Ser Pro Glu Ala Gln
                405                 410                 415

Ala Ala Ala Ala Ala Lys Ala Ala Lys Tyr Gly Ala Ala Gly Ala Gly
                420                 425                 430

Val Leu Gly Gly Leu Val Pro Gly Pro Gln Ala Ala Val Pro Gly Val
            435                 440                 445

Pro Gly Thr Gly Gly Val Pro Gly Val Gly Thr Pro Ala Ala Ala Ala
        450                 455                 460

Ala Lys Ala Ala Lys Ala Ala Gln Phe Gly Leu Val Pro Gly Val
465                 470                 475                 480

Gly Val Ala Pro Gly Val Gly Val Ala Pro Gly Val Gly Val Ala Pro
                485                 490                 495

Gly Val Gly Leu Ala Pro Gly Val Gly Val Ala Pro Gly Val Gly Val
            500                 505                 510

Ala Pro Gly Val Gly Val Ala Pro Gly Ile Gly Pro Gly Gly Val Ala
        515                 520                 525

Ala Ala Ala Lys Ser Ala Ala Lys Val Ala Ala Lys Ala Gln Leu Arg
530                 535                 540

Ala Ala Ala Gly Leu Gly Ala Gly Ile Pro Gly Leu Gly Val Gly Val
545                 550                 555                 560

Gly Val Pro Gly Leu Gly Val Gly Ala Gly Val Pro Gly Leu Gly Val
                565                 570                 575

Gly Ala Gly Val Pro Gly Phe Gly Ala Gly Ala Asp Glu Gly Val Arg
            580                 585                 590

Arg Ser Leu Ser Pro Glu Leu Arg Glu Gly Asp Pro Ser Ser Gln
        595                 600                 605

His Leu Pro Ser Thr Pro Ser Ser Pro Arg Val Pro Gly Ala Leu Ala
610                 615                 620

Ala Ala Lys Ala Ala Lys Tyr Gly Ala Ala Val Pro Gly Val Leu Gly
625                 630                 635                 640

Gly Leu Gly Ala Leu Gly Gly Val Gly Ile Pro Gly Gly Val Val Gly
                645                 650                 655

Ala Gly Pro

<210> SEQ ID NO 36
<211> LENGTH: 1980
<212> TYPE: DNA
<213> ORGANISM: Artificial Sequence
```

<220> FEATURE:
<223> OTHER INFORMATION: Description of Artificial Sequence: Synthetic polynucleotide

<400> SEQUENCE: 36

```
ggtggcgtac caggcgcaat tcctgggggt gtcccaggcg gtgtttttta tccgggcgcc      60
ggtcttggcg cactgggtgg cggtgcactg ggcccgggcg gcaaaccgct gaaaccggta     120
ccaggtggtt tagcaggcgc cggcttaggc gcaggtctgg gagcatttcc ggcagttacc     180
tttccagggg cactggttcc tggaggtgtg gccgatgcag ccgcggcata taaagccgct     240
aaagccggtg cgggtttagg aggcgtccca ggtgtcggtg gcctgggtgt tagcgccggt     300
gcagttgttc cgcagccggg agcaggggtt aaacctggta aagtgccggg agtaggtctg     360
ccaggcgttt atcctggtgg tgttttgccg ggtgcccgtt ttccgggcgt tggtgttctt     420
ccaggcgtgc cgaccggagc cggtgttaaa ccgaaagccc ccggtgttgg aggtgcattt     480
gcaggcatcc cggagttggg cccgtttggt ggtccgcaac ctggggttcc gttaggttat     540
ccgattaaag caccgaaact gcccggcggt tatggtctgc cgtacacaac cggtaaactg     600
ccgtatggtt atggcccggg tggagttgcg ggtgcagcag gtaaagcggg ttatcctacc     660
ggaaccggtg taggtccgca ggccgctgct gccgccgccg caaaagcagc ggctaaattt     720
ggcgccggag cagcgggtgt tctgcctgga gttggtggtg cgggcgtgcc aggggtacct     780
ggtgcaattc cgggtattgg tggtattgcc ggtgtcggca ccccggccgc ggcagctgcg     840
gcagcggcgg ctgccaaagc tgctaaatac ggtgccgcgg cgggtctggt gccaggaggt     900
ccgggttttg gtccgggagt ggttggcgtg cctggcgcag gcgttcctgg tgtgggcgtt     960
ccaggtgcag ggattcctgt tgtgcctggt gccggtattc ccggcgcggc cgttccgggg    1020
gtggttagcc cggaagccgc agcgaaggct gcggcaaagg cagcaaagta tggcgcacgc    1080
ccaggagtcg gcgtgggtgg tatcccgacc tatggggtgg gcgcaggggg ttttcctggt    1140
ttcggcgtag gtgtaggagg tataccgggc gtggccggtg taccaggggt tggtggcgtc    1200
cctggtgttg gcggtgtgcc aggtgttggt atttcaccgg aagcacaggc agcagccgca    1260
gctaaggcag cgaaatatgg tgccgccggc gcaggagttt taggtgggct ggttccgggc    1320
ccgcaggcag ctgtgccggg ggttccaggc accggtggtg tccctggagt cggtacgccg    1380
gctgcagcgg cagccaaagc ggctgcgaaa gcagcacagt ttggcttagt accgggtgtg    1440
ggagttgccc ccggcgttgg cgttgctcca ggggtgggtg ttgctcctgg cgtcggtctg    1500
gctcctggag tggcgtagc acccggtgtg gggtggccc cggtgttgg ggttgcaccg    1560
ggtatcggtc cgggcggtgt cgcagcagca gctaaaagcg cggcgaaagt tgcggccaaa    1620
gcccaactgc gcgccgccgc gggcctcggt gcaggtattc cggggctggg tgtcggagtt    1680
ggagtcccgg gtttgggcgt gggcgcggga gttccgggac tgggagtggg tgccggagtt    1740
cctggctttg gtgcaggcgc agatgaaggt gttcgtcgta gcctgagtcc ggaactgcgt    1800
gaaggtgatc cgagtagcag ccagcatctg ccgagcaccc cgagcagccc gcgtgttccg    1860
ggtgcattag ctgcagcaaa agccgccaag tatggtgcag ccgtgccggg cgtcttaggt    1920
ggtctgggcg ccctgggtgg tgtaggcatt ccgggaggtg ttgtgggtgc aggaccgtaa    1980
```

<210> SEQ ID NO 37
<211> LENGTH: 622
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

```
Gly Gly Val Pro Gly Ala Ile Pro Gly Gly Val Pro Gly Gly Val Phe
1               5                   10                  15
Tyr Pro Gly Ala Gly Leu Gly Ala Leu Gly Gly Ala Leu Gly Pro
            20                  25                  30
Gly Gly Lys Pro Leu Lys Pro Val Pro Gly Gly Leu Ala Gly Ala Gly
            35                  40                  45
Leu Gly Ala Gly Leu Gly Ala Phe Pro Ala Val Thr Phe Pro Gly Ala
50                  55                  60
Leu Val Pro Gly Gly Val Ala Asp Ala Ala Ala Tyr Lys Ala Ala
65                  70                  75                  80
Lys Ala Gly Ala Gly Leu Gly Gly Val Pro Gly Val Gly Gly Leu Gly
                85                  90                  95
Val Ser Ala Gly Ala Val Val Pro Gln Pro Gly Ala Gly Val Lys Pro
                100                 105                 110
Gly Lys Val Pro Gly Val Gly Leu Pro Gly Val Tyr Pro Gly Gly Val
            115                 120                 125
Leu Pro Gly Ala Arg Phe Pro Gly Val Gly Val Leu Pro Gly Val Pro
130                 135                 140
Thr Gly Ala Gly Val Lys Pro Lys Ala Pro Gly Val Gly Gly Ala Phe
145                 150                 155                 160
Ala Gly Ile Pro Gly Val Gly Pro Phe Gly Gly Pro Gln Pro Gly Val
                165                 170                 175
Pro Leu Gly Tyr Pro Ile Lys Ala Pro Lys Leu Pro Gly Gly Tyr Gly
            180                 185                 190
Leu Pro Tyr Thr Thr Gly Lys Leu Pro Tyr Gly Tyr Gly Pro Gly Gly
            195                 200                 205
Val Ala Gly Ala Ala Gly Lys Ala Gly Tyr Pro Thr Gly Thr Gly Val
            210                 215                 220
Gly Pro Gln Ala Ala Ala Ala Ala Ala Lys Ala Ala Lys Phe
225                 230                 235                 240
Gly Ala Gly Ala Ala Gly Val Leu Pro Gly Val Gly Gly Ala Gly Val
                245                 250                 255
Pro Gly Val Pro Gly Ala Ile Pro Gly Ile Gly Gly Ile Ala Gly Val
                260                 265                 270
Gly Thr Pro Ala Ala Ala Ala Ala Ala Ala Ala Lys Ala Ala
            275                 280                 285
Lys Tyr Gly Ala Ala Ala Gly Leu Val Pro Gly Gly Pro Gly Phe Gly
            290                 295                 300
Pro Gly Val Val Gly Val Pro Gly Ala Gly Val Pro Gly Val Gly Val
305                 310                 315                 320
Pro Gly Ala Gly Ile Pro Val Val Pro Gly Ala Gly Ile Pro Gly Ala
                325                 330                 335
Ala Val Pro Gly Val Val Ser Pro Glu Ala Ala Lys Ala Ala
            340                 345                 350
Lys Ala Ala Lys Tyr Gly Ala Arg Pro Gly Val Gly Val Gly Gly Ile
            355                 360                 365
Pro Thr Tyr Gly Val Gly Ala Gly Gly Phe Pro Gly Phe Val Gly
            370                 375                 380
Val Gly Gly Ile Pro Gly Val Ala Gly Val Pro Gly Val Gly Gly Val
385                 390                 395                 400
```

```
Pro Gly Val Gly Gly Val Pro Gly Val Gly Ile Ser Pro Glu Ala Gln
            405                 410                 415

Ala Ala Ala Ala Ala Lys Ala Ala Lys Tyr Gly Ala Ala Gly Ala Gly
        420                 425                 430

Val Leu Gly Gly Leu Val Pro Gly Pro Gln Ala Ala Val Pro Gly Val
        435                 440                 445

Pro Gly Thr Gly Gly Val Pro Gly Val Gly Thr Pro Ala Ala Ala Ala
        450                 455                 460

Ala Lys Ala Ala Ala Lys Ala Ala Gln Phe Gly Leu Val Pro Gly Val
465                 470                 475                 480

Gly Val Ala Pro Gly Val Gly Val Ala Pro Gly Val Gly Val Ala Pro
                485                 490                 495

Gly Val Gly Leu Ala Pro Gly Val Gly Val Ala Pro Gly Val Gly Val
            500                 505                 510

Ala Pro Gly Val Gly Val Ala Pro Gly Ile Gly Pro Gly Gly Val Ala
        515                 520                 525

Ala Ala Ala Lys Ser Ala Ala Lys Val Ala Ala Lys Ala Gln Leu Arg
        530                 535                 540

Ala Ala Ala Gly Leu Gly Ala Gly Ile Pro Gly Leu Gly Val Gly Val
545                 550                 555                 560

Gly Val Pro Gly Leu Gly Val Gly Ala Gly Val Pro Gly Leu Gly Val
                565                 570                 575

Gly Ala Gly Val Pro Gly Phe Gly Ala Gly Ala Asp Glu Gly Val Arg
            580                 585                 590

Arg Ser Leu Ser Pro Glu Leu Arg Glu Gly Asp Pro Ser Ser Ser Gln
        595                 600                 605

His Leu Pro Ser Thr Pro Ser Ser Pro Arg Val Pro Gly Ala
    610                 615                 620

<210> SEQ ID NO 38
<211> LENGTH: 1869
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
ggtggcgtac caggcgcaat tcctgggggt gtcccaggcg gtgttttta tccgggcgcc    60 ggtcttggcg cactgggtgg cggtgcactg ggcccgggcg gcaaaccgct gaaaccggta   120
ccaggtggtt tagcaggcgc cggcttaggc gcaggtctgg gagcatttcc ggcagttacc   180
tttccagggg cactggttcc tggaggtgtg gccgatgcag ccgcggcata taaagccgct   240
aaagccggtg cgggtttagg aggcgtccca ggtgtcggtg gcctgggtgt tagcgccggt   300
gcagttgttc cgcagccggg agcaggggtt aaacctggta aagtgccggg agtaggtctg   360
ccaggcgttt atcctggtgg tgttttgccg ggtgcccgtt ttccgggcgt tggtgttctt   420
ccaggcgtgc cgaccggagc cggtgttaaa ccgaaagccc ccggtgttgg aggtgcattt   480
gcaggcatcc cggagttggc ccgtttggt ggtccgcaac ctggggttcc gttaggttat   540
ccgattaaag caccgaaact gcccggcggt tatggtctgc cgtacacaac cggtaaactg   600
ccgtatggtt atggcccggg tggagttgcg ggtgcagcag gtaaagcggg ttatcctacc   660
ggaaccggtg taggtccgca ggccgctgct ccgccgccg caaaagcagc ggctaaattt   720
ggcgccggag cagcgggtgt tctgcctgga gttggtggtc cgggcgtgcc aggggtacct   780
```

```
ggtgcaattc cgggtattgg tggtattgcc ggtgtcggca ccccggccgc ggcagctgcg      840
gcagcggcgg ctgccaaagc tgctaaatac ggtgccgcgg cgggtctggt gccaggaggt      900
ccgggttttg gtccgggagt ggttggcgtg cctggcgcag gcgttcctgg tgtgggcgtt      960
ccaggtgcag ggattcctgt tgtgcctggt gccggtattc ccggcgcggc cgttccgggg     1020
gtggttagcc cggaagccgc agcgaaggct gcggcaaagg cagcaaagta tggcgcacgc     1080
ccaggagtcg gcgtgggtgg tatcccgacc tatggggtgg gcgcagggGg ttttcctggt     1140
ttcggcgtag gtgtaggagg tataccgggc gtggccggtg taccaggggt tggtggcgtc     1200
cctggtgttg gcggtgtgcc aggtgttggt atttcaccgg aagcacaggc agcagccgca     1260
gctaaggcag cgaaatatgg tgccgccggc gcaggagttt taggtgggct ggttccgggc     1320
ccgcaggcag ctgtgccggg ggttccaggc accggtggtg tccctggagt cggtacgccg     1380
gctgcagcgg cagccaaagc ggctgcgaaa gcagcacagt ttggcttagt accgggtgtg     1440
ggagttgccc ccggcgttgg cgttgctcca ggggtgggtg ttgctcctgg cgtcggtctg     1500
gctcctggag tgggcgtagc accggtgtgt ggggtggccc cgggtgttgg ggttgcaccg     1560
ggtatcggtc cgggcggtgt cgcagcagca gctaaaagcg cggcgaaagt tgcggccaaa     1620
gcccaactgc gcgccgccgc gggcctcggt gcaggtattc cggggctggg tgtcggagtt     1680
ggagtcccgg gtttgggcgt gggcgcggga gttccgggac tgggagtggg tgccggagtt     1740
cctggctttg gtgcaggcgc agatgaaggt gttcgtcgta gcctgagtcc ggaactgcgt     1800
gaaggtgatc cgagtagcag ccagcatctg ccgagcaccc cgagcagccc gcgtgttccg     1860
ggtgcataa                                                             1869
```

<210> SEQ ID NO 39
<211> LENGTH: 527
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gly Gly Val Pro Gly Ala Ile Pro Gly Gly Val Pro Gly Gly Val Phe
1               5                   10                  15

Tyr Pro Gly Ala Gly Leu Gly Ala Leu Gly Gly Ala Leu Gly Pro
            20                  25                  30

Gly Gly Lys Pro Leu Lys Pro Val Pro Gly Gly Leu Ala Gly Ala Gly
        35                  40                  45

Leu Gly Ala Gly Leu Gly Ala Phe Pro Ala Val Thr Phe Pro Gly Ala
    50                  55                  60

Leu Val Pro Gly Gly Val Ala Asp Ala Ala Ala Ala Tyr Lys Ala Ala
65                  70                  75                  80

Lys Ala Gly Ala Gly Leu Gly Gly Val Pro Gly Val Gly Gly Leu Gly
                85                  90                  95

Val Ser Ala Gly Ala Val Val Pro Gln Pro Gly Ala Gly Val Lys Pro
            100                 105                 110

Gly Lys Val Pro Gly Val Gly Leu Pro Gly Val Tyr Pro Gly Gly Val
        115                 120                 125

Leu Pro Gly Ala Arg Phe Pro Gly Val Gly Val Leu Pro Gly Val Pro
    130                 135                 140

Thr Gly Ala Gly Val Lys Pro Lys Ala Pro Gly Val Gly Gly Ala Phe
145                 150                 155                 160

```
Ala Gly Ile Pro Gly Val Gly Pro Phe Gly Gly Pro Gln Pro Gly Val
            165                 170                 175

Pro Leu Gly Tyr Pro Ile Lys Ala Pro Lys Leu Pro Gly Gly Tyr Gly
        180                 185                 190

Leu Pro Tyr Thr Thr Gly Lys Leu Pro Tyr Gly Tyr Gly Pro Gly Gly
        195                 200                 205

Val Ala Gly Ala Ala Gly Lys Ala Gly Tyr Pro Thr Gly Thr Gly Val
        210                 215                 220

Gly Pro Gln Ala Ala Ala Ala Ala Ala Lys Ala Ala Lys Phe
225             230                 235                 240

Gly Ala Gly Ala Ala Gly Val Leu Pro Gly Val Gly Gly Ala Gly Val
                245                 250                 255

Pro Gly Val Pro Gly Ala Ile Pro Gly Ile Gly Gly Ile Ala Gly Val
            260                 265                 270

Gly Thr Pro Ala Ala Ala Ala Ala Ala Ala Ala Ala Lys Ala Ala
            275                 280                 285

Lys Tyr Gly Ala Ala Ala Gly Leu Val Pro Gly Pro Gly Phe Gly
    290                 295                 300

Pro Gly Val Val Gly Val Pro Gly Ala Gly Val Pro Gly Val Gly Val
305                 310                 315                 320

Pro Gly Ala Gly Ile Pro Val Val Pro Gly Ala Gly Ile Pro Gly Ala
            325                 330                 335

Ala Val Pro Gly Val Val Ser Pro Glu Ala Ala Lys Ala Ala Ala
            340                 345                 350

Lys Ala Ala Lys Tyr Gly Ala Arg Pro Gly Val Gly Val Gly Gly Ile
            355                 360                 365

Pro Thr Tyr Gly Val Gly Ala Gly Gly Phe Pro Gly Phe Gly Val Gly
    370                 375                 380

Val Gly Gly Ile Pro Gly Val Ala Gly Val Pro Gly Val Gly Gly Val
385                 390                 395                 400

Pro Gly Val Gly Gly Val Pro Gly Val Gly Ile Ser Pro Glu Ala Gln
            405                 410                 415

Ala Ala Ala Ala Ala Lys Ala Ala Lys Tyr Gly Ala Gly Ala Gly
            420                 425                 430

Val Leu Gly Gly Leu Val Pro Gly Pro Gln Ala Ala Val Pro Gly Val
            435                 440                 445

Pro Gly Thr Gly Gly Val Pro Gly Val Gly Thr Pro Ala Ala Ala Ala
    450                 455                 460

Ala Lys Ala Ala Ala Lys Ala Ala Gln Phe Gly Leu Val Pro Gly Val
465                 470                 475                 480

Gly Val Ala Pro Gly Val Gly Val Ala Pro Gly Val Gly Val Ala Pro
            485                 490                 495

Gly Val Gly Leu Ala Pro Gly Val Gly Val Ala Pro Gly Val Gly Val
            500                 505                 510

Ala Pro Gly Val Gly Val Ala Pro Gly Ile Gly Pro Gly Gly Val
            515                 520                 525

<210> SEQ ID NO 40
<211> LENGTH: 1584
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
```

```
ggtggcgtac caggcgcaat tcctgggggt gtcccaggcg gtgttttta tccgggcgcc    60 ggtcttggcg cactgggtgg cggtgcactg ggcccgggcg gcaaaccgct gaaaccggta   120
ccaggtggtt tagcaggcgc cggcttaggc gcaggtctgg gagcatttcc ggcagttacc   180
tttccagggg cactggttcc tggaggtgtg gccgatgcag ccgcggcata taagccgct    240 aaagccggtg cgggtttagg aggcgtccca ggtgtcggtg gcctgggtgt tagcgccggt   300
gcagttgttc cgcagccggg agcagggggtt aaacctggta aagtgccggg agtaggtctg   360
ccaggcgttt atcctggtgg tgttttgccg ggtgcccgtt ttccgggcgt tggtgttctt   420
ccaggcgtgc cgaccggagc cggtgttaaa ccgaaagccc ccggtgttgg aggtgcattt   480
gcaggcatcc cgggagttgg cccgtttggt ggtccgcaac ctggggttcc gttaggttat   540
ccgattaaag caccgaaact gcccggcggt tatggtctgc cgtacacaac cggtaaactg   600
ccgtatggtt atggcccggg tggagttgcg ggtgcagcag gtaaagcggg ttatcctacc   660
ggaaccggtg taggtccgca ggccgctgct gccgccgccg caaaagcagc ggctaaattt   720
ggcgccggag cagcgggtgt tctgcctgga gttggtggtg cgggcgtgcc agggggtacct   780 ggtgcaattc cgggtattgg tggtattgcc ggtgtcggca ccccggccgc ggcagctgcg   840
gcagcggcgg ctgccaaagc tgctaaatac ggtgccgcgg cgggtctggt gccaggaggt   900
ccgggttttg gtccgggagt ggttggcgtg cctggcgcag gcgttcctgg tgtgggcgtt   960
ccaggtgcag ggattcctgt tgtgcctggt gccggtattc ccggcgcggc cgttccgggg  1020
gtggttagcc cggaagccgc agcgaaggct gcggcaaagg cagcaaagta tggcgcacgc  1080
ccaggagtcg gcgtgggtgg tatcccgacc tatgggtgg gcgcaggggg ttttcctggt  1140
ttcggcgtag gtgtaggagg tataccgggc gtggccggtg taccaggggt tggtggcgtc  1200
cctggtgttg gcggtgtgcc aggtgttggt atttcaccgg aagcacaggc agcagccgca  1260
gctaaggcag cgaaatatgg tgccgccggc gcaggagttt taggtgggct ggttccgggc  1320
ccgcaggcag ctgtgccggg ggttccaggc accggtggtg tccctggagt cggtacgccg  1380
gctgcagcgg cagccaaagc ggctgcgaaa gcagcacagt ttggcttagt accgggtgtg  1440
ggagttgccc ccggcgttgg cgttgctcca ggggtgggtg ttgctcctgg cgtcggtctg  1500
gctcctggag tgggcgtagc acccggtgtg ggggtggccc cgggtgttgg ggttgcaccg  1560
ggtatcggtc cgggcggtgt ctaa                                         1584
```

<210> SEQ ID NO 41
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gly Val Leu Pro Gly Val Gly Gly Ala Gly Val Pro Gly Val Pro Gly
1               5                   10                  15

Ala Ile Pro Gly Ile Gly Gly Ile Ala Gly Val Gly Thr Pro Ala Ala
            20                  25                  30

Ala Ala Ala Ala Ala Ala Ala Lys Ala Ala Lys Tyr Gly Ala Ala
        35                  40                  45

Ala Gly Leu Val Pro Gly Gly Pro Gly Phe Gly Pro Gly Val Val Gly
    50                  55                  60

Val Pro Gly Ala Gly Val Pro Gly Val Gly Val Pro Gly Ala Gly Ile

```
            65                  70                  75                  80
        Pro Val Val Pro Gly Ala Gly Ile Pro Gly Ala Ala Val Pro Gly Val
                        85                  90                  95

Val Ser Pro Glu Ala Ala Ala Lys Ala Ala Lys Ala Ala Lys Tyr
                    100                 105                 110

Gly Ala Arg Pro Gly Val Gly Gly Ile Pro Thr Tyr Gly Val
                    115                 120                 125

Gly Ala Gly Gly Phe Pro Gly Phe Gly Val Val Gly Gly Ile Pro
                130                 135                 140

Gly Val Ala Gly Val Pro Gly Val Gly Val Pro Gly Val Gly Gly
        145                 150                 155                 160

Val Pro Gly Val Gly Ile Ser Pro Glu Ala Gln Ala Ala Ala Ala
                        165                 170                 175

Lys Ala Ala Lys Tyr Gly Ala Ala Gly Ala Gly Val Leu Gly Gly Leu
                    180                 185                 190

Val Pro Gly Pro Gln Ala Ala Val Pro Gly Val Pro Gly Thr Gly Gly
                    195                 200                 205

Val Pro Gly Val Gly Thr Pro Ala Ala Ala Ala Lys Ala Ala
                210                 215                 220

Lys Ala Ala Gln Phe Gly Leu Val Pro Gly Val Gly Val Ala Pro Gly
        225                 230                 235                 240

Val Gly Val Ala Pro Gly Val Gly Val Ala Pro Gly Val Gly Leu Ala
                        245                 250                 255

Pro Gly Val Gly Val Ala Pro Gly Val Gly Val Ala Pro Gly Val Gly
                    260                 265                 270

Val Ala Pro Gly Ile Gly Pro Gly Gly Val Ala Ala Ala Lys Ser
                    275                 280                 285

Ala Ala Lys Val Ala Ala Lys Ala Gln Leu Arg Ala Ala Ala Gly Leu
                290                 295                 300

Gly Ala Gly Ile Pro Gly Leu Gly Val Gly Val Gly Val Pro Gly Leu
        305                 310                 315                 320

Gly Val Gly Ala Gly Val Pro Gly Leu Gly Val Gly Ala Gly Val Pro
                        325                 330                 335

Gly Phe Gly Ala Gly Ala Asp Glu Gly Val Arg Arg Ser Leu Ser Pro
                        340                 345                 350

Glu Leu Arg Glu Gly Asp Pro Ser Ser Ser Gln His Leu Pro Ser Thr
                    355                 360                 365

Pro Ser Ser Pro Arg Val Pro Gly Ala Leu Ala Ala Ala Lys Ala Ala
                    370                 375                 380

Lys Tyr Gly Ala Ala Val Pro Gly Val Leu Gly Gly Leu Gly Ala Leu
        385                 390                 395                 400

Gly Gly Val Gly Ile Pro Gly Gly Val Val Gly Ala Gly Pro Ala Ala
                        405                 410                 415

Ala Ala Ala Ala Ala Lys Ala Ala Lys Ala Ala Gln Phe Gly Leu
                    420                 425                 430

Val Gly Ala Ala Gly Leu Gly Gly Leu Gly Val Gly Gly Leu Gly Val
                    435                 440                 445

Pro Gly Val Gly Gly Leu Gly Gly Ile Pro Pro Ala Ala Ala Ala Lys
                    450                 455                 460

Ala Ala Lys Tyr Gly Ala Ala Gly Leu Gly Gly Val Leu Gly Gly Ala
        465                 470                 475                 480

Gly Gln Phe Pro Leu Gly Gly Val Ala Ala Arg Pro Gly Phe Gly Leu
                    485                 490                 495
```

Ser Pro Ile Phe Pro Gly Gly Ala Cys Leu Gly Lys Ala Cys Gly Arg
                500                 505                 510

Lys Arg Lys
        515

<210> SEQ ID NO 42
<211> LENGTH: 1548
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42

| | | | | |
|---|---|---|---|---|
| ggtgttctgc | ctggagttgg | tggtgcgggc | gtgccagggg | tacctggtgc aattccgggt | 60 |
| attggtggta | ttgccggtgt | cggcaccccg | gccgcggcag | ctgcggcagc ggcggctgcc | 120 |
| aaagctgcta | atacggtgc | cgcggcgggt | ctggtgccag | gaggtccggg ttttggtccg | 180 |
| ggagtggttg | gcgtgcctgg | cgcaggcgtt | cctggtgtgg | gcgttccagg tgcagggatt | 240 |
| cctgttgtgc | ctggtgccgg | tattcccggc | gcggccgttc | cggggtggt tagcccggaa | 300 |
| gccgcagcga | aggctgcggc | aaaggcagca | agtatggcg | cacgcccagg agtcggcgtg | 360 |
| ggtggtatcc | cgacctatgg | ggtgggcgca | ggggttttc | ctggtttcgg cgtaggtgta | 420 |
| ggaggtatac | cgggcgtggc | cggtgtacca | ggggttggtg | gcgtccctgg tgttggcggt | 480 |
| gtgccaggtg | ttggtatttc | accggaagca | caggcagcag | ccgcagctaa ggcagcgaaa | 540 |
| tatggtgccg | ccggcgcagg | agttttaggt | gggctggttc | cgggcccgca ggcagctgtg | 600 |
| ccggggttc | caggcaccgg | tggtgtccct | ggagtcggta | cgccggctgc agcggcagcc | 660 |
| aaagcggctg | cgaaagcagc | acagtttggc | ttagtaccgg | gtgtgggagt tgcccccggc | 720 |
| gttggcgttg | ctccagggt | gggtgttgct | cctggcgtcg | gtctggctcc tggagtgggc | 780 |
| gtagcacccg | gtgtggggt | ggccccgggt | gttgggttg | caccgggtat cggtccgggc | 840 |
| ggtgtcgcag | cagcagctaa | agcgcggcg | aaagttgcgg | ccaaagccca actgcgcgcc | 900 |
| gccgcgggcc | tcggtgcagg | tattccgggg | ctgggtgtcg | gagttggagt cccgggttg | 960 |
| ggcgtgggcg | cgggagttcc | gggactggga | gtgggtgccg | gagttcctgg ctttggtgca | 1020 |
| ggcgcagatg | aagtgttcg | tcgtagcctg | agtccggaac | tgcgtgaagg tgatccgagt | 1080 |
| agcagccagc | atctgccgag | cacccccgagc | agcccgcgtg | ttccgggtgc attagctgca | 1140 |
| gcaaaagccg | ccaagtatgg | tgcagccgtg | ccgggcgtct | taggtggtct gggcgccctg | 1200 |
| ggtggtgtag | gcattccggg | aggtgttgtg | ggtgcaggac | cggccgccgc agctgcggcc | 1260 |
| gccaaagcag | ctgcaaaagc | ggcccagttt | ggtttagtgg | gcgccgcagg tttaggcggt | 1320 |
| ttaggtgtgg | gtggactggg | tgtacctggc | gtaggcggtc | tgggtggaat tccgcccgca | 1380 |
| gcggccgcga | aagcggcaaa | atatggcgcg | gcaggcctgg | gcggcgtgct gggtggggca | 1440 |
| ggtcagtttc | cgctgggcgg | ggttgccgca | cgtccgggat | ttggtctgag cccgattttc | 1500 |
| cctggcggcg | catgtctggg | taaagcatgt | ggtcgtaaac | gtaaataa | 1548 |

<210> SEQ ID NO 43
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 43

Gly Leu Val Pro Gly Pro Gly Phe Gly Pro Gly Val Val Gly Val
1               5                   10                  15

Pro Gly Ala Gly Val Pro Gly Val Gly Val Pro Gly Ala Gly Ile Pro
            20                  25                  30

Val Val Pro Gly Ala Gly Ile Pro Gly Ala Ala Val Pro Gly Val Val
            35                  40                  45

Ser Pro Glu Ala Ala Ala Lys Ala Ala Lys Ala Ala Lys Tyr Gly
    50                  55                  60

Ala Arg Pro Gly Val Gly Val Gly Ile Pro Thr Tyr Gly Val Gly
65                  70                  75                  80

Ala Gly Gly Phe Pro Gly Phe Gly Val Gly Val Gly Ile Pro Gly
                85                  90                  95

Val Ala Gly Val Pro Gly Val Gly Val Pro Gly Val Gly Gly Val
                100                 105                 110

Pro Gly Val Gly Ile Ser Pro Glu Ala Gln Ala Ala Ala Ala Lys
                115                 120                 125

Ala Ala Lys Tyr Gly Ala Ala Gly Ala Gly Val Leu Gly Gly Leu Val
    130                 135                 140

Pro Gly Pro Gln Ala Ala Val Pro Gly Val Pro Gly Thr Gly Gly Val
145                 150                 155                 160

Pro Gly Val Gly Thr Pro Ala Ala Ala Ala Lys Ala Ala Ala Lys
                165                 170                 175

Ala Ala Gln Phe Gly Leu Val Pro Gly Val Gly Val Ala Pro Gly Val
                180                 185                 190

Gly Val Ala Pro Gly Val Gly Val Ala Pro Gly Val Gly Leu Ala Pro
        195                 200                 205

Gly Val Gly Val Ala Pro Gly Val Gly Val Ala Pro Gly Val Gly Val
        210                 215                 220

Ala Pro Gly Ile Gly Pro Gly Gly Val Ala Ala Ala Lys Ser Ala
225                 230                 235                 240

Ala Lys Val Ala Ala Lys Ala Gln Leu Arg Ala Ala Ala Gly Leu Gly
            245                 250                 255

Ala Gly Ile Pro Gly Leu Gly Val Gly Val Gly Val Pro Gly Leu Gly
                260                 265                 270

Val Gly Ala Gly Val Pro Gly Leu Gly Val Gly Ala Gly Val Pro Gly
            275                 280                 285

Phe Gly Ala Gly Ala Asp Glu Gly Val Arg Arg Ser Leu Ser Pro Glu
    290                 295                 300

Leu Arg Glu Gly Asp Pro Ser Ser Ser Gln His Leu Pro Ser Thr Pro
305                 310                 315                 320

Ser Ser Pro Arg Val Pro Gly Ala Leu Ala Ala Lys Ala Ala Lys
                325                 330                 335

Tyr Gly Ala Ala Val Pro Gly Val Leu Gly Gly Leu Gly Ala Leu Gly
            340                 345                 350

Gly Val Gly Ile Pro Gly Gly Val Val Gly Ala Gly Pro Ala Ala Ala
            355                 360                 365

Ala Ala Ala Ala Lys Ala Ala Lys Ala Ala Gln Phe Gly Leu Val
    370                 375                 380

Gly Ala Ala Gly Leu Gly Gly Leu Gly Val Gly Gly Leu Gly Val Pro
385                 390                 395                 400

Gly Val Gly Gly Leu Gly Gly Ile Pro Pro Ala Ala Ala Ala Lys Ala
            405                 410                 415
```

Ala Lys Tyr Gly Ala Ala Gly Leu Gly Gly Val Leu Gly Gly Ala Gly
          420                 425                 430

Gln Phe Pro Leu Gly Gly Val Ala Ala Arg Pro Gly Phe Gly Leu Ser
        435                 440                 445

Pro Ile Phe Pro Gly Gly Ala Cys Leu Gly Lys Ala Cys Gly Arg Lys
    450                 455                 460

Arg Lys
465

<210> SEQ ID NO 44
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
ggtctggtgc caggaggtcc gggttttggt ccgggagtgg ttggcgtgcc tggcgcaggc      60
gttcctggtg tgggcgttcc aggtgcaggg attcctgttg tgcctggtgc cggtattccc     120
ggcgcggccg ttccgggggt ggttagcccg gaagccgcag cgaaggctgc ggcaaaggca     180
gcaaagtatg gcgcacgccc aggagtcggc gtgggtggta tcccgaccta tggggtgggc     240 gcaggggggtt ttcctggttt cggcgtaggt gtaggaggta taccgggcgt ggccggtgta     300
ccaggggttg gtggcgtccc tggtgttggc ggtgtgccag gtgttggtat ttcaccggaa     360
gcacaggcag cagccgcagc taaggcagcg aaatatggtg ccgccggcgc aggagtttta     420
ggtgggctgg ttccgggccc gcaggcagct gtgccggggg ttccaggcac cggtggtgtc     480
cctggagtcg gtacgccggc tgcagcggca gccaaagcgg ctgcgaaagc agcacagttt     540
ggcttagtac cgggtgtggg agttgccccc ggcgttggcg ttgctccagg ggtgggtgtt     600
gctcctggcg tcggtctggc tcctggagtg gcgtagcac ccggtgtggg ggtggccccg     660
ggtgttgggg ttgcaccggg tatcggtccg ggcggtgtcg cagcagcagc taaaagcgcg     720
gcgaaagttg cggccaaagc ccaactgcgc gccgccgcgg gcctcggtgc aggtattccg     780
gggctgggtg tcggagttgg agtcccgggt ttgggcgtgg gcgcgggagt tccgggactg     840
ggagtgggtg ccggagttcc tggctttggt gcaggcgcag atgaaggtgt tcgtcgtagc     900
ctgagtccgg aactgcgtga aggtgatccg agtagcagcc agcatctgcc gagcaccccg     960
agcagcccgc gtgttccggg tgcattagct gcagcaaaag ccgccaagta tggtgcagcc    1020
gtgccgggcg tcttaggtgg tctgggcgcc ctgggtggtg taggcattcc gggaggtgtt    1080
gtgggtgcag gaccggccgc cgcagctgcg gccgccaaag cagctgcaaa agcggcccag    1140
tttggtttag tgggcgccgc aggtttaggc ggtttaggtg tgggtggact gggtgtacct    1200
ggcgtaggcg gtctggggtgg aattccgccc gcagcggccg cgaaagcggc aaaatatggc    1260
gcggcaggcc tgggcggcgt gctgggtggg gcaggtcagt ttccgctggg cggggttgcc    1320
gcacgtccgg gatttggtct gagcccgatt ttccctggcg gcgcatgtct gggtaaagca    1380
tgtggtcgta aacgtaaata a                                             1401

<210> SEQ ID NO 45
<211> LENGTH: 460
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 45

```
Gly Gly Val Pro Gly Ala Ile Pro Gly Gly Val Pro Gly Gly Val Phe
1               5                   10                  15

Tyr Pro Gly Ala Gly Leu Gly Ala Leu Gly Gly Ala Leu Gly Pro
            20                  25                  30

Gly Gly Lys Pro Leu Lys Pro Val Pro Gly Gly Leu Ala Gly Ala Gly
            35                  40                  45

Leu Gly Ala Gly Leu Gly Ala Phe Pro Ala Val Thr Phe Pro Gly Ala
50                  55                  60

Leu Val Pro Gly Gly Val Ala Asp Ala Ala Ala Tyr Lys Ala Ala
65                  70                  75                  80

Lys Ala Gly Ala Gly Leu Gly Gly Val Pro Gly Val Gly Gly Leu Gly
                85                  90                  95

Val Ser Ala Gly Ala Val Val Pro Gln Pro Gly Ala Gly Val Lys Pro
            100                 105                 110

Gly Lys Val Pro Gly Val Gly Leu Pro Gly Val Tyr Pro Gly Gly Val
            115                 120                 125

Leu Pro Gly Ala Arg Phe Pro Gly Val Gly Val Leu Pro Gly Val Pro
130                 135                 140

Thr Gly Ala Gly Val Lys Pro Lys Ala Pro Gly Val Gly Gly Ala Phe
145                 150                 155                 160

Ala Gly Ile Pro Gly Val Gly Pro Phe Gly Gly Pro Gln Pro Gly Val
            165                 170                 175

Pro Leu Gly Tyr Pro Ile Lys Ala Pro Lys Leu Pro Gly Tyr Gly
            180                 185                 190

Leu Pro Tyr Thr Thr Gly Lys Leu Pro Tyr Gly Tyr Gly Pro Gly Gly
            195                 200                 205

Val Ala Gly Ala Ala Gly Lys Ala Gly Tyr Pro Thr Gly Thr Gly Val
            210                 215                 220

Gly Pro Gln Ala Ala Ala Ala Ala Ala Lys Ala Ala Lys Phe
225                 230                 235                 240

Gly Ala Gly Ala Ala Gly Val Leu Pro Gly Val Gly Gly Ala Gly Val
            245                 250                 255

Pro Gly Val Pro Gly Ala Ile Pro Gly Ile Gly Gly Ile Ala Gly Val
            260                 265                 270

Gly Thr Pro Ala Ala Ala Ala Ala Ala Ala Lys Ala Ala
            275                 280                 285

Lys Tyr Gly Ala Ala Ala Gly Leu Val Pro Gly Pro Gly Phe Gly
            290                 295                 300

Pro Gly Val Val Gly Val Pro Gly Ala Gly Val Pro Gly Val Gly Val
305                 310                 315                 320

Pro Gly Ala Gly Ile Pro Val Val Pro Gly Ala Gly Ile Pro Gly Ala
            325                 330                 335

Ala Val Pro Gly Val Val Ser Pro Glu Ala Ala Lys Ala Ala
            340                 345                 350

Lys Ala Ala Lys Tyr Gly Ala Arg Pro Gly Val Gly Val Gly Gly Ile
            355                 360                 365

Pro Thr Tyr Gly Val Gly Ala Gly Gly Phe Pro Gly Phe Gly Val Gly
            370                 375                 380

Val Gly Gly Ile Pro Gly Val Ala Gly Val Pro Gly Val Gly Gly Val
385                 390                 395                 400
```

Pro Gly Val Gly Gly Val Pro Gly Val Gly Ile Ser Pro Glu Ala Gln
                405                 410                 415

Ala Ala Ala Ala Ala Lys Ala Ala Lys Tyr Gly Ala Ala Gly Ala Gly
            420                 425                 430

Val Leu Gly Gly Leu Val Pro Gly Pro Gln Ala Ala Val Pro Gly Val
        435                 440                 445

Pro Gly Thr Gly Gly Val Pro Gly Val Gly Thr Pro
    450                 455                 460

<210> SEQ ID NO 46
<211> LENGTH: 1383
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46

| | |
|---|---|
| ggtggcgtac caggcgcaat tcctgggggt gtcccaggcg gtgtttttta tccgggcgcc | 60 |
| ggtcttggcg cactgggtgg cggtgcactg ggcccgggcg gcaaaccgct gaaaccggta | 120 |
| ccaggtggtt tagcaggcgc cggcttaggc gcaggtctgg gagcatttcc ggcagttacc | 180 |
| tttccagggg cactggttcc tggaggtgtg gccgatgcag ccgcggcata taaagccgct | 240 |
| aaagccggtg cgggtttagg aggcgtccca ggtgtcggtg gctgggtgt tagcgccggt | 300 |
| gcagttgttc cgcagccggg agcaggggtt aaacctggta aagtgccggg agtaggtctg | 360 |
| ccaggcgttt atcctggtgg tgttttgccg ggtgcccgtt ttccgggcgt tggtgttctt | 420 |
| ccaggcgtgc cgaccggagc cggtgttaaa ccgaaagccc ccggtgttgg aggtgcattt | 480 |
| gcaggcatcc cggagttgg cccgtttggt ggtccgcaac ctgggggtcc gttaggttat | 540 |
| ccgattaaag caccgaaact gccggcggt tatggtctgc cgtacacaac cggtaaactg | 600 |
| ccgtatggtt atggcccggg tggagttgcg ggtgcagcag gtaaagcggg ttatcctacc | 660 |
| ggaaccggtg taggtccgca ggccgctgct gccgccgccg caaaagcagc ggctaaattt | 720 |
| ggcgccggag cagcgggtgt tctgcctgga gttggtggtg cgggcgtgcc aggggtacct | 780 |
| ggtgcaattc cgggtattgg tggtattgcc ggtgtcggca ccccgccgc ggcagctgcg | 840 |
| gcagcggcgg ctgccaaagc tgctaaatac ggtgccgcgg cgggtctggt gccaggaggt | 900 |
| ccgggttttg gtccgggagt ggttggcgtg cctggcgcag gcgttcctgg tgtgggcgtt | 960 |
| ccaggtgcag ggattcctgt tgtgcctggt gccggtattc ccggcgcggc cgttccgggg | 1020 |
| gtggttagcc cggaagccgc agcgaaggct gcggcaaagg cagcaaagta tggcgcacgc | 1080 |
| ccaggagtcg gcgtgggtgg tatcccgacc tatggggtgg gcgcaggggg ttttcctggt | 1140 |
| ttcggcgtag gtgtaggagg tataccgggc gtggccggtg taccagggt tggtggcgtc | 1200 |
| cctggtgttg gcggtgtgcc aggtgttggt atttcaccgg aagcacaggc agcagccgca | 1260 |
| gctaaggcag cgaaatatgg tgccgccggc gcagagttt aggtgggct ggttccgggc | 1320 |
| ccgcaggcag ctgtgccggg ggttccaggc accggtggtg tccctggagt cggtacgccg | 1380 |
| taa | 1383 |

<210> SEQ ID NO 47
<211> LENGTH: 416
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Gly Gly Val Pro Gly Ala Ile Pro Gly Gly Val Pro Gly Gly Phe
1               5                   10                  15

Tyr Pro Gly Ala Gly Leu Gly Ala Leu Gly Gly Ala Leu Gly Pro
            20                  25                  30

Gly Gly Lys Pro Leu Lys Pro Val Pro Gly Gly Leu Ala Gly Ala Gly
            35                  40                  45

Leu Gly Ala Gly Leu Gly Ala Phe Pro Ala Val Thr Phe Pro Gly Ala
50                  55                  60

Leu Val Pro Gly Gly Val Ala Asp Ala Ala Ala Tyr Lys Ala Ala
65                  70                  75                  80

Lys Ala Gly Ala Gly Leu Gly Gly Val Pro Gly Val Gly Gly Leu Gly
                85                  90                  95

Val Ser Ala Gly Ala Val Pro Gln Pro Gly Ala Gly Val Lys Pro
                100                 105                 110

Gly Lys Val Pro Gly Val Gly Leu Pro Gly Val Tyr Pro Gly Gly Val
            115                 120                 125

Leu Pro Gly Ala Arg Phe Pro Gly Val Gly Val Leu Pro Gly Val Pro
130                 135                 140

Thr Gly Ala Gly Val Lys Pro Lys Ala Pro Gly Val Gly Gly Ala Phe
145                 150                 155                 160

Ala Gly Ile Pro Gly Val Gly Pro Phe Gly Pro Gln Pro Gly Val
                165                 170                 175

Pro Leu Gly Tyr Pro Ile Lys Ala Pro Lys Leu Pro Gly Tyr Gly
            180                 185                 190

Leu Pro Tyr Thr Thr Gly Lys Leu Pro Tyr Gly Tyr Gly Pro Gly Gly
            195                 200                 205

Val Ala Gly Ala Ala Gly Lys Ala Gly Tyr Pro Thr Gly Thr Gly Val
210                 215                 220

Gly Pro Gln Ala Ala Ala Ala Ala Ala Lys Ala Ala Ala Lys Phe
225                 230                 235                 240

Gly Ala Gly Ala Ala Gly Val Leu Pro Gly Val Gly Gly Ala Gly Val
                245                 250                 255

Pro Gly Val Pro Gly Ala Ile Pro Gly Ile Gly Gly Ile Ala Gly Val
            260                 265                 270

Gly Thr Pro Ala Ala Ala Ala Ala Ala Ala Ala Lys Ala Ala
                275                 280                 285

Lys Tyr Gly Ala Ala Ala Gly Leu Val Pro Gly Gly Pro Gly Phe Gly
290                 295                 300

Pro Gly Val Val Gly Val Pro Gly Ala Gly Val Pro Gly Val Gly Val
305                 310                 315                 320

Pro Gly Ala Gly Ile Pro Val Val Pro Gly Ala Gly Ile Pro Gly Ala
                325                 330                 335

Ala Val Pro Gly Val Val Ser Pro Glu Ala Ala Lys Ala Ala Ala
                340                 345                 350

Lys Ala Ala Lys Tyr Gly Ala Arg Pro Gly Val Gly Val Gly Gly Ile
                355                 360                 365

Pro Thr Tyr Gly Val Gly Ala Gly Gly Phe Pro Gly Phe Gly Val Gly
            370                 375                 380

Val Gly Gly Ile Pro Gly Val Ala Gly Val Pro Gly Val Gly Gly Val
385                 390                 395                 400

Pro Gly Val Gly Gly Val Pro Gly Val Gly Ile Ser Pro Glu Ala Gln
```

<210> SEQ ID NO 48
<211> LENGTH: 1251
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 48

```
ggtggcgtac caggcgcaat tcctgggggt gtcccaggcg gtgtttttta tccgggcgcc      60
ggtcttggcg cactgggtgg cggtgcactg ggcccgggcg gcaaaccgct gaaaccggta     120
ccaggtggtt tagcaggcgc cggcttaggc gcaggtctgg gagcatttcc ggcagttacc     180
tttccagggg cactggttcc tggaggtgtg gccgatgcag ccgcggcata taaagccgct     240
aaagccggtg cgggtttagg aggcgtccca ggtgtcggtg gcctgggtgt tagcgccggt     300
gcagttgttc cgcagccggg agcagggggtt aaacctggta aagtgccggg agtaggtctg     360
ccaggcgttt atcctggtgg tgttttgccg ggtgcccgtt ttccgggcgt tggtgttctt     420
ccaggcgtgc cgaccggagc cggtgttaaa ccgaaagccc ccggtgttgg aggtgcattt     480
gcaggcatcc cgggagttgg cccgtttggt ggtccgcaac ctggggttcc gttaggttat     540
ccgattaaag caccgaaact gcccggcggt tatggtctgc cgtacacaac cggtaaactg     600
ccgtatggtt atggcccggg tggagttgcg ggtgcagcag gtaaagcggg ttatcctacc     660
ggaaccggtg taggtccgca ggccgctgct gccgccgccg caaaagcagc ggctaaattt     720
ggcgccggag cagcgggtgt tctgcctgga gttggtggtg cgggcgtgcc aggggtacct     780
ggtgcaattc cgggtattgg tggtattgcc ggtgtcggca ccccggccgc ggcagctgcg     840
gcagcggcgg ctgccaaagc tgctaaatac ggtgccgcgg cgggtctggt gccaggaggt     900
ccgggttttg gtccgggagt ggttggcgtg cctggcgcag gcgttcctgg tgtgggcgtt     960
ccaggtgcag ggattcctgt tgtgcctggt gccggtattc ccggcgcggc cgttccgggg    1020
gtggttagcc cggaagccgc agcgaaggct gcggcaaagg cagcaaagta tggcgcacgc    1080
ccaggagtcg gcgtgggtgg tatcccgacc tatggggtgg gcgcagggg ttttcctggt    1140
ttcggcgtag gtgtaggagg tataccgggc gtggccggtg taccagggggt tggtggcgtc    1200
cctggtgttg gcggtgtgcc aggtgttggt atttcaccgg aagcacagta a            1251
```

<210> SEQ ID NO 49
<211> LENGTH: 401
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 49

```
Arg Pro Gly Val Gly Val Gly Gly Ile Pro Thr Tyr Gly Val Gly Ala
1               5                   10                  15

Gly Gly Phe Pro Gly Phe Gly Val Gly Val Gly Gly Ile Pro Gly Val
            20                  25                  30

Ala Gly Val Pro Gly Val Gly Gly Val Pro Gly Val Gly Gly Val Pro
        35                  40                  45

Gly Val Gly Ile Ser Pro Glu Ala Gln Ala Ala Ala Ala Lys Ala
    50                  55                  60

Ala Lys Tyr Gly Ala Ala Gly Ala Gly Val Leu Gly Gly Leu Val Pro
```

```
                65                  70                  75                  80
Gly Pro Gln Ala Ala Val Pro Gly Val Pro Gly Thr Gly Gly Val Pro
                    85                  90                  95
Gly Val Gly Thr Pro Ala Ala Ala Ala Lys Ala Ala Ala Lys Ala
                100                 105                 110
Ala Gln Phe Gly Leu Val Pro Gly Val Gly Val Ala Pro Gly Val Gly
                115                 120                 125
Val Ala Pro Gly Val Gly Val Ala Pro Gly Val Gly Leu Ala Pro Gly
145                 150                 155                 160
Val Gly Val Ala Pro Gly Val Gly Val Ala Pro Gly Val Gly Val Ala
145                 150                 155                 160
Pro Gly Ile Gly Pro Gly Val Ala Ala Ala Lys Ser Ala Ala
                165                 170                 175
Lys Val Ala Ala Lys Ala Gln Leu Arg Ala Ala Ala Gly Leu Gly Ala
            180                 185                 190
Gly Ile Pro Gly Leu Gly Val Gly Val Gly Val Pro Gly Leu Gly Val
            195                 200                 205
Gly Ala Gly Val Pro Gly Leu Gly Val Gly Ala Gly Val Pro Gly Phe
            210                 215                 220
Gly Ala Gly Ala Asp Glu Gly Val Arg Arg Ser Leu Ser Pro Glu Leu
225                 230                 235                 240
Arg Glu Gly Asp Pro Ser Ser Ser Gln His Leu Pro Ser Thr Pro Ser
                245                 250                 255
Ser Pro Arg Val Pro Gly Ala Leu Ala Ala Lys Ala Ala Lys Tyr
                260                 265                 270
Gly Ala Ala Val Pro Gly Val Leu Gly Gly Leu Gly Ala Leu Gly Gly
            275                 280                 285
Val Gly Ile Pro Gly Gly Val Val Gly Ala Gly Pro Ala Ala Ala Ala
            290                 295                 300
Ala Ala Ala Lys Ala Ala Ala Lys Ala Ala Gln Phe Gly Leu Val Gly
305                 310                 315                 320
Ala Ala Gly Leu Gly Gly Leu Gly Val Gly Gly Leu Gly Val Pro Gly
                325                 330                 335
Val Gly Gly Leu Gly Gly Ile Pro Pro Ala Ala Ala Lys Ala Ala
                340                 345                 350
Lys Tyr Gly Ala Ala Gly Leu Gly Gly Val Leu Gly Gly Ala Gly Gln
                355                 360                 365
Phe Pro Leu Gly Gly Val Ala Ala Arg Pro Gly Phe Gly Leu Ser Pro
                370                 375                 380
Ile Phe Pro Gly Gly Ala Cys Leu Gly Lys Ala Cys Gly Arg Lys Arg
385                 390                 395                 400
Lys

<210> SEQ ID NO 50
<211> LENGTH: 1206
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
cgcccaggag tcggcgtggg tggtatcccg acctatgggg tgggcgcagg gggttttcct      60
ggtttcggcg taggtgtagg aggtataccg ggcgtggccg gtgtaccagg ggttggtggc     120
```

-continued

```
gtccctggtg ttggcggtgt gccaggtgtt ggtatttcac cggaagcaca ggcagcagcc    180
gcagctaagg cagcgaaata tggtgccgcc ggcgcaggag ttttaggtgg gctggttccg    240
ggcccgcagg cagctgtgcc gggggttcca ggcaccggtg tgtccctgg agtcggtacg     300 ccggctgcag cggcagccaa agcggctgcg aaagcagcac agtttggctt agtaccgggt    360
gtgggagttg cccccggcgt tggcgttgct ccaggggtgg gtgttgctcc tggcgtcggt    420
ctggctcctg gagtgggcgt agcacccggt gtggggtgg ccccgggtgt tgggttgca     480 ccgggtatcg gtccgggcgg tgtcgcagca gcagctaaaa gcgcggcgaa agttgcggcc    540
aaagcccaac tgcgcgccgc cgcgggcctc ggtgcaggta ttccggggct gggtgtcgga    600
gttggagtcc cgggtttggg cgtgggcgcg ggagttccgg gactgggagt gggtgccgga    660
gttcctggct ttggtgcagg cgcagatgaa ggtgttcgtc gtagcctgag tccggaactg    720
cgtgaaggtg atccgagtag cagccagcat ctgccgagca ccccgagcag cccgcgtgtt    780
ccgggtgcat tagctgcagc aaaagccgcc aagtatggtg cagccgtgcc gggcgtctta    840
ggtggtctgg gcgccctggg tggtgtaggc attccgggag gtgttgtggg tgcaggaccg    900
gccgccgcag ctgcggccgc caaagcagct gcaaaagcgg cccagtttgg tttagtgggc    960
gccgcaggtt taggcggttt aggtgtgggt ggactgggtg tacctggcgt aggcggtctg   1020
ggtggaattc cgcccgcagc ggccgcgaaa gcggcaaaat atggcgcggc aggcctgggc   1080
ggcgtgctgg gtggggcagg tcagtttccg ctgggcgggg ttgccgcacg tccgggattt   1140
ggtctgagcc cgattttccc tggcggcgca tgtctgggta agcatgtgg tcgtaaacgt    1200 aaataa                                                              1206
```

<210> SEQ ID NO 51
<211> LENGTH: 371
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 51

```
Gly Gly Val Pro Gly Ala Ile Pro Gly Gly Val Pro Gly Gly Val Phe
 1               5                  10                  15

Tyr Pro Gly Ala Gly Leu Gly Ala Leu Gly Gly Ala Leu Gly Pro
            20                  25                  30

Gly Gly Lys Pro Leu Lys Pro Val Pro Gly Gly Leu Ala Gly Ala Gly
        35                  40                  45

Leu Gly Ala Gly Leu Gly Ala Phe Pro Ala Val Thr Phe Pro Gly Ala
    50                  55                  60

Leu Val Pro Gly Gly Val Ala Asp Ala Ala Ala Tyr Lys Ala Ala
65                  70                  75                  80

Lys Ala Gly Ala Gly Leu Gly Gly Val Pro Gly Val Gly Gly Leu Gly
                85                  90                  95

Val Ser Ala Gly Ala Val Val Pro Gln Pro Gly Ala Gly Val Lys Pro
            100                 105                 110

Gly Lys Val Pro Gly Val Gly Leu Pro Gly Val Tyr Pro Gly Gly Val
        115                 120                 125

Leu Pro Gly Ala Arg Phe Pro Gly Val Gly Val Leu Pro Gly Val Pro
    130                 135                 140

Thr Gly Ala Gly Val Lys Pro Lys Ala Pro Gly Val Gly Gly Ala Phe
145                 150                 155                 160
```

-continued

Ala Gly Ile Pro Gly Val Gly Pro Phe Gly Pro Gln Pro Gly Val
             165                 170                 175

Pro Leu Gly Tyr Pro Ile Lys Ala Pro Lys Leu Pro Gly Gly Tyr Gly
        180                 185                 190

Leu Pro Tyr Thr Thr Gly Lys Leu Pro Tyr Gly Tyr Gly Pro Gly Gly
        195                 200                 205

Val Ala Gly Ala Ala Gly Lys Ala Gly Tyr Pro Thr Gly Thr Gly Val
        210                 215                 220

Gly Pro Gln Ala Ala Ala Ala Ala Ala Lys Ala Ala Lys Phe
225                 230                 235                 240

Gly Ala Gly Ala Ala Gly Val Leu Pro Gly Val Gly Gly Ala Gly Val
                245                 250                 255

Pro Gly Val Pro Gly Ala Ile Pro Gly Ile Gly Ile Ala Gly Val
            260                 265                 270

Gly Thr Pro Ala Ala Ala Ala Ala Ala Ala Ala Lys Ala Ala
            275                 280                 285

Lys Tyr Gly Ala Ala Ala Gly Leu Val Pro Gly Pro Gly Phe Gly
        290                 295                 300

Pro Gly Val Val Gly Val Pro Gly Ala Gly Val Pro Gly Val Gly Val
305                 310                 315                 320

Pro Gly Ala Gly Ile Pro Val Val Pro Gly Ala Gly Ile Pro Gly Ala
                325                 330                 335

Ala Val Pro Gly Val Val Ser Pro Glu Ala Ala Lys Ala Ala Ala
            340                 345                 350

Lys Ala Ala Lys Tyr Gly Ala Arg Pro Gly Val Gly Val Gly Gly Ile
        355                 360                 365

Pro Thr Tyr
    370

<210> SEQ ID NO 52
<211> LENGTH: 1116
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
ggtggcgtac caggcgcaat tcctgggggt gtcccaggcg gtgtttttta tccgggcgcc      60
ggtcttggcg cactgggtgg cggtgcactg ggcccgggcg gcaaaccgct gaaaccggta     120
ccaggtggtt tagcaggcgc cggcttaggc gcaggtctgg gagcatttcc ggcagttacc     180
tttccagggg cactggttcc tggaggtgtg gccgatgcag ccgcggcata taaagccgct     240
aaagccggtg cgggtttagg aggcgtccca ggtgtcggtg gcctgggtgt tagcgccggt     300
gcagttgttc cgcagccggg agcagggggtt aaacctggta agtgccggg agtaggtctg     360 ccaggcgttt atcctggtgg tgttttgccg ggtgcccgtt ttccgggcgt tggtgttctt     420
ccaggcgtgc cgaccggagc cggtgttaaa ccgaaagccc ccggtgttgg aggtgcattt     480
gcaggcatcc cggagttgg cccgtttggt ggtccgcaac ctggggttcc gttaggttat     540
ccgattaaag caccgaaact gcccggcggt tatggtctgc cgtacacaac cggtaaactg     600
ccgtatggtt atggcccggg tggagttgcg ggtgcagcag gtaaagcggg ttatcctacc     660
ggaaccggtg taggtccgca ggccgctgct ccgccgccg caaaagcagc ggctaaattt     720
ggcgccggag cagcgggtgt tctgcctgga gttggtggtg cgggcgtgcc aggggtacct     780

-continued

```
ggtgcaattc cgggtattgg tggtattgcc ggtgtcggca ccccggccgc ggcagctgcg      840
gcagcggcgg ctgccaaagc tgctaaatac ggtgccgcgg cgggtctggt gccaggaggt      900
ccgggttttg gtccgggagt ggttggcgtg cctggcgcag gcgttcctgg tgtgggcgtt      960
ccaggtgcag ggattcctgt tgtgcctggt gccggtattc ccggcgcggc cgttccgggg     1020
gtggttagcc cggaagccgc agcgaaggct gcggcaaagg cagcaaagta tggcgcacgc     1080
ccaggagtcg gcgtgggtgg tatcccgacc tattaa                               1116
```

<210> SEQ ID NO 53
<211> LENGTH: 345
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 53

```
Gly Gly Val Pro Gly Ala Ile Pro Gly Gly Val Pro Gly Gly Val Phe
  1               5                  10                  15

Tyr Pro Gly Ala Gly Leu Gly Ala Leu Gly Gly Ala Leu Gly Pro
             20                  25                  30

Gly Gly Lys Pro Leu Lys Pro Val Pro Gly Gly Leu Ala Gly Ala Gly
         35                  40                  45

Leu Gly Ala Gly Leu Gly Ala Phe Pro Ala Val Thr Phe Pro Gly Ala
 50                  55                  60

Leu Val Pro Gly Gly Val Ala Asp Ala Ala Ala Ala Tyr Lys Ala Ala
 65                  70                  75                  80

Lys Ala Gly Ala Gly Leu Gly Val Pro Gly Val Gly Leu Gly
             85                  90                  95

Val Ser Ala Gly Ala Val Val Pro Gln Pro Gly Ala Gly Val Lys Pro
                100                 105                 110

Gly Lys Val Pro Gly Val Gly Leu Pro Gly Val Tyr Pro Gly Gly Val
            115                 120                 125

Leu Pro Gly Ala Arg Phe Pro Gly Val Gly Val Leu Pro Gly Val Pro
        130                 135                 140

Thr Gly Ala Gly Val Lys Pro Lys Ala Pro Gly Val Gly Gly Ala Phe
145                 150                 155                 160

Ala Gly Ile Pro Gly Val Gly Pro Phe Gly Pro Gln Pro Gly Val
                165                 170                 175

Pro Leu Gly Tyr Pro Ile Lys Ala Pro Lys Leu Pro Gly Gly Tyr Gly
            180                 185                 190

Leu Pro Tyr Thr Thr Gly Lys Leu Pro Tyr Gly Tyr Gly Pro Gly Gly
        195                 200                 205

Val Ala Gly Ala Ala Gly Lys Ala Gly Tyr Pro Thr Gly Thr Gly Val
            210                 215                 220

Gly Pro Gln Ala Ala Ala Ala Ala Ala Lys Ala Ala Lys Phe
225                 230                 235                 240

Gly Ala Gly Ala Ala Gly Val Leu Pro Gly Val Gly Ala Gly Val
                245                 250                 255

Pro Gly Val Pro Gly Ala Ile Pro Gly Ile Gly Ile Ala Gly Val
            260                 265                 270

Gly Thr Pro Ala Ala Ala Ala Ala Ala Ala Ala Lys Ala Ala
        275                 280                 285

Lys Tyr Gly Ala Ala Ala Gly Leu Val Pro Gly Gly Pro Gly Phe Gly
            290                 295                 300
```

```
Pro Gly Val Val Gly Val Pro Gly Ala Gly Val Pro Gly Val Gly Val
305                 310                 315                 320

Pro Gly Ala Gly Ile Pro Val Val Pro Gly Ala Gly Ile Pro Gly Ala
                325                 330                 335

Ala Val Pro Gly Val Val Ser Pro Glu
            340                 345

<210> SEQ ID NO 54
<211> LENGTH: 1038
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
ggtggcgtac caggcgcaat tcctgggggt gtcccaggcg gtgtttttta ccgggcgcc       60 ggtcttggcg cactgggtgg cggtgcactg ggcccgggcg gcaaaccgct gaaaccggta    120
ccaggtggtt tagcaggcgc cggcttaggc gcaggtctgg gagcatttcc ggcagttacc    180
tttccagggg cactggttcc tggaggtgtg gccgatgcag ccgcggcata taaagccgct    240
aaagccggtg cgggtttagg aggcgtccca ggtgtcggtg gcctgggtgt tagcgccggt    300
gcagttgttc cgcagccggg agcagggggtt aaacctggta aagtgccggg agtaggtctg    360
ccaggcgttt atcctggtgg tgttttgccg ggtgcccgtt ttccgggcgt tggtgttctt    420
ccaggcgtgc cgaccggagc cggtgttaaa ccgaaagccc ccggtgttgg aggtgcattt    480
gcaggcatcc cgggagttgg cccgtttggt ggtccgcaac ctggggttcc gttaggttat    540
ccgattaaag caccgaaact gcccggcggt tatggtctgc cgtacacaac cggtaaactg    600
ccgtatggtt atggcccggg tggagttgcg ggtgcagcag gtaaagcggg ttatcctacc    660
ggaaccggtg taggtccgca ggccgctgct gccgccgccg caaaagcagc ggctaaattt    720
ggcgccggag cagcgggtgt tctgcctgga gttggtggtg cgggcgtgcc aggggtacct    780
ggtgcaattc cgggtattgg tggtattgcc ggtgtcggca ccccggccgc ggcagctgcg    840
gcagcggcgg ctgccaaagc tgctaaatac ggtgccgcgg cgggtctggt gccaggaggt    900
ccgggttttg gtccgggagt ggttggcgtg cctggcgcag cgttcctgg tgtgggcgtt     960 ccaggtgcag ggattcctgt tgtgcctggt gccggtattc ccggcgcggc cgttccgggg   1020
gtggttagcc cggaataa                                                 1038

<210> SEQ ID NO 55
<211> LENGTH: 336
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Lys Tyr Gly Ala Ala Gly Ala Gly Val Leu Gly Gly Leu Val Pro Gly
1               5                   10                  15

Pro Gln Ala Ala Val Pro Gly Val Pro Gly Thr Gly Gly Val Pro Gly
            20                  25                  30

Val Gly Thr Pro Ala Ala Ala Ala Lys Ala Ala Lys Ala Ala
        35                  40                  45

Gln Phe Gly Leu Val Pro Gly Val Gly Val Ala Pro Gly Val Gly Val
    50                  55                  60
```

Ala Pro Gly Val Gly Val Ala Pro Gly Val Gly Leu Ala Pro Gly Val
 65                  70                  75                  80

Gly Val Ala Pro Gly Val Gly Val Ala Pro Gly Val Gly Val Ala Pro
                 85                  90                  95

Gly Ile Gly Pro Gly Gly Val Ala Ala Ala Lys Ser Ala Ala Lys
            100                 105                 110

Val Ala Ala Lys Ala Gln Leu Arg Ala Ala Gly Leu Gly Ala Gly
            115                 120                 125

Ile Pro Gly Leu Gly Val Gly Val Gly Val Pro Gly Leu Gly Val Gly
130                 135                 140

Ala Gly Val Pro Gly Leu Gly Val Gly Ala Gly Val Pro Gly Phe Gly
145                 150                 155                 160

Ala Gly Ala Asp Glu Gly Val Arg Arg Ser Leu Ser Pro Glu Leu Arg
                165                 170                 175

Glu Gly Asp Pro Ser Ser Ser Gln His Leu Pro Ser Thr Pro Ser Ser
            180                 185                 190

Pro Arg Val Pro Gly Ala Leu Ala Ala Lys Ala Ala Lys Tyr Gly
            195                 200                 205

Ala Ala Val Pro Gly Val Leu Gly Gly Leu Gly Ala Leu Gly Gly Val
210                 215                 220

Gly Ile Pro Gly Gly Val Val Gly Ala Gly Pro Ala Ala Ala Ala Ala
225                 230                 235                 240

Ala Ala Lys Ala Ala Ala Lys Ala Ala Gln Phe Gly Leu Val Gly Ala
                245                 250                 255

Ala Gly Leu Gly Gly Leu Gly Val Gly Gly Leu Gly Val Pro Gly Val
            260                 265                 270

Gly Gly Leu Gly Gly Ile Pro Pro Ala Ala Ala Lys Ala Ala Lys
            275                 280                 285

Tyr Gly Ala Ala Gly Leu Gly Gly Val Leu Gly Gly Ala Gly Gln Phe
            290                 295                 300

Pro Leu Gly Gly Val Ala Ala Arg Pro Gly Phe Gly Leu Ser Pro Ile
305                 310                 315                 320

Phe Pro Gly Gly Ala Cys Leu Gly Lys Ala Cys Gly Arg Lys Arg Lys
                325                 330                 335

<210> SEQ ID NO 56
<211> LENGTH: 1011
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
aaatatggtg ccgccggcgc aggagtttta ggtgggctgg ttccgggccc gcaggcagct    60
gtgccggggg ttccaggcac cggtggtgtc cctggagtcg gtacgccggc tgcagcggca   120
gccaaagcgg ctgcgaaagc agcacagttt ggcttagtac cgggtgtggg agttgccccc   180
ggcgttggcg ttgctccagg ggtgggtgtt gctcctggcg tcggtctggc tcctggagtg   240
ggcgtagcac ccggtgtggg ggtggccccg ggtgttgggg ttgcaccggg tatcggtccg   300
ggcggtgtcg cagcagcagc taaagcgcg gcgaaagttg cggccaaagc ccaactgcgc   360
gccgccgcgg gcctcggtgc aggtattccg gggctgggtg tcggagttgg agtcccgggt   420
ttgggcgtgg gcgcgggagt tccgggactg ggagtgggtg ccggagttcc tggctttggt   480

```
gcaggcgcag atgaaggtgt tcgtcgtagc ctgagtccgg aactgcgtga aggtgatccg    540
agtagcagcc agcatctgcc gagcaccccg agcagcccgc gtgttccggg tgcattagct    600
gcagcaaaag ccgccaagta tggtgcagcc gtgccgggcg tcttaggtgg tctgggcgcc    660
ctgggtggtg taggcattcc gggaggtgtt gtgggtgcag accggccgc cgcagctgcg     720 gccgccaaag cagctgcaaa agcggcccag tttggtttag tgggcgccgc aggtttaggc    780
ggtttaggtg tgggtggact gggtgtacct ggcgtaggcg gtctgggtgg aattccgccc    840
gcagcggccg cgaaagcggc aaaatatggc gcggcaggcc tgggcggcgt gctgggtggg    900
gcaggtcagt ttccgctggg cggggttgcc gcacgtccgg gatttggtct gagcccgatt    960
ttccctggcg gcgcatgtct gggtaaagca tgtggtcgta aacgtaaata a            1011
```

<210> SEQ ID NO 57
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

```
Gln Phe Gly Leu Val Pro Gly Val Gly Val Ala Pro Gly Val Gly Val
1               5                   10                  15

Ala Pro Gly Val Gly Val Ala Pro Gly Val Gly Leu Ala Pro Gly Val
            20                  25                  30

Gly Val Ala Pro Gly Val Gly Val Ala Pro Gly Val Gly Val Ala Pro
        35                  40                  45

Gly Ile Gly Pro Gly Gly Val Ala Ala Ala Lys Ser Ala Ala Lys
    50                  55                  60

Val Ala Ala Lys Ala Gln Leu Arg Ala Ala Gly Leu Gly Ala Gly
65                  70                  75                  80

Ile Pro Gly Leu Gly Val Gly Val Gly Val Pro Gly Leu Gly Val Gly
                85                  90                  95

Ala Gly Val Pro Gly Leu Gly Val Gly Ala Gly Val Pro Gly Phe Gly
            100                 105                 110

Ala Gly Ala Asp Glu Gly Val Arg Arg Ser Leu Ser Pro Glu Leu Arg
        115                 120                 125

Glu Gly Asp Pro Ser Ser Ser Gln His Leu Pro Ser Thr Pro Ser Ser
    130                 135                 140

Pro Arg Val Pro Gly Ala Leu Ala Ala Ala Lys Ala Ala Lys Tyr Gly
145                 150                 155                 160

Ala Ala Val Pro Gly Val Leu Gly Gly Leu Gly Ala Leu Gly Gly Val
                165                 170                 175

Gly Ile Pro Gly Gly Val Val Gly Ala Gly Pro Ala Ala Ala Ala Ala
            180                 185                 190

Ala Ala Lys Ala Ala Lys Ala Ala Gln Phe Gly Leu Val Gly Ala
        195                 200                 205

Ala Gly Leu Gly Gly Leu Gly Val Gly Gly Leu Gly Val Pro Gly Val
    210                 215                 220

Gly Gly Leu Gly Gly Ile Pro Pro Ala Ala Ala Lys Ala Ala Lys
225                 230                 235                 240

Tyr Gly Ala Ala Gly Leu Gly Gly Val Leu Gly Gly Ala Gly Gln Phe
                245                 250                 255

Pro Leu Gly Gly Val Ala Ala Arg Pro Gly Phe Gly Leu Ser Pro Ile
            260                 265                 270
```

```
              Phe Pro Gly Gly Ala Cys Leu Gly Lys Ala Cys Gly Arg Lys Arg Lys
                          275                 280                 285
```

<210> SEQ ID NO 58
<211> LENGTH: 867
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58

```
cagtttggct tagtaccggg tgtgggagtt gccccggcg ttggcgttgc tccagggtg      60 ggtgttgctc ctggcgtcgg tctggctcct ggagtgggcg tagcacccgg tgtggggtg     120 gccccgggtg ttggggttgc accgggtatc ggtccgggcg tgtcgcagc agcagctaaa    180 agcgcggcga aagttgcggc caaagcccaa ctgcgcgccg ccgcgggcct cggtgcaggt   240
attccggggc tgggtgtcgg agttggagtc ccgggtttgg gcgtgggcgc gggagttccg   300
ggactgggag tgggtgccgg agttcctggc tttggtgcag gcgcagatga aggtgttcgt   360
cgtagcctga gtccggaact gcgtgaaggt gatccgagta gcagccagca tctgccgagc   420
accccgagca gcccgcgtgt tccgggtgca ttagctgcag caaaagccgc caagtatggt   480
gcagccgtgc cggcgtctt aggtggtctg ggcgccctgg gtggtgtagg cattccggga   540
ggtgttgtgg gtgcaggacc ggccgccgca gctgcggccg ccaaagcagc tgcaaaagcg   600
gcccagtttg gtttagtggg cgccgcaggt ttaggcggtt taggtgtggg tggactgggg   660
gtacctggcg taggcggtct gggtggaatt ccgcccgcag cggccgcgaa agcggcaaaa   720
tatggcgcgg caggcctggg cggcgtgctg ggtgggcag gtcagtttcc gctgggcggg   780
gttgccgcac gtccgggatt tggtctgagc ccgattttcc ctggcggcgc atgtctgggt   840
aaagcatgtg gtcgtaaacg taaataa                                      867
```

<210> SEQ ID NO 59
<211> LENGTH: 275
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

```
Gly Gly Val Pro Gly Ala Ile Pro Gly Gly Val Pro Gly Gly Val Phe
1               5                   10                  15

Tyr Pro Gly Ala Gly Leu Gly Ala Leu Gly Gly Ala Leu Gly Pro
            20                  25                  30

Gly Gly Lys Pro Leu Lys Pro Val Pro Gly Gly Leu Ala Gly Ala Gly
        35                  40                  45

Leu Gly Ala Gly Leu Gly Ala Phe Pro Ala Val Thr Phe Pro Gly Ala
 50                  55                  60

Leu Val Pro Gly Gly Val Ala Asp Ala Ala Ala Tyr Lys Ala Ala
65                  70                  75                  80

Lys Ala Gly Ala Gly Leu Gly Gly Val Pro Val Gly Gly Leu Gly
                85                  90                  95

Val Ser Ala Gly Ala Val Val Pro Gln Pro Gly Ala Gly Val Lys Pro
            100                 105                 110

Gly Lys Val Pro Gly Val Gly Leu Pro Gly Val Tyr Pro Gly Gly Val
        115                 120                 125
```

Leu Pro Gly Ala Arg Phe Pro Gly Val Gly Val Leu Pro Gly Val Pro
        130                 135                 140

Thr Gly Ala Gly Val Lys Pro Lys Ala Pro Gly Val Gly Gly Ala Phe
145                 150                 155                 160

Ala Gly Ile Pro Gly Val Gly Pro Phe Gly Gly Pro Gln Pro Gly Val
                165                 170                 175

Pro Leu Gly Tyr Pro Ile Lys Ala Pro Lys Leu Pro Gly Gly Tyr Gly
            180                 185                 190

Leu Pro Tyr Thr Thr Gly Lys Leu Pro Tyr Gly Tyr Gly Pro Gly Gly
        195                 200                 205

Val Ala Gly Ala Ala Gly Lys Ala Gly Tyr Pro Thr Gly Thr Gly Val
    210                 215                 220

Gly Pro Gln Ala Ala Ala Ala Ala Ala Lys Ala Ala Ala Lys Phe
225                 230                 235                 240

Gly Ala Gly Ala Ala Gly Val Leu Pro Gly Val Gly Gly Ala Gly Val
                245                 250                 255

Pro Gly Val Pro Gly Ala Ile Pro Gly Ile Gly Gly Ile Ala Gly Val
            260                 265                 270

Gly Thr Pro
    275

<210> SEQ ID NO 60
<211> LENGTH: 828
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
ggtggcgtac caggcgcaat tcctgggggt gtcccaggcg gtgttttta tccgggcgcc      60 ggtcttggcg cactgggtgg cggtgcactg ggcccgggcg gcaaaccgct gaaaccggta     120
ccaggtggtt tagcaggcgc cggcttaggc gcaggtctgg gagcatttcc ggcagttacc     180
tttccagggg cactggttcc tggaggtgtg gccgatgcag ccgcggcata taagccgct     240 aaagccggtg cgggtttagg aggcgtccca ggtgtcggtg gcctgggtgt tagcgccggt     300
gcagttgttc cgcagccggg agcagggggtt aaacctggta aagtgccggg agtaggtctg     360
ccaggcgttt atcctggtgg tgttttgccg ggtgcccgtt ttccgggcgt tggtgttctt     420
ccaggcgtgc cgaccggagc cggtgttaaa ccgaaagccc ccggtgttgg aggtgcattt     480
gcaggcatcc cgggagttgg cccgtttggt ggtccgcaac ctggggttcc gttaggttat     540
ccgattaaag caccgaaact gcccggcggt tatggtctgc cgtacacaac cggtaaactg     600
ccgtatggtt atggcccggg tggagttgcg ggtgcagcag gtaaagcggg ttatcctacc     660
ggaaccggtg taggtccgca ggccgctgct gccgccgccg caaaagcagc ggctaaattt     720
ggcgccggag cagcgggtgt tctgcctgga gttggtggtg cgggcgtgcc aggggtacct     780
ggtgcaattc cgggtattgg tggtattgcc ggtgtcggca ccccgtaa                 828

<210> SEQ ID NO 61
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gly Gly Val Pro Gly Ala Ile Pro Gly Val Pro Gly Gly Val Phe
1               5                   10                  15

Tyr Pro Gly Ala Gly Leu Gly Ala Leu Gly Gly Ala Leu Gly Pro
            20                  25                  30

Gly Gly Lys Pro Leu Lys Pro Val Pro Gly Gly Leu Ala Gly Ala Gly
        35                  40                  45

Leu Gly Ala Gly Leu Gly Ala Phe Pro Ala Val Thr Phe Pro Gly Ala
50                  55                  60

Leu Val Pro Gly Gly Val Ala Asp Ala Ala Ala Tyr Lys Ala Ala
65                  70                  75                  80

Lys Ala Gly Ala Gly Leu Gly Val Pro Gly Val Gly Leu Gly
                85                  90                  95

Val Ser Ala Gly Ala Val Pro Gln Pro Gly Ala Gly Val Lys Pro
            100                 105                 110

Gly Lys Val Pro Gly Val Gly Leu Pro Gly Val Tyr Pro Gly Gly Val
            115                 120                 125

Leu Pro Gly Ala Arg Phe Pro Gly Val Gly Val Leu Pro Gly Val Pro
    130                 135                 140

Thr Gly Ala Gly Val Lys Pro Lys Ala Pro Gly Val Gly Gly Ala Phe
145                 150                 155                 160

Ala Gly Ile Pro Gly Val Gly Pro Phe Gly Pro Gln Pro Gly Val
                165                 170                 175

Pro Leu Gly Tyr Pro Ile Lys Ala Pro Lys Leu Pro Gly Gly Tyr Gly
            180                 185                 190

Leu Pro Tyr Thr Thr Gly Lys Leu Pro Tyr Gly Tyr Gly Pro Gly Gly
        195                 200                 205

Val Ala Gly Ala Ala Gly Lys Ala Gly Tyr Pro Thr Gly Thr Gly Val
    210                 215                 220

Gly Pro Gln
225

<210> SEQ ID NO 62
<211> LENGTH: 684
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
ggtggcgtac caggcgcaat tcctgggggt gtcccaggcg gtgttttta tccgggcgcc      60 ggtcttggcg cactgggtgg cggtgcactg ggcccgggcg gcaaaccgct gaaaccggta    120
ccaggtggtt tagcaggcgc cggcttaggc gcaggtctgg gagcatttcc ggcagttacc    180
tttccagggg cactggttcc tggaggtgtg gccgatgcag ccgcggcata taaagccgct    240
aaagccggtg cgggtttagg aggcgtccca ggtgtcggtg gcctgggtgt tagcgccggt    300
gcagttgttc cgcagccggg agcaggggtt aaacctggta aagtgccggg agtaggtctg    360
ccaggcgttt atcctggtgg tgttttgccg ggtgcccgtt ttccgggcgt tggtgttctt    420
ccaggcgtgc cgaccggagc cggtgttaaa ccgaaagccc ccggtgttgg aggtgcattt    480
gcaggcatcc cgggagttgg cccgtttggt ggtccgcaac ctgggggttcc gttaggttat    540 ccgattaaag caccgaaact gcccggcggt tatggtctgc cgtacacaac cggtaaactg    600
ccgtatggtt atgcccgggg tggagttgcg ggtgcagcag gtaaagcggg ttatcctacc    660
ggaaccggtg taggtccgca gtaa 684

<210> SEQ ID NO 63
<211> LENGTH: 219
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 63

Gln Leu Arg Ala Ala Gly Leu Gly Ala Gly Ile Pro Gly Leu Gly
1               5                   10                  15

Val Gly Val Gly Val Pro Gly Leu Gly Val Gly Ala Gly Val Pro Gly
            20                  25                  30

Leu Gly Val Gly Ala Gly Val Pro Gly Phe Gly Ala Gly Ala Asp Glu
        35                  40                  45

Gly Val Arg Arg Ser Leu Ser Pro Glu Leu Arg Glu Gly Asp Pro Ser
    50                  55                  60

Ser Ser Gln His Leu Pro Ser Thr Pro Ser Ser Pro Arg Val Pro Gly
65                  70                  75                  80

Ala Leu Ala Ala Ala Lys Ala Ala Lys Tyr Gly Ala Ala Val Pro Gly
                85                  90                  95

Val Leu Gly Gly Leu Gly Ala Leu Gly Gly Val Gly Ile Pro Gly Gly
            100                 105                 110

Val Val Gly Ala Gly Pro Ala Ala Ala Ala Ala Lys Ala Ala
        115                 120                 125

Ala Lys Ala Ala Gln Phe Gly Leu Val Gly Ala Ala Gly Leu Gly Gly
130                 135                 140

Leu Gly Val Gly Gly Leu Gly Val Pro Gly Val Gly Leu Gly Gly
145                 150                 155                 160

Ile Pro Pro Ala Ala Ala Ala Lys Ala Ala Lys Tyr Gly Ala Ala Gly
                165                 170                 175

Leu Gly Gly Val Leu Gly Gly Ala Gly Gln Phe Pro Leu Gly Gly Val
            180                 185                 190

Ala Ala Arg Pro Gly Phe Gly Leu Ser Pro Ile Phe Pro Gly Gly Ala
        195                 200                 205

Cys Leu Gly Lys Ala Cys Gly Arg Lys Arg Lys
    210                 215

<210> SEQ ID NO 64
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 64
caactgcgcg ccgccgcggg cctcggtgca ggtattccgg ggctgggtgt cggagttgga      60
gtcccgggtt tgggcgtggg cgcgggagtt ccgggactgg gagtgggtgc cggagttcct     120
ggctttggtg caggcgcaga tgaaggtgtt cgtcgtagcc tgagtccgga actgcgtgaa     180
ggtgatccga gtagcagcca gcatctgccg agcaccccga gcagcccgcg tgttccgggt     240
gcattagctg cagcaaaagc cgccaagtat ggtgcagccg tgccgggcgt cttaggtggt     300
ctgggcgccc tgggtggtgt aggcattccg ggaggtgttg tgggtgcagg accggccgcc     360

```
gcagctgcgg ccgccaaagc agctgcaaaa gcggcccagt ttggtttagt gggcgccgca    420
ggtttaggcg gtttaggtgt gggtggactg ggtgtacctg gcgtaggcgg tctgggtgga    480
attccgcccg cagcggccgc gaaagcggca aaatatggcg cggcaggcct gggcggcgtg    540
ctgggtgggg caggtcagtt tccgctgggc ggggttgccg cacgtccggg atttggtctg    600
agcccgattt tccctggcgg cgcatgtctg ggtaaagcat gtggtcgtaa acgtaaataa    660
```

<210> SEQ ID NO 65
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

```
Val Pro Gly Val Leu Gly Gly Leu Gly Ala Leu Gly Gly Val Gly Ile
1               5                   10                  15

Pro Gly Gly Val Val Gly Ala Gly Pro Ala Ala Ala Ala Ala Ala Ala
            20                  25                  30

Lys Ala Ala Ala Lys Ala Ala Gln Phe Gly Leu Val Gly Ala Ala Gly
        35                  40                  45

Leu Gly Gly Leu Gly Val Gly Gly Leu Gly Val Pro Gly Val Gly Gly
    50                  55                  60

Leu Gly Gly Ile Pro Pro Ala Ala Ala Ala Lys Ala Ala Lys Tyr Gly
65                  70                  75                  80

Ala Ala Gly Leu Gly Gly Val Leu Gly Gly Ala Gly Gln Phe Pro Leu
                85                  90                  95

Gly Gly Val Ala Ala Arg Pro Gly Phe Gly Leu Ser Pro Ile Phe Pro
            100                 105                 110

Gly Gly Ala Cys Leu Gly Lys Ala Cys Gly Arg Lys Arg Lys
        115                 120                 125
```

<210> SEQ ID NO 66
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66

```
gtgccgggcg tcttaggtgg tctgggcgcc ctgggtggtg taggcattcc gggaggtgtt    60
gtgggtgcag gaccggccgc cgcagctgcg gccgccaaag cagctgcaaa agcggcccag    120
tttggtttag tgggcgccgc aggtttaggc ggtttaggtg tgggtggact gggtgtacct    180
ggcgtaggcg gtctgggtgg aattccgccc gcagcggccg cgaaagcggc aaaatatggc    240
gcggcaggcc tgggcggcgt gctgggtggg caggtcagt ttccgctggg cggggttgcc    300
gcacgtccgg gatttggtct gagcccgatt ttccctggcg gcgcatgtct gggtaaagca    360
tgtggtcgta aacgtaaata a                                              381
```

<210> SEQ ID NO 67
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Phe Gly Leu Val Gly Ala Ala Gly Leu Gly Gly Leu Val Gly
1               5                   10                  15

Gly Leu Gly Val Pro Gly Val Gly Leu Gly Gly Ile Pro Pro Ala
            20                  25                  30

Ala Ala Ala Lys Ala Ala Lys Tyr Gly Ala Ala Gly Leu Gly Val
        35                  40                  45

Leu Gly Gly Ala Gly Gln Phe Pro Leu Gly Gly Val Ala Ala Arg Pro
    50                  55                  60

Gly Phe Gly Leu Ser Pro Ile Phe Pro Gly Gly Ala Cys Leu Gly Lys
65                  70                  75                  80

Ala Cys Gly Arg Lys Arg Lys
                85

<210> SEQ ID NO 68
<211> LENGTH: 264
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
cagtttggtt tagtgggcgc cgcaggttta ggcggtttag gtgtgggtgg actgggtgta      60
cctggcgtag gcggtctggg tggaattccg cccgcagcgg ccgcgaaagc ggcaaaatat    120
ggcgcggcag gcctgggcgg cgtgctgggt ggggcaggtc agtttccgct ggcgggggtt    180
gccgcacgtc cgggatttgg tctgagcccg attttccctg gcggcgcatg tctgggtaaa    240
gcatgtggtc gtaaacgtaa ataa                                          264

<210> SEQ ID NO 69
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gly Gly Val Pro Gly Ala Ile Pro Gly Gly Val Pro Gly Gly Val Phe
1               5                   10                  15

Tyr Pro Gly Ala Gly Leu Gly Ala Leu Gly Gly Ala Leu Gly Pro
            20                  25                  30

Gly Gly Lys Pro Leu Lys Pro Val Pro Gly Gly Leu Ala Gly Ala Gly
        35                  40                  45

Leu Gly Ala Gly Leu Gly Ala Phe Pro Ala Val Thr Phe Pro Gly Ala
    50                  55                  60

Leu Val Pro Gly Gly Val Ala Asp
65                  70

<210> SEQ ID NO 70
<211> LENGTH: 219
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
ggtggcgtac caggcgcaat tcctgggggt gtcccaggcg gtgttttta tccgggcgcc       60

```
ggtcttggcg cactgggtgg cggtgcactg ggcccgggcg gcaaaccgct gaaaccggta    120
ccaggtggtt tagcaggcgc cggcttaggc gcaggtctgg gagcatttcc ggcagttacc    180
tttccagggg cactggttcc tggaggtgtg gccgattaa                           219
```

<210> SEQ ID NO 71
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gly Leu Gly Gly Val Leu Gly Gly Ala Gly Gln Phe Pro Leu Gly Gly
1               5                   10                  15

Val Ala Ala Arg Pro Gly Phe Gly Leu Ser Pro Ile Phe Pro Gly Gly
            20                  25                  30

Ala Cys Leu Gly Lys Ala Cys Gly Arg Lys Arg Lys
        35                  40

<210> SEQ ID NO 72
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72

```
ggcctgggcg gcgtgctggg tggggcaggt cagtttccgc tgggcggggt tgccgcacgt    60
ccgggatttg gtctgagccc gattttccct ggcggcgcat gtctgggtaa agcatgtggt    120
cgtaaacgta ataa                                                     135
```

<210> SEQ ID NO 73
<211> LENGTH: 636
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73

```
atgaaaaaga tttggctggc gctggctggt ttagttttag cgtttagcgc atcggcggcg    60
cagtatgaag atgcaggttt tccgggtctg cctggtccgg caggcgaacc gggtcgtcat    120
ggtaaagatg gtctgatggg tagtccgggt tttaaaggtg aagcaggttc accgggtgca    180
cctggtcagt atggcacccg tgtgaaccgg gtattccgg gatttccggg taatcgtggc    240
ctgatgggtc agaaaggtga aattggtccg cctggtcagc agggtaaaaa aggcgcaccg    300
ggtatgccag gactgatggg ttcaaatggc agtccgggtc agccaggcac accgggttca    360
aaaggtagca aggcgaacc tggtattcag ggtatgcctg gtgcaagcgg tctgaaaggc    420
gagccaggtg ccaccggttc tccgggtgaa ccaggttata tgggtctgcc aggtatccaa    480
ggcaaaaaag gtgataaagg taatcagggc gaaaaaggca ttcagggcca gaaaggcgaa    540
aatggccgtc agggtattcc aggccagcag ggcatccagg tcatcatgg tgcaaaaggt    600 gaacgtggtg aaaagggcga accaggtgtt cgttaa                             636
```

<210> SEQ ID NO 74

<211> LENGTH: 211
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 74

```
Met Lys Lys Ile Trp Leu Ala Leu Ala Gly Leu Val Leu Ala Phe Ser
1               5                   10                  15
Ala Ser Ala Ala Gln Tyr Glu Asp Ala Gly Phe Pro Gly Leu Pro Gly
            20                  25                  30
Pro Ala Gly Glu Pro Gly Arg His Gly Lys Asp Gly Leu Met Gly Ser
        35                  40                  45
Pro Gly Phe Lys Gly Glu Ala Gly Ser Pro Gly Ala Pro Gly Gln Asp
    50                  55                  60
Gly Thr Arg Gly Glu Pro Gly Ile Pro Gly Phe Pro Gly Asn Arg Gly
65                  70                  75                  80
Leu Met Gly Gln Lys Gly Glu Ile Gly Pro Pro Gly Gln Gly Lys
                85                  90                  95
Lys Gly Ala Pro Gly Met Pro Gly Leu Met Gly Ser Asn Gly Ser Pro
            100                 105                 110
Gly Gln Pro Gly Thr Pro Gly Ser Lys Gly Ser Lys Gly Glu Pro Gly
        115                 120                 125
Ile Gln Gly Met Pro Gly Ala Ser Gly Leu Lys Gly Glu Pro Gly Ala
    130                 135                 140
Thr Gly Ser Pro Gly Glu Pro Gly Tyr Met Gly Leu Pro Gly Ile Gln
145                 150                 155                 160
Gly Lys Lys Gly Asp Lys Gly Asn Gln Gly Glu Lys Gly Ile Gln Gly
                165                 170                 175
Gln Lys Gly Glu Asn Gly Arg Gln Gly Ile Pro Gly Gln Gln Gly Ile
            180                 185                 190
Gln Gly His His Gly Ala Lys Gly Glu Arg Gly Glu Lys Gly Glu Pro
        195                 200                 205
Gly Val Arg
    210
```

<210> SEQ ID NO 75
<211> LENGTH: 565
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 75

```
tgcaggtttt ccgggtctgc ctggtccggc aggcgaaccg ggtcgtcatg gtaaagatgg     60
tctgatgggt agtccgggtt ttaaaggtga agcaggttca ccgggtgcac ctggtcagga    120
tggcacccgt ggtgaaccgg gtattccggg atttccgggt aatcgtggcc tgatgggtca    180
gaaaggtgaa attggtccgc ctggtcagca gggtaaaaaa ggcgcaccgg gtatgccagg    240
actgatgggt tcaaatggca gtccgggtca gccaggcaca ccgggttcaa aaggtagcaa    300
aggcgaacct ggtattcagg gtatgcctgg tgcaagcggt ctgaaaggcg agccaggtgc    360
caccggttct ccgggtgaac caggttatat gggtctgcca ggtatccaag gcaaaaaagg    420
tgataaaggt aatcagggcg aaaaaggcat tcagggccag aaaggcgaaa atggccgtca    480
gggtattcca ggccagcagg gcatccaggg tcatcatggt gcaaaaggtg aacgtggtga    540
```
aaagggcgaa ccaggtgttc gttaa                                        565

<210> SEQ ID NO 76
<211> LENGTH: 187
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Ala Gly Phe Pro Gly Leu Pro Gly Pro Ala Gly Glu Pro Gly Arg His
1               5                   10                  15

Gly Lys Asp Gly Leu Met Gly Ser Pro Gly Phe Lys Gly Glu Ala Gly
            20                  25                  30

Ser Pro Gly Ala Pro Gly Gln Asp Gly Thr Arg Gly Glu Pro Gly Ile
        35                  40                  45

Pro Gly Phe Pro Gly Asn Arg Gly Leu Met Gly Gln Lys Gly Glu Ile
    50                  55                  60

Gly Pro Pro Gly Gln Gln Gly Lys Lys Gly Ala Pro Gly Met Pro Gly
65                  70                  75                  80

Leu Met Gly Ser Asn Gly Ser Pro Gly Gln Pro Gly Thr Pro Gly Ser
                85                  90                  95

Lys Gly Ser Lys Gly Glu Pro Gly Ile Gln Met Pro Gly Ala Ser
            100                 105                 110

Gly Leu Lys Gly Glu Pro Gly Ala Thr Gly Ser Pro Gly Glu Pro Gly
        115                 120                 125

Tyr Met Gly Leu Pro Gly Ile Gln Lys Lys Gly Asp Lys Gly Asn
    130                 135                 140

Gln Gly Glu Lys Gly Ile Gln Gln Lys Gly Glu Asn Gly Arg Gln
145                 150                 155                 160

Gly Ile Pro Gly Gln Gln Gly Ile Gln Gly His His Gly Ala Lys Gly
                165                 170                 175

Glu Arg Gly Glu Lys Gly Glu Pro Gly Val Arg
            180                 185

<210> SEQ ID NO 77
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
atgaaaaaga tttggctggc gctggctggt ttagttttag cgtttagcgc atcggcggcg      60
cagtatgaag atatgggtcc gcctggtagc cgtggtgcaa gtggtccggc aggcgttcgt     120
ggtccgaatg gtgatgcagg tcgtccgggt gaaccgggtc tgatgggtcc tcgtggtctg     180
cctggttcac cgggtaatat tggtcctgca ggtaaagaag gtccggttgg tctgccaggt     240
attgatggcc gtccgggtcc gattggtcca gccggtgcac gtggtgaacc tggcaatatt     300
ggttttccgg gtcctaaagg tccgaccggt gatccgggta aaaatggtga taaaggtcat     360
gcaggtctgg caggcgcacg cggtgcacct ggtccggatg gtaataatgg tgcacagggt     420
ccaccgggtc cgcagggtgt tcaaggtggt aaaggcgaac agggtcctgc cggtcctccg     480
ggttttcagg gactgcctgg tccgagcggt cctgcgggtg aagttggtaa acctggtgaa     540

```
cgcggtctgc atggtgaatt tggcctgcct gggcctgcag gtccgcgtgg cgaacgtggt    600
ccgccaggtg aaagcggtgc agcaggtccg acaggttaa                           639
```

<210> SEQ ID NO 78
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

```
Met Lys Lys Ile Trp Leu Ala Leu Ala Gly Leu Val Leu Ala Phe Ser
1               5                   10                  15

Ala Ser Ala Ala Gln Tyr Glu Asp Met Gly Pro Pro Gly Ser Arg Gly
            20                  25                  30

Ala Ser Gly Pro Ala Gly Val Arg Gly Pro Asn Gly Asp Ala Gly Arg
        35                  40                  45

Pro Gly Glu Pro Gly Leu Met Gly Pro Arg Gly Leu Pro Gly Ser Pro
    50                  55                  60

Gly Asn Ile Gly Pro Ala Gly Lys Glu Gly Pro Val Gly Leu Pro Gly
65                  70                  75                  80

Ile Asp Gly Arg Pro Gly Pro Ile Gly Pro Ala Gly Ala Arg Gly Glu
                85                  90                  95

Pro Gly Asn Ile Gly Phe Pro Gly Pro Lys Gly Pro Thr Gly Asp Pro
            100                 105                 110

Gly Lys Asn Gly Asp Lys Gly His Ala Gly Leu Ala Gly Ala Arg Gly
        115                 120                 125

Ala Pro Gly Pro Asp Gly Asn Asn Gly Ala Gln Gly Pro Pro Gly Pro
    130                 135                 140

Gln Gly Val Gln Gly Gly Lys Gly Glu Gln Gly Pro Ala Gly Pro Pro
145                 150                 155                 160

Gly Phe Gln Gly Leu Pro Gly Pro Ser Gly Pro Ala Gly Glu Val Gly
                165                 170                 175

Lys Pro Gly Glu Arg Gly Leu His Gly Glu Phe Gly Leu Pro Gly Pro
            180                 185                 190

Ala Gly Pro Arg Gly Glu Arg Gly Pro Pro Gly Glu Ser Gly Ala Ala
        195                 200                 205

Gly Pro Thr Gly
    210
```

<210> SEQ ID NO 79
<211> LENGTH: 567
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79

```
atgggtccgc ctggtagccg tggtgcaagt ggtccggcag gcgttcgtgg tccgaatggt    60
gatgcaggtc gtccgggtga accgggtctg atgggtcctc gtggtctgcc tggttcaccg    120
ggtaatattg gtcctgcagg taaagaaggt ccggttggtc tgccaggtat tgatggccgt    180
ccgggtccga ttggtccagc cggtgcacgt ggtgaacctg gcaatattgg ttttccgggt    240
cctaaaggtc cgaccggtga tccgggtaaa aatggtgata aggtcatgc aggtctggca    300 ggcgcacgcg gtgcacctgg tccggatggt aataatggtg cacagggtcc accgggtccg    360
```

```
cagggtgttc aaggtggtaa aggcgaacag ggtcctgccg gtcctccggg ttttcaggga    420
ctgcctggtc cgagcggtcc tgcgggtgaa gttggtaaac ctggtgaacg cggtctgcat    480
ggtgaatttg gcctgcctgg gcctgcaggt ccgcgtggcg aacgtggtcc gccaggtgaa    540
agcggtgcag caggtccgac aggttaa                                        567
```

<210> SEQ ID NO 80
<211> LENGTH: 188
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 80

```
Met Gly Pro Pro Gly Ser Arg Gly Ala Ser Gly Pro Ala Gly Val Arg
1               5                   10                  15

Gly Pro Asn Gly Asp Ala Gly Arg Pro Gly Glu Pro Gly Leu Met Gly
            20                  25                  30

Pro Arg Gly Leu Pro Gly Ser Pro Gly Asn Ile Gly Pro Ala Gly Lys
        35                  40                  45

Glu Gly Pro Val Gly Leu Pro Gly Ile Asp Gly Arg Pro Gly Pro Ile
    50                  55                  60

Gly Pro Ala Gly Ala Arg Gly Glu Pro Gly Asn Ile Gly Phe Pro Gly
65                  70                  75                  80

Pro Lys Gly Pro Thr Gly Asp Pro Gly Lys Asn Gly Asp Lys Gly His
                85                  90                  95

Ala Gly Leu Ala Gly Ala Arg Gly Ala Pro Gly Pro Asp Gly Asn Asn
            100                 105                 110

Gly Ala Gln Gly Pro Pro Gly Pro Gln Gly Val Gln Gly Gly Lys Gly
        115                 120                 125

Glu Gln Gly Pro Ala Gly Pro Pro Gly Phe Gln Gly Leu Pro Gly Pro
    130                 135                 140

Ser Gly Pro Ala Gly Glu Val Gly Lys Pro Gly Glu Arg Gly Leu His
145                 150                 155                 160

Gly Glu Phe Gly Leu Pro Gly Pro Ala Gly Pro Arg Gly Glu Arg Gly
                165                 170                 175

Pro Pro Gly Glu Ser Gly Ala Ala Gly Pro Thr Gly
            180                 185
```

<210> SEQ ID NO 81
<211> LENGTH: 612
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 81

```
atgaaaaaga tttggctggc gctggctggt ttagttttag cgtttagcgc atcggcggcg    60
cagtatgaag atggttttca gggtcctgcc ggtgaaccgg gtgaacctgg tcagacaggt    120
ccggcaggcg cacgtggtcc tgcaggtcct cctggtaaag ccggtgaaga tggtcatccg    180
ggtaaaccgg tcgtcctggt gaacgtggt gttgttggtc cgcagggtgc ccgtggtttt    240
ccgggtactc cgggtctgcc aggttttaaa ggtattcgtg gtcataatgg tctggatggt    300
ctgaaaggtc agcctggtgc accgggtgtt aaaggtgaac aggtgctccc gggtgaaaat    360
```

| ggcacaccgg gtcagaccgg tgcgcgtggt ctgcctggcg aacgcggtcg tgttggtgca | 420 |
| cctggtccag ccggtgcacg cggtagtgat ggtagcgttg gtccggttgg tccagcgggt | 480 |
| ccgattggta gcgcaggtcc accgggtttt ccaggcgcac cgggtccgaa aggtgaaatt | 540 |
| ggtgcagttg gtaatgcagg ccctgccggt ccagcaggac cgcgtggtga agttggcctg | 600 |
| cctggtctgt aa | 612 |

<210> SEQ ID NO 82
<211> LENGTH: 203
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 82

Met Lys Lys Ile Trp Leu Ala Leu Ala Gly Leu Val Leu Ala Phe Ser
1               5                   10                  15
Ala Ser Ala Ala Gln Tyr Glu Asp Gly Phe Gln Gly Pro Ala Gly Glu
            20                  25                  30
Pro Gly Glu Pro Gly Gln Thr Gly Pro Ala Gly Ala Arg Gly Pro Ala
        35                  40                  45
Gly Pro Pro Gly Lys Ala Gly Glu Asp Gly His Pro Gly Lys Pro Gly
    50                  55                  60
Arg Pro Gly Glu Arg Gly Val Val Gly Pro Gln Gly Ala Arg Gly Phe
65                  70                  75                  80
Pro Gly Thr Pro Gly Leu Pro Gly Phe Lys Gly Ile Arg Gly His Asn
                85                  90                  95
Gly Leu Asp Gly Leu Lys Gly Gln Pro Gly Ala Pro Gly Val Lys Gly
            100                 105                 110
Glu Pro Gly Ala Pro Gly Glu Asn Gly Thr Pro Gly Gln Thr Gly Ala
        115                 120                 125
Arg Gly Leu Pro Gly Glu Arg Gly Arg Val Gly Ala Pro Gly Pro Ala
    130                 135                 140
Gly Ala Arg Gly Ser Asp Gly Ser Val Gly Pro Val Gly Pro Ala Gly
145                 150                 155                 160
Pro Ile Gly Ser Ala Gly Pro Pro Gly Phe Pro Gly Ala Pro Gly Pro
                165                 170                 175
Lys Gly Glu Ile Gly Ala Val Gly Asn Ala Gly Pro Ala Gly Pro Ala
            180                 185                 190
Gly Pro Arg Gly Glu Val Gly Leu Pro Gly Leu
        195                 200

<210> SEQ ID NO 83
<211> LENGTH: 540
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 83

| ggttttcagg gtcctgccgg tgaaccgggt gaacctggtc agacaggtcc ggcaggcgca | 60 |
| cgtggtcctg caggtcctcc tggtaaagcc ggtgaagatg gtcatccggg taaaccgggt | 120 |
| cgtcctggtg aacgtggtgt tgttggtccg cagggtgccc gtggttttcc gggtactccg | 180 |
| ggtctgccag gttttaaagg tattcgtggt cataatggtc tggatggtct gaaaggtcag | 240 |

```
cctggtgcac cgggtgttaa aggtgaacca ggtgctccgg gtgaaaatgg cacaccgggt    300
cagaccggtg cgcgtggtct gcctggcgaa cgcggtcgtg ttggtgcacc tggtccagcc    360
ggtgcacgcg gtagtgatgg tagcgttggt ccggttggtc cagcgggtcc gattggtagc    420
gcaggtccac cgggttttcc aggcgcaccg gtccgaaag gtgaaattgg tgcagttggt     480
aatgcaggcc ctgccggtcc agcaggaccg cgtggtgaag ttggcctgcc tggtctgtaa    540
```

<210> SEQ ID NO 84
<211> LENGTH: 179
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gly Phe Gln Gly Pro Ala Gly Glu Pro Gly Glu Pro Gly Gln Thr Gly
1               5                   10                  15

Pro Ala Gly Ala Arg Gly Pro Ala Gly Pro Pro Gly Lys Ala Gly Glu
            20                  25                  30

Asp Gly His Pro Gly Lys Pro Gly Arg Pro Gly Glu Arg Gly Val Val
        35                  40                  45

Gly Pro Gln Gly Ala Arg Gly Phe Pro Gly Thr Pro Gly Leu Pro Gly
    50                  55                  60

Phe Lys Gly Ile Arg Gly His Asn Gly Leu Asp Gly Leu Lys Gly Gln
65                  70                  75                  80

Pro Gly Ala Pro Gly Val Lys Gly Glu Pro Gly Ala Pro Gly Glu Asn
                85                  90                  95

Gly Thr Pro Gly Gln Thr Gly Ala Arg Gly Leu Pro Gly Glu Arg Gly
            100                 105                 110

Arg Val Gly Ala Pro Gly Pro Ala Gly Ala Arg Gly Ser Asp Gly Ser
        115                 120                 125

Val Gly Pro Val Gly Pro Ala Gly Pro Ile Gly Ser Ala Gly Pro Pro
    130                 135                 140

Gly Phe Pro Gly Ala Pro Gly Pro Lys Gly Glu Ile Gly Ala Val Gly
145                 150                 155                 160

Asn Ala Gly Pro Ala Gly Pro Ala Gly Pro Arg Gly Glu Val Gly Leu
                165                 170                 175

Pro Gly Leu

<210> SEQ ID NO 85
<211> LENGTH: 689
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85

```
gtccgcaggg tgttgttggt gcagatggta agacggtac cccgggtgaa aaggagaac      60 agggacgtac aggtgcagca ggtaaacagg gcagcccggg tgccgatggt gcccgtggcc    120
cgctgggtag cattggtcag cagggtgcaa gaggcgaacc gggcgatccg ggtagtccgg    180
gcctgcgtgg tgatacgggt ctggccggtg ttaaaggcgt tgcaggtcct tcaggtcgtc    240
caggtcaacc gggtgcaaat ggtctgccgg tgttaatgg tcgtggcggt ctggaacgtg     300
gtctggcagg accgccgggt cctgatggtc gccgcggtga acgggttca ccgggtattg     360
```

```
ccggtgccct gggtaaacca ggtctggaag gtccgaaagg ttatcctggt ctgcgcggtc    420
gtgatggtac caatggcaaa cgtggcgaac agggcgaaac cggtccagat ggtgttcgtg    480
gtattccggg taacgatggt cagagcggta accgggcat tgatggtatt gatggcacca    540
atggtcagcc tggcgaagca ggttatcagg gtggtcgcgg tacccgtggt cagctgggtg    600
aaacaggtga tgttggtcag aatggtgatc gcggcgcacc gggtccggat ggtagcaaag    660
gtagcgccgg tcgtccgggt ttacgttaa                                      689
```

<210> SEQ ID NO 86
<211> LENGTH: 229
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 86

```
Gly Pro Gln Gly Val Val Gly Ala Asp Gly Lys Asp Gly Thr Pro Gly
 1               5                  10                  15

Glu Lys Gly Glu Gln Gly Arg Thr Gly Ala Ala Gly Lys Gln Gly Ser
            20                  25                  30

Pro Gly Ala Asp Gly Ala Arg Gly Pro Leu Gly Ser Ile Gly Gln Gln
        35                  40                  45

Gly Ala Arg Gly Glu Pro Gly Asp Pro Gly Ser Pro Gly Leu Arg Gly
    50                  55                  60

Asp Thr Gly Leu Ala Gly Val Lys Gly Val Ala Gly Pro Ser Gly Arg
65                  70                  75                  80

Pro Gly Gln Pro Gly Ala Asn Gly Leu Pro Gly Val Asn Gly Arg Gly
                85                  90                  95

Gly Leu Glu Arg Gly Leu Ala Gly Pro Pro Gly Pro Asp Gly Arg Arg
           100                 105                 110

Gly Glu Thr Gly Ser Pro Gly Ile Ala Gly Ala Leu Gly Lys Pro Gly
       115                 120                 125

Leu Glu Gly Pro Lys Gly Tyr Pro Gly Leu Arg Gly Arg Asp Gly Thr
   130                 135                 140

Asn Gly Lys Arg Gly Glu Gln Gly Glu Thr Gly Pro Asp Gly Val Arg
145                 150                 155                 160

Gly Ile Pro Gly Asn Asp Gly Gln Ser Gly Lys Pro Gly Ile Asp Gly
                165                 170                 175

Ile Asp Gly Thr Asn Gly Gln Pro Gly Glu Ala Gly Tyr Gln Gly Gly
           180                 185                 190

Arg Gly Thr Arg Gly Gln Leu Gly Glu Thr Gly Asp Val Gly Gln Asn
       195                 200                 205

Gly Asp Arg Gly Ala Pro Gly Pro Asp Gly Ser Lys Gly Ser Ala Gly
   210                 215                 220

Arg Pro Gly Leu Arg
225
```

<210> SEQ ID NO 87
<211> LENGTH: 2283
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 87

```
ggtggcgtac caggcgcaat tcctgggggt gtcccaggcg gtgttttta tccgggcgcc    60
ggtcttggcg cactgggtgg cggtgcactg ggcccgggcg gcaaaccgct gaaaccggta   120
ccaggtggtt tagcaggcgc cggcttaggc gcaggtctgg gagcatttcc ggcagttacc   180
tttccagggg cactggttcc tggaggtgtg gccgatgcag ccgcggcata taaagccgct   240
aaagccggtg cgggtttagg aggcgtccca ggtgtcggtg gcctgggtgt tagcgccggt   300
gcagttgttc cgcagccggg agcagggggtt aaacctggta aagtgccggg agtaggtctg   360
ccaggcgttt atcctggtgg tgttttgccg ggtgcccgtt ttccgggcgt tggtgttctt   420
ccaggcgtgc cgaccggagc cggtgttaaa ccgaaagccc ccggtgttgg aggtgcattt   480
gcaggcatcc cgggagttgg cccgtttggt ggtccgcaac ctggggttcc gttaggttat   540
ccgattaaag caccgaaact gcccggcggt tatggtctgc cgtacacaac cggtaaactg   600
ccgtatggtt atggcccggg tggagttgcg ggtgcagcag gtaaagcggg ttatcctacc   660
ggaaccggtg taggtccgca ggccgctgct ccgccgccg caaaagcagc ggctaaattt   720
ggcgccggag cagcgggtgt tctgcctgga gttggtggtg cgggcgtgcc aggggtacct   780
ggtgcaattc cgggtattgg tggtattgcc ggtgtcggca ccccggccgc ggcagctgcg   840
gcagcggcgg ctgccaaagc tgctaaatac ggtgccgcgg cgggtctggt gccaggaggt   900
ccgggttttg gtccgggagt ggttggcgtg cctggcgcag gcgttcctgg tgtgggcgtt   960
ccaggtgcag ggattcctgt tgtgcctggt gccggtattc ccggcgcggc cgttccgggg  1020
gtggttagcc cggaagccgc agcgaaggct gcggcaaagg cagcaaagta tggcgcacgc  1080
ccaggagtcg cgctgggtgg tatcccgacc tatggggtgg gcgcagggg ttttcctggt  1140
ttcggcgtag gtgtaggagg tataccgggc gtggccggtg taccagggt tggtggcgtc  1200
cctggtgttg gcgtgtgcc aggtgttggt atttcaccgg aagcacaggc agcagccgca  1260
gctaaggcag cgaaatatgg tgccgccggc gcaggagttt taggtgggct ggttccgggc  1320
ccgcaggcag ctgtgccggg ggttccaggc accggtggtg tccctggagt cggtacgccg  1380
gctgcagcgg cagccaaagc ggctgcgaaa gcagcacagt ttggcttagt accgggtgtg  1440
ggagttgccc ccggcgttgg cgttgctcca ggggtgggtg ttgctcctgg cgtcggtctg  1500
gctcctggag tgggcgtagc acccggtgtg gggtggccc cgggtgttgg ggttgcaccg  1560
ggtatcggtc cgggcggtgt cgcagcagca gctaaaagcg cggcgaaagt tgcggccaaa  1620
gcccaactgc gcgccgccgc gggcctcggt gcaggtattc cggggctggg tgtcggagtt  1680
ggagtcccgg gtttgggcgt gggcgcggga gttccgggac tgggagtggg tgccggagtt  1740
cctggctttg gtgcaggcgc agatgaaggt gttcgtcgta gcctgagtcc ggaactgcgt  1800
gaaggtgatc cgagtagcag ccagcatctg ccgagcaccc cgagcagccc gcgtgttccg  1860
ggtgcattag ctgcagcaaa agccgccaag tatggtgcag ccgtgccggg cgtcttaggt  1920
ggtctgggcg ccctgggtgg tgtaggcatt ccggggaggtg ttgtgggtgc aggaccggcc  1980
gccgcagctg cggccgccaa agcagctgca aaagcggccc agtttggttt agtgggcgcc  2040
gcaggtttag gcggtttagg tgtgggtgga ctgggtgtac ctggcgtagg cggtctgggt  2100
ggaattccgc ccgcagcggc cgcgaaagcg gcaaaatatg gcgcggcagg cctgggcggc  2160
gtgctgggtg gggcaggtca gtttccgctg gcgggggttg ccgcacgtcc gggatttggt  2220
ctgagcccga ttttccctgg cggcgcatgt ctgggtaaag catgtggtcg taaacgtaaa  2280
taa                                                                2283
```

```
<210> SEQ ID NO 88
<211> LENGTH: 760
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gly Gly Val Pro Gly Ala Ile Pro Gly Val Pro Gly Gly Val Phe
1               5                   10                  15

Tyr Pro Gly Ala Gly Leu Gly Ala Leu Gly Gly Ala Leu Gly Pro
                20                  25                  30

Gly Gly Lys Pro Leu Lys Pro Val Pro Gly Gly Leu Ala Gly Ala Gly
            35                  40                  45

Leu Gly Ala Gly Leu Gly Ala Phe Pro Ala Val Thr Phe Pro Gly Ala
    50                  55                  60

Leu Val Pro Gly Gly Val Ala Asp Ala Ala Ala Tyr Lys Ala Ala
65                  70                  75                  80

Lys Ala Gly Ala Gly Leu Gly Gly Val Pro Gly Val Gly Leu Gly
                85                  90                  95

Val Ser Ala Gly Ala Val Val Pro Gln Pro Gly Ala Gly Val Lys Pro
            100                 105                 110

Gly Lys Val Pro Gly Val Gly Leu Pro Gly Val Tyr Pro Gly Gly Val
            115                 120                 125

Leu Pro Gly Ala Arg Phe Pro Gly Val Gly Val Leu Pro Gly Val Pro
    130                 135                 140

Thr Gly Ala Gly Val Lys Pro Lys Ala Pro Gly Val Gly Ala Phe
145                 150                 155                 160

Ala Gly Ile Pro Gly Val Gly Pro Phe Gly Gly Pro Gln Pro Gly Val
                165                 170                 175

Pro Leu Gly Tyr Pro Ile Lys Ala Pro Lys Leu Pro Gly Gly Tyr Gly
            180                 185                 190

Leu Pro Tyr Thr Thr Gly Lys Leu Pro Tyr Gly Tyr Gly Pro Gly Gly
        195                 200                 205

Val Ala Gly Ala Ala Gly Lys Ala Gly Tyr Pro Thr Gly Thr Gly Val
    210                 215                 220

Gly Pro Gln Ala Ala Ala Ala Ala Ala Lys Ala Ala Ala Lys Phe
225                 230                 235                 240

Gly Ala Gly Ala Ala Gly Val Leu Pro Gly Val Gly Ala Gly Val
                245                 250                 255

Pro Gly Val Pro Gly Ala Ile Pro Gly Ile Gly Ile Ala Gly Val
            260                 265                 270

Gly Thr Pro Ala Ala Ala Ala Ala Ala Ala Ala Lys Ala Ala
        275                 280                 285

Lys Tyr Gly Ala Ala Ala Gly Leu Val Pro Gly Gly Pro Gly Phe Gly
    290                 295                 300

Pro Gly Val Val Gly Val Pro Gly Ala Gly Val Pro Gly Val Gly Val
305                 310                 315                 320

Pro Gly Ala Gly Ile Pro Val Val Pro Gly Ala Gly Ile Pro Gly Ala
                325                 330                 335

Ala Val Pro Gly Val Val Ser Pro Glu Ala Ala Lys Ala Ala Ala
            340                 345                 350

Lys Ala Ala Lys Tyr Gly Ala Arg Pro Gly Val Gly Val Gly Gly Ile
        355                 360                 365
```

Pro Thr Tyr Gly Val Gly Ala Gly Gly Phe Pro Gly Phe Gly Val Gly
    370                 375                 380

Val Gly Gly Ile Pro Gly Val Ala Gly Val Pro Gly Val Gly Gly Val
385                 390                 395                 400

Pro Gly Val Gly Gly Val Pro Gly Val Gly Ile Ser Pro Glu Ala Gln
                405                 410                 415

Ala Ala Ala Ala Ala Lys Ala Ala Lys Tyr Gly Ala Ala Gly Ala Gly
            420                 425                 430

Val Leu Gly Gly Leu Val Pro Gly Pro Gln Ala Ala Val Pro Gly Val
            435                 440                 445

Pro Gly Thr Gly Gly Val Pro Gly Val Gly Thr Pro Ala Ala Ala Ala
    450                 455                 460

Ala Lys Ala Ala Ala Lys Ala Ala Gln Phe Gly Leu Val Pro Gly Val
465                 470                 475                 480

Gly Val Ala Pro Gly Val Gly Val Ala Pro Gly Val Gly Val Ala Pro
                485                 490                 495

Gly Val Gly Leu Ala Pro Gly Val Gly Val Ala Pro Gly Val Gly Val
            500                 505                 510

Ala Pro Gly Val Gly Val Ala Pro Gly Ile Gly Pro Gly Gly Val Ala
            515                 520                 525

Ala Ala Ala Lys Ser Ala Ala Lys Val Ala Lys Ala Gln Leu Arg
    530                 535                 540

Ala Ala Ala Gly Leu Gly Ala Gly Ile Pro Gly Leu Gly Val Gly Val
545                 550                 555                 560

Gly Val Pro Gly Leu Gly Val Gly Ala Gly Val Pro Gly Leu Gly Val
                565                 570                 575

Gly Ala Gly Val Pro Gly Phe Gly Ala Gly Ala Asp Glu Gly Val Arg
            580                 585                 590

Arg Ser Leu Ser Pro Glu Leu Arg Glu Gly Asp Pro Ser Ser Ser Gln
            595                 600                 605

His Leu Pro Ser Thr Pro Ser Ser Pro Arg Val Pro Gly Ala Leu Ala
    610                 615                 620

Ala Ala Lys Ala Ala Lys Tyr Gly Ala Ala Val Pro Gly Val Leu Gly
625                 630                 635                 640

Gly Leu Gly Ala Leu Gly Gly Val Gly Ile Pro Gly Gly Val Val Gly
                645                 650                 655

Ala Gly Pro Ala Ala Ala Ala Ala Ala Lys Ala Ala Lys Ala
            660                 665                 670

Ala Gln Phe Gly Leu Val Gly Ala Ala Gly Leu Gly Gly Leu Gly Val
    675                 680                 685

Gly Gly Leu Gly Val Pro Gly Val Gly Gly Leu Gly Gly Ile Pro Pro
690                 695                 700

Ala Ala Ala Ala Lys Ala Ala Lys Tyr Gly Ala Ala Gly Leu Gly Gly
705                 710                 715                 720

Val Leu Gly Gly Ala Gly Gln Phe Pro Leu Gly Gly Val Ala Ala Arg
                725                 730                 735

Pro Gly Phe Gly Leu Ser Pro Ile Phe Pro Gly Gly Ala Cys Leu Gly
            740                 745                 750

Lys Ala Cys Gly Arg Lys Arg Lys
            755                 760

<210> SEQ ID NO 89
<211> LENGTH: 429
<212> TYPE: PRT

-continued

<213> ORGANISM: Podocoryna carnea

<400> SEQUENCE: 89

```
Gly Pro Gln Gly Val Val Gly Ala Asp Gly Lys Asp Gly Thr Pro Gly
1               5                   10                  15

Glu Lys Gly Glu Gln Gly Arg Thr Gly Ala Ala Gly Lys Gln Gly Ser
            20                  25                  30

Pro Gly Ala Asp Gly Ala Arg Gly Pro Leu Gly Ser Ile Gly Gln Gln
        35                  40                  45

Gly Ala Arg Gly Glu Pro Gly Asp Pro Gly Ser Pro Gly Leu Arg Gly
    50                  55                  60

Asp Thr Gly Leu Ala Gly Val Lys Gly Val Ala Gly Pro Ser Gly Arg
65                  70                  75                  80

Pro Gly Gln Pro Gly Ala Asn Gly Leu Pro Gly Val Asn Gly Arg Gly
                85                  90                  95

Gly Leu Arg Gly Lys Pro Gly Ala Lys Gly Ile Ala Gly Ser Asp Gly
            100                 105                 110

Glu Ala Gly Glu Ser Gly Ala Pro Gly Gln Ser Gly Pro Thr Gly Pro
        115                 120                 125

Arg Gly Gln Arg Gly Pro Ser Gly Glu Asp Gly Asn Pro Gly Leu Gln
    130                 135                 140

Gly Leu Pro Gly Ser Asp Gly Glu Pro Gly Glu Glu Gly Gln Pro Gly
145                 150                 155                 160

Arg Ser Gly Gln Pro Gly Gln Gly Pro Arg Gly Ser Pro Gly Glu
                165                 170                 175

Val Gly Pro Arg Gly Ser Lys Gly Pro Ser Gly Asp Arg Gly Asp Arg
            180                 185                 190

Gly Glu Arg Gly Val Pro Gly Gln Thr Gly Ser Ala Gly Asn Val Gly
        195                 200                 205

Glu Asp Gly Glu Gln Gly Gly Lys Gly Val Asp Gly Ala Ser Gly Pro
    210                 215                 220

Ser Gly Ala Leu Gly Ala Arg Gly Pro Pro Gly Ser Arg Gly Asp Thr
225                 230                 235                 240

Gly Ala Val Gly Pro Gly Pro Thr Gly Arg Ser Gly Leu Pro Gly
                245                 250                 255

Asn Ala Gly Gln Lys Gly Pro Ser Gly Glu Pro Gly Ser Pro Gly Lys
            260                 265                 270

Ala Gly Ser Ala Gly Glu Gln Gly Pro Pro Gly Lys Asp Gly Ser Asn
        275                 280                 285

Gly Glu Pro Gly Ser Pro Gly Lys Glu Gly Glu Arg Gly Leu Ala Gly
    290                 295                 300

Pro Pro Gly Pro Asp Gly Arg Arg Gly Glu Thr Gly Ser Pro Gly Ile
305                 310                 315                 320

Ala Gly Ala Leu Gly Lys Pro Gly Leu Glu Gly Pro Lys Gly Tyr Pro
                325                 330                 335

Gly Leu Arg Gly Arg Asp Gly Thr Asn Gly Lys Arg Gly Glu Gln Gly
            340                 345                 350

Glu Thr Gly Pro Asp Gly Val Arg Gly Ile Pro Gly Asn Asp Gly Gln
        355                 360                 365

Ser Gly Lys Pro Gly Ile Asp Gly Ile Asp Gly Thr Asn Gly Gln Pro
    370                 375                 380

Gly Glu Ala Gly Tyr Gln Gly Gly Arg Gly Thr Arg Gly Gln Leu Gly
385                 390                 395                 400
```

```
Glu Thr Gly Asp Val Gly Gln Asn Gly Asp Arg Gly Ala Pro Gly Pro
            405                 410                 415

Asp Gly Ser Lys Gly Ser Ala Gly Arg Pro Gly Leu Arg
            420                 425

<210> SEQ ID NO 90
<211> LENGTH: 570
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90
ggtccgcagg gtgttgttgg tgcagatggt aaagacggta ccccgggtaa tgcaggtcag      60
aaaggtccgt caggtgaacc tggcagccct ggtaaagcag gtagtgccgg tgagcagggt     120
ccgccgggca agatggtag taatggtgag ccgggtagcc ctggcaaaga aggtgaacgt     180
ggtctggcag accgccggg tcctgatggt cgccgcggtg aaacgggttc accgggtatt     240
gccggtgccc tgggtaaacc aggtctggaa ggtccgaaag gttatcctgg tctgcgcggt     300
cgtgatggta ccaatggcaa acgtggcgaa cagggcgaaa ccggtccaga tggtgttcgt     360
ggtattccgg gtaacgatgg tcagagcggt aaaccgggca ttgatggtat tgatggcacc     420
aatggtcagc ctggcgaagc aggttatcag ggtggtcgcg gtacccgtgg tcagctgggt     480
gaaacaggtg atgttggtca gaatggtgat cgcggcgcac cgggtccgga tggtagcaaa     540
ggtagcgccg gtcgtccggg tttacgttaa                                       570

<210> SEQ ID NO 91
<211> LENGTH: 189
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Gly Pro Gln Gly Val Val Gly Ala Asp Gly Lys Asp Gly Thr Pro Gly
1               5                   10                  15

Asn Ala Gly Gln Lys Gly Pro Ser Gly Glu Pro Gly Ser Pro Gly Lys
            20                  25                  30

Ala Gly Ser Ala Gly Glu Gln Gly Pro Pro Gly Lys Asp Gly Ser Asn
        35                  40                  45

Gly Glu Pro Gly Ser Pro Gly Lys Glu Gly Arg Gly Leu Ala Gly
    50                  55                  60

Pro Pro Gly Pro Asp Gly Arg Arg Gly Glu Thr Gly Ser Pro Gly Ile
65                  70                  75                  80

Ala Gly Ala Leu Gly Lys Pro Gly Leu Glu Gly Pro Lys Gly Tyr Pro
            85                  90                  95

Gly Leu Arg Gly Arg Asp Gly Thr Asn Gly Lys Arg Gly Glu Gln Gly
            100                 105                 110

Glu Thr Gly Pro Asp Gly Val Arg Gly Ile Pro Gly Asn Asp Gly Gln
        115                 120                 125

Ser Gly Lys Pro Gly Ile Asp Gly Ile Asp Gly Thr Asn Gly Gln Pro
    130                 135                 140

Gly Glu Ala Gly Tyr Gln Gly Gly Arg Gly Thr Arg Gly Gln Leu Gly
145                 150                 155                 160

Glu Thr Gly Asp Val Gly Gln Asn Gly Asp Arg Gly Ala Pro Gly Pro
```

Asp Gly Ser Lys Gly Ser Ala Gly Arg Pro Gly Leu Arg
            180                 185

<210> SEQ ID NO 92
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Met Lys Lys Ile Trp Leu Ala Leu Ala Gly Leu Val Leu Ala Phe Ser
1               5                   10                  15

Ala Ser Ala Gly Asp Gln Gly Pro Val Gly Arg Thr Gly Glu Val Gly
            20                  25                  30

Ala Val Gly Pro Pro Gly Phe Ala Gly Glu Lys Gly Pro Ser Gly Glu
        35                  40                  45

Ala Gly Thr Ala Gly Pro Pro Gly Thr Pro Gly Pro Gln Gly Leu Leu
    50                  55                  60

Gly Ala Pro Gly Ile Leu Gly Leu Pro Gly Ser Arg Gly Glu Arg Gly
65                  70                  75                  80

Leu Pro Gly Val Ala Gly Ala Val Gly Glu Pro Gly Pro Leu Gly Ile
                85                  90                  95

Ala Gly Pro Pro Gly Ala Arg Gly Pro Pro Gly Ala Val Gly Ser Pro
            100                 105                 110

Gly Val Asn Gly Ala Pro Gly Glu Ala Gly Arg Asp Gly Asn Pro Gly
        115                 120                 125

Asn Asp Gly Pro Pro Gly Arg Asp Gly Gln Pro Gly His Lys Gly Glu
    130                 135                 140

Arg Gly Tyr Pro Gly Asn Ile Gly Pro Val Gly Ala Ala Gly Ala Pro
145                 150                 155                 160

Gly Pro His Gly Pro Val Gly Pro Ala Gly Lys His Gly Asn Arg Gly
                165                 170                 175

Glu Thr Gly Pro Ser Gly Pro Val Gly Pro Ala Gly Ala Val Gly Pro
            180                 185                 190

Arg Gly Pro Ser Gly Pro Gln Gly Ile Arg Gly Asp Lys Gly Glu Pro
        195                 200                 205

Gly Glu Lys Gly Pro Arg Gly Leu Pro Gly Leu Gly Asp Tyr Lys Asp
    210                 215                 220

Asp Asp Asp Lys
225

<210> SEQ ID NO 93
<211> LENGTH: 687
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93
atgaaaaaga tttggctggc gctggctggt ttagttttag cgtttagcgc atcggcgggt      60
gatcagggtc cggttggtcg taccggtgaa gttggtgcag tcggccgccc gggttttgcg     120
ggtgaaaaag cccgtcagg tgaagcaggc accgctggcc ctcctggcac gcctggccca     180
cagggtttac tgggcgcacc tggaattctg ggactgccgg gcagccgtgg agaacgcggt     240

```
ttaccaggtg ttgccggtgc cgttggtgaa cctggtccac tgggcattgc agggccgcct    300
ggcgcacggg gaccgcctgg tgctgttggt agtccgggtg tgaatggtgc tccgggtgaa    360
gccggtcgtg acggtaatcc gggaaatgac ggcccgccag gccgcgatgg tcagccgggt    420
cataaaggtg agcgtggtta cccaggtaat attggtccag tcggtgccgc cggtgcgccg    480
ggtcctcatg gccctgtcgg tccagccggt aaacatggta atcgcggtga gacaggtccg    540
tcaggaccag tgggccctgc tggcgcagtc ggtccgcgcg ggccgagtgg ccctcagggt    600
attcgtggcg ataaagggga accgggcgaa aaagggccgc ggggtctgcc aggcctgggt    660
gactacaaag acgacgacga caaataa                                        687
```

<210> SEQ ID NO 94
<211> LENGTH: 228
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 94

```
Met Lys Lys Ile Trp Leu Ala Leu Ala Gly Leu Val Leu Ala Phe Ser
1               5                   10                  15

Ala Ser Ala Lys Gly His Asn Gly Leu Gln Gly Leu Pro Gly Ile Ala
            20                  25                  30

Gly His His Gly Asp Gln Gly Ala Pro Gly Ser Val Gly Pro Ala Gly
        35                  40                  45

Pro Arg Gly Pro Ala Gly Pro Ser Gly Pro Ala Gly Lys Asp Gly Arg
    50                  55                  60

Thr Gly His Pro Gly Thr Val Gly Pro Ala Gly Ile Arg Gly Pro Gln
65                  70                  75                  80

Gly His Gln Gly Pro Ala Gly Pro Pro Gly Pro Gly Pro Pro Gly
                85                  90                  95

Pro Pro Gly Val Ser Gly Gly Gly Tyr Asp Phe Gly Tyr Asp Gly Asp
                100                 105                 110

Phe Tyr Arg Ala Asp Gln Pro Arg Ser Ala Pro Ser Leu Arg Pro Lys
            115                 120                 125

Asp Tyr Glu Val Asp Ala Thr Leu Lys Ser Leu Asn Asn Gln Ile Glu
    130                 135                 140

Thr Leu Leu Thr Pro Glu Gly Ser Arg Lys Asn Pro Ala Arg Thr Cys
145                 150                 155                 160

Arg Asp Leu Arg Leu Ser His Pro Glu Trp Ser Ser Gly Tyr Tyr Trp
                165                 170                 175

Ile Asp Pro Asn Gln Gly Cys Thr Met Asp Ala Ile Lys Val Tyr Cys
            180                 185                 190

Asp Phe Ser Thr Gly Glu Thr Cys Ile Arg Ala Gln Pro Glu Asn Ile
        195                 200                 205

Pro Ala Lys Asn Trp Tyr Arg Ser Ser Lys Asp Gly Asp Tyr Lys Asp
    210                 215                 220

Asp Asp Asp Lys
225
```

<210> SEQ ID NO 95
<211> LENGTH: 687
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 95

```
atgaaaaaga tttggctggc gctggctggt ttagttttag cgtttagcgc atcggcgaaa    60
ggtcacaatg gactgcaagg cctgccaggt attgcaggtc atcatggtga tcaaggtgcc   120
ccgggaagcg ttggtccggc ggggccgaga ggccctgcgg gaccttcagg tccggcaggc   180
aaagatggtc ggacaggcca tccgggcacc gttggccctg caggaattcg tggaccgcag   240
ggtcatcagg gacctgctgg tccgccaggt cccccgggcc ctccgggacc accgggtgtt   300
agtggtggtg gttatgattt tggctatgat ggtgattttt atcgtgcaga tcagccgcgt   360
agcgcaccga gcctgcgtcc taaagattat gaagttgatg caaccctgaa aagcctgaat   420
aatcagattg aaacactgct gacaccggaa ggtagccgta aaaatccggc ccgtacctgt   480
cgtgatctgc gtctgagcca cccggaatgg agcagcggtt attattggat tgatccgaat   540
caaggttgta ccatggatgc aattaaagtt tattgtgatt ttagcacagg tgaaacatgt   600
atccgtgcac agccggaaaa tattccggcc aaaaattggt atcgtagtag caaagatggt   660
gactacaaag acgacgacga caaataa                                        687
```

<210> SEQ ID NO 96
<211> LENGTH: 262
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 96

```
Met Lys Lys Ile Trp Leu Ala Leu Ala Gly Leu Val Leu Ala Phe Ser
1               5                   10                  15

Ala Ser Ala Tyr Glu Val Asp Ala Thr Leu Lys Ser Leu Asn Asn Gln
                20                  25                  30

Ile Glu Thr Leu Leu Thr Pro Glu Gly Ser Arg Lys Asn Pro Ala Arg
            35                  40                  45

Thr Cys Arg Asp Leu Arg Leu Ser His Pro Glu Trp Ser Ser Gly Tyr
        50                  55                  60

Tyr Trp Ile Asp Pro Asn Gln Gly Cys Thr Met Asp Ala Ile Lys Val
65                  70                  75                  80

Tyr Cys Asp Phe Ser Thr Gly Glu Thr Cys Ile Arg Ala Gln Pro Glu
                85                  90                  95

Asn Ile Pro Ala Lys Asn Trp Tyr Arg Ser Ser Lys Asp Lys His
                100                 105                 110

Val Trp Leu Gly Glu Thr Ile Asn Ala Gly Ser Gln Phe Glu Tyr Asn
            115                 120                 125

Val Glu Gly Val Thr Ser Lys Glu Met Ala Thr Gln Leu Ala Phe Met
        130                 135                 140

Arg Leu Leu Ala Asn Tyr Ala Ser Gln Asn Ile Thr Tyr His Cys Lys
145                 150                 155                 160

Asn Ser Ile Ala Tyr Met Asp Glu Glu Thr Gly Asn Leu Lys Lys Ala
                165                 170                 175

Val Ile Leu Gln Gly Ser Asn Asp Val Glu Leu Val Ala Glu Gly Asn
            180                 185                 190

Ser Arg Phe Thr Tyr Thr Val Leu Val Asp Gly Cys Ser Lys Lys Thr
        195                 200                 205
```

Asn Glu Trp Gly Lys Thr Ile Ile Glu Tyr Lys Thr Asn Lys Pro Ser
    210                 215                 220

Arg Leu Pro Phe Leu Asp Ile Ala Pro Leu Asp Ile Gly Gly Ala Asp
225                 230                 235                 240

Gln Glu Phe Phe Val Asp Ile Gly Pro Val Cys Phe Lys Gly Asp Tyr
                245                 250                 255

Lys Asp Asp Asp Asp Lys
            260

<210> SEQ ID NO 97
<211> LENGTH: 788
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
tgaaaaagat tggctggcg ctggctggtt tagttttagc gtttagcgca tcggcgtatg      60
aagttgatgc aaccctgaaa agcctgaata atcagattga aacactgctg acaccggaag   120
gtagccgtaa aaatccggcc cgtacctgtc gtgatctgcg tctgagccac ccggaatgga   180
gcagcggtta ttattggatt gatccgaatc aaggttgtac catggatgca attaaagttt   240
attgtgattt tagcacaggt gaaacatgta tccgtgcaca gccggaaaat attccggcca   300
aaaattggta tcgtagtagc aaagataaaa acatgtgtg gctgggtgaa accattaatg   360
caggtagcca gtttgaatac aatgttgaag gtgttaccag caagaaatg gcaacacagc   420 tggcatttat gcgtctgctg gcaaattatg caagccagaa tattacatat cattgtaaaa   480
atagcattgc atatatggat gaagaaaccg gtaatctgaa aaaagcagtt attctgcagg   540
gtagcaatga tgttgaactg gttgccgaag gtaatagccg ttttacatat accgttctgg   600
ttgatggttg tagcaaaaaa accaatgaat ggggtaaaac catcattgaa atataaaacca   660 acaaaccgag ccgtctgccg tttctggata tcgctccgct ggatattggt ggtgccgatc   720
aggaattttt tgtcgatatc ggtcctgtgt gttttaaagg tgactacaaa gacgacgacg   780
acaaataa                                                             788

<210> SEQ ID NO 98
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Met Lys Lys Ile Trp Leu Ala Leu Ala Gly Leu Val Leu Ala Phe Ser
1               5                   10                  15

Ala Ser Ala Gly Gly Val Pro Gly Ala Ile Pro Gly Gly Val Pro Gly
            20                  25                  30

Gly Val Phe Tyr Pro Gly Ala Gly Leu Gly Ala Leu Gly Gly Gly Ala
        35                  40                  45

Leu Gly Pro Gly Gly Lys Pro Leu Lys Pro Val Pro Gly Gly Leu Ala
    50                  55                  60

Gly Ala Gly Leu Gly Ala Gly Leu Gly Ala Phe Pro Ala Val Thr Phe
65                  70                  75                  80

Pro Gly Ala Leu Val Pro Gly Gly Val Ala Asp Ala Ala Ala Ala Tyr
                85                  90                  95

Lys Ala Ala Lys Ala Gly Ala Gly Leu Gly Val Pro Val Gly
            100                 105                 110

Gly Leu Gly Val Ser Ala Gly Ala Val Val Pro Gln Pro Gly Ala Gly
                115                 120                 125

Val Lys Pro Gly Lys Val Pro Gly Val Gly Leu Pro Gly Val Tyr Pro
    130                 135                 140

Gly Gly Val Leu Pro Gly Ala Arg Phe Pro Gly Val Gly Val Leu Pro
145                 150                 155                 160

Gly Val Pro Thr Gly Ala Gly Val Lys Pro Lys Ala Pro Val Gly
                165                 170                 175

Gly Ala Phe Ala Gly Ile Pro Gly Val Gly Pro Phe Gly Gly Pro Gln
                180                 185                 190

Pro Gly Val Pro Leu Gly Tyr Pro Ile Lys Ala Pro Lys Leu Pro Gly
        195                 200                 205

Gly Tyr Gly Leu Pro Tyr Thr Thr Gly Lys Leu Gly Asp Tyr Lys Asp
    210                 215                 220

Asp Asp Asp Lys
225

<210> SEQ ID NO 99
<211> LENGTH: 687
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99
atgaaaaaga tttggctggc gctggctggt ttagttttag cgtttagcgc atcggcgggt      60
ggcgtaccag gcgcaattcc tgggggtgtc ccaggcggtg ttttttatcc gggcgccggt     120
cttggcgcac tggtggcgg tgcactgggc ccgggcggca aaccgctgaa accggtacca      180
ggtggtttag caggcgccgg cttaggcgca ggtctgggag catttccggc agttaccttt     240
ccaggggcac tggttcctgg aggtgtggcc gatgcagccg cggcatataa agccgctaaa     300
gccggtgcgg gtttaggagg cgtcccaggt gtcggtggcc tggtgttag cgccggtgca     360 gttgttccgc agccgggagc aggggttaaa cctggtaaag tgccgggagt aggtctgcca     420
ggcgtttatc ctggtggtgt tttgccgggt gcccgttttc cggcgttgg tgttcttcca     480 ggcgtgccga ccggagccgg tgttaaaccg aaagcccccg tgttggagg tgcatttgca     540 ggcatcccgg gagttggccc gtttggtggt ccgcaacctg gggttccgtt aggttatccg     600
attaaagcac cgaaactgcc cggcggttat ggtctgccgt acacaaccgg taaactgggt     660
gactacaaag acgacgacga caaataa                                         687

<210> SEQ ID NO 100
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Met Lys Lys Ile Trp Leu Ala Leu Ala Gly Leu Val Leu Ala Phe Ser
1               5                   10                  15

Ala Ser Ala Pro Tyr Gly Tyr Gly Pro Gly Gly Val Ala Gly Ala Ala
            20                  25                  30

```
Gly Lys Ala Gly Tyr Pro Thr Gly Thr Gly Val Gly Pro Gln Ala Ala
            35                  40                  45
Ala Ala Ala Ala Ala Lys Ala Ala Lys Phe Gly Ala Gly Ala Ala
    50                  55                  60
Gly Val Leu Pro Gly Val Gly Gly Ala Gly Val Pro Gly Val Pro Gly
65                  70                  75                  80
Ala Ile Pro Gly Ile Gly Gly Ile Ala Gly Val Gly Thr Pro Ala Ala
                85                  90                  95
Ala Ala Ala Ala Ala Ala Ala Lys Ala Ala Lys Tyr Gly Ala Ala
            100                 105                 110
Ala Gly Leu Val Pro Gly Gly Pro Gly Phe Gly Pro Gly Val Val Gly
            115                 120                 125
Val Pro Gly Ala Gly Val Pro Gly Val Gly Val Pro Gly Ala Gly Ile
            130                 135                 140
Pro Val Val Pro Gly Ala Gly Ile Pro Gly Ala Ala Val Pro Gly Val
145                 150                 155                 160
Val Ser Pro Glu Ala Ala Ala Lys Ala Ala Lys Ala Ala Lys Tyr
                165                 170                 175
Gly Ala Arg Pro Gly Val Gly Val Gly Gly Ile Pro Thr Tyr Gly Val
            180                 185                 190
Gly Ala Gly Gly Phe Pro Gly Phe Gly Val Gly Val Gly Ile Pro
            195                 200                 205
Gly Val Ala Gly Val Pro Gly Val Gly Val Gly Asp Tyr Lys Asp
            210                 215                 220
Asp Asp Asp Lys
225

<210> SEQ ID NO 101
<211> LENGTH: 687
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101
atgaaaaaga tttggctggc gctggctggt ttagttttag cgtttagcgc atcggcgccg      60
tatggttatg gcccgggtgg agttgcgggt gcagcaggta agcgggttta tcctaccgga     120
accggtgtag gtccgcaggc cgctgctgcc gccgccgcaa agcagcggc taaatttggc     180 gccggagcag cgggtgttct gcctggagtt ggtggtgcgg cgtgccagg ggtacctggt     240 gcaattccgg gtattggtgg tattgccggt gtcggcaccc cggccgcggc agctgcggca     300
gcggcggctg ccaaagctgc taaatacggt gccgcgcgg gtctggtgcc aggaggtccg     360
ggttttggtc cgggagtggt tggcgtgcct ggcgcaggcg ttcctggtgt gggcgttcca     420
ggtgcaggga ttcctgttgt gcctggtgcc ggtattcccg gcgcggccgt tccggggtg     480 gttagcccgg aagccgcagc gaaggctgcg gcaaaggcag caaagtatgg cgcacgccca     540
ggagtcggcg tgggtggtat cccgacctat ggggtgggcg caggggggttt tcctggtttc     600 ggcgtaggtg taggaggtat accgggcgtg gccggtgtac caggggttgg tggcgtcggt     660
gactacaaag acgacgacga caaataa                                         687

<210> SEQ ID NO 102
<211> LENGTH: 273
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 102

```
Met Lys Lys Ile Trp Leu Ala Leu Ala Gly Leu Val Leu Ala Phe Ser
1               5                   10                  15
Ala Ser Ala Pro Val Gly Arg Arg Gly Pro Lys Gly Ser Arg Gly Asp
            20                  25                  30
Pro Gly Asp Gly Gly Ala Ala Gly Pro Lys Gly Pro Glu Gly Val Asp
        35                  40                  45
Gly Leu Ile Gly Glu Pro Gly Gln Pro Gly Pro Ile Gly Ala Glu Gly
    50                  55                  60
Ser Ser Gly Leu Glu Gly Phe Leu Gly Asp Lys Gly Ser Lys Gly Ala
65                  70                  75                  80
Arg Gly Gly Pro Gly Asn Arg Gly Arg Pro Gly Gln Asp Gly Val Pro
                85                  90                  95
Gly Gln Asp Gly Arg Ala Gly Glu Lys Gly Glu Gly Glu Thr Gly
            100                 105                 110
Asp Arg Gly Gln Gln Gly Leu Arg Gly Lys Val Gly Asp Pro Gly Leu
        115                 120                 125
Val Gly Asp Leu Gly Ala Gln Gly Pro Gln Gly Ser Gln Gly Leu Val
    130                 135                 140
Gly Pro Pro Gly Ile Pro Gly Glu Pro Gly Ser Gly Glu Pro Gly
145                 150                 155                 160
Asp Gln Gly Pro Arg Gly Pro Glu Gly Gln Gly Ser Pro Gly Val
                165                 170                 175
Arg Gly Gly Arg Gly Glu Arg Gly Thr Pro Gly Ala Val Gly Pro Lys
            180                 185                 190
Gly Pro Pro Gly Lys Asn Gly Ala Asp Gly Pro Arg Gly Leu Pro Gly
        195                 200                 205
Ala Ser Gly Pro Pro Gly Ser Pro Gly Asn Gln Gly Pro Glu Gly Ser
    210                 215                 220
Arg Gly Ala Asp Gly Asn Asn Gly Phe Pro Gly Asp Asp Gly Glu Asn
225                 230                 235                 240
Gly Leu Val Gly Ile Pro Gly Glu Pro Gly Pro Lys Gly Ala Arg Gly
                245                 250                 255
Thr Arg Gly Glu Leu Gly Lys Thr Gly Asp Tyr Lys Asp Asp Asp
            260                 265                 270
Lys
```

<210> SEQ ID NO 103
<211> LENGTH: 822
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 103

```
atgaaaaaga tttggctggc gctggctggt ttagttttag cgtttagcgc atcggcgccg    60
gttggtcgtc gtggtccgaa aggtagccgt ggtgatcctg gtgatggtgg tgcagcaggt   120
cctaaaggtc cggaaggtgt tgatggtctg attggtgaac cgggtcagcc tggtccgatt   180
ggcgcagaag gtagcagcgg tctggaaggt tttctgggtg ataaaggtag caaaggtgca   240
```

```
cgtggtggtc cgggtaatcg cggtcgtcct ggtcaggatg gtgttccggg tcaagatggt    300
cgtgccggtg aaaaaggtga aggtggtgaa accggtgatc gcggtcagca gggtctgcgt    360
ggtaaagttg gtgatccagg tctggtgggt gatctgggtg cacagggtcc gcagggtagc    420
caaggtctgg ttggtccgcc tggtattccg ggtgaacctg gtagcggtgg cgaaccgggt    480
gatcagggtc ctcgcggtcc agaaggtcct cagggttcac cgggtgttcg cggtggtcgt    540
ggtgaacgtg gtacaccggg tgcagttgga ccgaaaggtc cgccaggtaa aaatggtgca    600
gatggtccgc gtggtctgcc tggtgcaagc ggtcctccgg gtagtcctgg taaccagggt    660
cctgaaggtt ctcgtggtgc cgatggtaat aatggttttc aggtgatga tggtgaaaat    720 ggcctggttg gtatccctgg cgaaccaggt ccaaaaggcg cacgcggtac acgcggtgaa    780
ctgggtaaaa ccggtgacta caaagacgac gacgacaaat aa                      822
```

<210> SEQ ID NO 104
<211> LENGTH: 450
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 104

```
Met Lys Lys Ile Trp Leu Ala Leu Ala Gly Leu Val Leu Ala Phe Ser
1               5                   10                  15

Ala Ser Ala Gly Arg Gly Gly Pro Ala Gly Leu Gln Gly Ala Ala Gly
            20                  25                  30

Asn Pro Gly Asp Pro Gly Asp Arg Gly Gln Ala Gly Glu Ile Gly Leu
        35                  40                  45

Pro Gly Thr Glu Gly Gln Arg Gly Gln Gly Gly Ser Arg Gly Asp Asp
    50                  55                  60

Gly Ile Gly Gly Gln Ser Gly Thr Asp Gly Asp Pro Gly Asn Asp Gly
65                  70                  75                  80

Val Ala Gly Ile Arg Gly Ala Arg Gly Glu Pro Gly Ala Thr Gly Pro
                85                  90                  95

Glu Gly Ala Ala Gly Gln Lys Gly Asp Arg Gly Arg Phe Gly Glu Gln
            100                 105                 110

Gly Arg Pro Gly Asn Asp Gly Pro Gly Arg Arg Gly Arg Val Gly
        115                 120                 125

Asn Leu Gly Glu Thr Gly Ala Glu Gly Asp Glu Gly Thr Arg Gly Tyr
    130                 135                 140

Thr Gly Asp Arg Gly Pro Glu Gly Ala Ile Gly Ile Ser Gly Val Thr
145                 150                 155                 160

Gly Asn Pro Gly Pro Gln Gly Ile Lys Gly Pro Pro Gly Asp Thr Gly
                165                 170                 175

His Pro Gly Arg Gln Gly Pro Ser Gly Pro Gln Gly Pro Pro Gly Ile
            180                 185                 190

Pro Gly Thr Asp Gly Leu Thr Ile His Asn Leu Ile Lys Pro Pro Ser
        195                 200                 205

Gln Phe Phe Asp Ala Thr Ser Ser Ser Asp Pro Leu Thr Asp Ala Val
    210                 215                 220

Val Glu Ser Ile Leu Lys Ser Phe Gln Tyr Ala Glu Leu Glu Ile Asp
225                 230                 235                 240

Leu Thr Lys Lys Pro Asp Gly Thr Met Lys Tyr Pro Ala Ile Ser Cys
                245                 250                 255
```

Asp Asp Leu His Lys Asp Tyr Pro Gln Leu Pro Ser Gly Asn Tyr Thr
            260                 265                 270

Leu Asp Pro Asn Gly Gly Cys Lys Asn Asp Ala Phe Glu Thr Tyr Cys
        275                 280                 285

Glu Phe Asn Asn Ser Val Lys Met Cys Leu Thr Pro Lys Ile Pro Thr
    290                 295                 300

Leu Leu Pro Met Gly Thr Tyr Lys Tyr Tyr Val Asn Ser Glu Gly Tyr
305                 310                 315                 320

Tyr Ser Pro Asn Asp Phe Gly Leu Asn Leu Arg Phe Glu Tyr Tyr
                325                 330                 335

Gly Ser Val Thr Gln Leu Lys Phe Leu Gln Thr Lys Ala Thr Arg Val
            340                 345                 350

Thr Gln Thr Ile Arg Val Leu Cys Lys Asn Tyr Asp Pro Leu His Lys
        355                 360                 365

Gln Pro Val Phe Ile Gly Met Asn Asp Glu Thr Val Met Asp Glu Pro
    370                 375                 380

Arg Met Glu Glu Asn Gln Cys Gln Tyr Phe Asn Gly Leu Ser Ala His
385                 390                 395                 400

Val Glu Leu Glu Leu Ser Ser Asn Asp Pro Ser Tyr Leu Pro Ile Tyr
                405                 410                 415

Glu Met Arg Leu Tyr Leu Gly Arg Lys Thr Asn Glu Glu Leu Gly Ile
            420                 425                 430

Glu Leu Gly Asp Leu Cys Phe Glu Tyr Gly Asp Tyr Lys Asp Asp Asp
        435                 440                 445

Asp Lys
    450

<210> SEQ ID NO 105
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105
atgaaaaaga tttggctggc gctggctggt ttagttttag cgtttagcgc atcggcggt      60 cgtggcggtc cggcaggtct gcagggtgct gcaggtaatc ctggcgaccc tggcgatcgt    120
ggtcaggcag gcgaaattgg tctgccaggc accgaaggtc agcgtggtca aggtggttca    180
cgtggtgatg acgtattgg tggtcagagc ggcaccgatg cgatccggg taacgatggt      240 gttgcaggta ttcgtggtgc acgcggagaa cctggtgcca ccggacctga aggtgcagcc    300
ggtcagaaag gtgatcgtgg ccgttttggc aacagggtc gtccgggaaa tgatggtcca    360
ccgggtcgcc gtggccgtgt gggcaatctg gtgaaacag gtgccgaagg tgatgaaggc    420
acccgtggtt atacaggtga ccgtggaccg gaaggcgcaa ttggtattag cggtgtgacc    480
ggtaatccgg gtccacaggg cattaaaggc cctccgggtg atacgggtca tccgggtcgt    540
cagggaccga gcggtccgca aggaccaccg ggtattccag gtacagatgg cctgaccatt    600
cataatctga ttaaaccgcc tagccagttt tttgatgcaa ccagcagcag cgatccgctg    660
accgatgcag ttgttgaaag cattctgaaa tcttttcagt atgccagct ggaaattgac    720 ctgaccaaaa aaccggatgg caccatgaaa tatccggcaa ttagctgtga tgatctgcac    780
aaagattatc cgcagctgcc gagcggtaat tatacccctg gatccgaatg gtggttgtaaa    840 aatgatgcct ttgaaaccta ttgcgagttc aacaatagcg tgaaaatgtg tctgaccccg    900

```
aaaattccga cactgctgcc gatgggcacc tataaatact atgttaatag cgagggttac    960
tacagcccga atgattttgg tctgaatctg cgcttttttg agtattatgg tagcgttacc   1020
cagctgaaat ttctgcagac caaagcaacc cgtgttaccc agaccattcg tgttctgtgt   1080
aaaaactatg atccgctgca taaacagccg gttttttattg gtatgaatga cgaaaccgtt   1140
atggatgaac cgcgtatgga agaaaatcag tgccagtatt ttaacggtct gagcgcacat   1200
gttgaactgg aactgagcag caatgatccg agctatctgc cgatttatga aatgcgtctg   1260
tatctgggtc gtaaaaccaa tgaagaactg ggcattgaac tgggcgatct gtgttttgaa   1320
tatggtgact acaaagacga cgacgacaaa taa                                1353
```

<210> SEQ ID NO 106
<211> LENGTH: 286
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

```
Met Lys Lys Ile Trp Leu Ala Leu Ala Gly Leu Val Leu Ala Phe Ser
1               5                   10                  15

Ala Ser Ala Glu Lys Thr Ser Ser Lys Val Ala Leu Met Thr Val Leu
            20                  25                  30

Val Val Ile Thr Gly Ala Leu Ile Ile Glu Gly Thr Ser Ile Thr Arg
        35                  40                  45

Gly Ser Thr His Val Asn Arg Gly Leu Arg Lys Arg Gln Thr Ser Glu
    50                  55                  60

Asp Asn Cys Glu Ala Val Lys Val Gly Leu Pro Gly Arg Asp Gly Arg
65                  70                  75                  80

Glu Gly Pro Pro Gly Pro Pro Gly Pro Ala Gly Arg Asp Gly Arg Asp
                85                  90                  95

Ala Val Cys Ser Asn Gln Thr Thr Gly Leu Gly Ala Lys Gly Asp Arg
            100                 105                 110

Gly Pro Pro Gly Thr Pro Gly Phe Pro Gly Glu Val Gly Arg Pro Gly
        115                 120                 125

Pro Pro Gly Ala Asp Gly Ile Pro Gly Pro Gln Gly Glu Arg Gly Ala
    130                 135                 140

Val Gly Pro Gly Gly Lys Pro Gly Pro Arg Gly Glu Val Gly Thr Pro
145                 150                 155                 160

Gly Ala Asp Gly Ala Asp Gly Ala Thr Gly Ala Thr Gly Val Gln Gly
                165                 170                 175

Pro Asp Gly Ala Lys Gly Glu Lys Gly Ala Ser Gly Thr Ala Gly Leu
            180                 185                 190

Lys Gly Glu Lys Gly Asp Thr Cys Ile Pro Asp Ser Asn Ser Thr Leu
        195                 200                 205

Gly Met Pro Gly Thr Pro Gly Ala Gly Gly Ser Lys Gly Gln Lys Gly
    210                 215                 220

Glu Ser Gly Ile Val Gly Pro Lys Gly Glu Arg Gly Glu Ile Gly Thr
225                 230                 235                 240

Pro Gly His Pro Gly Phe Arg Gly Ala Asp Gly Glu Pro Gly His Lys
                245                 250                 255

Gly Val Pro Gly Arg Ala Gly Ala Gln Gly Asp Arg Gly Asp Pro Gly
            260                 265                 270
```

Asp Asp Gly Leu Thr Gly Asp Tyr Lys Asp Asp Asp Lys
        275                 280                 285

<210> SEQ ID NO 107
<211> LENGTH: 861
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107
atgaaaaaga tttggctggc gctggctggt ttagttttag cgtttagcgc atcggcggaa      60
aaaaccagca gcaaagttgc actgatgacc gttctggttg ttattaccgg tgcactgatt     120
attgaaggca ccagcattac ccgtggtagc acccatgtta atcgtggtct gcgtaaacgt     180
cagaccagcg aagataattg tgaagcagtt aaagttggtc tgccaggtcg tgatggtcgt     240
gaaggtcctc cgggtccgcc tggtccggct ggcagagatg ccgtgatgc agtttgtagc      300 aatcagacca ccgtctgggt tgcaaaaggt gatcgtggtc cgccaggtac accgggtttt    360
ccgggtgaag ttggccgtcc gggtccaccg ggtgcagatg gtattccggg tcctcagggt    420
gaacgtggtg cagttggtcc tggtggtaaa cctggtccgc gtggtgaagt gggcaccct     480 ggtgccgatg gcgcagatgg tgcaaccggt gcgaccggtg ttcagggtcc tgatggtgcc    540
aaaggcgaaa aggtgcaag cggcaccgca ggtctgaaag gtgagaaagg cgatacctgt     600
attccggata gcaatagcac cctgggtatg cctggtacac aggtgccgg tggtagcaaa     660 ggccagaaag tgaaagtgg tattgttggt ccgaaaggcg aacgcggtga aattggcaca    720
ccgggtcatc ctggttttcg tggtgcggat ggtgaaccag gtcataaagg tgttccgggt    780
cgtgccggtg cgcagggtga tcgcggtgat ccgggtgatg atggtctgac cggtgactac    840
aaagacgacg acgacaaata a                                              861

<210> SEQ ID NO 108
<211> LENGTH: 512
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Met Lys Lys Ile Trp Leu Ala Leu Ala Gly Leu Val Leu Ala Phe Ser
1               5                   10                  15

Ala Ser Ala Gly Phe Pro Gly Ala Pro Gly Ala Asp Gly Ala Pro Gly
            20                  25                  30

Gln Lys Gly Glu Leu Gly Ala Val Gly Pro Gln Gly Thr Pro Gly Leu
        35                  40                  45

Ser Gly Pro Ser Gly Pro Thr Gly Pro Pro Gly Pro Lys Gly Val Arg
    50                  55                  60

Gly Ala Pro Gly Ser Ser Gly Ala Lys Gly Asp Ala Gly Asn Pro Gly
65                  70                  75                  80

Asp Asp Gly Pro Val Gly Pro Gln Gly Val Pro Gly Val Asp Gly Ser
                85                  90                  95

Pro Gly Gln Lys Gly Glu Thr Gly Arg Val Gly Pro Arg Gly His Asp
            100                 105                 110

Gly Ile Asn Gly Thr Pro Gly Glu Asp Gly Ala Thr Gly Phe Pro Gly
        115                 120                 125

```
Pro Asp Gly Ala Lys Gly Glu Lys Gly Thr Ser Gly Thr Ala Gly Leu
130                 135                 140

Lys Gly Glu Lys Gly Asp Thr Cys Ile Pro Asp Ser Asn Ser Thr Leu
145                 150                 155                 160

Gly Met Pro Gly Thr Pro Gly Ala Gly Trp Ser Lys Gly Gln Lys Gly
                165                 170                 175

Glu Ser Gly Ile Val Gly Pro Lys Gly Glu Lys Gly Glu Ile Gly Thr
                180                 185                 190

Pro Gly Pro Pro Gly Phe Arg Gly Ala Asp Gly Glu Pro Gly Gln Arg
            195                 200                 205

Gly Glu Pro Gly Arg Ala Gly Ala Gln Gly Glu Arg Gly Ala Pro Gly
210                 215                 220

Asn Asn Gly Arg Asp Gly Phe Pro Gly Asp Pro Gly Ala Asp Gly Ala
225                 230                 235                 240

Pro Gly Gln Lys Gly Glu Leu Gly Ala Ile Gly His Pro Gly Phe Ser
                245                 250                 255

Gly Pro Ser Gly Pro Ser Gly Pro Thr Gly Pro Pro Gly Pro Lys Gly
            260                 265                 270

Val Arg Gly Ala Gln Gly Arg Pro Gly Asp Arg Gly Ser Pro Gly Asp
            275                 280                 285

Val Gly Pro Ile Gly Ala Pro Gly Pro Pro Gly Ala Asp Gly Val Pro
            290                 295                 300

Gly Leu Thr Gly Val Gln Gly Arg Asp Gly Pro Lys Gly Glu Ser Ala
305                 310                 315                 320

Ser Ser Gly Ala Val Tyr Val Arg Trp Gly Arg Thr Thr Cys Pro Ser
                325                 330                 335

Gly Ala Asp Val Val Tyr Ser Gly Arg Ala Ala Gly Ala Lys Tyr Asp
                340                 345                 350

His Ser Gly Gly Thr Ser Asp His His Cys Leu Pro Asn Asn Pro Gln
            355                 360                 365

Tyr Leu Ser Glu Asp Asp Thr Asn Ala Leu Gly Ala Gln Leu Tyr Gly
            370                 375                 380

Val Glu Tyr Glu Ile Arg Asp Arg Ser Ser Pro Tyr Asn Ser Leu Asp
385                 390                 395                 400

Gln Ser Asp Met Pro Cys Val Val Cys Asn Ala Asn Gly Arg Ser Gln
                405                 410                 415

Leu Leu Met Val Pro Ala Arg Tyr Thr Cys Pro Thr Gly Trp Ser Arg
                420                 425                 430

Glu Tyr Tyr Gly Tyr Met Met Ser Glu Gly Lys Ala Lys Asn Arg Glu
            435                 440                 445

Gly Arg Lys Thr Thr Ile Cys Met Asp Phe Ser Ala Glu Ala Val Pro
450                 455                 460

Gly Ser Gly Ala Asn Thr Asn Pro Ser Pro Gly Ile Met Met Arg Ala
465                 470                 475                 480

Asn Cys Asn Gly Leu Ala Cys Pro Pro Tyr Gln Ser Asn Thr Pro Leu
                485                 490                 495

Thr Cys Ala Val Cys Thr Lys Gly Asp Tyr Lys Asp Asp Asp Asp Lys
            500                 505                 510

<210> SEQ ID NO 109
<211> LENGTH: 1539
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 109

```
atgaaaaaga tttggctggc gctggctggt ttagttttag cgtttagcgc atcggcggt      60
tttcctggcg ctccgggtgc cgacggtgct ccgggtcaaa aggtgaact gggtgccgtg     120
ggtccgcagg gcactccggg tctgagtggt cctagtggtc cgaccggtcc accaggtcca    180
aaaggcgtgc gtggtgcacc gggtagcagc ggagccaaag gtgatgcagg taaccctggt    240
gatgacggtc cggttggtcc acagggcgtt ccaggtgttg atggtagccc tggccaaaag    300
ggtgaaaccg tcgtgtggg tcctcgtggt catgatggta ttaatggcac cccaggtgaa    360
gatggtgcga caggctttcc aggtccggat ggcgcaaagg gtgagaaggg caccagcggt    420
acagctggcc tgaagggcga aaagggcgat acatgcatcc cggattcaaa ttcaacactg    480
ggcatgccag gtacgcctgg cgcaggttgg agtaaaggac aaaaaggcga atcaggcatt    540
gtgggaccta aaggcgagaa gggtgagatt ggtactccgg accgccagg ctttcgcggt    600
gcagacggcg aaccgggtca gcgtggcgaa cctggtcgtg caggcgcaca aggtgaacgc    660
ggagcccctg gtaataatgg acgtgatggc tttcctggtg atccaggtgc agatggcgca    720
cctggccaga aaggcgaact gggagcaatt ggtcatccgg gatttagcgg tccgtcaggt    780
ccgagcggac cgacaggtcc tcctggaccg aaaggtgtac gtggcgcaca gggtcgtcct    840
ggcgatcgtg gcagtccagg tgatgtgggt ccgattggtg cacctggtcc tccaggtgcg    900
gacggcgtgc tggtttaac aggtgtgcag ggtcgcgacg gtcctaaagg tgaatcagca    960
agcagcggtg cagtttatgt tcgttgggt cgtaccacct gtcctagcgg agcagatgtt   1020
gtttatagcg gtcgcgcagc cggtgcaaaa tatgatcatt caggtggcac ctcagatcat   1080
cattgtctgc gaataatcc gcagtatctg agcgaagatg ataccaatgc actgggtgca   1140
cagctgtatg gtgtggaata tgaaattcgt gatcgtagca gcccgtataa agcctggat   1200
cagagcgata tgccgtgtgt tgtttgtaat gcaaatggtc gtagccagct gctgatggtt   1260
ccggcacgtt atacatgccc gaccggttgg agccgtgaat attatggtta tatgatgagc   1320
gaaggcaaag ccaaaatcg cgaaggtcgt aaaaccacca tttgtatgga ttttagcgca   1380
gaagcagttc tggtagcgg tgcaaatacc aatccgagtc cgggtattat gatgcgtgca   1440
aattgtaatg gtctggcatg tccgccttat cagagcaata caccgctgac ctgtgccgtt   1500
tgtaccaaag gtgactacaa agacgacgac gacaaataa                         1539
```

<210> SEQ ID NO 110
<211> LENGTH: 219
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 110

```
Met Lys Lys Ile Trp Leu Ala Leu Ala Gly Leu Val Leu Ala Phe Ser
1               5                  10                  15

Ala Ser Ala Gly Pro Ala Gly Ala Lys Gly Pro Ser Gly Asp Ile Gly
            20                  25                  30

Arg Pro Gly Glu Ser Gly Ser Pro Gly Ala Arg Gly His Ser Gly Gln
        35                  40                  45

Pro Gly Arg Thr Gly Ile Ala Gly Asn Gln Gly Leu Pro Gly Thr Ala
    50                  55                  60
```

Gly Glu Glu Gly Arg Thr Gly Pro Pro Gly Ala Gly Leu Arg Gly
65                  70                  75                  80

Gln Ala Gly Met Met Gly Phe Pro Gly Pro Lys Gly Ala Ala Gly Leu
            85                  90                  95

Pro Gly Lys Pro Gly Asp Arg Gly Asn Val Gly Leu Ala Gly Pro Arg
        100                 105                 110

Gly Ala Pro Gly Lys Asp Gly Glu Val Gly Ala Gln Gly Pro Pro Gly
    115                 120                 125

Val Ala Gly Pro Thr Gly Pro Arg Gly Glu Thr Gly Leu Ala Gly Ser
130                 135                 140

Val Gly Phe Gln Gly Met Pro Gly Pro Ser Gly Ala Ala Gly Glu Pro
145                 150                 155                 160

Gly Lys Pro Gly Asn Gln Gly Leu Arg Gly Asp Ala Gly Ser Pro Gly
                165                 170                 175

Met Ile Gly Pro Arg Gly Glu Arg Gly Leu Pro Gly Glu Arg Gly Ala
            180                 185                 190

Ser Gly Ala Gln Gly Leu Leu Gly Pro Arg Gly Thr Ser Gly Ala Pro
        195                 200                 205

Gly Leu Gly Asp Tyr Lys Asp Asp Asp Lys
    210                 215

<210> SEQ ID NO 111
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111
atgaaaaaga tttggctggc gctggctggt ttagttttag cgtttagcgc atcggcgggt      60
ccggcaggcg caaaaggtcc gagcggtgat attggtcgtc cgggtgaaag cggtagtccg     120
ggtgcacgtg gtcatagcgg tcagcctggt cgtaccggta ttgcaggtaa tcagggtctg     180
cctggtacag ccggtgaaga aggtcgcacc ggtccgccag gtcctgcagg tctgcgtggt     240
caggcaggta tgatgggttt tccgggtccg aaaggtgcag cgggtctgcc aggcaaaccg     300
ggtgatcgtg gtaatgttgg tctggctggt ccgcgtggtg caccgggtaa agatggtgaa     360
gttggtgcac agggtcctcc gggtgttgca ggtccgaccg gtcctcgtgg tgaaaccggt     420
ctggcaggta gcgttggttt tcagggtatg ccaggtccgt caggtgcagc aggcgaacct     480
ggtaaaccgg gtaaccaggg cctgcgtggt gatgccggtt caccgggtat gattggtcca     540
cgcggtgaac gtggcctgcc tggcgaacgt ggtgcaagcg gtgcacaagg tctgctgggt     600
ccacgtggca cctcaggcgc accaggtctg ggtgactaca agacgacga cgacaaataa     660

<210> SEQ ID NO 112
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Met Lys Lys Ile Trp Leu Ala Leu Ala Gly Leu Val Leu Ala Phe Ser
1               5                   10                  15

Ala Ser Ala Gln Gly Ile Pro Gly Ser Ala Gly Lys Glu Gly Gly Lys
            20                  25                  30

```
Gly Asp Pro Gly Pro Leu Gly Ser Pro Gly Lys Pro Gly Pro Asp Gly
         35                  40                  45
Leu Arg Gly Phe Ala Gly Ala Arg Gly Leu Pro Gly Ala Ala Gly Pro
 50                  55                  60
Pro Gly Leu Lys Gly Ala Glu Gly Pro Met Gly Ala Pro Gly Leu Thr
 65                  70                  75                  80
Gly Ser Thr Gly Glu Arg Gly Pro Asn Gly Pro Ala Gly Ala Ile Gly
                 85                  90                  95
Leu Pro Gly Arg Pro Gly Pro Gly Pro Pro Gly Pro Val Gly Glu
                100                 105                 110
Lys Gly Asp Pro Gly Asp Lys Gly Leu Pro Gly Ala Gly Asp Asp
                115                 120                 125
Gly Val Gln Gly Ala Met Gly Leu Pro Gly Pro Ile Gly Ser Gln Gly
    130                 135                 140
Pro Pro Gly Asp Tyr Gly Asp Lys Gly Glu Leu Gly Lys Pro Gly Gln
145                 150                 155                 160
Lys Gly Ser Lys Gly Asp Lys Gly Glu Ser Gly Pro Pro Gly Pro Ile
                165                 170                 175
Gly Ile Gln Gly Pro Ile Gly His Pro Gly Pro Ile Gly Ser Asp Gly
            180                 185                 190
Ser Pro Gly Leu Arg Gly Tyr Leu Gly Met Arg Gly Gln Lys Gly Asp
        195                 200                 205
Asp Gly Ile Arg Gly Leu Pro Gly Ser Ala Gly Pro Val Gly Leu Gln
    210                 215                 220
Gly Leu Pro Gly Gly Asp Tyr Lys Asp Asp Asp Lys
225                 230                 235

<210> SEQ ID NO 113
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113
atgaaaaaga tttggctggc gctggctggt ttagttttag cgtttagcgc atcggcgcag      60
ggtattccgg gtagcgcagg taaagaaggt ggtaaaggcg atccgggtcc gctgggttca     120
ccgggtaaac cgggtcctga tggtctgcgt ggttttgccg gtgcacgtgg tctgcctggt     180
gcagcaggtc cgcctggtct gaaaggtgcc gaaggtccga tgggtgctcc gggtctgacc     240
ggtagcaccg gtgaacgcgg tccgaatggt ccggcaggcg caattggtct gccaggtcgt     300
cctggtggtc cgggtcctcc tggtccggtt ggtgaaaaag gtgatcctgg tgataaaggc     360
ctgcctggtc ctgccggtga tgatggtgtt cagggtgcca tgggcttacc gggtccgatt     420
ggtagccagg gtcctccggg tgattatggc gataaaggtg aactgggtaa acctggccag     480
aaaggtagca aaggtgacaa aggcgaaagc ggtccgccag gtccgatcgg cattcagggt     540
cctattggtc atccaggtcc aattggttca gatggctcac cgggactgcg tggctatctg     600
ggtatgcgtg gacagaaagg tgatgacggt attcgtggcc tgccaggtag tgcaggtccg     660
gtgggtctgc agggactgcc tggtggtgac tacaaagacg acgacgacaa ataa          714

<210> SEQ ID NO 114
<211> LENGTH: 254
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 114

```
Met Lys Lys Ile Trp Leu Ala Leu Ala Gly Leu Val Leu Ala Phe Ser
 1               5                  10                  15
Ala Ser Ala Lys Gly Glu Thr Gly Glu Ala Gly Asp Pro Gly Thr Pro
             20                  25                  30
Gly Glu Pro Gly Ile Ala Gly Pro Lys Gly Asp Val Gly Asp Lys Gly
         35                  40                  45
Asp Ala Gly Pro Pro Gly Ala Ala Gly Pro Ala Gly Val Lys Gly Pro
     50                  55                  60
Pro Gly Glu Asp Gly Ala Lys Gly Asp Val Gly Pro Ala Gly Phe Pro
 65                  70                  75                  80
Gly Asp Pro Gly Pro Thr Gly Glu Pro Gly Val Pro Gly Met Asp Gly
                 85                  90                  95
Gly Val Gly Glu Lys Gly Ser Leu Gly Asp Pro Gly Leu Thr Gly Pro
            100                 105                 110
Arg Gly Ala Ser Gly Glu Pro Gly Pro Pro Gly Ser Pro Gly Lys Arg
        115                 120                 125
Gly Pro Pro Gly Pro Ala Gly Pro Glu Gly Arg Glu Gly Leu Lys Gly
    130                 135                 140
Ser Lys Gly Ser Pro Gly Gln Glu Gly Pro Val Gly Arg Thr Gly Pro
145                 150                 155                 160
Ile Gly Pro Gln Gly Ser Pro Gly Asn Val Gly Pro Lys Gly Leu Arg
                165                 170                 175
Gly Ile Pro Gly Pro Thr Gly Gln Gly Leu Leu Gly Pro Pro Gly
            180                 185                 190
Gln Ala Gly Pro Pro Gly Pro Met Gly Pro Pro Gly Met Pro Gly Leu
        195                 200                 205
Arg Gly Ala Gln Gly Leu Lys Gly Asp Lys Gly His Val Gly Leu Ile
    210                 215                 220
Gly Leu Ile Gly Pro Pro Gly Glu Met Gly Glu Lys Gly Asp Gln Gly
225                 230                 235                 240
Leu Pro Gly Ile Gln Gly Asp Tyr Lys Asp Asp Asp Lys
                245                 250
```

<210> SEQ ID NO 115
<211> LENGTH: 765
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 115

```
atgaaaaaga tttggctggc gctggctggt ttagttttag cgtttagcgc atcggcgaaa      60
ggtgaaaccg gtgaagcggg tgatccgggt acaccgggtg aacctggtat tgcaggtccg     120
aaaggtgatg ttggtgataa aggtgacgca ggtccgcctg gtgcagcagg tccggcaggc     180
gttaaaggtc ctccgggtga agatggtgca aaaggcgacg ttggtcctgc aggttttcct     240
ggcgatccgg gtccgactgg tgaaccgggt gtgccaggta tggatggtgg tgtgggtgaa     300
aaaggtagcc tgggtgatcc tggtctgacc ggtccgcgtg gcgcaagtgg tgaaccaggt     360
ccaccgggta gtccgggtaa acgtggtcct cctggaccgg ctggtccgga aggtcgtgaa     420
```

```
ggtctgaaag gtagcaaagg ttcaccgggt caagaaggtc cggttggtcg taccggtccg    480
attggtccgc agggctcacc gggtaatgtt ggtcctaaag gtctgcgtgg tattccgggt    540
cctacaggcg aacagggtct gctgggtccg ccaggccaag caggtcctcc aggtcctatg    600
ggtccacctg gtatgcctgg cctgcgtggt gcccagggcc tgaaaggcga taaaggccat    660
gttggtctga ttggcctgat tggtccacca ggtgaaatgg gagaaaaagg cgatcagggc    720
ctgcctggta ttcagggtga ctacaaagac gacgacgaca aataa                    765
```

<210> SEQ ID NO 116
<211> LENGTH: 30
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: MISC_FEATURE
<222> LOCATION: (1)..(30)
<223> OTHER INFORMATION: This sequence may encompass 2-30 residues

<400> SEQUENCE: 116

His His His His His His His His His His His His His His His His
1               5                   10                  15

His His His His His His His His His His His His His His
                20                  25                  30

<210> SEQ ID NO 117
<211> LENGTH: 20
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: MISC_FEATURE
<222> LOCATION: (1)..(20)
<223> OTHER INFORMATION: This sequence may encompass 2-20 residues

<400> SEQUENCE: 117

His His His His His His His His His His His His His His His His
1               5                   10                  15

His His His His
                20

<210> SEQ ID NO 118
<211> LENGTH: 15
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: MISC_FEATURE
<222> LOCATION: (1)..(15)
<223> OTHER INFORMATION: This sequence may encompass 5-15 residues

<400> SEQUENCE: 118

His His His His His His His His His His His His His His His
1               5                   10                  15

<210> SEQ ID NO 119
<211> LENGTH: 18
<212> TYPE: PRT
<213> ORGANISM: Artificial Sequence
<220> FEATURE:

<223> OTHER INFORMATION: Description of Artificial Sequence: Synthetic
      His tag
<220> FEATURE:
<221> NAME/KEY: MISC_FEATURE
<222> LOCATION: (1)..(18)
<223> OTHER INFORMATION: This sequence may encompass 5-18 residues

<400> SEQUENCE: 119

His His His His His His His His His His His His His His His His
1               5                   10                  15

His His

<210> SEQ ID NO 120
<211> LENGTH: 16
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: MISC_FEATURE
<222> LOCATION: (1)..(16)
<223> OTHER INFORMATION: This sequence may encompass 5-16 residues

<400> SEQUENCE: 120

His His His His His His His His His His His His His His His His
1               5                   10                  15

<210> SEQ ID NO 121
<211> LENGTH: 14
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: MISC_FEATURE
<222> LOCATION: (1)..(14)
<223> OTHER INFORMATION: This sequence may encompass 5-14 residues

<400> SEQUENCE: 121

His His His His His His His His His His His His His His
1               5                   10

<210> SEQ ID NO 122
<211> LENGTH: 13
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: MISC_FEATURE
<222> LOCATION: (1)..(13)
<223> OTHER INFORMATION: This sequence may encompass 5-13 residues

<400> SEQUENCE: 122

His His His His His His His His His His His His His
1               5                   10

<210> SEQ ID NO 123
<211> LENGTH: 12
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: MISC_FEATURE
<222> LOCATION: (1)..(12)

<223> OTHER INFORMATION: This sequence may encompass 5-12 residues

<400> SEQUENCE: 123

His His His His His His His His His His His His
1               5                   10

<210> SEQ ID NO 124
<211> LENGTH: 11
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: MISC_FEATURE
<222> LOCATION: (1)..(11)
<223> OTHER INFORMATION: This sequence may encompass 5-11 residues

<400> SEQUENCE: 124

His His His His His His His His His His His
1               5                   10

<210> SEQ ID NO 125
<211> LENGTH: 10
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: MISC_FEATURE
<222> LOCATION: (1)..(10)
<223> OTHER INFORMATION: This sequence may encompass 5-10 residues

<400> SEQUENCE: 125

His His His His His His His His His His
1               5                   10

<210> SEQ ID NO 126
<211> LENGTH: 12
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: MISC_FEATURE
<222> LOCATION: (1)..(12)
<223> OTHER INFORMATION: This sequence may encompass 6-12 residues

<400> SEQUENCE: 126

His His His His His His His His His His His His
1               5                   10

<210> SEQ ID NO 127
<211> LENGTH: 11
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: MISC_FEATURE
<222> LOCATION: (1)..(11)
<223> OTHER INFORMATION: This sequence may encompass 6-11 residues

<400> SEQUENCE: 127

His His His His His His His His His His His
1               5                   10

<210> SEQ ID NO 128
<211> LENGTH: 10
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: MISC_FEATURE
<222> LOCATION: (1)..(10)
<223> OTHER INFORMATION: This sequence may encompass 7-10 residues

<400> SEQUENCE: 128

His His His His His His His His His His
1               5                   10

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      9xHis tag

<400> SEQUENCE: 129

His His His His His His His His His
1               5

<210> SEQ ID NO 130
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(150)
<223> OTHER INFORMATION: This sequence may encompass 2-50 "Gly Glu Lys"
      repeating units

<400> SEQUENCE: 130

Gly Glu Lys Gly Glu Lys Gly Glu Lys Gly Glu Lys Gly Glu Lys Gly
1               5                   10                  15

Glu Lys Gly Glu Lys Gly Glu Lys Gly Glu Lys Gly Glu Lys Gly Glu
                20                  25                  30

Lys Gly Glu Lys Gly Glu Lys Gly Glu Lys Gly Glu Lys Gly Glu Lys
            35                  40                  45

Gly Glu Lys Gly Glu Lys Gly Glu Lys Gly Glu Lys Gly Glu Lys Gly
        50                  55                  60

Glu Lys Gly Glu Lys Gly Glu Lys Gly Glu Lys Gly Glu Lys Gly Glu
65                  70                  75                  80

Lys Gly Glu Lys Gly Glu Lys Gly Glu Lys Gly Glu Lys Gly Glu Lys
                85                  90                  95

Gly Glu Lys Gly Glu Lys Gly Glu Lys Gly Glu Lys Gly Glu Lys Gly
            100                 105                 110

Glu Lys Gly Glu Lys Gly Glu Lys Gly Glu Lys Gly Glu Lys Gly Glu
        115                 120                 125

Lys Gly Glu Lys Gly Glu Lys Gly Glu Lys Gly Glu Lys Gly Glu Lys
    130                 135                 140

Gly Glu Lys Gly Glu Lys
145                 150

```
<210> SEQ ID NO 131
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(150)
<223> OTHER INFORMATION: This sequence may encompass 2-50 "Gly Asp Lys"
      repeating units

<400> SEQUENCE: 131

Gly Asp Lys Gly Asp Lys Gly Asp Lys Gly Asp Lys Gly
1               5                   10                  15

Asp Lys Gly Asp Lys Gly Asp Lys Gly Asp Lys Gly Asp
            20                  25                  30

Lys Gly Asp Lys Gly Asp Lys Gly Asp Lys Gly Asp Lys
        35                  40                  45

Gly Asp Lys Gly Asp Lys Gly Asp Lys Gly Asp Lys Gly
50                  55                  60

Asp Lys Gly Asp Lys Gly Asp Lys Gly Asp Lys Gly Asp
65                  70                  75                  80

Lys Gly Asp Lys Gly Asp Lys Gly Asp Lys Gly Asp Lys
            85                  90                  95

Gly Asp Lys Gly Asp Lys Gly Asp Lys Gly Asp Lys Gly
            100                 105                 110

Asp Lys Gly Asp Lys Gly Asp Lys Gly Asp Lys Gly Asp
        115                 120                 125

Lys Gly Asp Lys Gly Asp Lys Gly Asp Lys Gly Asp Lys
    130                 135                 140

Gly Asp Lys Gly Asp Lys
145                 150

<210> SEQ ID NO 132
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(120)
<223> OTHER INFORMATION: This sequence may encompass 2-40 "Gly Glu Lys"
      repeating units

<400> SEQUENCE: 132

Gly Glu Lys Gly Glu Lys Gly Glu Lys Gly Glu Lys Gly
1               5                   10                  15

Glu Lys Gly Glu Lys Gly Glu Lys Gly Glu Lys Gly Glu
            20                  25                  30

Lys Gly Glu Lys Gly Glu Lys Gly Glu Lys Gly Glu Lys
        35                  40                  45

Gly Glu Lys Gly Glu Lys Gly Glu Lys Gly Glu Lys Gly
    50                  55                  60

Glu Lys Gly Glu Lys Gly Glu Lys Gly Glu Lys Gly Glu
65                  70                  75                  80

Lys Gly Glu Lys Gly Glu Lys Gly Glu Lys Gly Glu Lys
            85                  90                  95
```

Gly Glu Lys Gly Glu Lys Gly Glu Lys Gly Glu Lys Gly
            100                 105                 110

Glu Lys Gly Glu Lys Gly Glu Lys
        115                 120

<210> SEQ ID NO 133
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(120)
<223> OTHER INFORMATION: This sequence may encompass 2-40 "Gly Asp Lys"
      repeating units

<400> SEQUENCE: 133

Gly Asp Lys Gly Asp Lys Gly Asp Lys Gly Asp Lys Gly Asp Lys Gly
1               5                   10                  15

Asp Lys Gly Asp Lys Gly Asp Lys Gly Asp Lys Gly Asp Lys Gly Asp
            20                  25                  30

Lys Gly Asp Lys Gly Asp Lys Gly Asp Lys Gly Asp Lys Gly Asp Lys
        35                  40                  45

Gly Asp Lys Gly Asp Lys Gly Asp Lys Gly Asp Lys Gly Asp Lys Gly
    50                  55                  60

Asp Lys Gly Asp Lys Gly Asp Lys Gly Asp Lys Gly Asp Lys Gly Asp
65                  70                  75                  80

Lys Gly Asp Lys Gly Asp Lys Gly Asp Lys Gly Asp Lys Gly Asp Lys
                85                  90                  95

Gly Asp Lys Gly Asp Lys Gly Asp Lys Gly Asp Lys Gly Asp Lys Gly
            100                 105                 110

Asp Lys Gly Asp Lys Gly Asp Lys
        115                 120

<210> SEQ ID NO 134
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(90)
<223> OTHER INFORMATION: This sequence may encompass 2-30 "Gly Glu Lys"
      repeating units

<400> SEQUENCE: 134

Gly Glu Lys Gly Glu Lys Gly Glu Lys Gly Glu Lys Gly Glu Lys Gly
1               5                   10                  15

Glu Lys Gly Glu Lys Gly Glu Lys Gly Glu Lys Gly Glu Lys Gly Glu
            20                  25                  30

Lys Gly Glu Lys Gly Glu Lys Gly Glu Lys Gly Glu Lys Gly Glu Lys
        35                  40                  45

Gly Glu Lys Gly Glu Lys Gly Glu Lys Gly Glu Lys Gly Glu Lys Gly
    50                  55                  60

Glu Lys Gly Glu Lys Gly Glu Lys Gly Glu Lys Gly Glu Lys Gly Glu
65                  70                  75                  80

Lys Gly Glu Lys Gly Glu Lys Gly Glu Lys
                85                  90

<210> SEQ ID NO 135
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(90)
<223> OTHER INFORMATION: This sequence may encompass 2-30 "Gly Asp Lys"
      repeating units

<400> SEQUENCE: 135

Gly Asp Lys Gly Asp Lys Gly Asp Lys Gly Asp Lys Gly Asp Lys Gly
1               5                   10                  15

Asp Lys Gly Asp Lys Gly Asp Lys Gly Asp Lys Gly Asp Lys Gly Asp
            20                  25                  30

Lys Gly Asp Lys Gly Asp Lys Gly Asp Lys Gly Asp Lys Gly Asp Lys
        35                  40                  45

Gly Asp Lys Gly Asp Lys Gly Asp Lys Gly Asp Lys Gly Asp Lys Gly
    50                  55                  60

Asp Lys Gly Asp Lys Gly Asp Lys Gly Asp Lys Gly Asp Lys Gly Asp
65                  70                  75                  80

Lys Gly Asp Lys Gly Asp Lys Gly Asp Lys
                85                  90

<210> SEQ ID NO 136
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(60)
<223> OTHER INFORMATION: This sequence may encompass 2-20 "Gly Glu Lys"
      repeating units

<400> SEQUENCE: 136

Gly Glu Lys Gly Glu Lys Gly Glu Lys Gly Glu Lys Gly Glu Lys Gly
1               5                   10                  15

Glu Lys Gly Glu Lys Gly Glu Lys Gly Glu Lys Gly Glu Lys Gly Glu
            20                  25                  30

Lys Gly Glu Lys Gly Glu Lys Gly Glu Lys Gly Glu Lys Gly Glu Lys
        35                  40                  45

Gly Glu Lys Gly Glu Lys Gly Glu Lys Gly Glu Lys
    50                  55                  60

<210> SEQ ID NO 137
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(60)
<223> OTHER INFORMATION: This sequence may encompass 2-20 "Gly Asp Lys"
      repeating units

<400> SEQUENCE: 137

```
Gly Asp Lys Gly Asp Lys Gly Asp Lys Gly Asp Lys Gly
1               5                   10                  15

Asp Lys Gly Asp Lys Gly Asp Lys Gly Asp Lys Gly Asp
            20                  25                  30

Lys Gly Asp Lys Gly Asp Lys Gly Asp Lys Gly Asp Lys
            35                  40                  45

Gly Asp Lys Gly Asp Lys Gly Asp Lys
            50                  55              60
```

<210> SEQ ID NO 138
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(45)
<223> OTHER INFORMATION: This sequence may encompass 2-15 "Gly Glu Lys"
      repeating units

<400> SEQUENCE: 138

```
Gly Glu Lys Gly Glu Lys Gly Glu Lys Gly Glu Lys Gly Glu Lys Gly
1               5                   10                  15

Glu Lys Gly Glu Lys Gly Glu Lys Gly Glu Lys Gly Glu Lys Gly Glu
            20                  25                  30

Lys Gly Glu Lys Gly Glu Lys Gly Glu Lys Gly Glu Lys
            35                  40                  45
```

<210> SEQ ID NO 139
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(45)
<223> OTHER INFORMATION: This sequence may encompass 2-15 "Gly Asp Lys"
      repeating units

<400> SEQUENCE: 139

```
Gly Asp Lys Gly Asp Lys Gly Asp Lys Gly Asp Lys Gly Asp Lys Gly
1               5                   10                  15

Asp Lys Gly Asp Lys Gly Asp Lys Gly Asp Lys Gly Asp Lys Gly Asp
            20                  25                  30

Lys Gly Asp Lys Gly Asp Lys Gly Asp Lys Gly Asp Lys
            35                  40                  45
```

<210> SEQ ID NO 140
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(30)
<223> OTHER INFORMATION: This sequence may encompass 2-10 "Gly Glu Lys"
      repeating units

<400> SEQUENCE: 140

```
Gly Glu Lys Gly Glu Lys Gly Glu Lys Gly Glu Lys Gly Glu Lys Gly
```

```
                1               5                  10                 15
Glu Lys Gly Glu Lys Gly Glu Lys Gly Glu Lys Gly Glu Lys
                20                 25                 30

<210> SEQ ID NO 141
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(30)
<223> OTHER INFORMATION: This sequence may encompass 2-10 "Gly Asp Lys"
      repeating units

<400> SEQUENCE: 141

Gly Asp Lys Gly Asp Lys Gly Asp Lys Gly Asp Lys Gly Asp Lys Gly
1               5                   10                  15
Asp Lys Gly Asp Lys Gly Asp Lys Gly Asp Lys Gly Asp Lys
                20                  25                  30

<210> SEQ ID NO 142
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(27)
<223> OTHER INFORMATION: This sequence may encompass 2-9 "Gly Glu Lys"
      repeating units

<400> SEQUENCE: 142

Gly Glu Lys Gly Glu Lys Gly Glu Lys Gly Glu Lys Gly Glu Lys Gly
1               5                   10                  15
Glu Lys Gly Glu Lys Gly Glu Lys Gly Glu Lys
                20                  25

<210> SEQ ID NO 143
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(27)
<223> OTHER INFORMATION: This sequence may encompass 2-9 "Gly Asp Lys"
      repeating units

<400> SEQUENCE: 143

Gly Asp Lys Gly Asp Lys Gly Asp Lys Gly Asp Lys Gly Asp Lys Gly
1               5                   10                  15
Asp Lys Gly Asp Lys Gly Asp Lys Gly Asp Lys
                20                  25

<210> SEQ ID NO 144
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MISC_FEATURE
<222> LOCATION: (1)..(24)
<223> OTHER INFORMATION: This sequence may encompass 2-8 "Gly Glu Lys"
      repeating units

<400> SEQUENCE: 144

Gly Glu Lys Gly Glu Lys Gly Glu Lys Gly Glu Lys Gly Glu Lys Gly
1               5                   10                  15

Glu Lys Gly Glu Lys Gly Glu Lys
            20

<210> SEQ ID NO 145
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(24)
<223> OTHER INFORMATION: This sequence may encompass 2-8 "Gly Asp Lys"
      repeating units

<400> SEQUENCE: 145

Gly Asp Lys Gly Asp Lys Gly Asp Lys Gly Asp Lys Gly Asp Lys Gly
1               5                   10                  15

Asp Lys Gly Asp Lys Gly Asp Lys
            20

<210> SEQ ID NO 146
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(21)
<223> OTHER INFORMATION: This sequence may encompass 2-7 "Gly Glu Lys"
      repeating units

<400> SEQUENCE: 146

Gly Glu Lys Gly Glu Lys Gly Glu Lys Gly Glu Lys Gly Glu Lys Gly
1               5                   10                  15

Glu Lys Gly Glu Lys
            20

<210> SEQ ID NO 147
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(21)
<223> OTHER INFORMATION: This sequence may encompass 2-7 "Gly Asp Lys"
      repeating units

<400> SEQUENCE: 147

Gly Asp Lys Gly Asp Lys Gly Asp Lys Gly Asp Lys Gly Asp Lys Gly
1               5                   10                  15

Asp Lys Gly Asp Lys
            20
```

```
<210> SEQ ID NO 148
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(18)
<223> OTHER INFORMATION: This sequence may encompass 2-6 "Gly Glu Lys"
      repeating units

<400> SEQUENCE: 148

Gly Glu Lys Gly Glu Lys Gly Glu Lys Gly Glu Lys Gly Glu Lys Gly
1               5                   10                  15

Glu Lys

<210> SEQ ID NO 149
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(18)
<223> OTHER INFORMATION: This sequence may encompass 2-6 "Gly Asp Lys"
      repeating units

<400> SEQUENCE: 149

Gly Asp Lys Gly Asp Lys Gly Asp Lys Gly Asp Lys Gly Asp Lys Gly
1               5                   10                  15

Asp Lys

<210> SEQ ID NO 150
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(15)
<223> OTHER INFORMATION: This sequence may encompass 2-5 "Gly Glu Lys"
      repeating units

<400> SEQUENCE: 150

Gly Glu Lys Gly Glu Lys Gly Glu Lys Gly Glu Lys Gly Glu Lys
1               5                   10                  15

<210> SEQ ID NO 151
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(15)
<223> OTHER INFORMATION: This sequence may encompass 2-5 "Gly Asp Lys"
      repeating units

<400> SEQUENCE: 151

Gly Asp Lys Gly Asp Lys Gly Asp Lys Gly Asp Lys Gly Asp Lys
```

```
                    -continued
1               5              10              15

<210> SEQ ID NO 152
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(12)
<223> OTHER INFORMATION: This sequence may encompass 2-4 "Gly Glu Lys"
      repeating units

<400> SEQUENCE: 152

Gly Glu Lys Gly Glu Lys Gly Glu Lys Gly Glu Lys
1               5                   10

<210> SEQ ID NO 153
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(12)
<223> OTHER INFORMATION: This sequence may encompass 2-4 "Gly Asp Lys"
      repeating units

<400> SEQUENCE: 153

Gly Asp Lys Gly Asp Lys Gly Asp Lys Gly Asp Lys
1               5                   10
```

What is claimed is:

1. A recombinant polypeptide comprising the amino acid sequence of SEQ ID NO: 1 having an internal truncation of from 50 amino acids to 250 amino acids.

2. The recombinant polypeptide of claim 1, wherein the recombinant polypeptide comprises the amino acid sequence according to SEQ ID NO: 91 or a fragment thereof.

3. The recombinant polypeptide of claim 1, wherein the recombinant polypeptide consists of the amino acid sequence according to SEQ ID NO: 91.

4. The recombinant polypeptide of claim 1, further comprising one or more selected from the group consisting of: a secretion tag, a histidine tag, a fluorescent protein, a protease cleavage site, and a beta-lactamase protein.

5. The recombinant polypeptide of claim 4, wherein the secretion tag is DsbA.

6. The recombinant polypeptide of claim 1, further comprising one or more GEK amino acid trimer repeats, one or more GDK trimer repeats, or a combination thereof.

7. A composition comprising from 0.005% w/w to 30% w/w of a recombinant polypeptide according to claim 1.

8. The composition of claim 7, wherein the recombinant polypeptide comprises the amino acid sequence according to SEQ ID NO: 91 or a fragment thereof.

9. The composition of claim 7, wherein the recombinant polypeptide consists of the amino acid sequence according to SEQ ID NO: 91.

10. The composition of claim 7, wherein the composition is formulated for topical application.

11. The composition of claim 10, wherein the composition comprises a topical carrier, a preservative, or both.

12. The composition of claim 11, wherein the topical carrier is selected from the group consisting of: a liposome, a biodegradable microcapsule, a lotion, a spray, an aerosol, a dusting powder, a biodegradable polymer, a mineral oil, a triglyceride oil, a silicone oil, glycerin, glycerin monostearate, an alcohol, an emulsifying agents, a liquid petroleum, a white petrolatum, propylene glycol, polyoxyethylene, polyoxypropylene, wax, sorbitan monostearate, polysorbate, cetyl ester wax, cetearyl alcohol, 2-octyldodecanol, benzyl alcohol, cyclomethicone, cyclopentasiloxane, water, and any combination thereof.

13. The composition of claim 11, wherein the preservative is selected from the group consisting of: tocopherol, diiodomethyl-p-tolylsulfone, 2-bromo-2-nitropropane-1,3-diol, cis isomer 1-(3-chloroallyl)-3,5,7-triaza-1-azoniaadamantane chloride, glutaraldehyde, 4,4-dimethyl oxazolidine, 7-ethylbicyclooxazolidine, methyl paraben, sorbic acid, rosemary extract, ethylenediaminetetraacetic acid (EDTA), and any combination thereof.

14. The composition of claim 10, wherein the composition is a cosmetic.

15. A method of treating the skin of a subject, the method comprising administering to the skin of a subject a composition according to claim 10, thereby treating the skin of the subject.

16. The method of claim 15, wherein the treating results in an increase in viability of keratinocytes, fibroblasts, or both, of the subject after exposure to ultraviolet (UV) radiation.

17. The method of claim 15, wherein the treating results in an increase in viability of keratinocytes, fibroblasts, or both, of the subject after exposure to urban dust.

18. The method of claim 15, wherein the treating results in a decrease in production of inflammatory cytokines.

19. The method of claim 15, wherein the subject is a human.

\* \* \* \* \*